United States Patent
Sakamoto et al.

(10) Patent No.: US 10,358,470 B2
(45) Date of Patent: **\*Jul. 23, 2019**

(54) GLYCOSYLATED POLYPEPTIDE AND PHARMACEUTICAL COMPOSITION CONTAINING SAME

(71) Applicant: GLYTECH, INC., Kyoto (JP)

(72) Inventors: Izumi Sakamoto, Kyoto (JP);
Kazuhiro Fukae, Kyoto (JP);
Katsunari Tezuka, Kyoto (JP);
Keisuke Tazuru, Kyoto (JP);
Masatoshi Maeda, Kyoto (JP);
Yasuhiro Kajihara, Kyoto (JP);
Takashi Tsuji, Kyoto (JP)

(73) Assignee: GLYTECH, INC., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/347,222

(22) PCT Filed: Sep. 28, 2012

(86) PCT No.: PCT/JP2012/075262
§ 371 (c)(1),
(2) Date: Mar. 25, 2014

(87) PCT Pub. No.: WO2013/047846
PCT Pub. Date: Apr. 4, 2013

(65) Prior Publication Data
US 2014/0369964 A1 Dec. 18, 2014

(30) Foreign Application Priority Data

Oct. 1, 2011 (JP) .................................. 2011-218793

(51) Int. Cl.
| C07K 14/565 | (2006.01) |
| A61K 38/00 | (2006.01) |
| C07K 1/02 | (2006.01) |
| A61K 38/21 | (2006.01) |
| C07K 1/107 | (2006.01) |

(52) U.S. Cl.
CPC ............ *C07K 14/565* (2013.01); *A61K 38/00* (2013.01); *A61K 38/215* (2013.01); *C07K 1/026* (2013.01); *C07K 1/1077* (2013.01)

(58) Field of Classification Search
None
See application file for complete search history.

(56) References Cited

U.S. PATENT DOCUMENTS

| 6,514,729 | B1 | 2/2003 | Bentzien |
| 6,572,853 | B1 | 6/2003 | Schneider-Fresenius et al. |
| 7,446,173 | B2 | 11/2008 | Pepinsky et al. |
| 7,700,314 | B2 * | 4/2010 | El-Tayar ............... A61K 47/60 435/68.1 |
| 7,829,659 | B2 | 11/2010 | Grabstein et al. |
| 7,985,731 | B2 | 7/2011 | Kajihara et al. |
| 2002/0119516 | A1 | 8/2002 | Paulson et al. |
| 2002/0160460 | A1 | 10/2002 | Paulson et al. |
| 2003/0124645 | A1 | 7/2003 | Paulson et al. |
| 2004/0115168 | A1 | 6/2004 | DeFrees et al. |
| 2004/0137581 | A1 | 7/2004 | Aguinaldo et al. |
| 2005/0221344 | A1* | 10/2005 | Welcher ............... C07K 14/555 435/6.14 |
| 2006/0040353 | A1 | 2/2006 | Davidson et al. |
| 2008/0003202 | A1* | 1/2008 | Guyon ................ C07K 14/565 424/85.6 |
| 2009/0043076 | A1 | 2/2009 | Carr et al. |
| 2009/0214472 | A1 | 8/2009 | Filpula et al. |
| 2010/0003721 | A1 | 1/2010 | Shin et al. |
| 2010/0145017 | A1 | 6/2010 | Narumi et al. |
| 2011/0172392 | A1 | 7/2011 | Kajihara et al. |
| 2011/0195897 | A1 | 8/2011 | Kajihara et al. |
| 2011/0262945 | A1* | 10/2011 | Kajihara ............... C07K 1/1077 435/23 |
| 2014/0058062 | A1 | 2/2014 | Kajihara et al. |
| 2014/0148585 | A1 | 5/2014 | Sugihara et al. |

FOREIGN PATENT DOCUMENTS

| EP | 237019 A2 | 9/1987 |
| EP | 2330114 A1 | 6/2011 |
| JP | 63-267296 | 11/1988 |
| JP | 2002-543790 A | 12/2002 |
| JP | 2002-543790 A | 12/2002 |
| JP | 2008-518631 A | 6/2008 |
| JP | 2008-518631 A | 6/2008 |
| JP | 2009242372 | 10/2009 |
| JP | 2011-024597 A | 2/2011 |
| RU | 2007103479 | 9/2008 |
| RU | 2014116550 | 10/2015 |
| WO | WO-00/23472 | 4/2000 |
| WO | WO 02/20033 A1 | 3/2002 |
| WO | WO 2002/074806 A2 | 9/2002 |
| WO | WO-03/075944 | 9/2003 |
| WO | WO 2004/020468 A2 | 3/2004 |
| WO | 2005019260 | 3/2005 |
| WO | WO 2005/019260 A1 | 3/2005 |
| WO | WO 2006020580 | 2/2006 |
| WO | WO-2007/110231 | 10/2007 |
| WO | WO 2009/017154 | 2/2009 |
| WO | WO-2009/017154 A1 | 2/2009 |
| WO | WO 2009/153960 A1 | 12/2009 |
| WO | WO-2009/153960 A1 | 12/2009 |
| WO | WO-2010/015722 | 2/2010 |

(Continued)

OTHER PUBLICATIONS

Kolchanov, 1988, Journal of Molecular Evolution, vol. 27, pp. 154-162.*

(Continued)

*Primary Examiner* — Joanne Hama
*Assistant Examiner* — Jegatheesan Seharaseyon
(74) *Attorney, Agent, or Firm* — Myers Bigel, P.A.

(57) ABSTRACT

The object of the present invention is to provide a glycosylated polypeptide having uniform sugar chain structure which has interferon β activity. It was found that a glycosylated polypeptide having uniform sugar chain structure as well as having interferon β activity can be prepared by a method comprising a step of synthesizing a glycosylated peptide fragment and at least two peptide fragments and a step of linking the glycosylated peptide fragment and the at least two peptide fragments.

22 Claims, 50 Drawing Sheets
Specification includes a Sequence Listing.

(56) References Cited

FOREIGN PATENT DOCUMENTS

| WO | WO 2010/021126 A1 | 2/2010 |
| WO | WO-2010/021126 A1 | 2/2010 |
| WO | WO 2012/051615 A1 | 4/2012 |
| WO | WO 2012/121206 A1 | 9/2012 |
| WO | WO 2013/002330 A1 | 1/2013 |

OTHER PUBLICATIONS

Pasquo, 2012, PLoS ONE, vol. 7, Issue 2, e32555.*
Bork, 2000, Genome Research 10:398-400.*
Bork et al., 1996, Trends in Genetics 12:425-427.*
Pakula et al. Annu. REv. Genet., vol. 23, pp. 289-310 (Year: 1989).*
Conibear et al., J.Chem. Soc. Rev., vol. 47, pp. 9046-9068. (Year: 2018).*
Extended European Search Report, EP12836998 dated Apr. 7, 2015, 9 pages.
Gross, G. et al., Interfereon-beta [synthetic construct]; Genbank accession AAA72975.1; Apr. 27, 1993.
Gawlitzek et al., "Characterization of changes in the glycosylation pattern of recombinant proteins from BHK-21 celss due to different culture conditions," J. Biotechnol., (1995), 42:117-131.
Haselberg et al., "Capillary electrophoresis mass spectrometry using nonconvalently coated capillaries for the analysis of biopharmaceuticals," Anal. Bioanal. Chem., (2001), 400:295-303.
Karpusas et al., "The crystal structure of human interferon β at 2.2-A resolution," Proc. Natl. Acad. Sci. (1997), 94:11813-11818.
Walsh et al., "Post-translational modifications in the context of therapeutic proteins," Nat. Biotechnol., (2006), 24(10):1241-1252.
International Searh Report for PCT Application No. PCT/JP2012/075262, dated Nov. 13, 2012.
Sakamoto et al., "Chemical Synthesis of Homogeneous Human Glycosyl-interferon-β That Exhibits Potent Antitumor Activity in Vivo", J. Am. Chem. Soc., 2012, 134:5428-5431.
Gawlitzek et al. "Characterization of changes in the glycosylation pattern of recombinant proteins from BHK-21 cells due to different culture conditions", *J. Biotechnol.* vol. 42: pp. 117-131 (1995).
Haselberg et al. "Capillary electrophoresis-mass spectrometry using noncovalently coated capillaries for the analysis of biopharmaceuticals", *Anal Bioanal Chem* vol. 400: pp. 295-303 (2011).
Imanishi, J. *Gan to Kagaku Ryoho* 21(16):2853-8 (1994) (abstract only).
Karpusas et al. "*The crystal structure of human interferon-β at 2.2-Å resolution*", PNAS 94: pp. 11813-11818 (1997).
Karpusas "*The structure of human interferon-β: implications for activity*", Cell. Mol. Life Sci. 54: pp. 1203-1216 (1998).
Revel, M. *Structure, Action, Differential Actions, and Medical Applications. In Growth Factors and Cytokines in Health and Disease.* vol. 2B: pp. 433-520, JAI Press Inc (1997).
Ruzicka et al. "*Binding of recombinant-produced interfereon beta ser to human lymphoblastoid cells*", Evidence for two binding domains. J Biological Chem. 262: pp. 16142-16149 (1987).
Senda et al. "*Three-dimensional crystal structure of recombinant murine interferon-β*", The EMBO J. 11(9): pp. 3193-3201 (1992).
Wadler and Schwartz "*New Advances in Interferon Therapy*", The Oncologist 2:254-267 (1997).
Greene T.W. et al, "Protective groups in organic synthesis", 2 edition, John Wiley & Sons, Inc, Canada, 1991, p. 473, line 293.
Russian Office Action corresponding to Russian Application No. 2007103479, dated Sep. 27, 2016, 7 pages.
Extended European Search Report corresponding to International Application No. PCT/JP2014/058127, dated Sep. 28, 2016, 8 pages.
International Search Report corresponding to PCT/JP2014/058127; dated Jun. 10, 2014.
Ishida et al., "Accelerated clearance of PEGylated liposomes in rats after repeated injections", *J. Control. Rel.*, 88, 2003. pp. 35-42.
Porter et al. "Novel Modified β-Interferons: Gene Cloning, Expression, and Biological Activity in Bacterial Extracts", *DNA*, vol. 5, No. 2, 1986, Mary Ann Liebert, Inc., Publishers, pp. 137-148.
Walsh et al. "Post-translational modifications in the context of therapeutic proteins", *Nature Biotechnology*, 24, pp. 1241-1252 (2006).
Runkle et al. "Systematic Mutational Mapping of Sites on Human Interferon-å-1a That Are Important for Receptor Binding and Functional Activity", *Biochemistry*, 39, pp. 2538-2551 (2000).
Miranda et al. "Accelerated chemical synthesis of peptides and small proteins", Proc. Natl. Acad. Sci. USA 96:1181-1186 (1999).
Chan, W.C. and White, P.D. "Fmoc Solid Phase Peptide Synthesis: A Practical Approach" Eds. Oxford University Press, 4 pages (2000).
Ghane, M. et. al., "Design Construction and Expression of a Synthetic βInterferon (IFN-B) Gene in *E. coli*", Pak. J. Biol. Sci., 9:2922-2926 (2006).

* cited by examiner

[Figure 1]
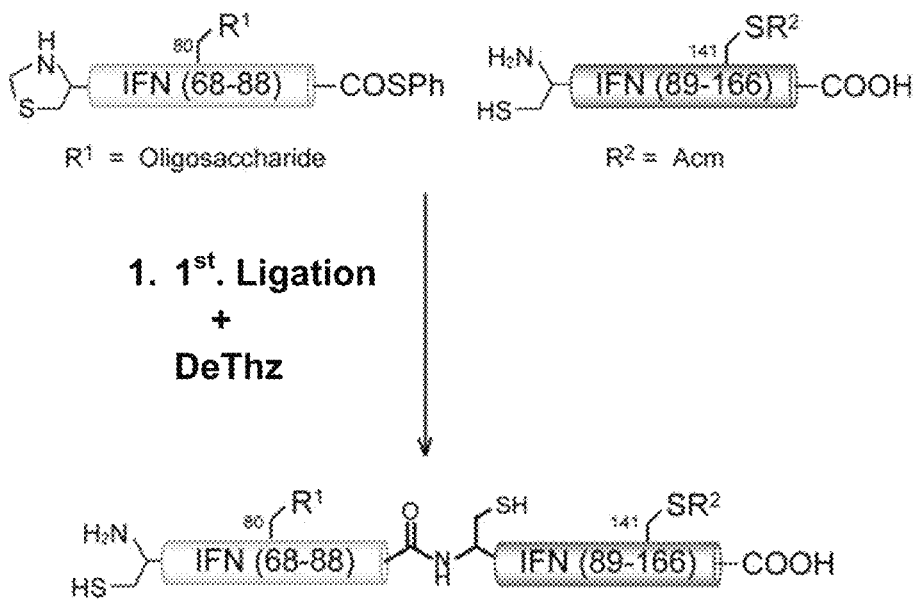
[Figure 2]
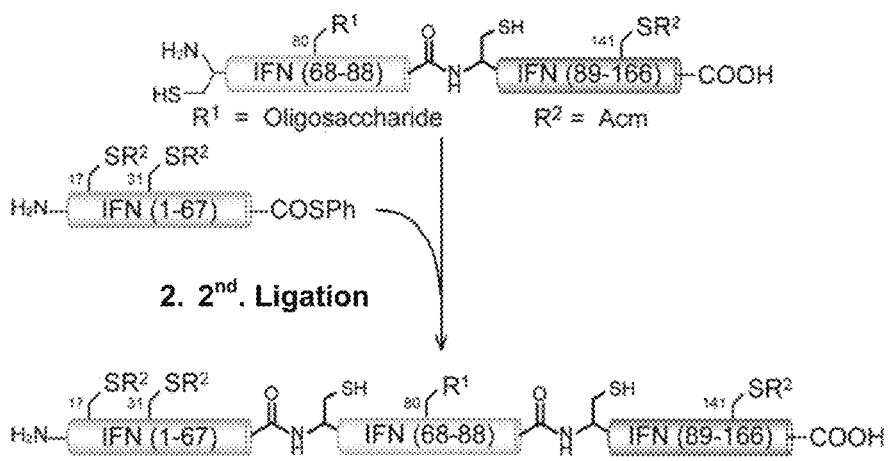

[Figure 3]
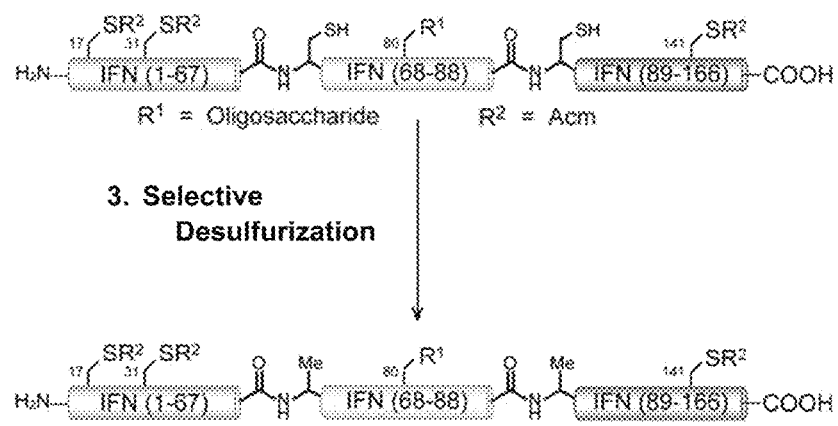
[Figure 4]
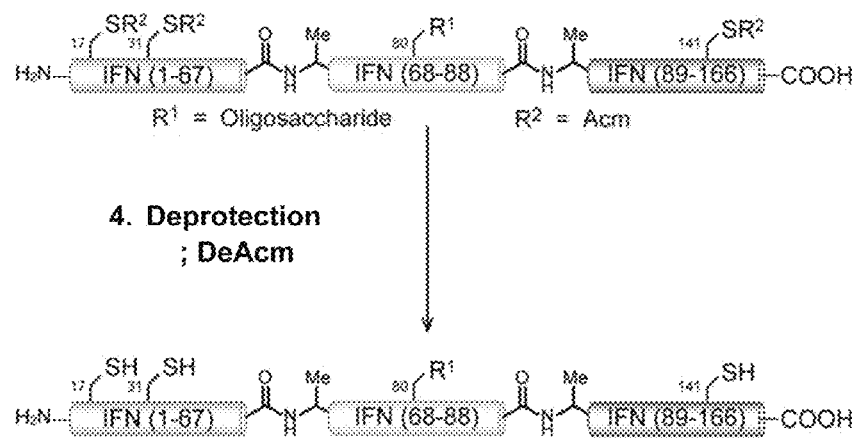

[Figure 5]
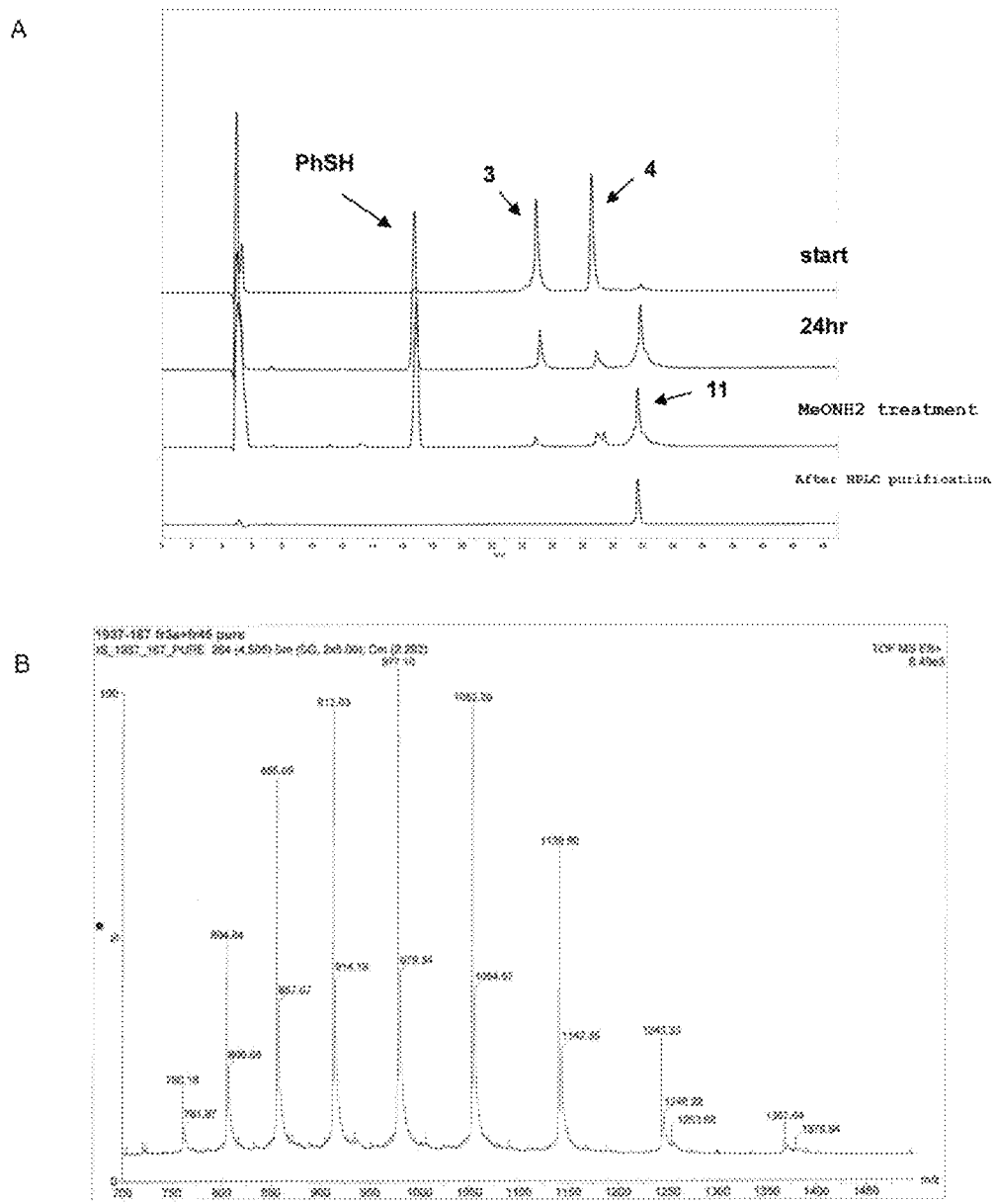

[Figure 6]

Peptide fragment (11) (SEQ ID NO. 16)

H₂N-Cys-Ile-Phe-Arg-Gln-Asp-Ser-Ser-Ser-Thr-Gly-Trp-
                    70

Asn(asialyloligosaccharide)-Glu-Thr-Ile-Val-Glu-Asn-Leu-Leu-Cys-
80

Asn-Val-Tyr-His-Gln-Ile-Asn-His-Leu-Lys-Thr-Val-Leu-Glu-Glu-Lys-
90                                          100

Leu-Glu-Lys-Glu-Asp-Phe-Thr-Arg-Gly-Lys-Leu-Met-Ser-Ser-Leu-His-
        110                                       120

Leu-Lys-Arg-Tyr-Tyr-Gly-Arg-Ile-Leu-His-Tyr-Leu-Lys-Ala-Lys-Glu-Tyr-
                130

Ser-His-Cys(Acm)-Ala-Trp-Thr-Ile-Val-Arg-Val-Glu-Ile-Leu-Arg-Asn-
140                                          150

Phe-Tyr-Phe-Ile-Asn-Arg-Leu-Thr-Gly-Tyr-Leu-Arg-Asn-CO₂H
            160

[Figure 7]
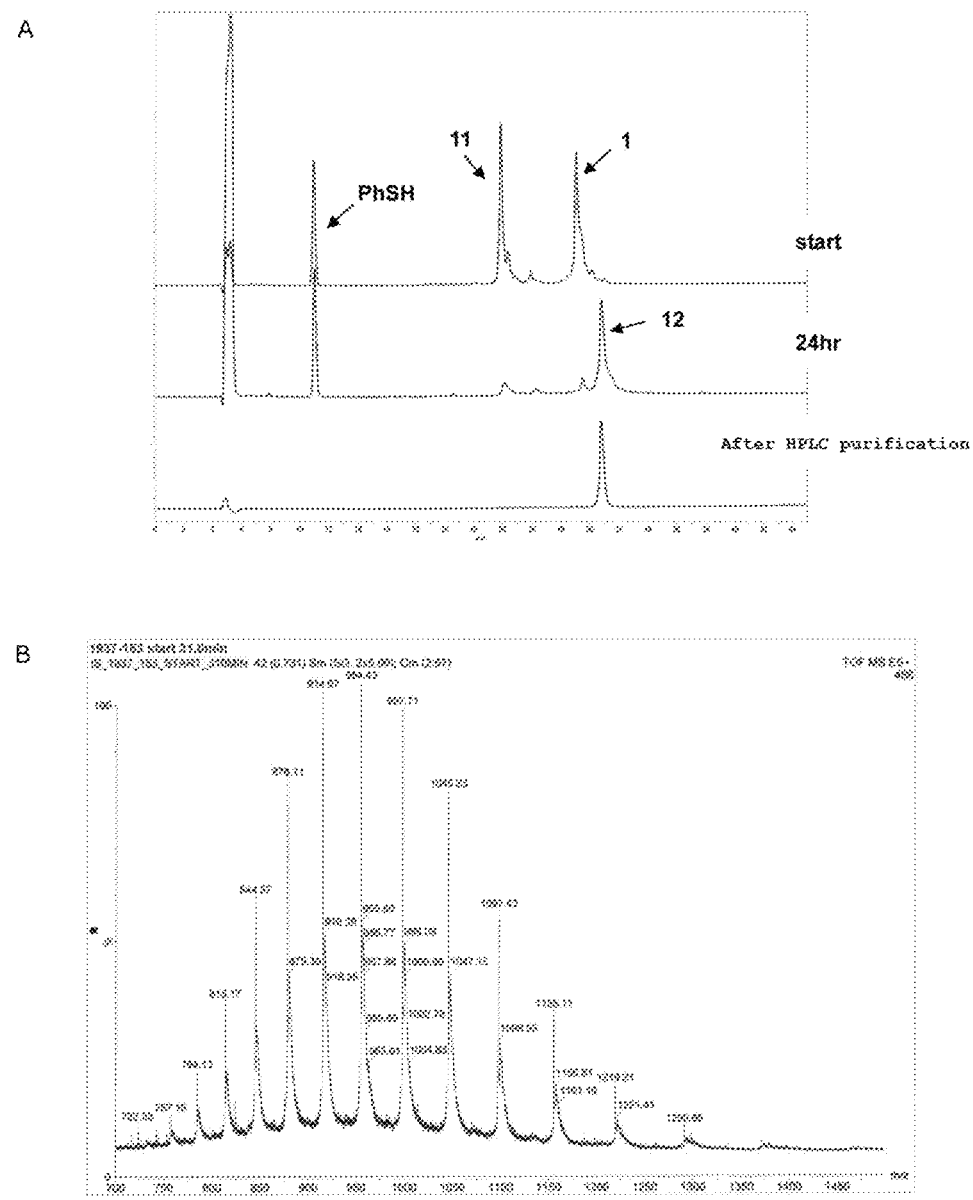

[Figure 8]

Peptide fragment (12) (SEQ ID NO. 17)

H$_2$N-Met-Ser-Tyr-Asn-Leu-Leu-Gly-Phe-Leu-Gln-Arg-Ser-Ser-Asn-Phe-Gln-Cys(Acm)-Gln-Lys-Leu-Leu-Trp-Gln-Leu-Asn-Gly-Arg-Leu-Glu-Tyr-Cys(Acm)-Leu-Lys-Asp-Arg-Met-Asn-Phe-Asp-Ile-Pro-Glu-Glu-Ile-Lys-Gln-Leu-Gln-Gln-Phe-Gln-Lys-Glu-Asp-Ala-Ala-Leu-Thr-Ile-Tyr-Glu-Met-Leu-Gln-Asn-Ile-Phe-Cys-Ile-Phe-Arg-Gln-Asp-Ser-Ser-Ser-Thr-Gly-Trp-Asn(asialyloligosaccharide)-Glu-Thr-Ile-Val-Glu-Asn-Leu-Leu-Cys-Asn-Val-Tyr-His-Gln-Ile-Asn-His-Leu-Lys-Thr-Val-Leu-Glu-Glu-Lys-Leu-Glu-Lys-Glu-Asp-Phe-Thr-Arg-Gly-Lys-Leu-Met-Ser-Ser-Leu-His-Leu-Lys-Arg-Tyr-Tyr-Gly-Arg-Ile-Leu-His-Tyr-Leu-Lys-Ala-Lys-Glu-Tyr-Ser-His-Cys(Acm)-Ala-Trp-Thr-Ile-Val-Arg-Val-Glu-Ile-Leu-Arg-Asn-Phe-Tyr-Phe-Ile-Asn-Arg-Leu-Thr-Gly-Tyr-Leu-Arg-Asn-CO$_2$H

[Figure 9]
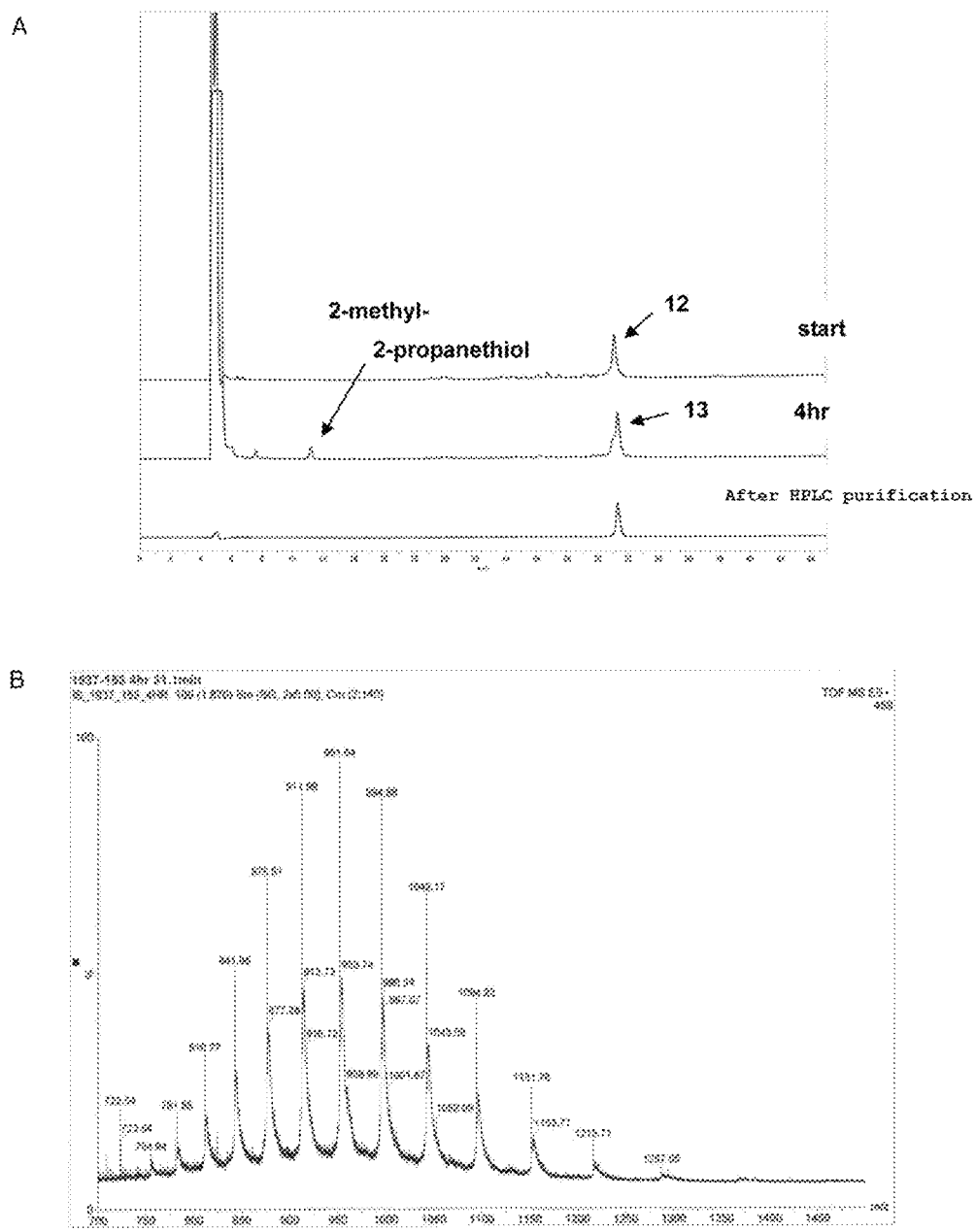

[Figure 10]

Peptide fragment (13) (SEQ ID NO. 18)

H₂N-Met-Ser-Tyr-Asn-Leu-Leu-Gly-Phe-Leu-Gln-Arg-Ser-Ser-Asn-Phe-
Gln-Cys(Acm)-Gln-Lys-Leu-Leu-Trp-Gln-Leu-Asn-Gly-Arg-Leu-Glu-Tyr-
Cys(Acm)-Leu-Lys-Asp-Arg-Met-Asn-Phe-Asp-Ile-Pro-Glu-Glu-Ile-Lys-
Gln-Leu-Gln-Gln-Phe-Gln-Lys-Glu-Asp-Ala-Ala-Leu-Thr-Ile-Tyr-Glu-Met-
Leu-Gln-Asn-Ile-Phe-Ala-Ile-Phe-Arg-Gln-Asp-Ser-Ser-Ser-Thr-Gly-Trp-
Asn(asialyloligosaccharide)-Glu-Thr-Ile-Val-Glu-Asn-Leu-Leu-
Ala-Asn-Val-Tyr-His-Gln-Ile-Asn-His-Leu-Lys-Thr-Val-Leu-Glu-Glu-Lys-
Leu-Glu-Lys-Glu-Asp-Phe-Thr-Arg-Gly-Lys-Leu-Met-Ser-Ser-Leu-His-
Leu-Lys-Arg-Tyr-Tyr-Gly-Arg-Ile-Leu-His-Tyr-Leu-Lys-Ala-Lys-Glu-Tyr-
Ser-His-Cys(Acm)-Ala-Trp-Thr-Ile-Val-Arg-Val-Glu-Ile-Leu-Arg-Asn-Phe-
Tyr-Phe-Ile-Asn-Arg-Leu-Thr-Gly-Tyr-Leu-Arg-Asn-CO₂H

[Figure 11]
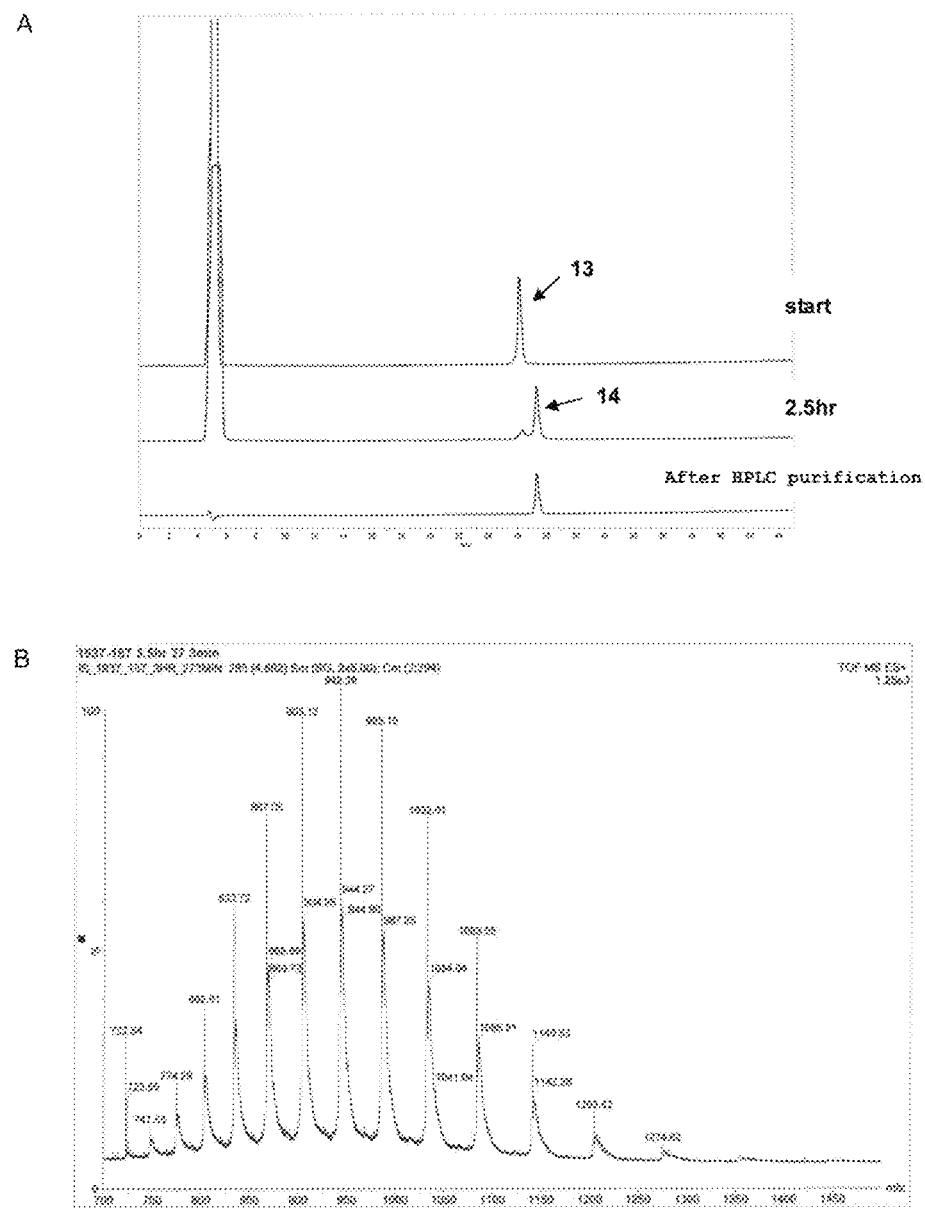

[Figure 12]

Peptide fragment (14) (SEQ ID NO. 19)

H₂N-Met-Ser-Tyr-Asn-Leu-Leu-Gly-Phe-Leu-Gln-Arg-Ser-Ser-Asn-Phe-Gln-Cys-Gln-Lys-Leu-Leu-Trp-Gln-Leu-Asn-Gly-Arg-Leu-Glu-Tyr-Cys-Leu-Lys-Asp-Arg-Met-Asn-Phe-Asp-Ile-Pro-Glu-Glu-Ile-Lys-Gln-Leu-Gln-Gln-Phe-Gln-Lys-Glu-Asp-Ala-Ala-Leu-Thr-Ile-Tyr-Glu-Met-Leu-Gln-Asn-Ile-Phe-Ala-Ile-Phe-Arg-Gln-Asp-Ser-Ser-Ser-Thr-Gly-Trp-Asn(asialyloligosaccharide)-Glu-Thr-Ile-Val-Glu-Asn-Leu-Leu-Ala-Asn-Val-Tyr-His-Gln-Ile-Asn-His-Leu-Lys-Thr-Val-Leu-Glu-Glu-Lys-Leu-Glu-Lys-Glu-Asp-Phe-Thr-Arg-Gly-Lys-Leu-Met-Ser-Ser-Leu-His-Leu-Lys-Arg-Tyr-Tyr-Gly-Arg-Ile-Leu-His-Tyr-Leu-Lys-Ala-Lys-Glu-Tyr-Ser-His-Cys-Ala-Trp-Thr-Ile-Val-Arg-Val-Glu-Ile-Leu-Arg-Asn-Phe-Tyr-Phe-Ile-Asn-Arg-Leu-Thr-Gly-Tyr-Leu-Arg-Asn-CO₂H

[Figure 13]
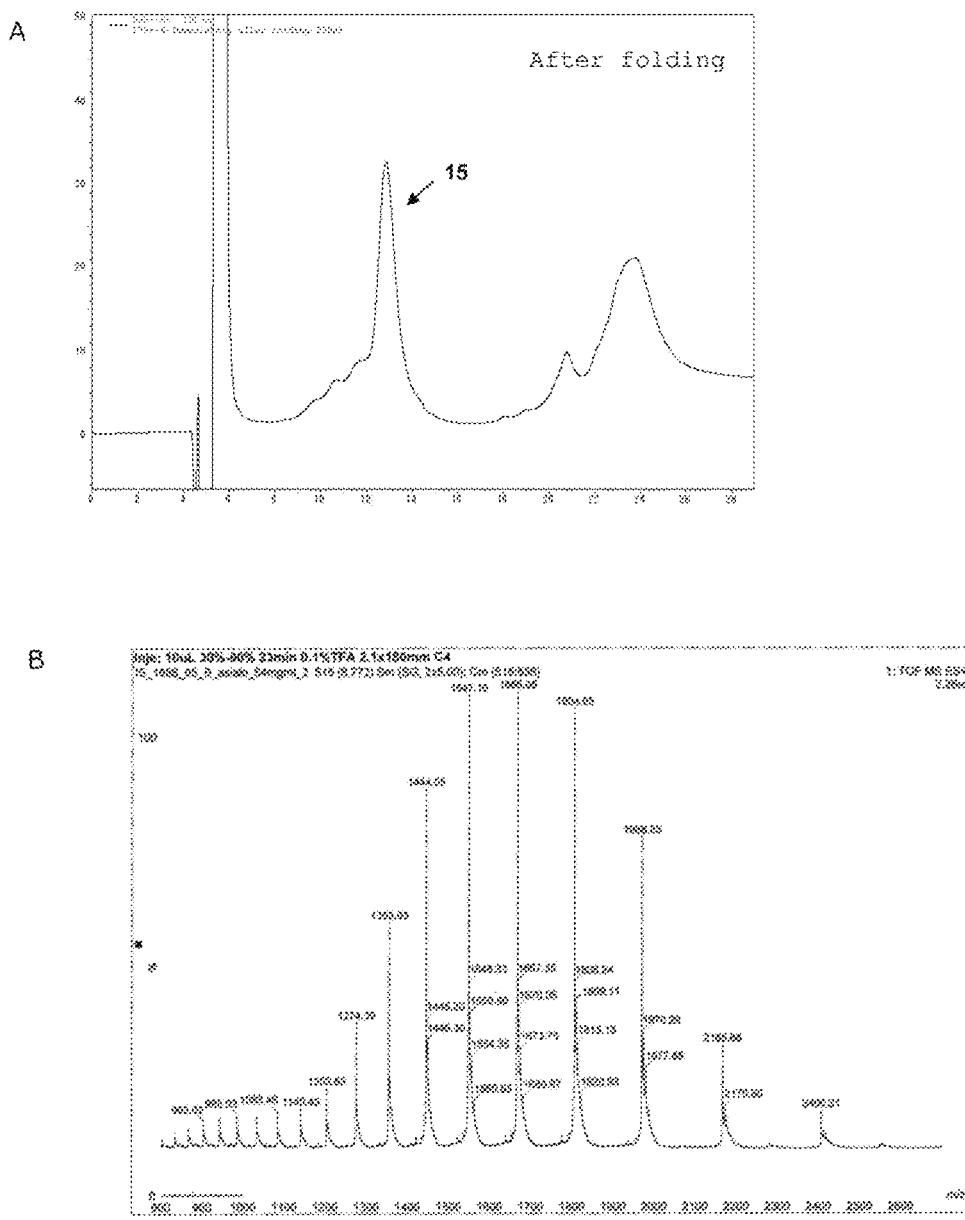

[Figure 14]

Peptide fragment (15) (SEQ ID NO. 20)

H₂N-Met-Ser-Tyr-Asn-Leu-Leu-Gly-Phe-Leu-Gln-Arg-Ser-Ser-Asn-Phe-
Gln-Cys-Gln-Lys-Leu-Leu-Trp-Gln-Leu-Asn-Gly-Arg-Leu-Glu-Tyr-Cys-
Leu-Lys-Asp-Arg-Met-Asn-Phe-Asp-Ile-Pro-Glu-Glu-Ile-Lys-Gln-Leu-
Gln-Gln-Phe-Gln-Lys-Glu-Asp-Ala-Ala-Leu-Thr-Ile-Tyr-Glu-Met-Leu-
Gln-Asn-Ile-Phe-Ala-Ile-Phe-Arg-Gln-Asp-Ser-Ser-Ser-Thr-Gly-Trp-
Asn(asialyloligosaccharide)-Glu-Thr-Ile-Val-Glu-Asn-Leu-Leu-Ala-
Asn-Val-Tyr-His-Gln-Ile-Asn-His-Leu-Lys-Thr-Val-Leu-Glu-Glu-Lys-
Leu-Glu-Lys-Glu-Asp-Phe-Thr-Arg-Gly-Lys-Leu-Met-Ser-Ser-Leu-His-
Leu-Lys-Arg-Tyr-Tyr-Gly-Arg-Ile-Leu-His-Tyr-Leu-Lys-Ala-Lys-Glu-Tyr-
Ser-His-Cys-Ala-Trp-Thr-Ile-Val-Arg-Val-Glu-Ile-Leu-Arg-Asn-Phe-
Tyr-Phe-Ile-Asn-Arg-Leu-Thr-Gly-Tyr-Leu-Arg-Asn-CO₂H

[Figure 16]
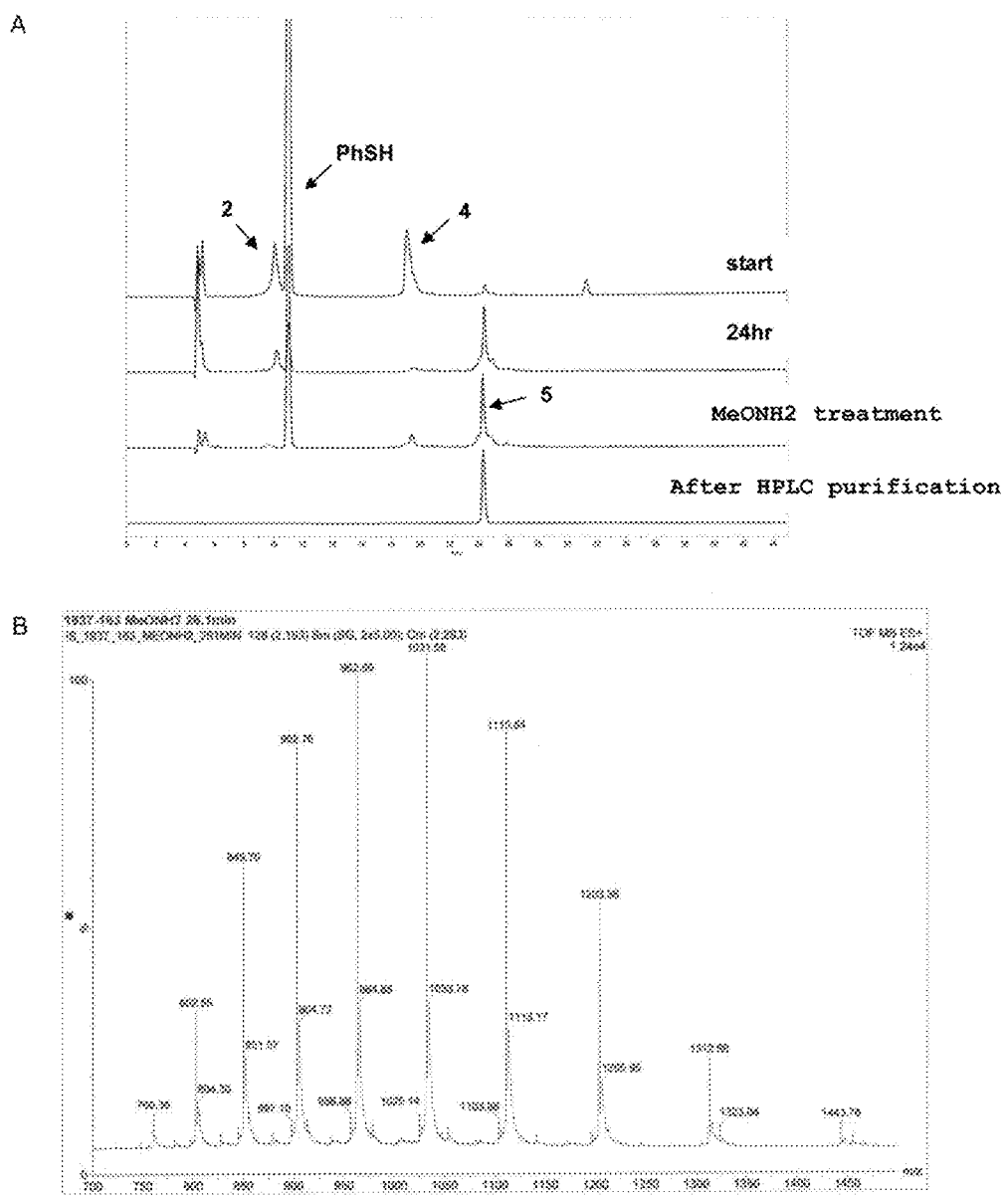

[Figure 17]

Peptide fragment (5) (SEQ ID NO. 21)

70
H₂N-Cys-Ile-Phe-Arg-Gln-Asp-Ser-Ser-Ser-Thr-Gly-Trp-

80
Asn(protected sialyloligosaccharide)-Glu-Thr-Ile-Val-Glu-Asn-Leu-Leu- 90                                          100
Cys-Asn-Val-Tyr-His-Gln-Ile-Asn-His-Leu-Lys-Thr-Val-Leu-Glu-Glu-Lys- 110                                              120
Leu-Glu-Lys-Glu-Asp-Phe-Thr-Arg-Gly-Lys-Leu-Met-Ser-Ser-Leu-His- 130
Leu-Lys-Arg-Tyr-Tyr-Gly-Arg-Ile-Leu-His-Tyr-Leu-Lys-Ala-Lys-Glu-Tyr- 140                                              150
Ser-His-Cys(Acm)-Ala-Trp-Thr-Ile-Val-Arg-Val-Glu-Ile-Leu-Arg-Asn-Phe- 160
Tyr-Phe-Ile-Asn-Arg-Leu-Thr-Gly-Tyr-Leu-Arg-Asn-CO₂H

[Figure 18]
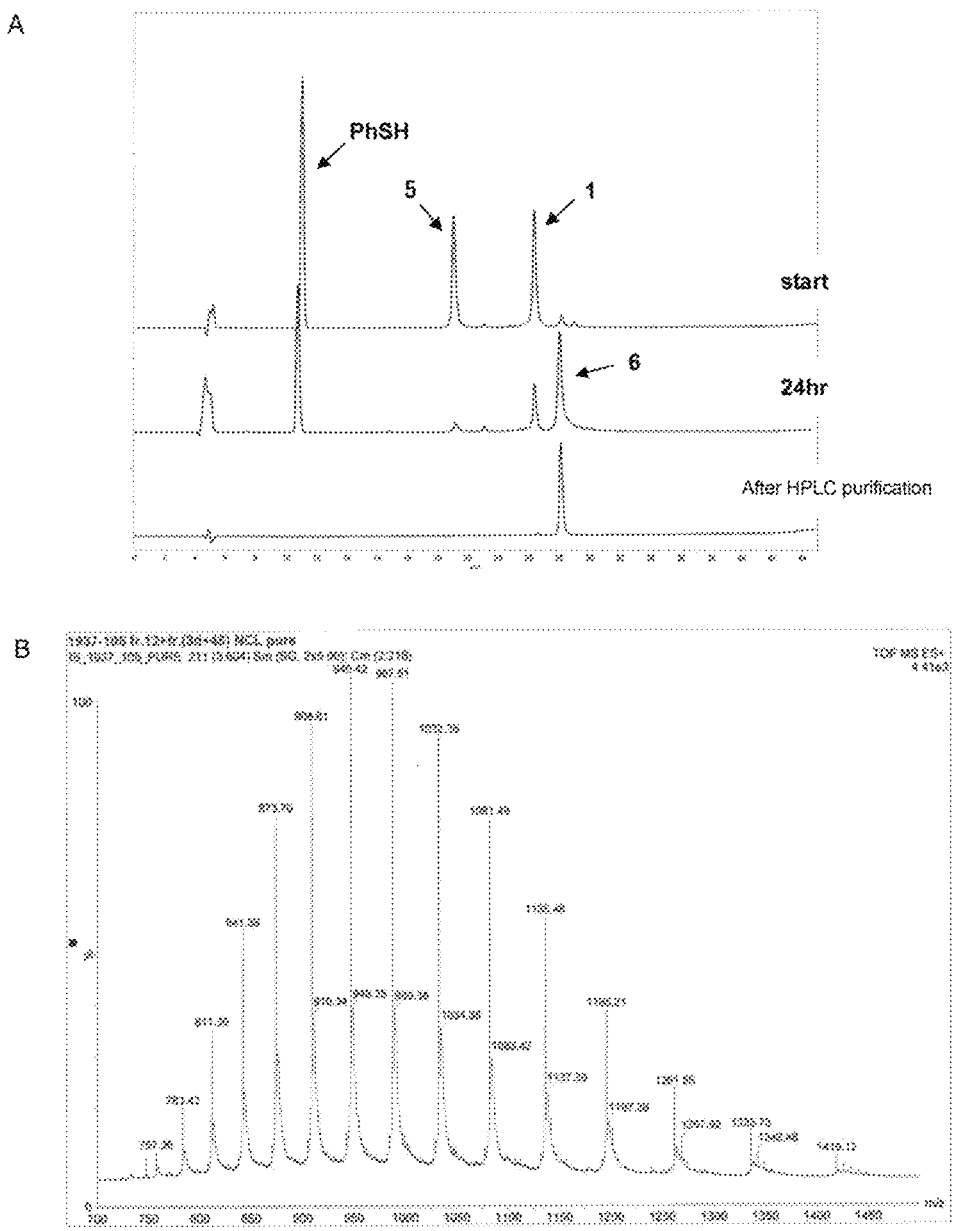

[Figure 19]

Peptide fragment (6) (SEQ ID NO. 22)

H₂N-Met-Ser-Tyr-Asn-Leu-Leu-Gly-Phe-Leu-Gln-Arg-Ser-Ser-Asn-Phe-Gln-Cys(Acm)-Gln-Lys-Leu-Leu-Trp-Gln-Leu-Asn-Gly-Arg-Leu-Glu-Tyr-Cys(Acm)-Leu-Lys-Asp-Arg-Met-Asn-Phe-Asp-Ile-Pro-Glu-Glu-Ile-Lys-Gln-Leu-Gln-Gln-Phe-Gln-Lys-Glu-Asp-Ala-Ala-Leu-Thr-Ile-Tyr-Glu-Met-Leu-Gln-Asn-Ile-Phe-Cys-Ile-Phe-Arg-Gln-Asp-Ser-Ser-Ser-Thr-Gly-Trp-Asn(protected sialyloligosaccharide)-Glu-Thr-Ile-Val-Glu-Asn-Leu-Leu-Cys-Asn-Val-Tyr-His-Gln-Ile-Asn-His-Leu-Lys-Thr-Val-Leu-Glu-Glu-Lys-Leu-Glu-Lys-Glu-Asp-Phe-Thr-Arg-Gly-Lys-Leu-Met-Ser-Ser-Leu-His-Leu-Lys-Arg-Tyr-Tyr-Gly-Arg-Ile-Leu-His-Tyr-Leu-Lys-Ala-Lys-Glu-Tyr-Ser-His-Cys(Acm)-Ala-Trp-Thr-Ile-Val-Arg-Val-Glu-Ile-Leu-Arg-Asn-Phe-Tyr-Phe-Ile-Asn-Arg-Leu-Thr-Gly-Tyr-Leu-Arg-Asn-CO₂H

[Figure 20]
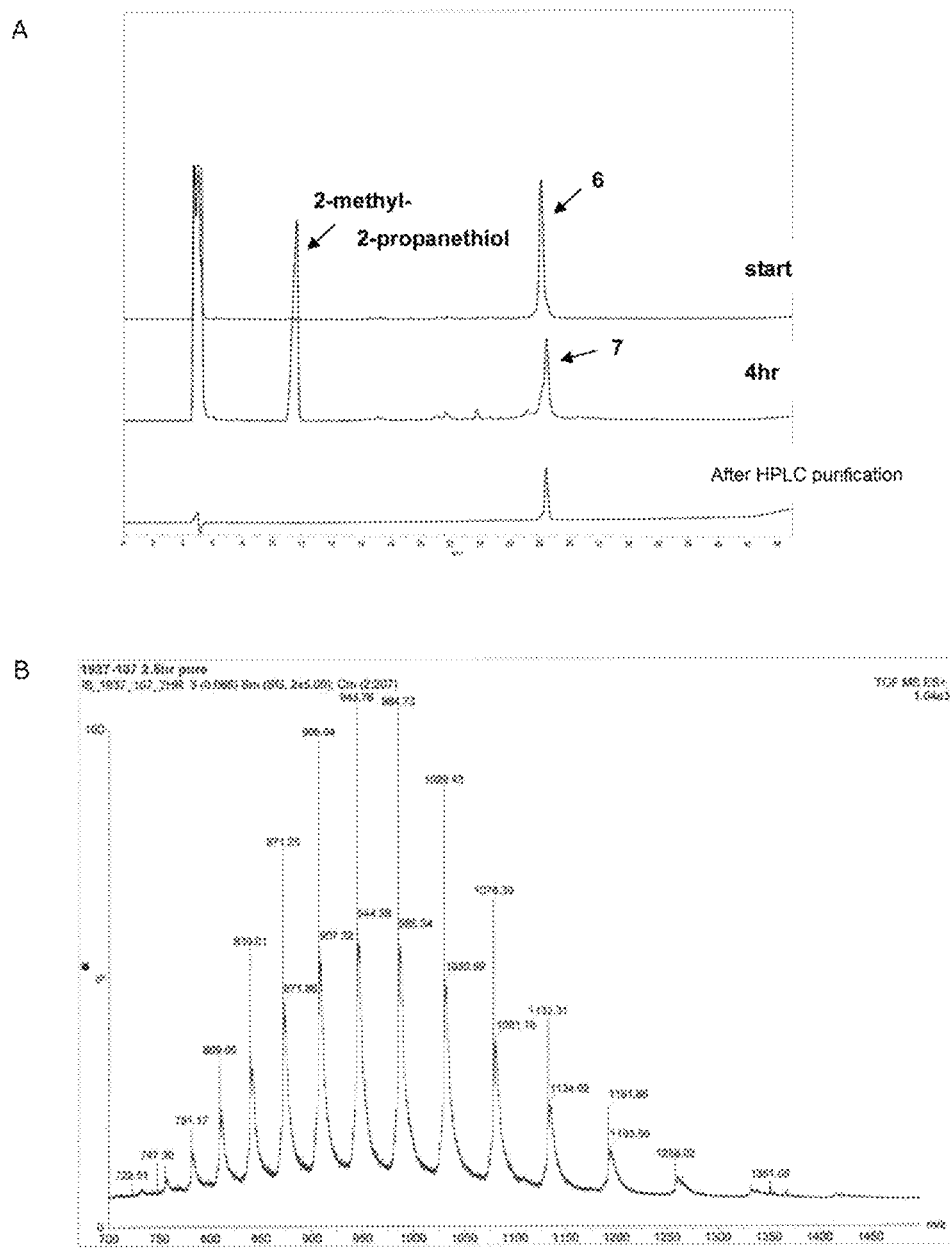

[Figure 21]

Peptide fragment (7) (SEQ ID NO. 23)

H₂N-Met-Ser-Tyr-Asn-Leu-Leu-Gly-Phe-Leu-Gln-Arg-Ser-Ser-Asn-Phe-
Gln-Cys(Acm)-Gln-Lys-Leu-Leu-Trp-Gln-Leu-Asn-Gly-Arg-Leu-Glu-Tyr-
Cys(Acm)-Leu-Lys-Asp-Arg-Met-Asn-Phe-Asp-Ile-Pro-Glu-Glu-Ile-Lys-Gln-
Leu-Gln-Gln-Phe-Gln-Lys-Glu-Asp-Ala-Ala-Leu-Thr-Ile-Tyr-Glu-Met-Leu-
Gln-Asn-Ile-Phe-Ala-Ile-Phe-Arg-Gln-Asp-Ser-Ser-Ser-Thr-Gly-Trp-
Asn(protected sialyloligosaccharide)-Glu-Thr-Ile-Val-Glu-Asn-Leu-Leu-
Ala-Asn-Val-Tyr-His-Gln-Ile-Asn-His-Leu-Lys-Thr-Val-Leu-Glu-Glu-Lys-
Leu-Glu-Lys-Glu-Asp-Phe-Thr-Arg-Gly-Lys-Leu-Met-Ser-Ser-Leu-His-
Leu-Lys-Arg-Tyr-Tyr-Gly-Arg-Ile-Leu-His-Tyr-Leu-Lys-Ala-Lys-Glu-Tyr-
Ser-His-Cys(Acm)-Ala-Trp-Thr-Ile-Val-Arg-Val-Glu-Ile-Leu-Arg-Asn-Phe-
Tyr-Phe-Ile-Asn-Arg-Leu-Thr-Gly-Tyr-Leu-Arg-Asn-CO₂H

[Figure 22]
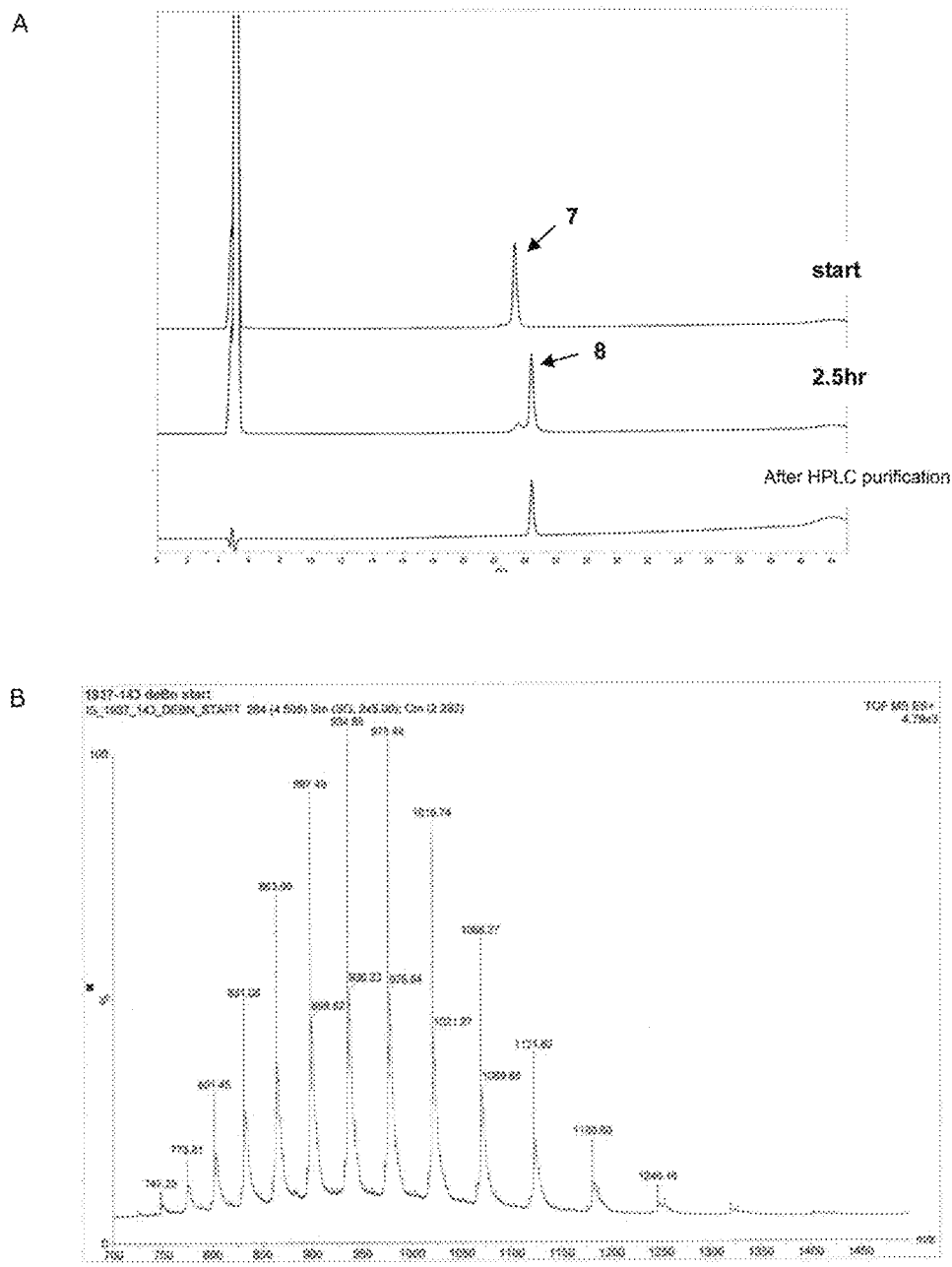

[Figure 23]

Peptide fragment (8) (SEQ ID NO. 24)

$$
\begin{aligned}
&\overset{1}{\text{H}_2\text{N-Met-Ser-Tyr-Asn-Leu-Leu-Gly-Phe-Leu-Gln-Arg-Ser-Ser-Asn-Phe-}} \\
&\overset{20}{\text{Gln-Cys-Gln-Lys-Leu-Leu-Trp-Gln-Leu-Asn-Gly-Arg-Leu-Glu-Tyr-Cys-}} \\
&\overset{40}{\text{Leu-Lys-Asp-Arg-Met-Asn-Phe-Asp-Ile-Pro-Glu-Glu-Ile-Lys-Gln-Leu-}} \\
&\overset{50}{\text{Gln-Gln-Phe-Gln-Lys-Glu-Asp-Ala-Ala-Leu-Thr-Ile-Tyr-Glu-Met-Leu-}} \\
&\overset{70}{\text{Gln-Asn-Ile-Phe-Ala-Ile-Phe-Arg-Gln-Asp-Ser-Ser-Ser-Thr-Gly-Trp-}} \\
&\overset{80}{\text{Asn(protected sialyloligosaccharide)-Glu-Thr-Ile-Val-Glu-Asn-Leu-Leu-}} \\
&\overset{90}{\text{Ala-Asn-Val-Tyr-His-Gln-Ile-Asn-His-Leu-Lys-Thr-Val-Leu-Glu-Glu-Lys-}} \\
&\overset{110}{\text{Leu-Glu-Lys-Glu-Asp-Phe-Thr-Arg-Gly-Lys-Leu-Met-Ser-Ser-Leu-His-}} \\
&\overset{130}{\text{Leu-Lys-Arg-Tyr-Tyr-Gly-Arg-Ile-Leu-His-Tyr-Leu-Lys-Ala-Lys-Glu-Tyr-}} \\
&\overset{140}{\text{Ser-His-Cys-Ala-Trp-Thr-Ile-Val-Arg-Val-Glu-Ile-Leu-Arg-Asn-Phe-}} \\
&\overset{160}{\text{Tyr-Phe-Ile-Asn-Arg-Leu-Thr-Gly-Tyr-Leu-Arg-Asn-CO}_2\text{H}}
\end{aligned}
$$

[Figure 24]
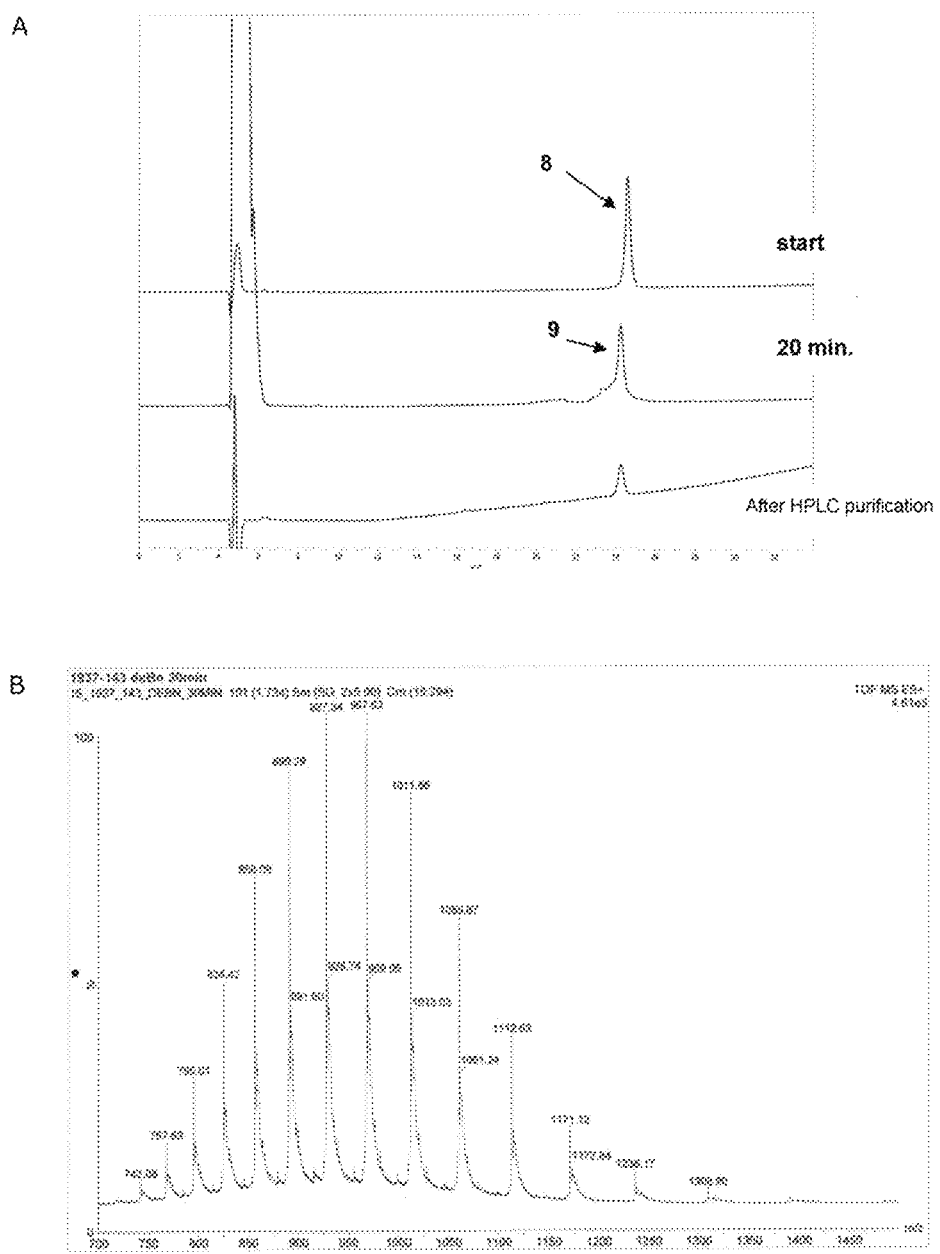

[Figure 25]

Peptide fragment (9) (SEQ ID NO. 25)

H$_2$N-Met-Ser-Tyr-Asn-Leu-Leu-Gly-Phe-Leu-Gln-Arg-Ser-Ser-Asn-Phe-Gln-Cys-Gln-Lys-Leu-Leu-Trp-Gln-Leu-Asn-Gly-Arg-Leu-Glu-Tyr-Cys-Leu-Lys-Asp-Arg-Met-Asn-Phe-Asp-Ile-Pro-Glu-Glu-Ile-Lys-Gln-Leu-Gln-Gln-Phe-Gln-Lys-Glu-Asp-Ala-Ala-Leu-Thr-Ile-Tyr-Glu-Met-Leu-Gln-Asn-Ile-Phe-Ala-Ile-Phe-Arg-Gln-Asp-Ser-Ser-Ser-Thr-Gly-Trp-Asn(sialyloligosaccharide)-Glu-Thr-Ile-Val-Glu-Asn-Leu-Leu-Ala-Asn-Val-Tyr-His-Gln-Ile-Asn-His-Leu-Lys-Thr-Val-Leu-Glu-Glu-Lys-Leu-Glu-Lys-Glu-Asp-Phe-Thr-Arg-Gly-Lys-Leu-Met-Ser-Ser-Leu-His-Leu-Lys-Arg-Tyr-Tyr-Gly-Arg-Ile-Leu-His-Tyr-Leu-Lys-Ala-Lys-Glu-Tyr-Ser-His-Cys-Ala-Trp-Thr-Ile-Val-Arg-Val-Glu-Ile-Leu-Arg-Asn-Phe-Tyr-Phe-Ile-Asn-Arg-Leu-Thr-Gly-Tyr-Leu-Arg-Asn-CO$_2$H

[Figure 26]
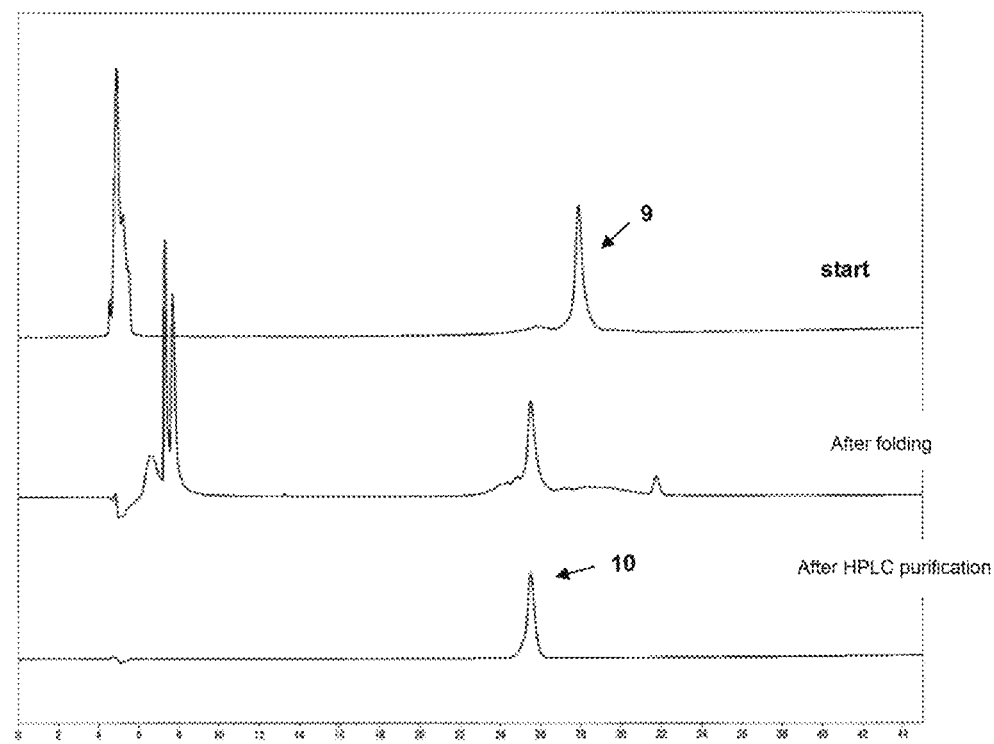

[Figure 27]

Peptide fragment (10) (SEQ ID NO. 26)

H₂N-Met-Ser-Tyr-Asn-Leu-Leu-Gly-Phe-Leu-Gln-Arg-Ser-Ser-Asn-Phe-Gln-Cys-Gln-Lys-Leu-Leu-Trp-Gln-Leu-Asn-Gly-Arg-Leu-Glu-Tyr-Cys-Leu-Lys-Asp-Arg-Met-Asn-Phe-Asp-Ile-Pro-Glu-Glu-Ile-Lys-Gln-Leu-Gln-Gln-Phe-Gln-Lys-Glu-Asp-Ala-Ala-Leu-Thr-Ile-Tyr-Glu-Met-Leu-Gln-Asn-Ile-Phe-Ala-Ile-Phe-Arg-Gln-Asp-Ser-Ser-Ser-Thr-Gly-Trp-Asn(sialyloligosaccharide)-Glu-Thr-Ile-Val-Glu-Asn-Leu-Leu-Ala-Asn-Val-Tyr-His-Gln-Ile-Asn-His-Leu-Lys-Thr-Val-Leu-Glu-Glu-Lys-Leu-Glu-Lys-Glu-Asp-Phe-Thr-Arg-Gly-Lys-Leu-Met-Ser-Ser-Leu-His-Leu-Lys-Arg-Tyr-Tyr-Gly-Arg-Ile-Leu-His-Tyr-Leu-Lys-Ala-Lys-Glu-Tyr-Ser-His-Cys-Ala-Trp-Thr-Ile-Val-Arg-Val-Glu-Ile-Leu-Arg-Asn-Phe-Tyr-Phe-Ile-Asn-Arg-Leu-Thr-Gly-Tyr-Leu-Arg-Asn-CO₂H

[Figure 29]
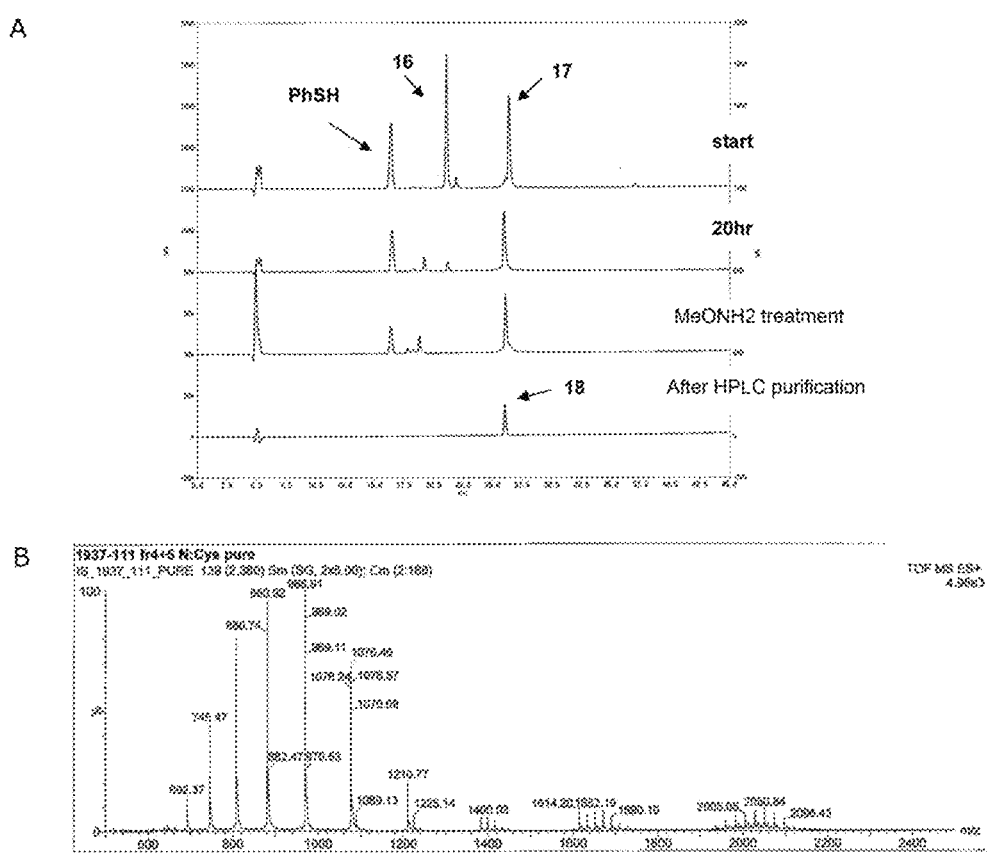

[Figure 30]
A
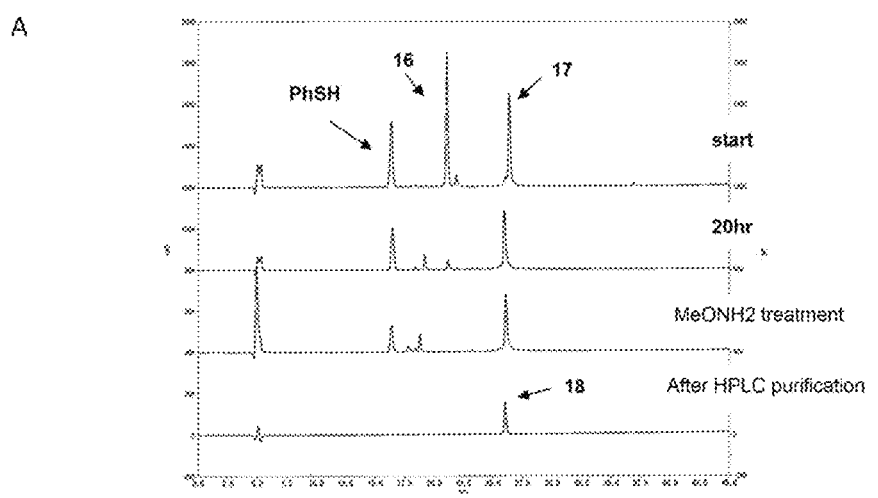
B
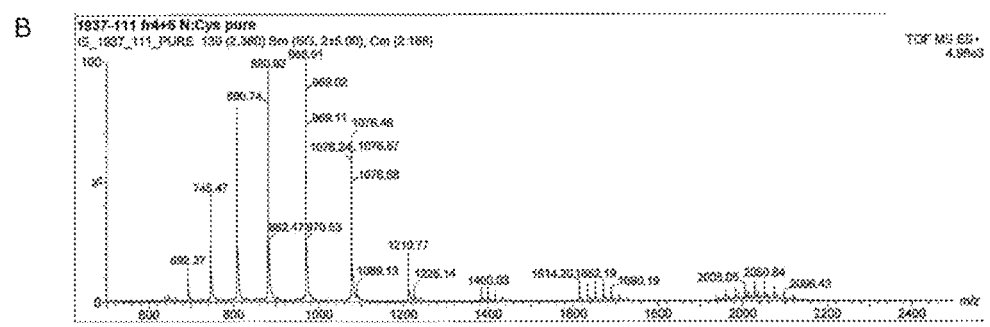

[Figure 31]
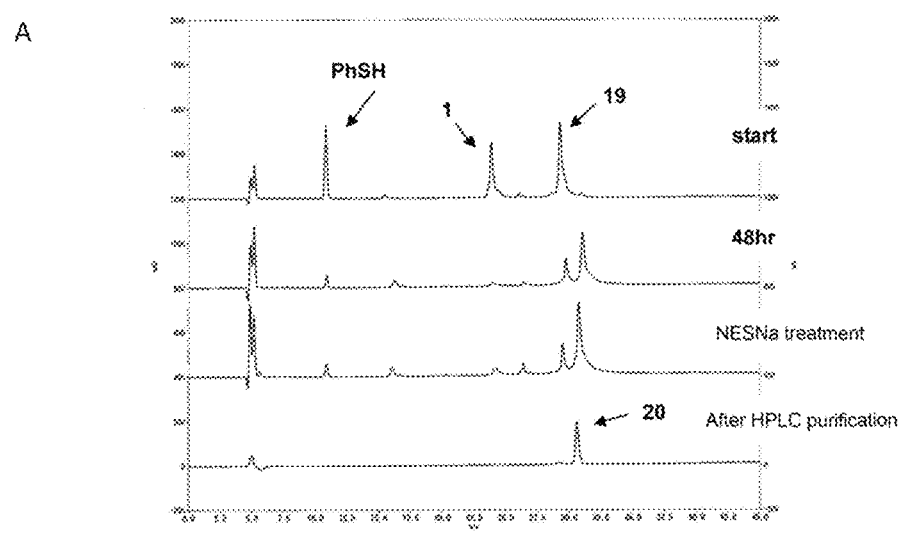
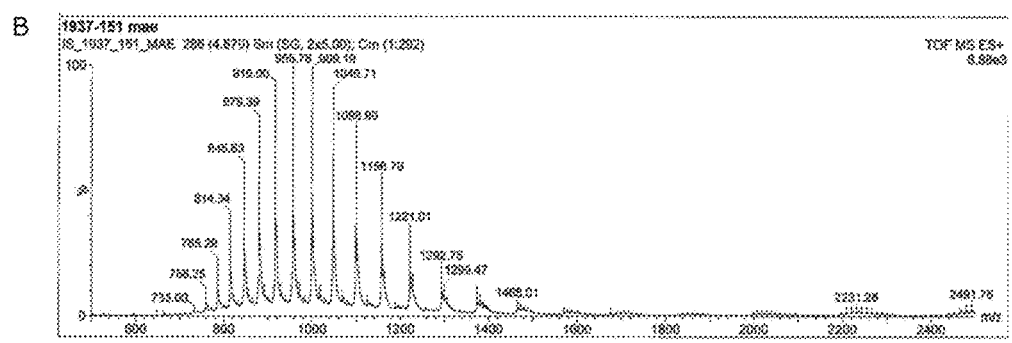

[Figure 32]
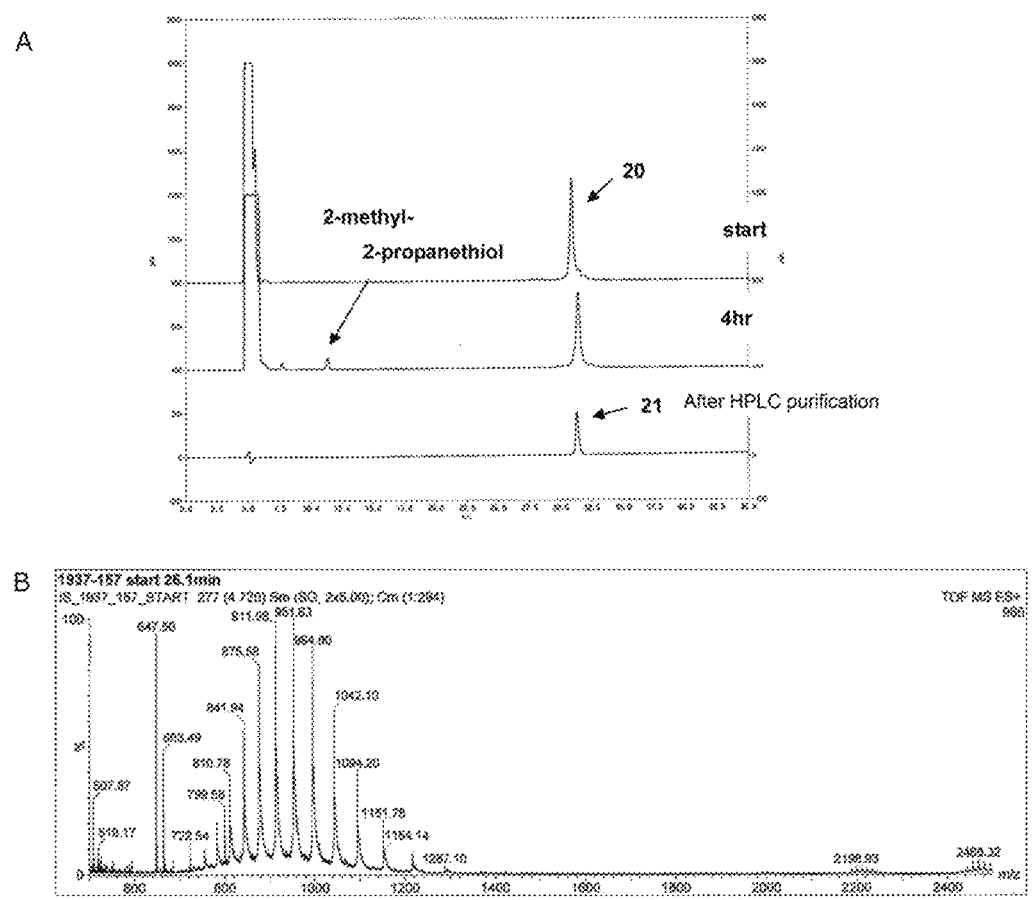

[Figure 33]
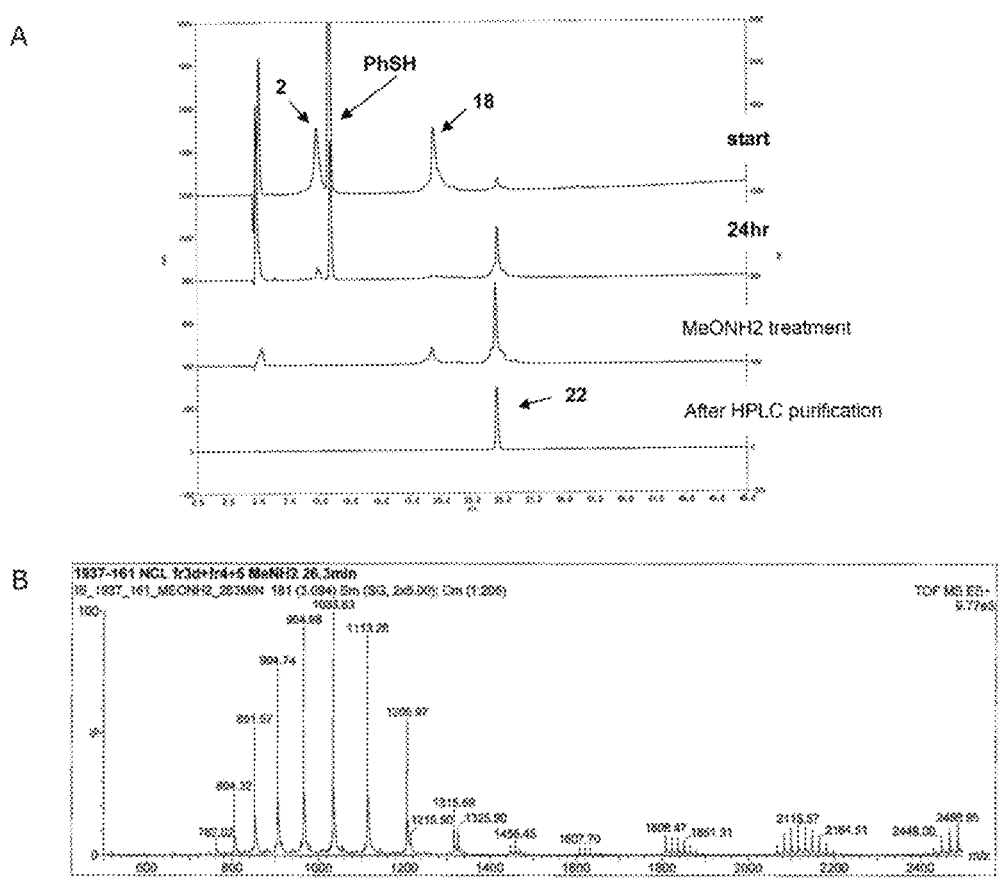

[Figure 34]
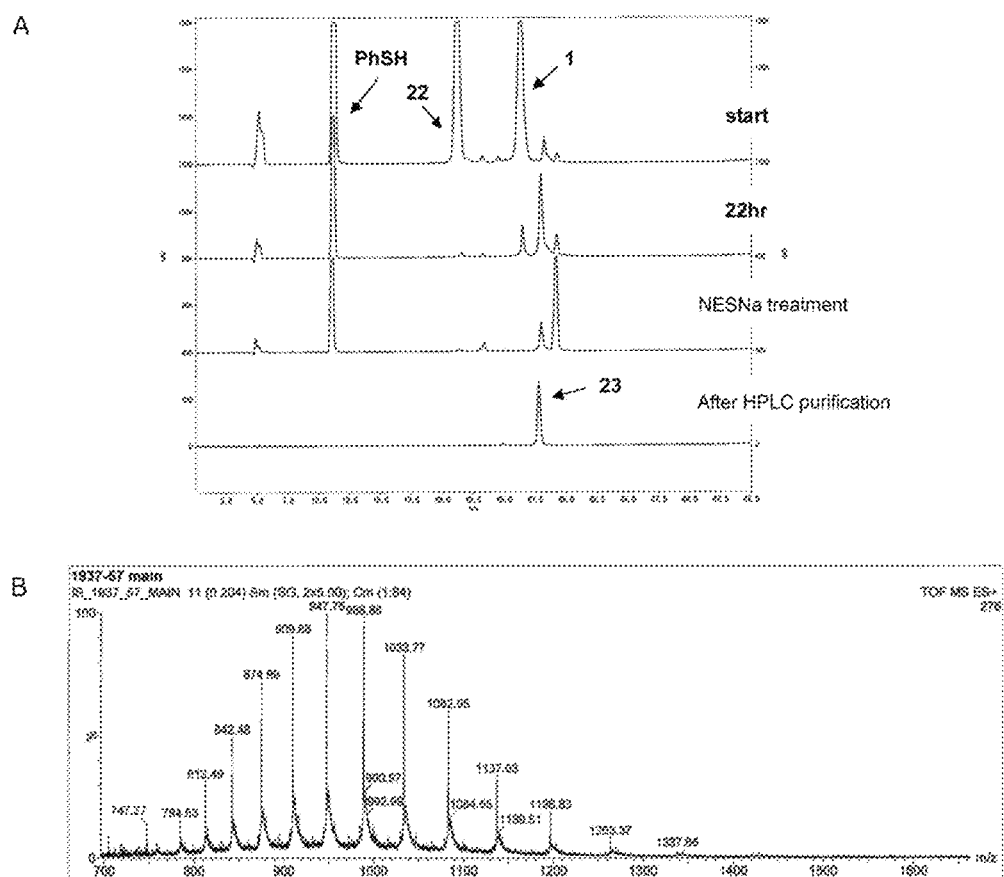

[Figure 35]
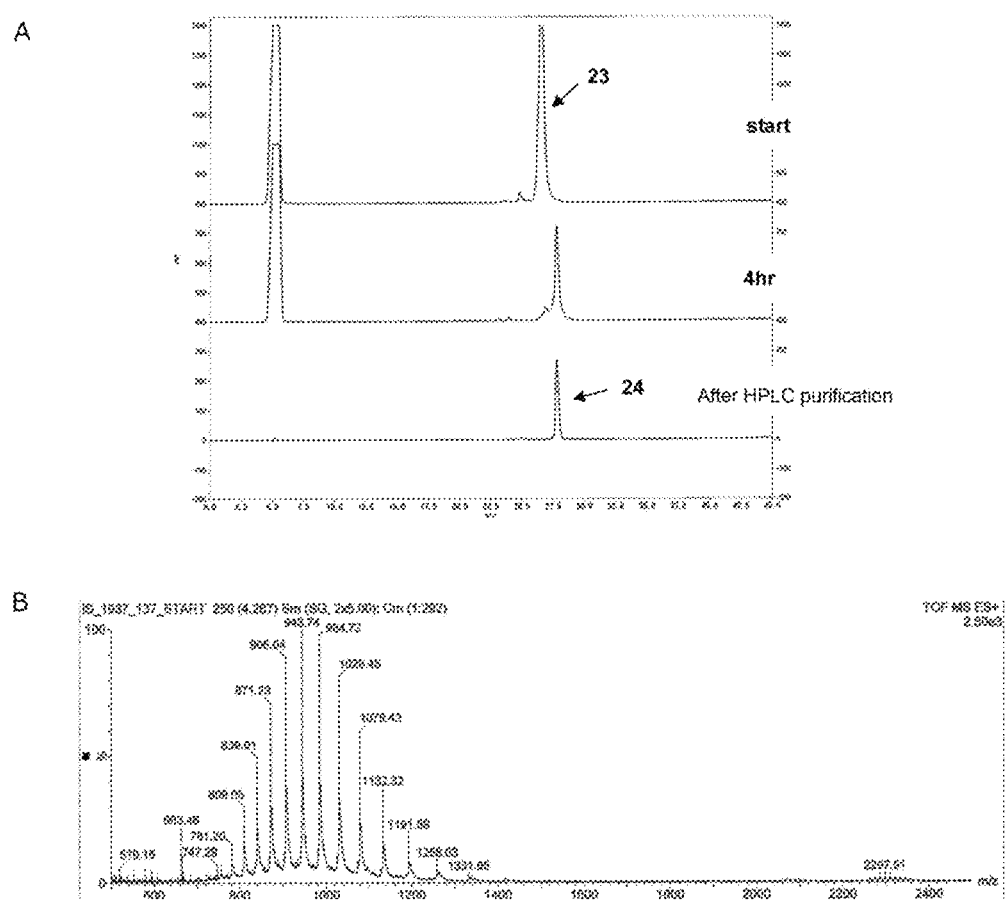

[Figure 36]
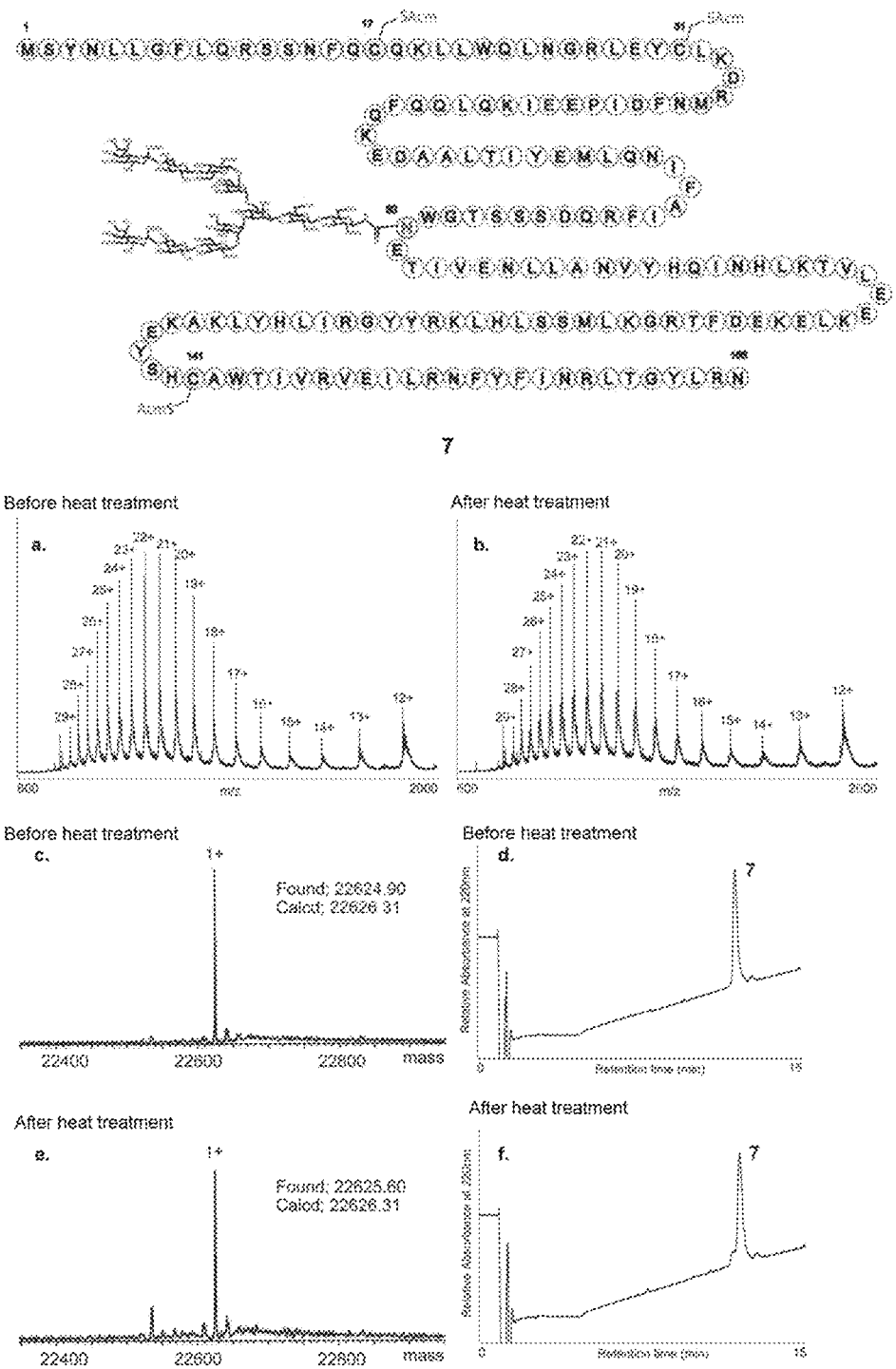

[Figure 37]
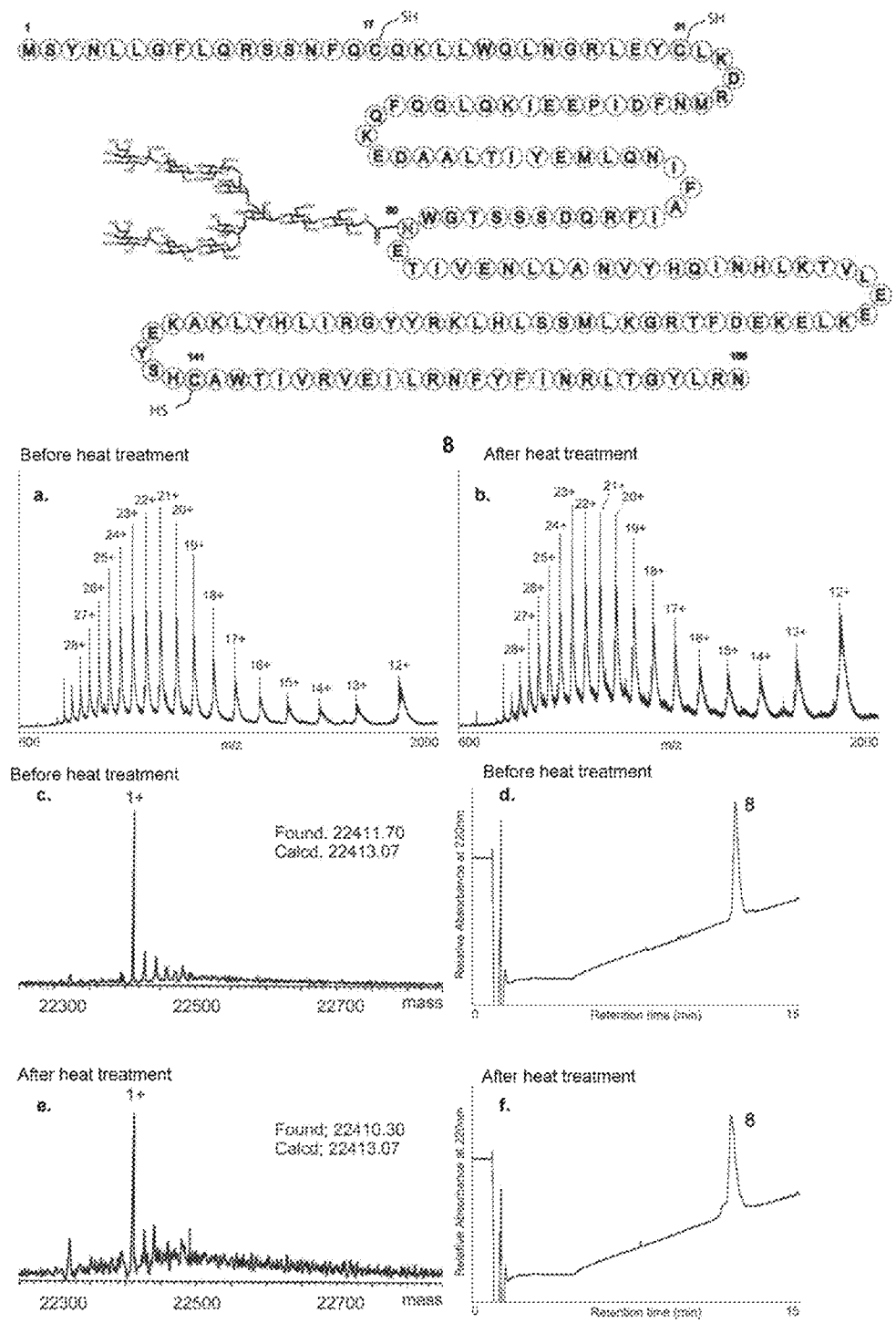

[Figure 38]
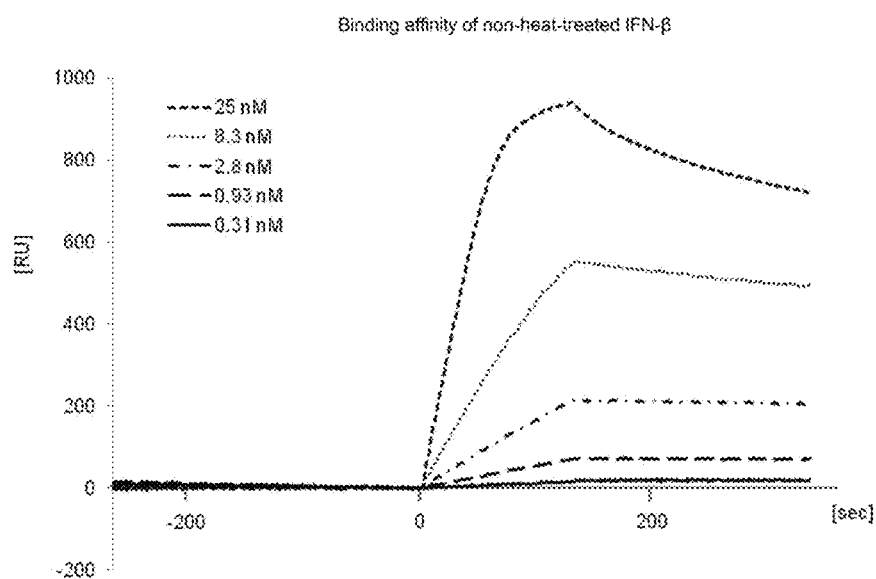
[Figure 39]
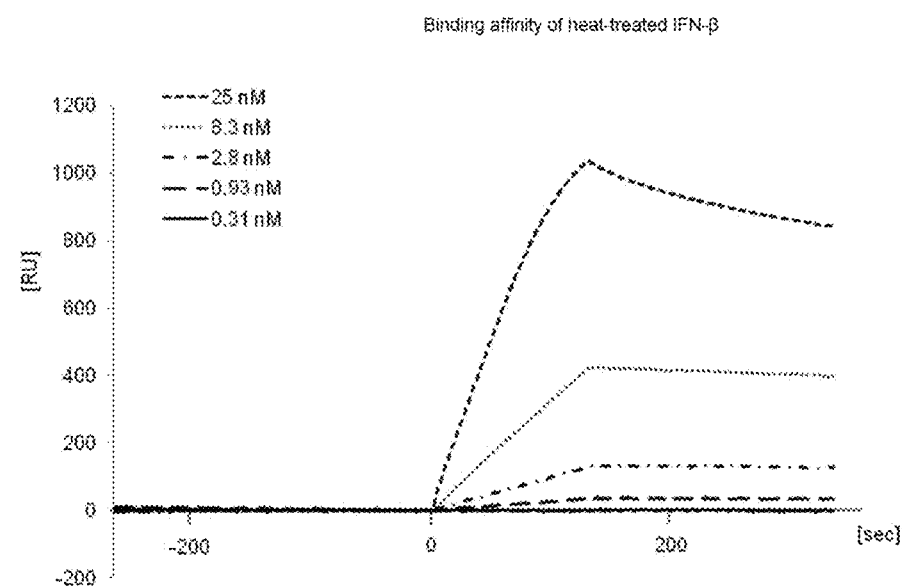

[Figure 40]
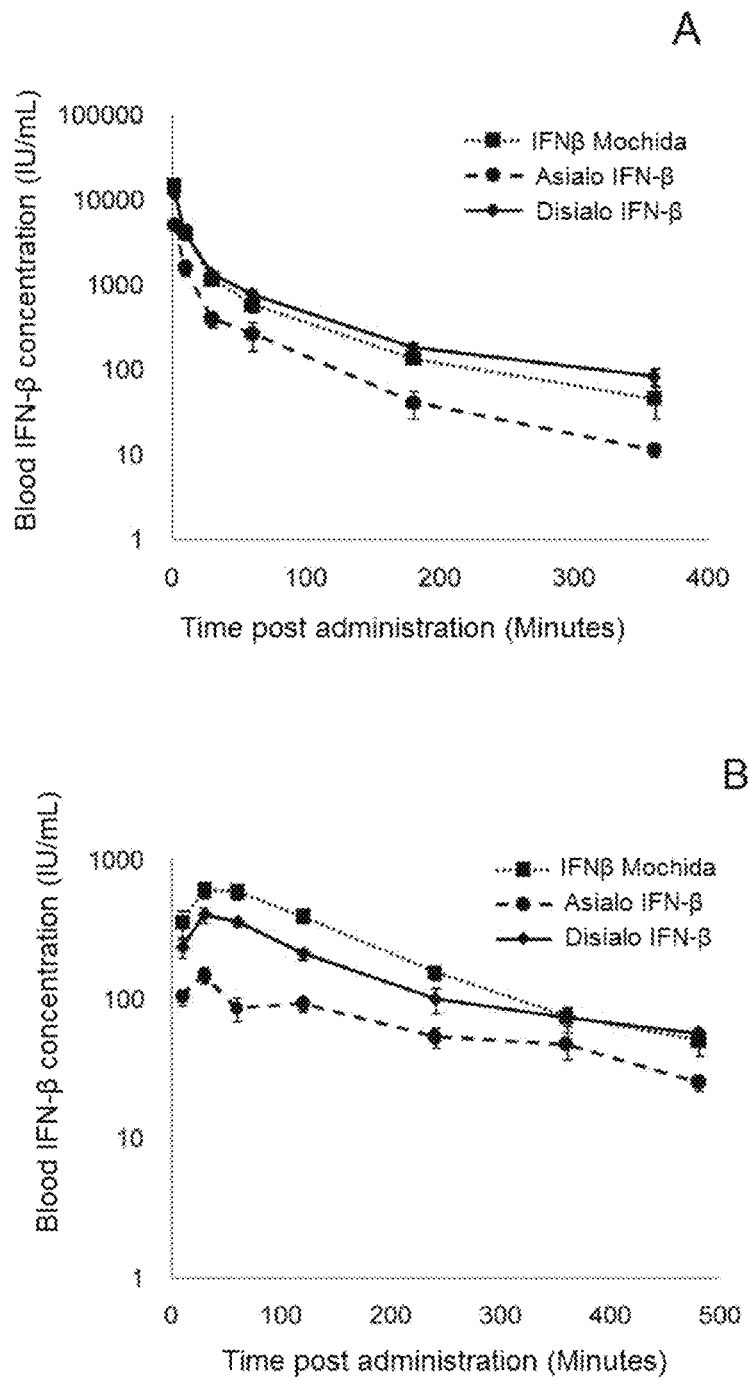

[Figure 41]
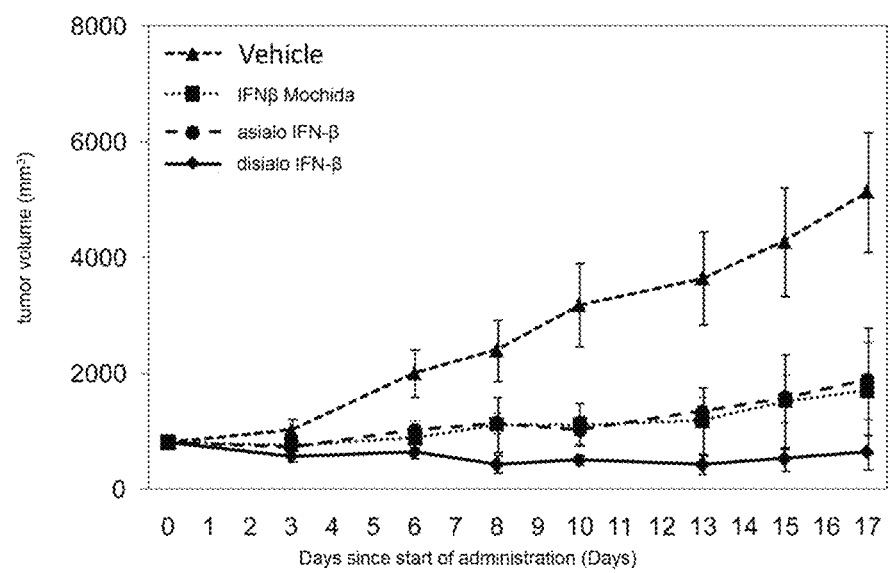
[Figure 42]
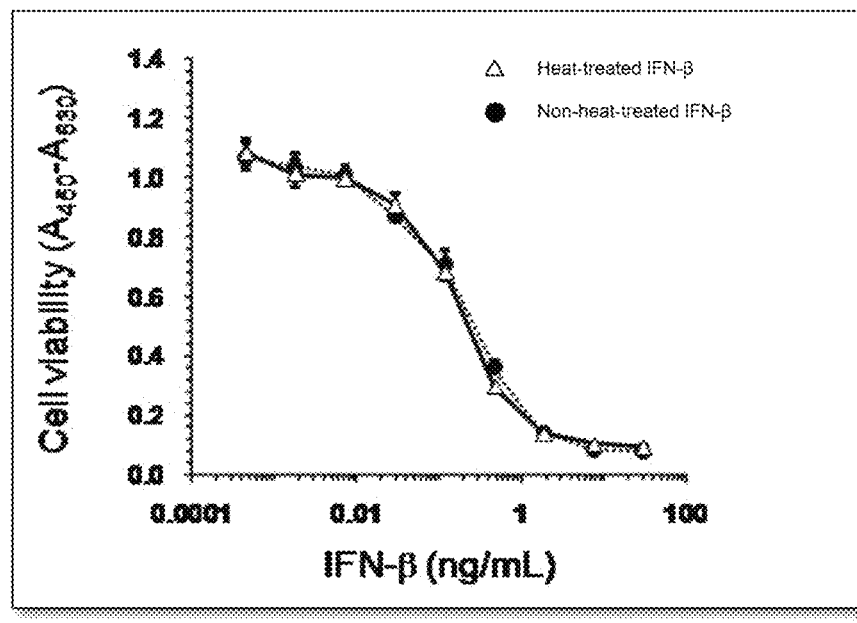

[Figure 43]
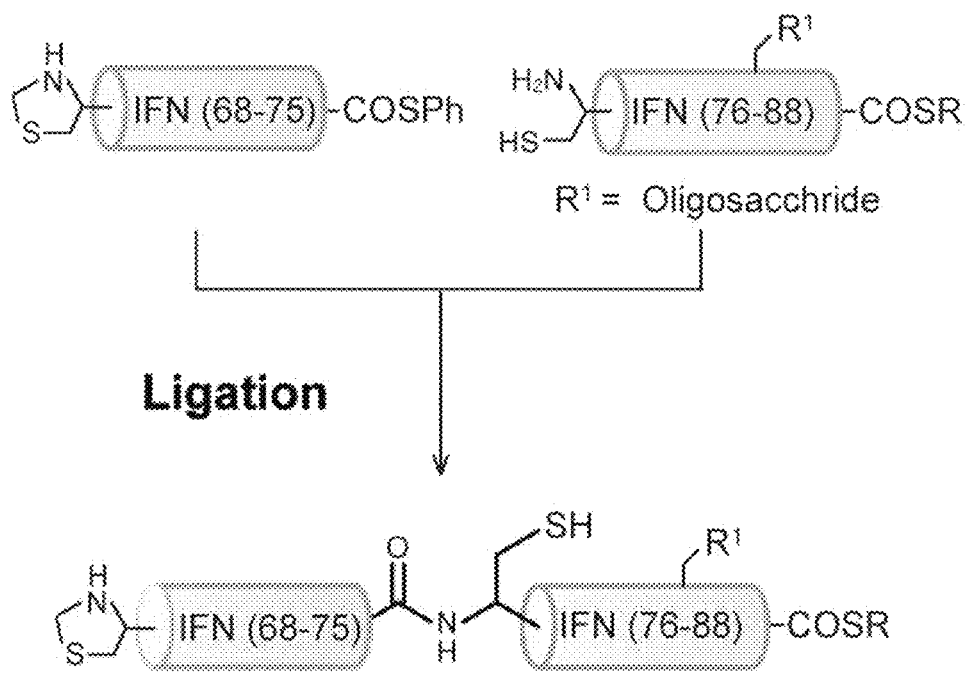
[Figure 44]
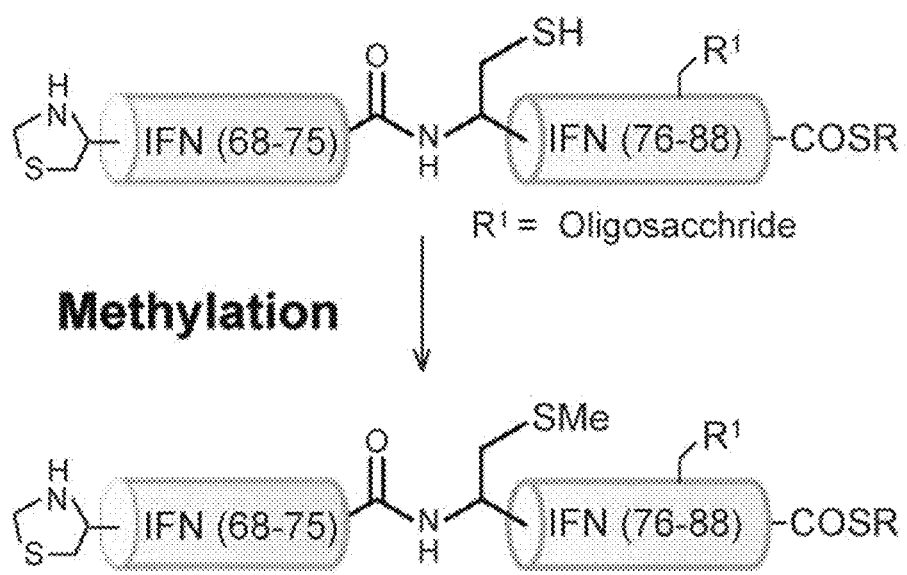

[Figure 45]
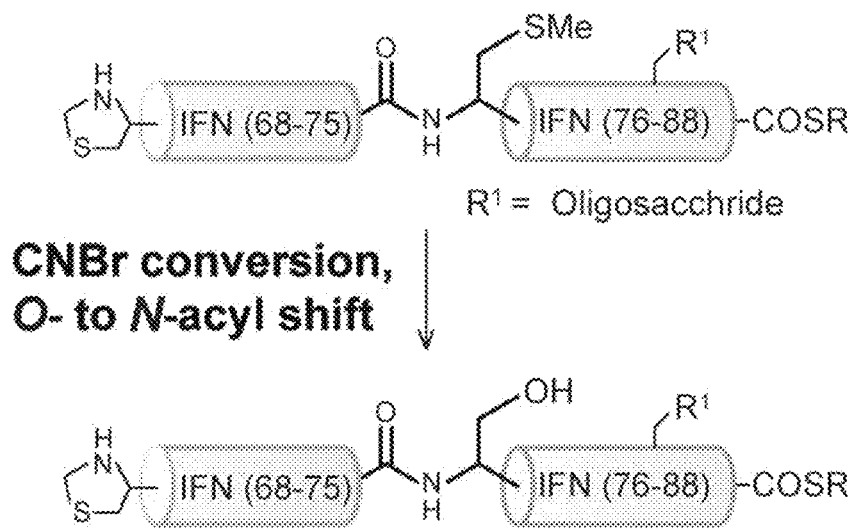

A

Figure 46, cont.
B
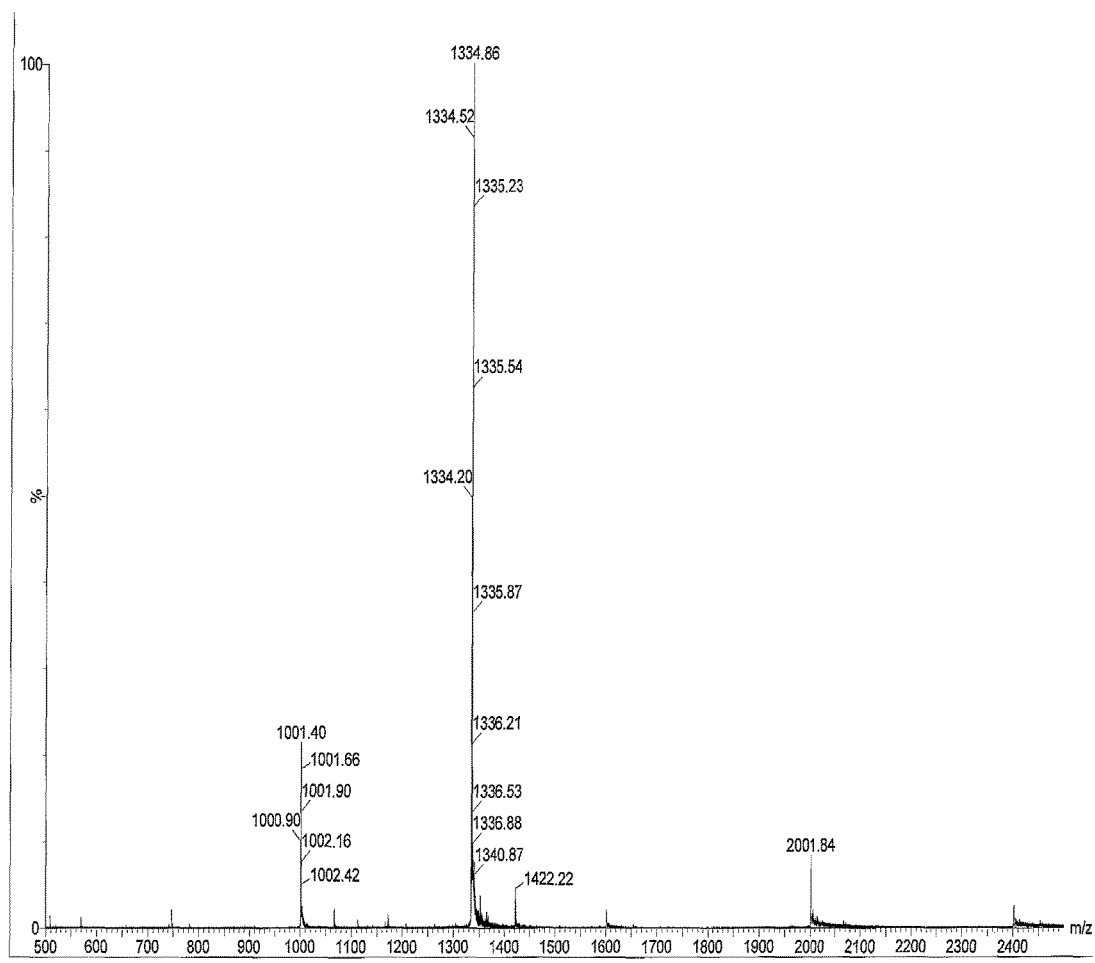

A

Figure 47, cont.
B
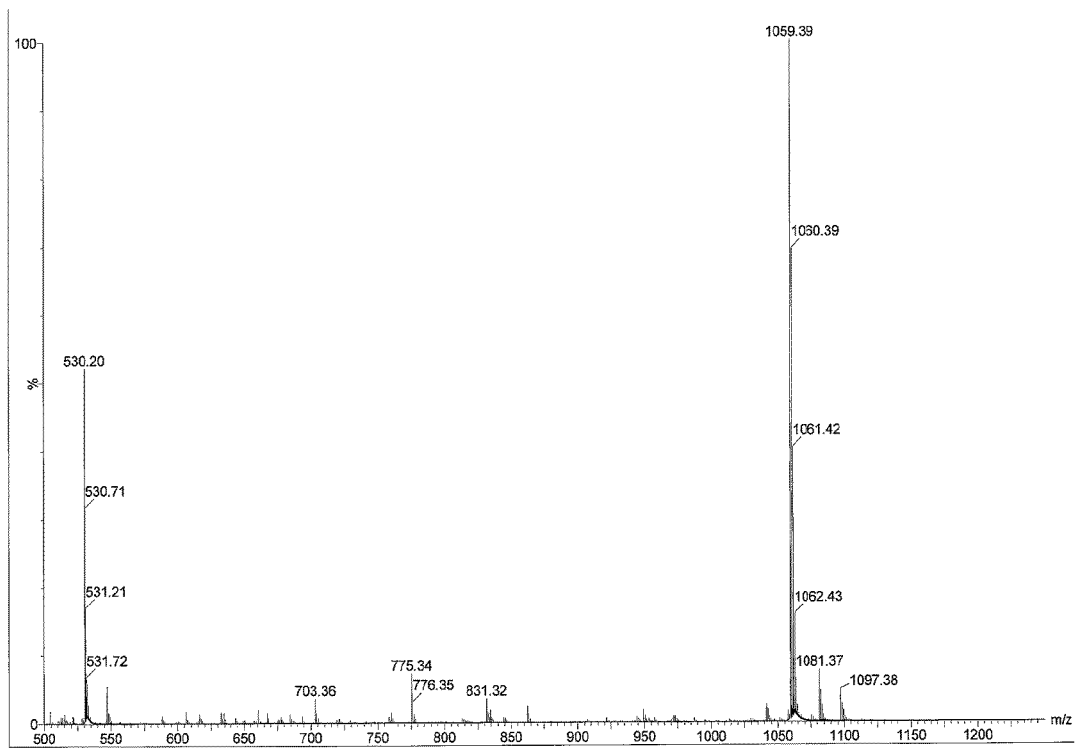

A

Figure 48, cont.
B
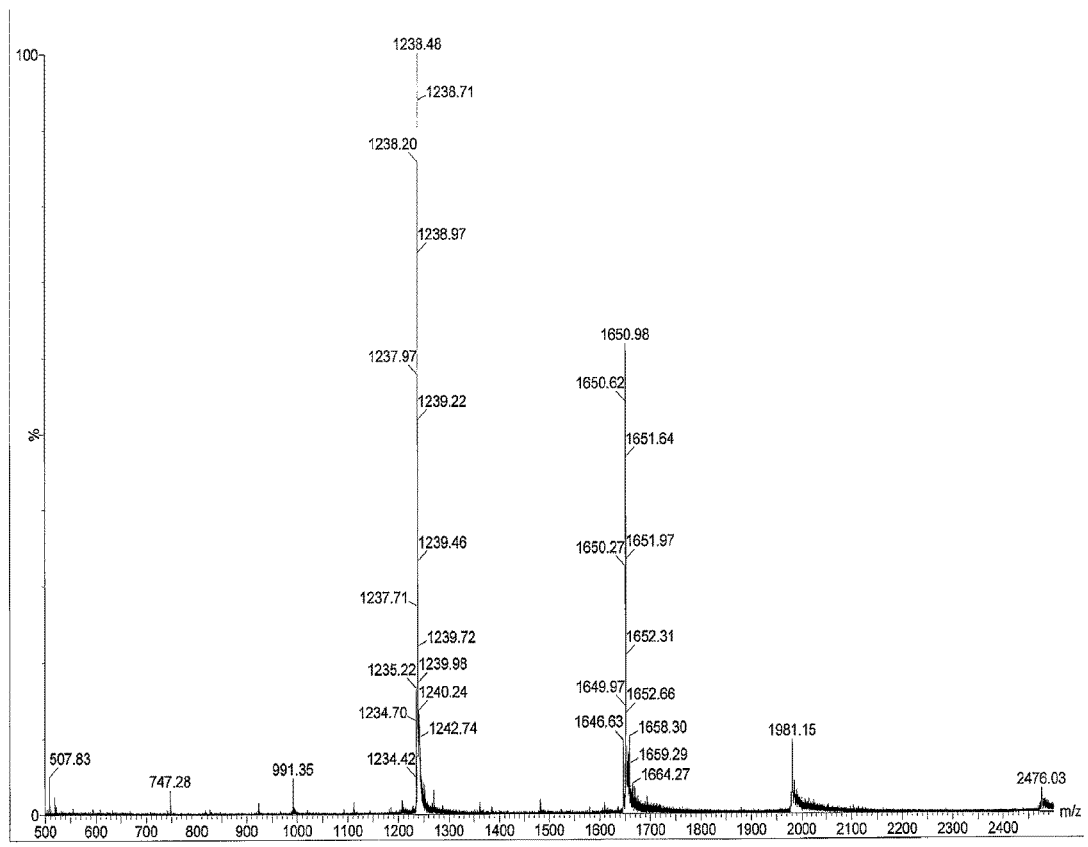

A

Figure 49, cont.
B
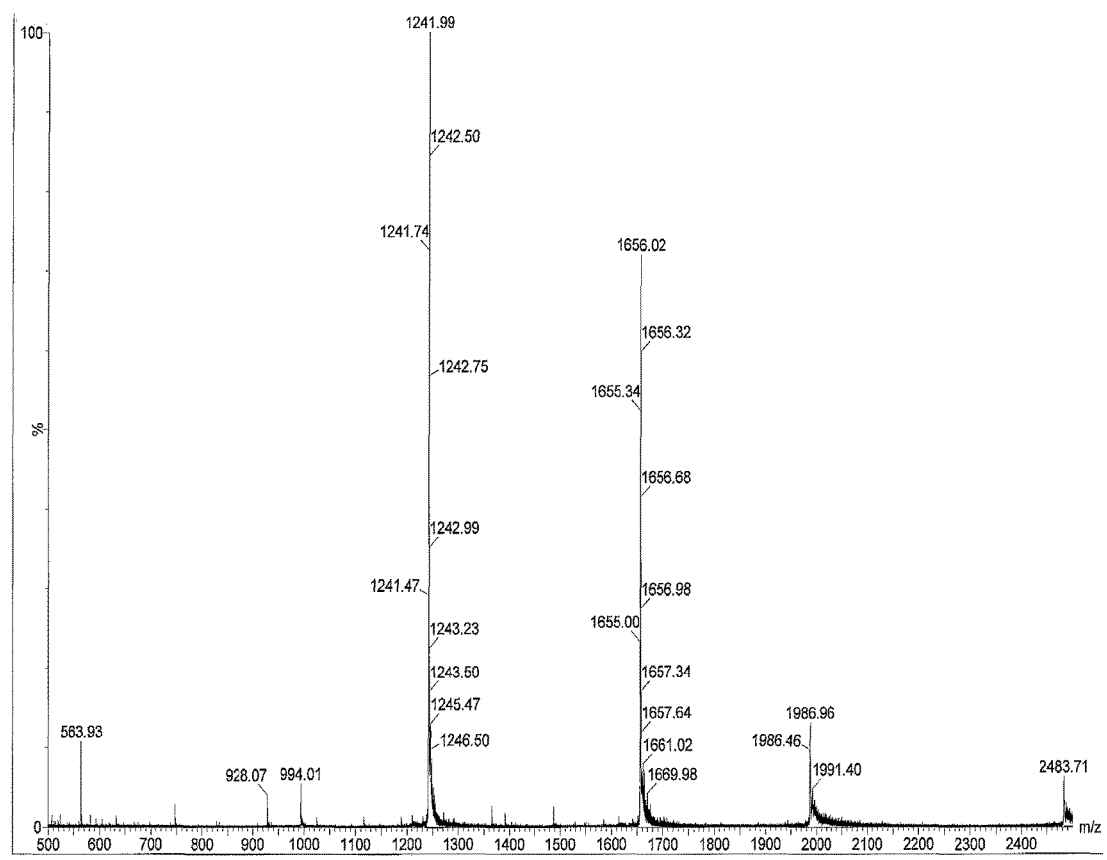

A

Figure 50, cont.
B
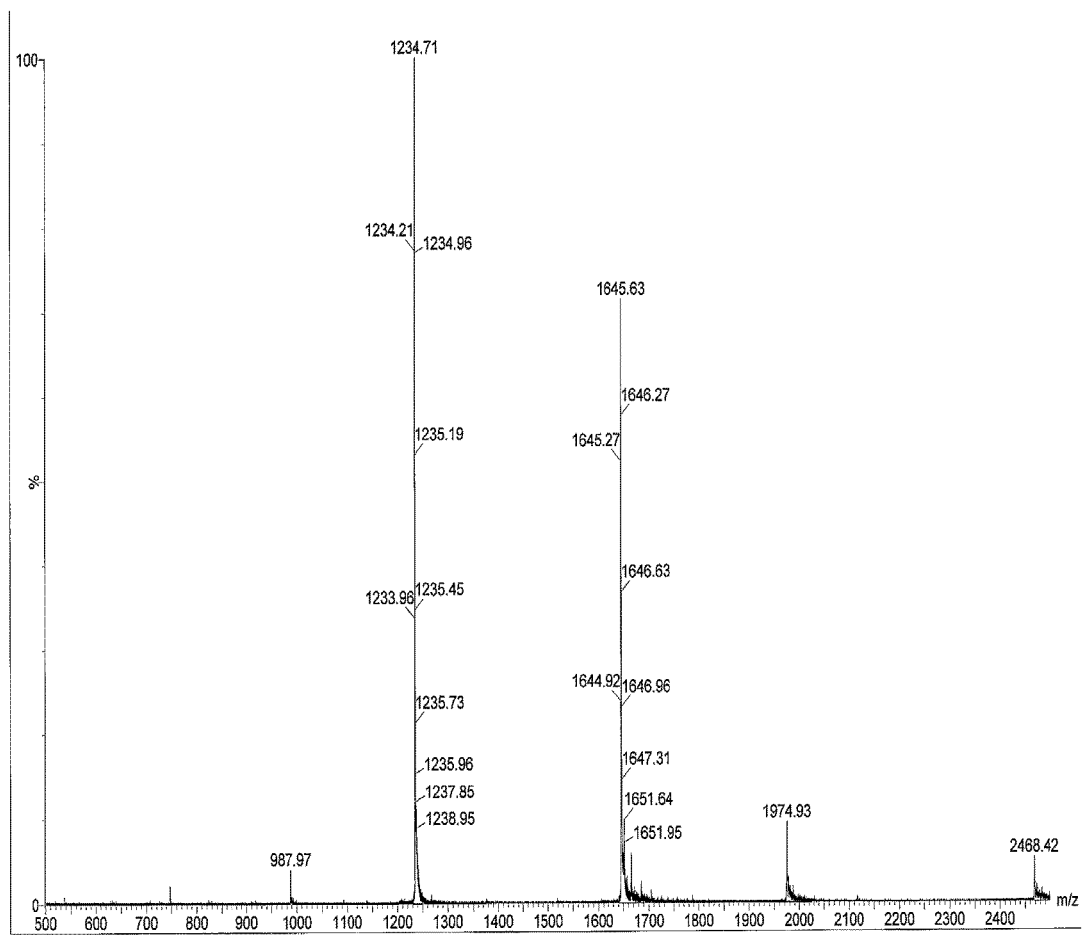

GLYCOSYLATED POLYPEPTIDE AND PHARMACEUTICAL COMPOSITION CONTAINING SAME

CROSS-REFERENCE TO RELATED APPLICATIONS

This application is the U.S. national stage application under 35 U.S.C. § 371 of International Patent Application No. PCT/JP2012/075262, filed on Sep. 28, 2012, which claims priority to Japan Application No. JP 2011-218793, filed on Oct. 1, 2011, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 30, 2014, is named 096025-0105_SL.txt and is 64,641 bytes in size.

TECHNICAL FIELD

The present invention relates to a glycosylated polypeptide and a pharmaceutical composition comprising said polypeptide.

BACKGROUND ART

Natural human interferon β (IFN-β) is a glycoprotein consisting of 166 amino acid residues. Interferon β belongs to the cytokine family, and is known to be involved in immunomodulation action, antiviral activity, and cell proliferation suppression action. Moreover, human interferon β has three Cys at positions 17, 31, and 141 of its amino acid sequence, and has a monoantennary complex-type N-linked oligosaccharide at asparagine at position 80. Moreover, it is known to have a disulfide bond at Cys at positions 31 and 141. Interferon β as a pharmaceutical is manufactured utilizing a cell expression system, and is classified into IFN-β-1a or IFN-β-1b depending on the difference in the host for expression. While IFN-β-1a is a glycoprotein, IFN-β-1b does not have an oligosaccharide. Further, IFN-β-1a having a sugar chain is known to have a more potent effect in immunogenicity, antiviral activity, and antitumor property compared to IFN-β-1b.

It is known that the sugar chain structure comprised in the glycoprotein has a strong influence on pharmacokinetics. In particular, the presence or absence of a sialic acid present at the non-reducing terminal of the sugar chain is known to have an influence on the extension of half-life in blood. However, previously biosynthesized IFN-β-1a is reported to have ununiform sugar chain structure in the polypeptide (for example, the result of analyzing the sugar chain structure ununiformity by CE-TOF-MS is described in Non-Patent Literature 1). Moreover, isolation of IFN—β having substantially uniform sugar chain structure from a synthesized IFN—β or a naturally-occurring IFN—β has not been reported. This has thus been an obstacle in presuming the sugar chain structure important for bioactivity.

In recent years, the biotechnology of utilizing a cell expression system has enabled the manufacture of bioactive protein formulations including interferons, such as insulin, erythropoietin, and G-CSF. In these protein formulations, it is reported that the glycosylation pattern of the protein renders variety to physical or chemical properties of the protein such as the folding step, or conformation property, stability, immune reaction, half-life in blood, and function of the protein in the biological system (Non-Patent Literature 2). Moreover, considering the crucial immunogenicity caused by a non-human-type sugar chain, the structure of the sugar chain added to these protein formulations is preferably a human-type sugar chain.

Such glycoprotein formulations have been manufactured by the cell expression system as the only method. However, as described above, the technology of such a cell expression system could not go the length of controlling the sugar chain structure, thereby causing ununiformity in the sugar chain structure in the glycoprotein manufactured (e.g. Non-Patent Literature 3). For this reason, there were problems such as variability of the quality between production lots or the inability to optimize the sugar chain. Accordingly, a method for preparing a uniform glycoprotein wherein the sugar chain structure is easily adjustable has been long desired, but currently, there is no report of synthesizing a human-type uniform glycoprotein showing bioactivity in vivo by chemical synthesis.

Moreover, a bioactive glycoprotein manufactured by a technology by such a cell expression system may comprise a virus or genetic material. Moreover, there is a possibility of contamination with such genetic material etc. also in the case of synthesizing a bioactive glycoprotein using a sugar chain prepared from a biologically-derived sample. Application of heat treatment that can disintegrate these genetic materials is desired in order to manufacture a safe protein formulation. However, currently, heat treatment on a bioactive glycoprotein formulation will inactivate the glycoprotein, and application of heat treatment has not been reported.

CITATION LIST

Non-Patent Literatures

[Non-Patent Literature 1] Anal Bioanall Chem (2011) 400: 295-303
[Non-Patent Literature 2] Nat. Biotechnol., 2006, 24, 1241-1252
[Non-Patent Literature 3] J. Biotechnol, 42, 117-131 (1995)

SUMMARY OF THE INVENTION

Problems to be Solved by the Invention

The object of the present invention is to provide a glycosylated polypeptide having uniform sugar chain structure which has interferon β activity.

Means for Solving the Problems

As a result of repeated research to solve the above problems, the present inventors succeeded in manufacturing a glycosylated polypeptide having uniform sugar chain structure which has interferon β activity.

In other words, the present invention relates to a glycosylated polypeptide characterized in that said glycosylated polypeptide is a polypeptide selected from the group consisting of:

(a) a polypeptide consisting of the amino acid sequence represented by SEQ ID NO. 1;

(b) a polypeptide consisting of the amino acid sequence represented by SEQ ID NO. 1 having one or a few amino acids deleted, substituted, or added;

(c) an interferon β analog; and (d) a polypeptide having 80% or more homology with a polypeptide consisting of the amino acid sequence represented by SEQ ID NO. 1;

wherein the polypeptide has a sugar chain at the amino acid corresponding to position 80 in interferon β and has interferon β activity, and said glycosylated polypeptide has substantially uniform sugar chains.

Here, one embodiment of the glycosylated polypeptide of the present invention is characterized in that said glycosylated polypeptide is prepared by chemical synthesis.

Moreover, another aspect of the present invention relates to a glycosylated polypeptide obtained by a method comprising a step of synthesizing a glycosylated peptide fragment and at least two peptide fragments and a step of linking said glycosylated peptide fragment and said at least two peptide fragments, characterized in that said glycosylated polypeptide is a polypeptide selected from the group consisting of:

(a) a polypeptide consisting of the amino acid sequence represented by SEQ ID NO. 1;

(b) a polypeptide consisting of the amino acid sequence represented by SEQ ID NO. 1 having one or a few amino acids deleted, substituted, or added;

(c) an interferon β analog; and (d) a polypeptide having 80% or more homology with a polypeptide consisting of the amino acid sequence represented by SEQ ID NO. 1;

wherein the polypeptide has a sugar chain at the amino acid corresponding to position 80 in interferon β and has interferon β activity.

Moreover, in one embodiment of the glycosylated polypeptide of the present invention, the glycosylated polypeptide relates to a glycosylated polypeptide obtained by a method comprising a step of synthesizing a glycosylated peptide fragment and at least two peptide fragments and a step of linking said glycosylated peptide fragment and said at least two peptide fragments, characterized in that said glycosylated polypeptide is a polypeptide selected from the group consisting of:

(a) a polypeptide consisting of the amino acid sequence represented by SEQ ID NO. 1;

(b) a polypeptide consisting of the amino acid sequence represented by SEQ ID NO. 1 having one or a few amino acids deleted, substituted, or added;

(c) an interferon β analog; and (d) a glycosylated polypeptide having 80% or more homology with a polypeptide consisting of the amino acid sequence represented by SEQ ID NO. 1;

wherein the polypeptide has a sugar chain at the amino acid corresponding to position 80 in interferon β and has interferon β activity.

Here, one embodiment of the glycosylated polypeptide of the present invention is characterized in that the sugar chain in said glycosylated polypeptide is an asparagine-linked sugar chain.

Moreover, one embodiment of the glycosylated polypeptide of the present invention is characterized in that the sugar chain in said glycosylated polypeptide is a disialo sugar chain represented by the following formula (a) or an asialo sugar chain represented by the following formula (b).

[Chemical Formula 1]

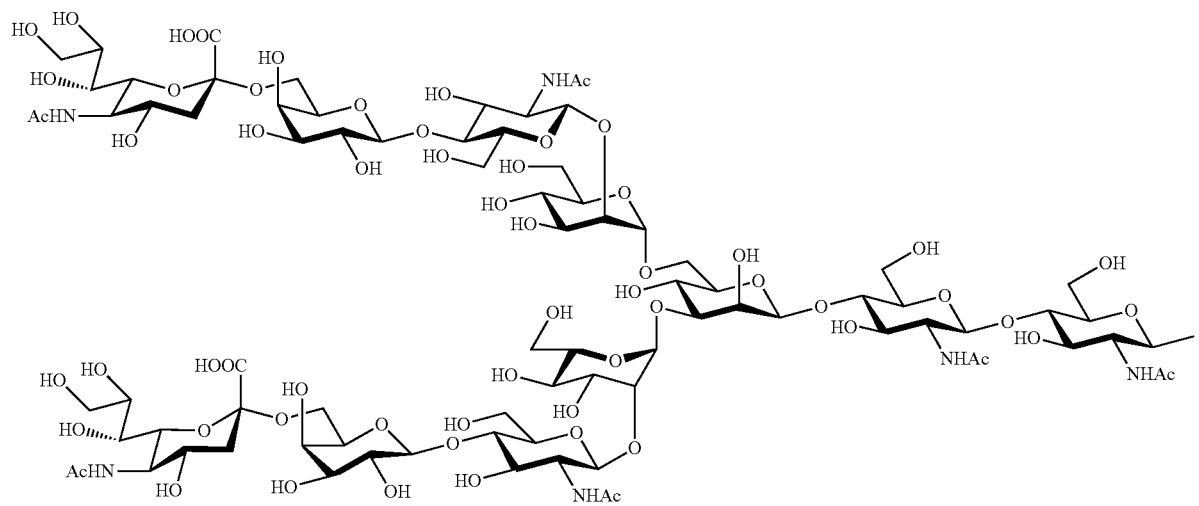

(a)

[Chemical Formula 2]

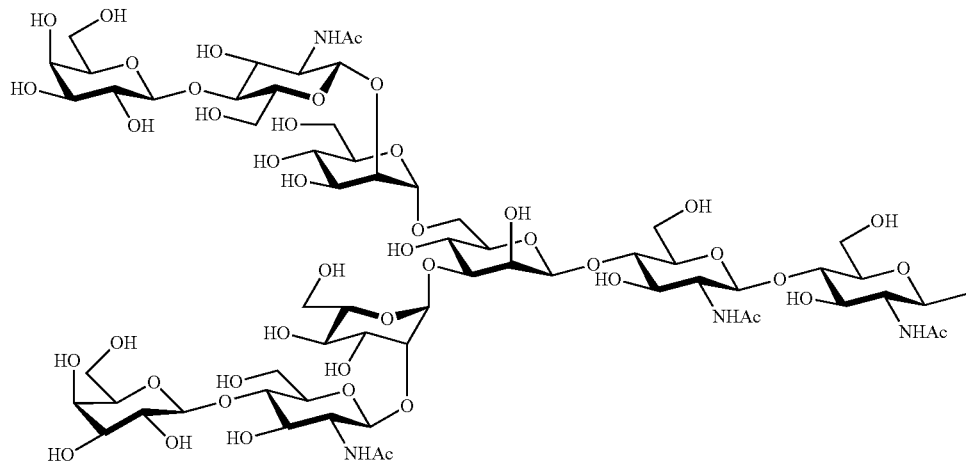

(b)

Moreover, one embodiment of the glycosylated polypeptide of the present invention is characterized in that Cys corresponding to positions 31 and 141 of interferon β forms a disulfide bond in said glycosylated polypeptide.

Moreover, one embodiment of the glycosylated polypeptide of the present invention is characterized in that said glycosylated polypeptide is heat-treated.

Moreover, one embodiment of the glycosylated polypeptide of the present invention is characterized in that said glycosylated polypeptide is 90% or more pure.

Moreover, another aspect of the present invention relates to a composition comprising said glycosylated polypeptide characterized in that the glycosylated polypeptides in said composition are substantially uniform.

Here, one embodiment of the composition of the present invention is characterized in that the glycosylated polypeptides in said composition are 90% or more uniform.

Moreover, one embodiment of the composition of the present invention is characterized in that said glycosylated polypeptide is 90% or more pure.

Moreover, the composition of the present invention is characterized in that it is a composition comprising a glycosylated polypeptide characterized in that said glycosylated polypeptide is a polypeptide selected from the group consisting of the following polypeptides (a)-(d):

(a) a polypeptide consisting of the amino acid sequence represented by SEQ ID NO. 1;

(b) a polypeptide consisting of the amino acid sequence represented by SEQ ID NO. 1 having one or a few amino acids deleted, substituted, or added;

(c) an interferon β analog; and (d) a polypeptide having 80% or more homology with a polypeptide consisting of the amino acid sequence represented by SEQ ID NO. 1;

wherein the polypeptide has a sugar chain at the amino acid corresponding to position 80 in interferon β and has interferon β activity, and the glycosylated polypeptides in said composition are substantially uniform.

Moreover, another aspect of the present invention relates to a pharmaceutical composition characterized in that it comprises (I) a glycosylated polypeptide according to any one of claims 1 to 7 and/or a pharmaceutically acceptable salt thereof and (II) a pharmaceutically acceptable carrier.

Here, one embodiment of the pharmaceutical composition of the present invention is characterized in that sugar chains are substantially uniform in said glycosylated polypeptide.

Moreover, one embodiment of the pharmaceutical composition of the present invention is characterized in that sugar chains are 90% or more uniform in said glycosylated polypeptide.

Moreover, one embodiment of the pharmaceutical composition of the present invention is characterized in that said glycosylated polypeptide is 90% or more pure.

Moreover, one embodiment of the pharmaceutical composition of the present invention is characterized in that it is employed for treating or preventing an interferon β-related disease.

Moreover, one embodiment of the pharmaceutical composition of the present invention is characterized in that said interferon β-related disease is at least one disease selected from the group consisting of a brain tumor including multi-glioblastoma, medulloblastoma, and astrocytoma, cutaneous malignant melanoma, chronic active hepatitis B, chronic hepatitis C, subacute sclerosing panencephalitis, compensated cirrhosis C, and multiple sclerosis.

Moreover, another aspect of the present invention relates to a method for treating or preventing an interferon β-related disease, characterized in administering an effective amount of said glycosylated polypeptide.

Here, one embodiment of the method of the present invention for treating or preventing an interferon β-related disease is characterized in that said interferon β-related disease is at least one disease selected from the group consisting of a brain tumor including multi-glioblastoma, medulloblastoma, and astrocytoma, cutaneous malignant melanoma, chronic active hepatitis B, chronic hepatitis C, subacute sclerosing panencephalitis, compensated cirrhosis C, and multiple sclerosis.

Moreover, another aspect of the present invention relates to a glycosylated polypeptide characterized in that the glycosylated polypeptide is a polypeptide selected from the group consisting of:

(a) a polypeptide consisting of the amino acid sequence represented by SEQ ID NO. 1;

(b) a polypeptide consisting of the amino acid sequence represented by SEQ ID NO. 1 having one or a few amino acids deleted, substituted, or added;

(c) an interferon β analog; and (d) a polypeptide having 80% or more homology with a polypeptide consisting of the amino acid sequence represented by SEQ ID NO. 1;

wherein the polypeptide has a sugar chain at the amino acid corresponding to position 80 in interferon β and has Cys corresponding to positions 17, 31, and 141 in interferon β protected by a protecting group.

Here, one embodiment of the glycosylated polypeptide of the present invention is characterized in that said sugar chain in said glycosylated polypeptide is a disialo sugar chain having the carboxy group of the sialic acid present at the sugar chain non-reducing terminal protected represented by the following formula (c) or an asialo sugar chain represented by the following formula (b).

[Chemical Formula 3]

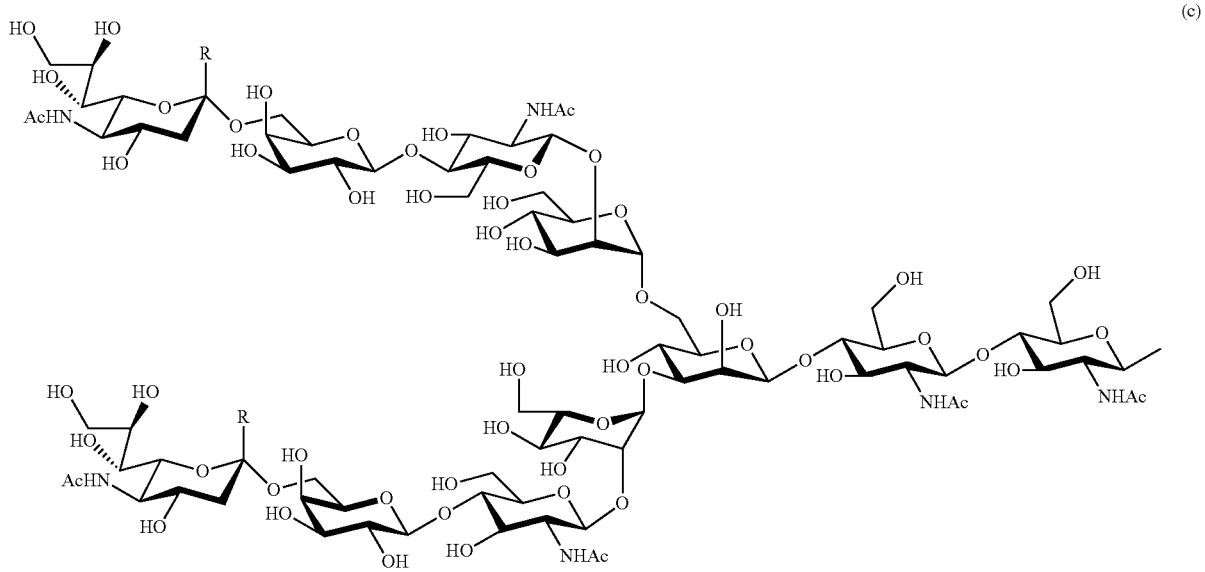

(c)

(wherein R represents —COOBn, —COOEt, —COOMe, —COOCH$_2$COPh, —COOCH$_2$PhOMe, —COOCH$_2$Ph(OMe)$_2$, —COOCH$_2$PhNO$_2$, or —COOCH$_2$Ph(NO$_2$)$_2$. Bn indicates a benzyl group, Et indicates an ethyl group, Me indicates a methyl group, and Ph indicates a phenyl group).

[Chemical Formula 4]

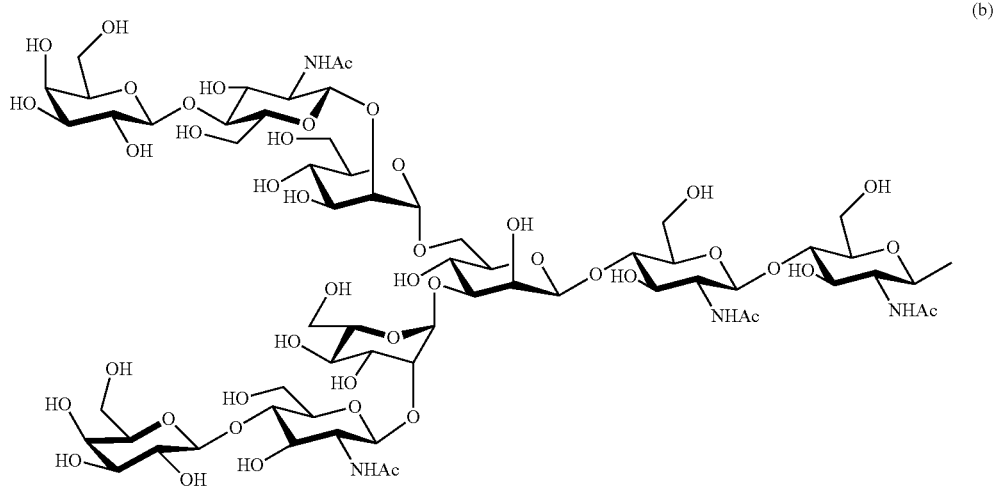

(b)

Moreover, one embodiment of the glycosylated polypeptide of the present invention is characterized in that Cys corresponding to said positions 17, 31, and 141 in interferon β are protected by any one protecting group selected from the group consisting of an Acm group, an alkoxymethyl group, a triphenylmethyl group, a t-butyl group, a benzyl group, and an ethyl group having the 13 position substituted in said glycosylated polypeptide.

Moreover, another aspect of the present invention relates to a method for manufacturing a glycosylated polypeptide, characterized in that it comprises a step of deprotecting Cys corresponding to said positions 17, 31, and 141 in interferon β protected by a protecting group in said glycosylated polypeptide having Cys protected.

Here, one embodiment of the method for manufacturing the glycosylated polypeptide of the present invention is characterized in that it further comprises a step of preparing said glycosylated polypeptide having Cys corresponding to positions 17, 31, and 141 in interferon β protected by a protecting group before said step of deprotecting Cys.

Moreover, one embodiment of the method for manufacturing the glycosylated polypeptide of the present invention is characterized in that the glycosylated polypeptide is heat-treated before the step of deprotecting the protecting group of Cys.

Moreover, another aspect of the present invention relates to a glycosylated polypeptide characterized in that the glycosylated polypeptide is a polypeptide selected from the group consisting of:
(a) a polypeptide consisting of the amino acid sequence represented by SEQ ID NO. 1;
(b) a polypeptide consisting of the amino acid sequence represented by SEQ ID NO. 1 having one or a few amino acids deleted, substituted, or added;
(c) an interferon β analog; and
(d) a glycosylated polypeptide having 80% or more homology with a polypeptide consisting of the amino acid sequence represented by SEQ ID NO. 1;
wherein the polypeptide has a sugar chain at the amino acid corresponding to position 80 in interferon β, and said sugar chain is a disialo sugar chain having the carboxy group of the sialic acid present at the sugar chain non-reducing terminal protected represented by the following formula (c).

(wherein R represents —COOBn, —COOEt, —COOMe, —COOCH$_2$COPh, —COOCH$_2$PhOMe, —COOCH$_2$Ph(OMe)$_2$, —COOCH$_2$PhNO$_2$, or —COOCH$_2$Ph(NO$_2$)$_2$. Bn indicates a benzyl group, Et indicates an ethyl group, Me indicates a methyl group, and Ph indicates a phenyl group).

Moreover, another aspect of the present invention relates to a method for manufacturing a glycosylated polypeptide, characterized in that it comprises a step of deprotecting the protecting group of the carboxy group of the sialic acid present at the sugar chain non-reducing terminal in said glycosylated polypeptide having a sugar chain having the carboxy group of the sialic acid protected.

Here, one embodiment of the method for manufacturing the glycosylated polypeptide of the present invention is characterized in that it further comprises a step of preparing said glycosylated polypeptide having a sugar chain having the carboxy group of the sialic acid protected before the deprotection step of the carboxy group of said sialic acid.

Moreover, the glycosylated polypeptide of the manufacturing method of the present invention is characterized in that it further comprises a step of folding said glycosylated polypeptide.

Effects of the Invention

Since the glycosylated polypeptide of the present invention has uniform sugar chain structure, there is little variability between lots and a glycosylated polypeptide having interferon β activity with stable quality can be provided. Moreover, the type of sugar chain bound can be made to be uniform, and the sugar chain structure can be optimized according to purpose.

Moreover, since the glycosylated polypeptide of the present invention can be heat-treated, contamination with a virus or an unknown genetic material can be prevented.

BRIEF DESCRIPTION OF THE DRAWINGS

FIG. 1 is a schematic diagram of a step of ligating glycopeptide fragment B having amino acids at positions 68-88 and peptide fragment C having amino acids at posi-

[Chemical Formula 5]

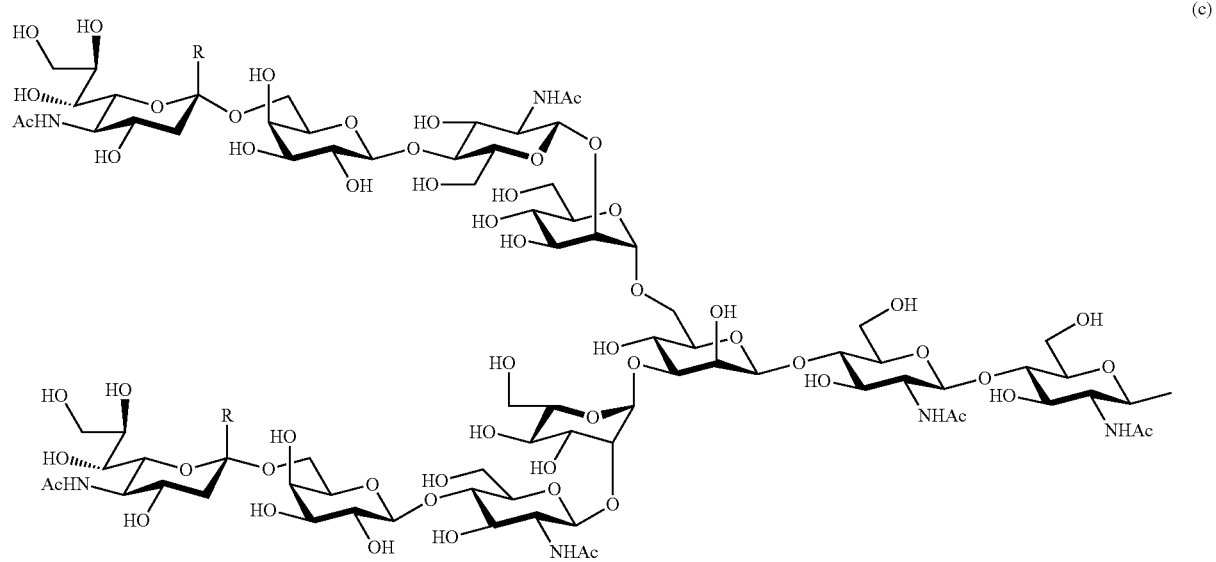

(c)

Figure 15:
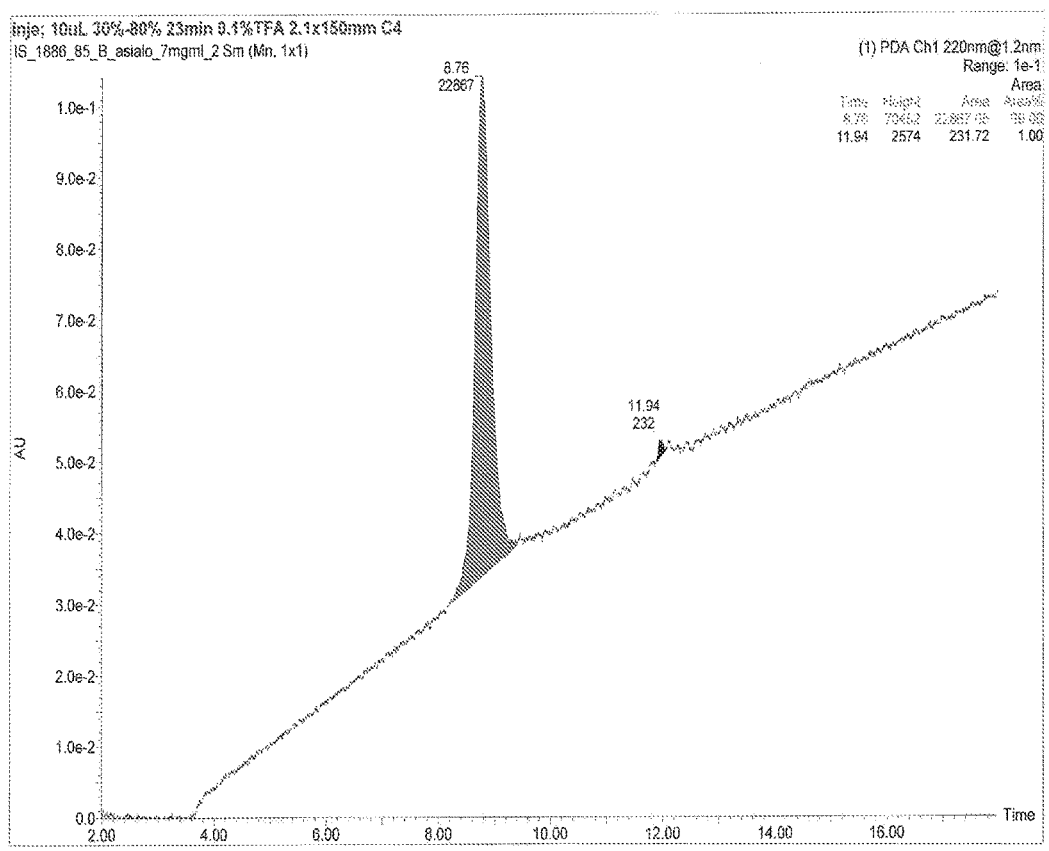

tions 89-166 in the amino acid sequence of interferon β in one embodiment of manufacturing the glycosylated polypeptide of the present invention.

FIG. 2 is a schematic diagram of a step of ligating peptide fragment A having amino acids at positions 1-67 and glycopeptide fragment (B+C) having amino acids at positions 68-166 in the amino acid sequence of interferon β in one embodiment of manufacturing the glycosylated polypeptide of the present invention.

FIG. 3 is a schematic diagram of a step of reducing a particular cysteine of glycopeptide fragment (A+B+C) having amino acids at positions 1-166 in the amino acid sequence of interferon β prepared by ligation into alanine in one embodiment of manufacturing the glycosylated polypeptide of the present invention.

FIG. 4 is a schematic diagram showing a step of deprotecting the protecting group of cysteine performed on glycopeptide fragment (A+B+C) having amino acids at positions 1-166 in the amino acid sequence of interferon β prepared by ligation after the reduction step into alanine in one embodiment of manufacturing the glycosylated polypeptide of the present invention.

FIG. 5 shows the HPLC (A) and ESI-MS (B) data of glycopeptide fragment (11) manufactured in one embodiment of manufacturing the glycosylated polypeptide of the present invention.

FIG. 6 shows the amino acid sequence of glycopeptide fragment (11) manufactured in one embodiment of manufacturing the glycosylated polypeptide of the present invention.

FIG. 7 shows the HPLC (A) and ESI-MS (B) data of glycopeptide fragment (12) manufactured in one embodiment of manufacturing the glycosylated polypeptide of the present invention.

FIG. 8 shows the amino acid sequence of glycopeptide fragment (12) manufactured in one embodiment of manufacturing the glycosylated polypeptide of the present invention.

FIG. 9 shows the HPLC (A) and ESI-MS (B) data of glycopeptide fragment (13) manufactured in one embodiment of manufacturing the glycosylated polypeptide of the present invention.

FIG. 10 shows the amino acid sequence of glycopeptide fragment (13) manufactured in one embodiment of manufacturing the glycosylated polypeptide of the present invention.

FIG. 11 shows the HPLC (A) and ESI-MS (B) data of glycopeptide fragment (14) manufactured in one embodiment of manufacturing the glycosylated polypeptide of the present invention.

FIG. 12 shows the amino acid sequence of glycopeptide fragment (14) manufactured in one embodiment of manufacturing the glycosylated polypeptide of the present invention.

FIG. 13 shows the HPLC (A) and ESI-MS (B) data of glycopeptide fragment (15) manufactured in one embodiment of manufacturing the glycosylated polypeptide of the present invention.

FIG. 14 shows the amino acid sequence of glycopeptide fragment (15) manufactured in one embodiment of manufacturing the glycosylated polypeptide of the present invention.

FIG. 15 shows the data of the purity of glycopeptide fragment (15) manufactured in one embodiment of manufacturing the glycosylated polypeptide of the present invention as measured by HPLC.

FIG. 16 shows the HPLC (A) and ESI-MS (B) data of glycopeptide fragment (5) manufactured in one embodiment of manufacturing the glycosylated polypeptide of the present invention.

FIG. 17 shows the amino acid sequence of glycopeptide fragment (5) manufactured in one embodiment of manufacturing the glycosylated polypeptide of the present invention.

FIG. 18 shows the HPLC (A) and ESI-MS (B) data of glycopeptide fragment (6) manufactured in one embodiment of manufacturing the glycosylated polypeptide of the present invention.

FIG. 19 shows the amino acid sequence of glycopeptide fragment (6) manufactured in one embodiment of manufacturing the glycosylated polypeptide of the present invention.

FIG. 20 shows the HPLC (A) and ESI-MS (B) data of glycopeptide fragment (7) manufactured in one embodiment of manufacturing the glycosylated polypeptide of the present invention.

FIG. 21 shows the amino acid sequence of glycopeptide fragment (7) manufactured in one embodiment of manufacturing the glycosylated polypeptide of the present invention.

FIG. 22 shows the HPLC (A) and ESI-MS (B) data of glycopeptide fragment (8) manufactured in one embodiment of manufacturing the glycosylated polypeptide of the present invention.

FIG. 23 shows the amino acid sequence of glycopeptide fragment (8) manufactured in one embodiment of manufacturing the glycosylated polypeptide of the present invention.

FIG. 24 shows the HPLC (A) and ESI-MS (B) data of glycopeptide fragment (9) manufactured in one embodiment of manufacturing the glycosylated polypeptide of the present invention.

FIG. 25 shows the amino acid sequence of glycopeptide fragment (9) manufactured in one embodiment of manufacturing the glycosylated polypeptide of the present invention.

FIG. 26 shows the HPLC data of glycopeptide fragment (10) manufactured in one embodiment of manufacturing the glycosylated polypeptide of the present invention.

FIG. 27 shows the amino acid sequence of glycopeptide fragment (10) manufactured in one embodiment of manufacturing the glycosylated polypeptide of the present invention.

Figure 28:
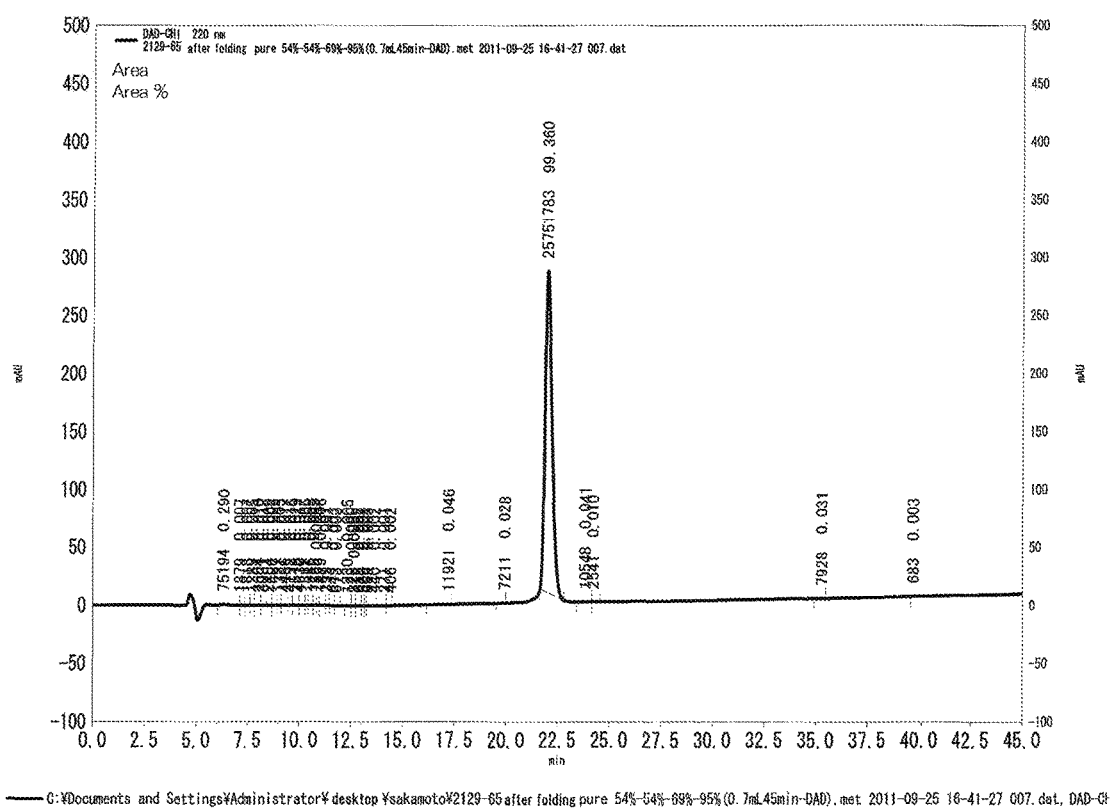

FIG. 28 shows the data of the purity of glycopeptide fragment (10) manufactured in one embodiment of manufacturing the glycosylated polypeptide of the present invention as measured by HPLC.

FIG. 29 shows the HPLC (A) and ESI-MS (B) data of peptide fragment (18) manufactured in one embodiment of manufacturing the glycosylated polypeptide of the present invention.

FIG. 30 shows the HPLC (A) and ESI-MS (B) data of glycopeptide fragment (19) manufactured in one embodiment of manufacturing the glycosylated polypeptide of the present invention.

FIG. 31 shows the HPLC (A) and ESI-MS (B) data of glycopeptide fragment (20) manufactured in one embodiment of manufacturing the glycosylated polypeptide of the present invention.

FIG. 32 shows the HPLC (A) and ESI-MS (B) data of glycopeptide fragment (21) manufactured in one embodiment of manufacturing the glycosylated polypeptide of the present invention.

FIG. 33 shows the HPLC (A) and ESI-MS (B) data of glycopeptide fragment (22) manufactured in one embodiment of manufacturing the glycosylated polypeptide of the present invention.

FIG. 34 shows the HPLC (A) and ESI-MS (B) data of glycopeptide fragment (23) manufactured in one embodiment of manufacturing the glycosylated polypeptide of the present invention.

FIG. 35 shows the HPLC (A) and ESI-MS (B) data of glycopeptide fragment (24) manufactured in one embodiment of manufacturing the glycosylated polypeptide of the present invention.

FIG. 36 shows a schematic diagram of the amino acid sequence (SEQ ID NO 23) of dibenzyl disialo sugar chain attached polypeptide (7) having Cys at positions 17, 31, and 141 protected with an Acm group which is one embodiment of the glycosylated polypeptide of the present invention, and HPLC and ESI-MS analysis data of said dibenzyl disialo sugar chain attached polypeptide (7) before and after heat treatment. FIGS. 36a and c show the ESI-MS data before heat treatment, and FIGS. 36b and e show the ESI-MS data after heat treatment. Moreover, FIG. 36d shows the HPLC analysis data before heat treatment, and FIG. 36f shows the HPLC analysis data after heat treatment.

FIG. 37 shows a schematic diagram of the amino acid sequence (SEQ ID NO 24) of dibenzyl disialo sugar chain attached polypeptide (8) having Cys at positions 17, 31, and 141 unprotected which is one embodiment of the glycosylated polypeptide of the present invention, and HPLC and ESI-MS analysis data of said dibenzyl disialo sugar chain attached polypeptide (8) before and after heat treatment. FIGS. 37a and c show the ESI-MS data before heat treatment, and FIGS. 37b and e show the ESI-MS data after heat treatment. Moreover, FIG. 37d shows the HPLC analysis data before heat treatment, and FIG. 37f shows the HPLC analysis data after heat treatment.

FIG. 38 shows the receptor affinity analysis data against IFN-α/β receptor 2 of a chemically synthesized glycosylated polypeptide (non-heat-treated) which is one embodiment of the present invention.

FIG. 39 shows the receptor affinity analysis data against IFN-α/β receptor 2 of a chemically synthesized glycosylated polypeptide (heat-treated) which is one embodiment of the present invention.

FIG. 40 shows the pharmacokinetics analysis data when a chemically synthesized glycosylated polypeptide which is one embodiment of the present invention was administered to mice. IFNβ Mochida prepared by biosynthesis was used as control. In FIG. 40, A shows the data when administered intravenously and B shows the data when administered subcutaneously.

FIG. 41 is the showing the antitumor activity of a chemically synthesized glycosylated polypeptide which is one embodiment of the present invention. PBS (vehicle group) and IFNβ Mochida prepared by biosynthesis were used as controls.

FIG. 42 shows the data comparing the cell proliferation suppression activity power a chemically synthesized glycosylated polypeptide which is one embodiment of the present invention between a heat-treated and a non-heat-treated polypeptide.

FIG. 43 is a schematic diagram showing a step of ligating peptide fragment B2 having amino acids at positions 68-75 and glycopeptide fragment B1 having amino acids at positions 76-88 in the amino acid sequence of interferon β in one embodiment of manufacturing the glycosylated polypeptide of the present invention.

FIG. 44 is a schematic diagram showing a step of methylating the thiol group (—SH) of a particular cysteine of glycopeptide fragment (B1+B2) having amino acids at positions 68-88 in the amino acid sequence of interferon β prepared by ligation into a methylthio group (—SMe) in one embodiment of manufacturing the glycosylated polypeptide of the present invention.

FIG. 45 is a schematic diagram showing a step of intramolecular acyl translocation in which the cysteine having a methylated thiol group (—SMe) on glycopeptide fragment (B1+B2) is converted into serine in one embodiment of manufacturing the glycosylated polypeptide of the present invention.

Figure 46:
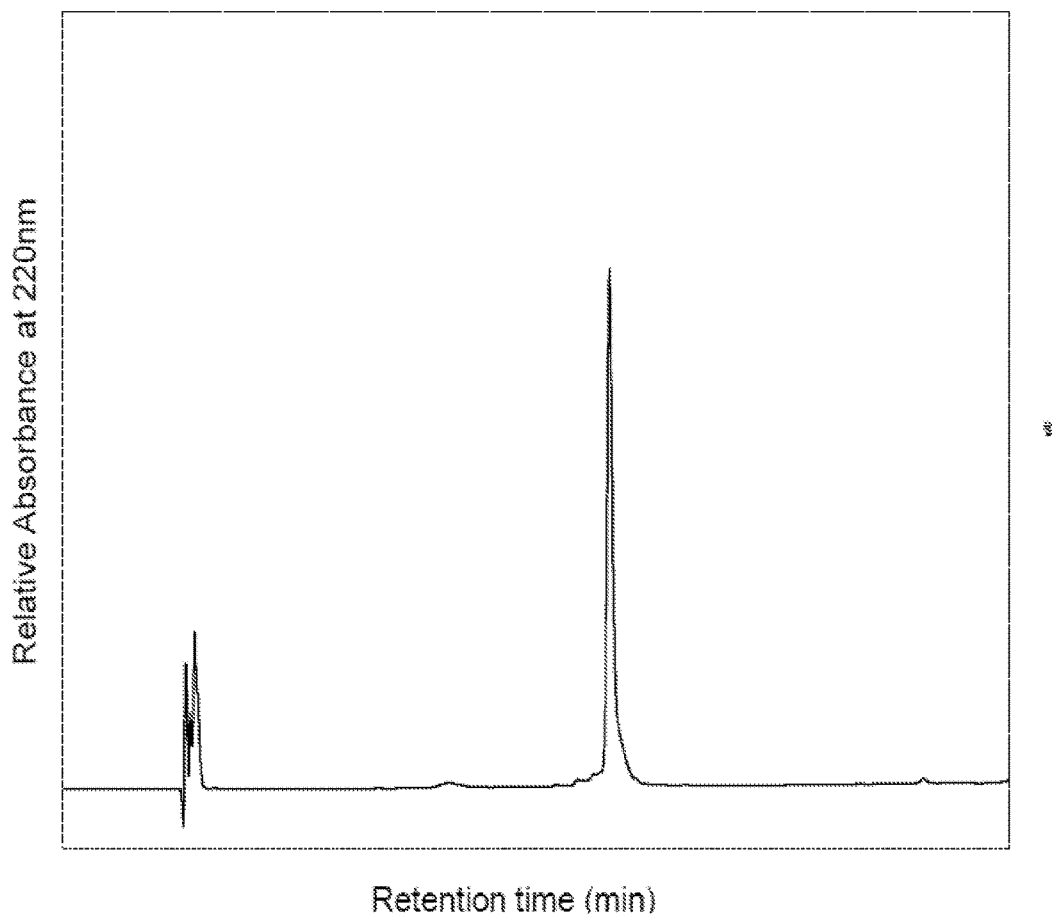

FIG. 46 shows the HPLC (A) and ESI-MS (B) data of glycopeptide fragment (25) manufactured in one embodiment of manufacturing the glycosylated polypeptide of the present invention.

Figure 47:
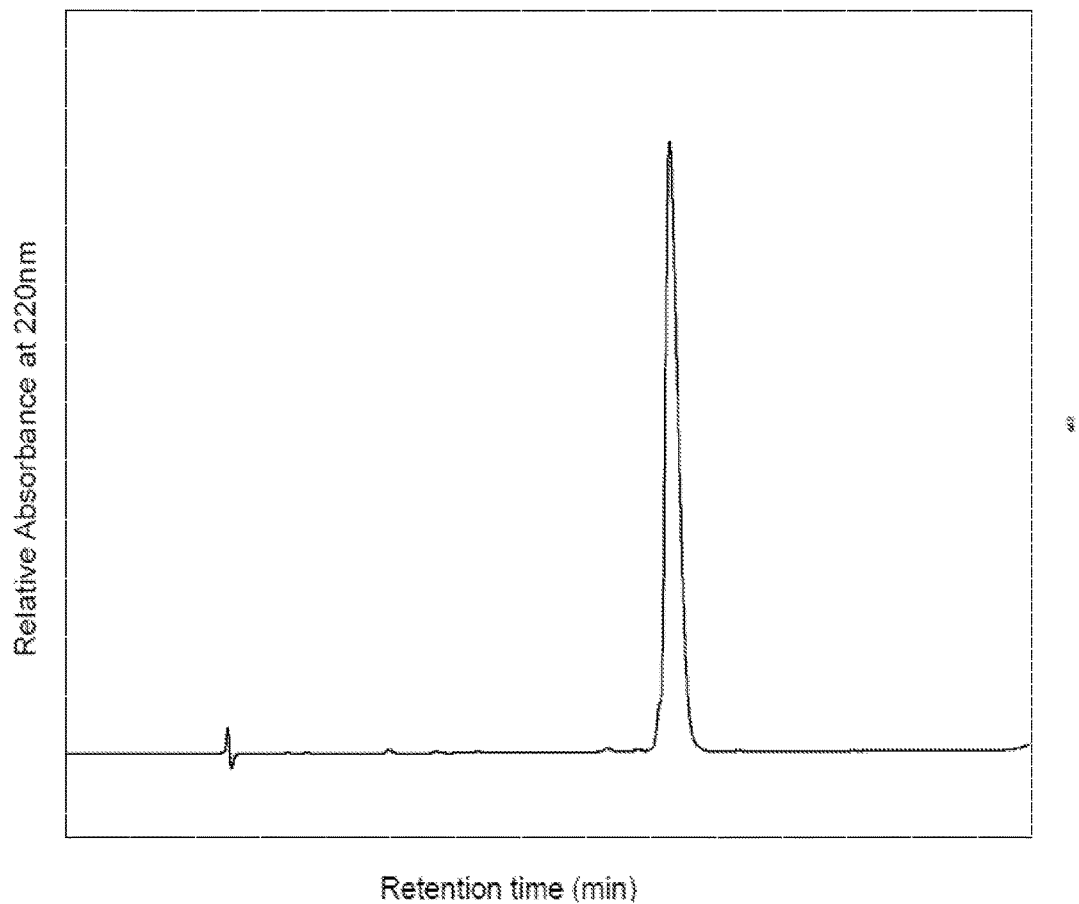

FIG. 47 shows the HPLC (A) and ESI-MS (B) data of peptide fragment (26) manufactured in one embodiment of manufacturing the glycosylated polypeptide of the present invention.

Figure 48:
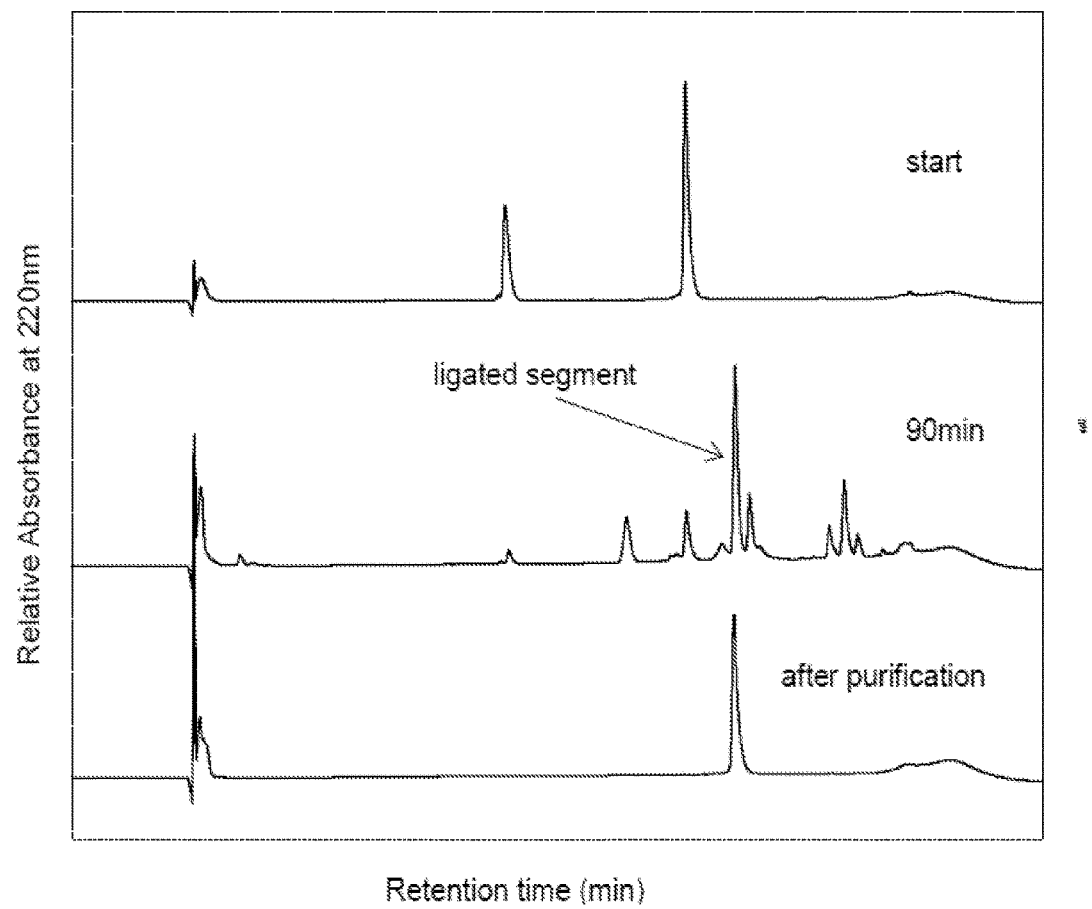

FIG. 48 shows the HPLC (A) and ESI-MS (B) data of glycopeptide fragment (27) manufactured in one embodiment of manufacturing the glycosylated polypeptide of the present invention.

Figure 49:
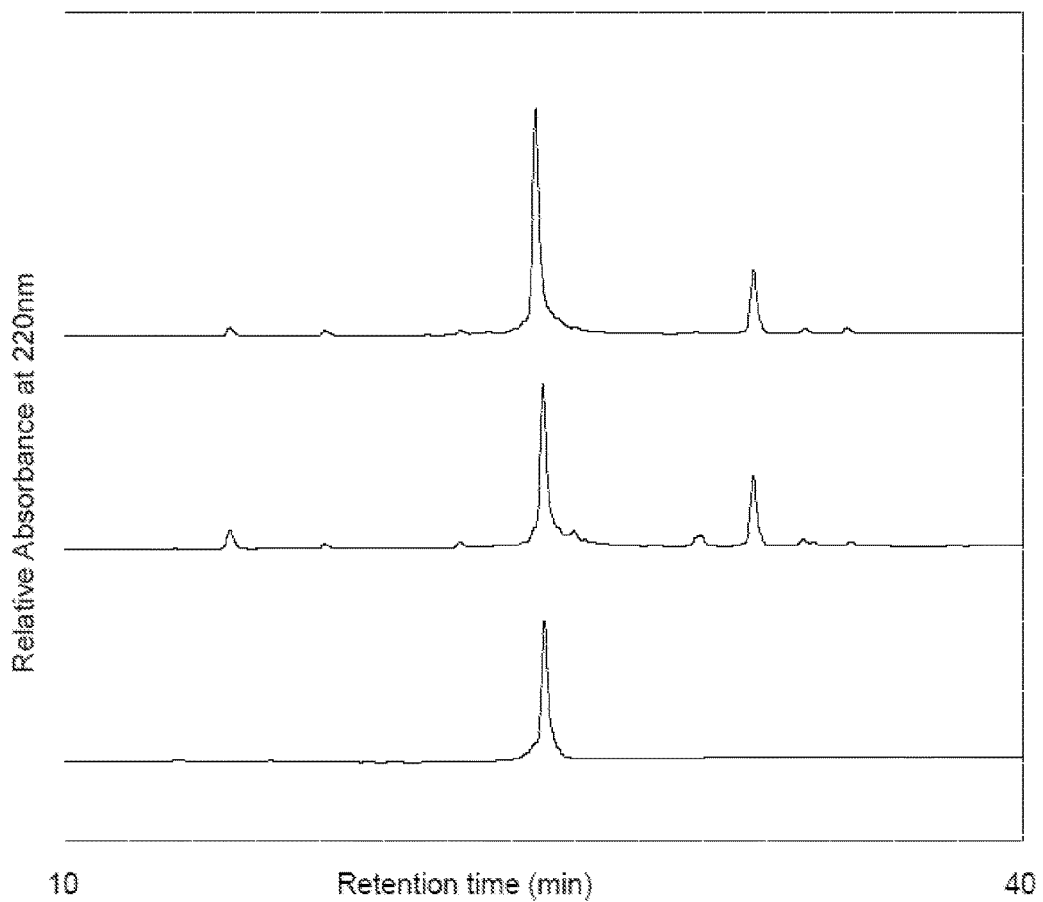

FIG. 49 shows the HPLC (A) and ESI-MS (B) data of glycopeptide fragment (28) manufactured in one embodiment of manufacturing the glycosylated polypeptide of the present invention.

Figure 50:
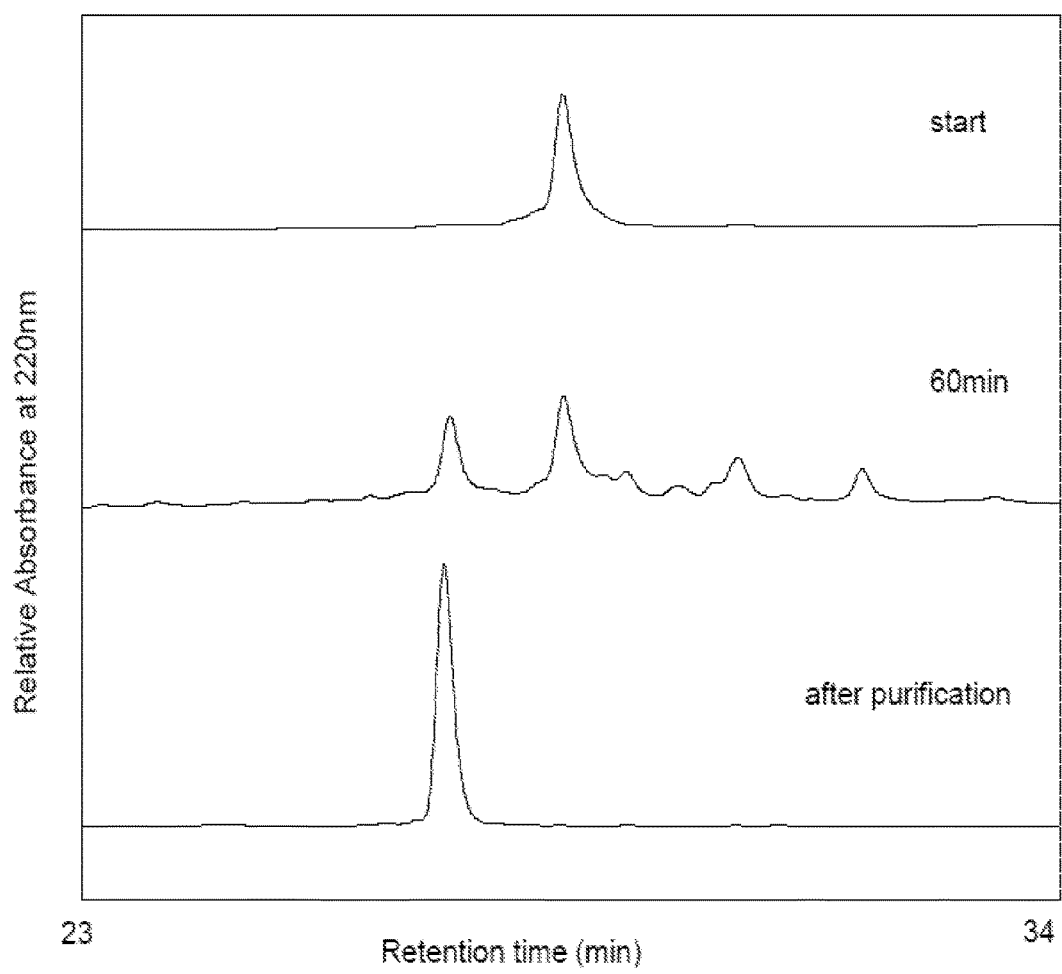

FIG. 50 shows the HPLC (A) and ESI-MS (B) data of glycopeptide fragment (29) manufactured in one embodiment of manufacturing the glycosylated polypeptide of the present invention.

DESCRIPTION OF EMBODIMENTS

An "interferon β" or "IFN-β" herein is a polypeptide having a sequence of 166 amino acids represented by SEQ ID NO. 1. Interferon β has a disulfide bond between cysteines at positions 31 and 141 in the amino acid sequence below. Moreover, an "interferon β" herein preferably has the amino acid sequence below (SEQ ID NO. 1), and corresponds to a human-type interferon β-1a having a sugar chain. Interferon β-1a has a sugar chain added to asparagine at position 80 in the amino acid sequence below.
Met-Ser-Tyr-Asn-Leu-Leu-Gly-Phe-Leu-Gln$^{10}$-Arg-Ser-Ser-Asn-Phe-Gln-Cys-Gln-Lys-Leu$^2$-Leu-Trp-Gln-Leu-Asn-Gly-Arg-Leu-Glu-Tyr$^{30}$-Cys-Leu-Lys-Asp-Arg-Met-Asn-Phe-Asp-Ile$^{40}$-Pro-Glu-Glu-Ile-Lys-Gln-Leu-Gln-Gln-Phe$^{50}$-Gln-Lys-Glu-Asp-Ala-Leu-Thr-Ile-Tyr$^{60}$-Glu-Met-Leu-Gln-Asn-Ile-Phe-Ala-Ile-Phe$^{70}$-Arg-Gln-Asp-Ser-Ser-Ser-Thr-Gly-Trp-Asn$^{80}$-Glu-Thr-Ile-Val-Glu-Asn-Leu-Leu-Ala-Asn$^{90}$-Val-Tyr-His-Gln-Ile-Asn-His-Leu-Lys-Thr$^{100}$-Val-Leu-Glu-Glu-Lys-Leu-Glu-Lys-Glu-Asp$^{110}$-Phe-Thr-Arg-Gly-Lys-Leu-Met-Ser-Ser-Leu$^{120}$-His-Leu-Lys-Arg-Tyr-Tyr-Gly-Arg-Ile-Leu$^{130}$-His-Tyr-Leu-Lys-Ala-Lys-Glu-Tyr-Ser-His$^{140}$-Cys-Ala-Trp-Thr-Ile-Val-Arg-Val-Glu-Ile$^{150}$-Leu-Arg-Asn-Phe-Tyr-Phe-Ile-Asn-Arg-Leu$^{160}$-Thr-Gly-Tyr-Leu-Arg-Asn$^{166}$ An "amino acid" herein is employed in its broadest meaning, and includes not only natural amino acids but also non-natural amino acids such as amino acid variants and derivatives. Those skilled in the art will recognize in light of this broad definition that examples of amino acids herein include, e.g., natural proteinogenic L-amino acids; D-amino acids; chemically modified amino acids such as amino acid variants and derivatives; natural non-proteinogenic amino acids such as norleucine, β-alanine, and ornithine; and chemically synthesized compounds having properties well-known in the art characteristic of amino acids. Examples of non-natural amino acids include an α-methylamino acid (such as α-methylalanine), a D-amino acid, a histidine-like amino acid (such as 2-amino-histidine, 3-hydroxy-histidine, homohistidine, α-fluoromethyl-histidine, and α-methyl-histidine), an amino acid having excess methylenes on the side chain ("homo" amino acid), and an amino acid in which the carboxylic functional group amino acid in the side chain is substituted with a sulfonate group (such as cysteic acid). In a preferred aspect, the amino acid contained in the compound of the present invention consists only of natural amino acids.

As used herein, when one or a few amino acids in the amino acid sequence are said to be deleted, substituted, or added, the number of amino acids substituted etc. is not particularly limited as long as interferon β activity is retained, but means that e.g. approximately 1, 2, 3, 4, 5, 6, 7, 8, 9, or 10 amino acids are different. Alternatively, it also includes the case where 20% or less and preferably 10% or less amino acids of the length of the entire amino acid sequence are different. The amino acid to be substituted or added may be a natural amino acid, a non-natural amino acid, or an amino acid analog, preferably a natural amino acid.

A "peptide fragment" herein refers to a peptide fragment having the sequence of a portion of the amino acid sequence of the ultimate glycosylated polypeptide when manufacturing the glycosylated polypeptide of the present invention. Moreover, a "glycosylated peptide fragment" or a "glycopeptide fragment" herein refers to a peptide fragment comprising a glycosylated amino acid in the amino acid sequence of such peptide fragment. The glycosylated polypeptide of the present invention is manufactured by linking a glycosylated peptide fragment and at least two peptide fragments.

An "interferon β analog" herein includes a polypeptide structurally similar to interferon β and/or a polypeptide having an overlapping structure with interferon β, e.g. a polypeptide having one of the amino acids or a few amino acids of interferon β amino acids conservatively substituted, a modified interferon β, an interferon β fragment having interferon β activity, and an elongated interferon β having interferon β activity.

"Having one of the amino acids or a few amino acids conservatively substituted" herein refers to an amino acid substitution in which the hydrophylicity and/or hydrophobicity index are similar between the original amino acid and the amino acid to be substituted, and wherein apparent reduction or dissipation of interferon β activity before and after such substitution is not caused.

A "modified interferon β" herein is a modified version of interferon β, including a naturally-occurring variant of interferon β or an artificially modified compound of interferon β. Examples of such modifications include, e.g., alkylation, acylation (such as acetylation), amidation, carboxylation, ester formation, disulfide bond formation, glycosylation, lipidation, phosphorylation, hydroxylation, and binding of a labeling component of/to one or more amino acid residues of interferon β.

An "interferon β fragment having interferon β activity" herein is a peptide having one or more amino acids deleted from the N- and/or C-terminals of interferon β which maintains activity towards interferon β receptor.

An "elongated interferon β having interferon β activity" herein is a peptide having one or more amino acids added to the N- and/or C-terminals of interferon β which maintains interferon β activity.

Examples of an interferon β analog described above can include the amino acid sequence known as interferon β-1b in which Met at position 1 is deleted and Cys at position 17 is substituted to Ser.

The glycosylated polypeptide of the present invention comprises a polypeptide consisting of an amino acid sequence having 80% or more homology with the amino acid sequence represented by SEQ ID NO. 1, wherein the glycosylated polypeptide has a sugar chain at the amino acid corresponding to position 80 in interferon β and has interferon β activity. When the glycosylated polypeptide of the present invention has 80% or more homology with SEQ ID NO. 1, it can preferably have 85% or more, 90% or more, 95% or more, or 99% or more homology.

An "amino acid corresponding to a particular position in interferon β" herein refers to an amino acid at the same position corresponding to the amino acid sequence of interferon β, as long as there is no addition or deletion etc. of an amino acid in the glycosylated polypeptide. Moreover, if an addition or deletion of an amino acid is present in the amino acid sequence of a glycosylated polypeptide, it refers to an amino acid at the position that takes into account the shift on the amino acid sequence by the addition or deletion of the amino acid. For example, in a glycosylated polypeptide having the sequence $Met_1$-$Ser_2$-$Tyr_3$-$Asn_4$- (SEQ ID NO: 49) from positions 1 to 4, when one amino acid (Trp) is added between the amino acids at positions 2 and 3 (Met-Ser-Trp-Tyr-Asn-) (SEQ ID NO: 50), the amino acid corresponding to the amino acid at position 3 (Tyr) refers to the amino acid (Tyr) in the glycosylated polypeptide which has been shifted one to the C-terminal side by the insertion of Trp.

A "sugar chain" herein refers to a compound made from a string of one or more unit sugars (monosaccharides and/or derivatives thereof). When there is a string of two or more unit sugars, each unit sugar is bound with each other by a dehydration condensation with a glycoside bond in between. Such sugar chains include, but are not limited to e.g. a wide range such as monosaccharides and polysaccharides contained in vivo (glucose, galactose, mannose, fucose, xylose, N-acetylglucosamine, N-acetylgalactosamine, sialic acid, and conjugates and derivatives thereof), as well as a sugar chain degraded or derived from conjugated biomolecules such as degraded polysaccharides, glycoproteins, proteoglycans, glycosaminoglycans, and glycolipids. The sugar chain may be linear or branched.

Moreover, a "sugar chain" herein also includes a sugar chain derivative, and examples of sugar chain derivatives include, but are not limited to, a sugar chain wherein the sugar constituting the sugar chain is e.g. a sugar having a carboxy group (such as aldonic acid in which C-position 1 is oxidized to become a carboxylic acid (such as D-gluconic acid which is oxidized D-glucose) and uronic acid in which the terminal C atom has become a carboxylic acid (D-glucuronic acid which is oxidized D-glucose)), a sugar having an amino group or an amino group derivative (such as D-glucosamine and D-galactosamine), a sugar having both amino and carboxy groups (such as N-glycoylneuraminic acid and N-acetylmuramic acid), a deoxylated sugar (such as 2-deoxy-D-ribose), a sulfated sugar comprising a sulfate group, and a phosphorylated sugar comprising a phosphate group.

A preferred sugar chain herein is a sugar chain that will not dissipate interferon β activity when added to the glycosylated polypeptide.

Such a sugar chain in the glycosylated polypeptide of the present invention is not particularly limited, and may be a sugar chain that exists as a glycoconjugate in vivo (such as a glycopeptide (or a glycoprotein), a proteoglycan, and a glycolipid), or it may be a sugar chain that does not exist as a glycoconjugate in vivo.

A sugar chain that exists as a glycoconjugate in vivo is preferred with respect to the fact that the glycosylated polypeptide of the present invention is administered in vivo. Examples of such sugar chains include N- or O-linked sugar chains which are sugar chains bound to a peptide (or a protein) in vivo as a glycopeptide (or a glycoprotein). An N-linked sugar chain is preferably employed. N-linked sugar chains can include, e.g., a high-mannose form, a complex form, or a hybrid form, particularly preferably a complex form.

In one preferred aspect of the present invention, the sugar chain in the glycosylated polypeptide of the present invention is a complex-type sugar chain. A complex-type sugar chain is characterized in that it comprises two or more types of monosaccharides, and has the basic structure shown below and a lactosamine structure shown by Galβ1-4GlcNAc.

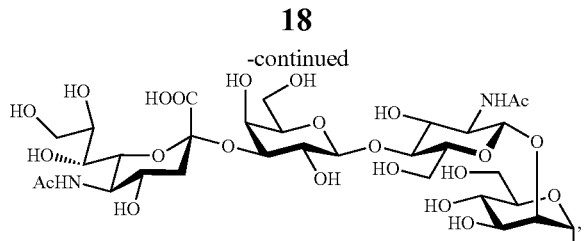

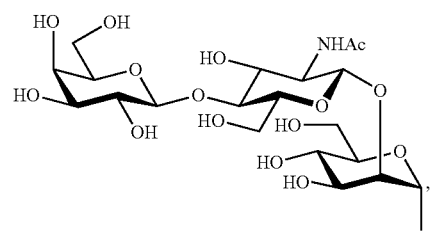

[Chemical Formula 6]

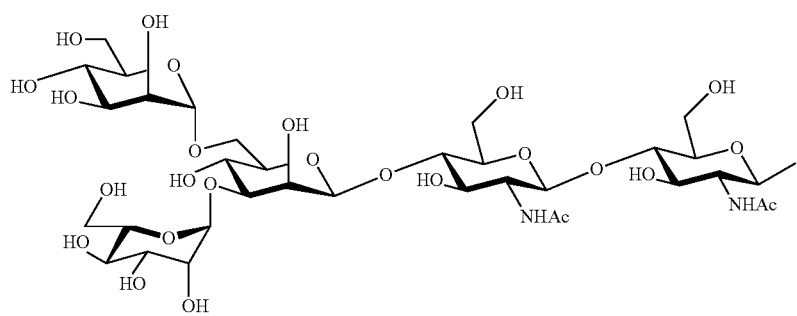

Examples of preferred complex-type sugar chains used herein include, e.g., a sugar chain represented by the following general formula:

[Chemical Formula 7]

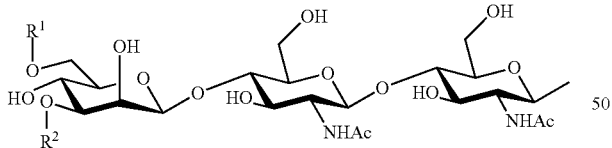

[wherein $R^1$ and $R^2$ are identical or different and are:

[Chemical Formula 8]

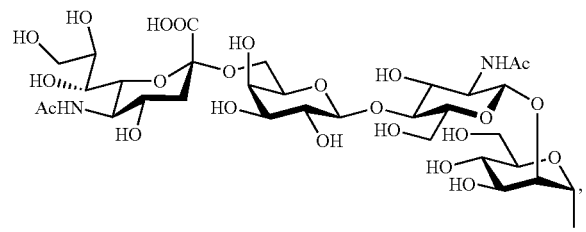

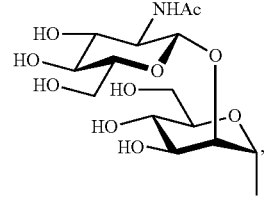

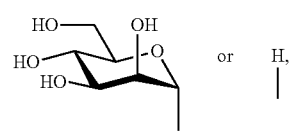

and Ac is an acetyl group].

Moreover, in the present invention, a complex-type sugar chain comprises a biantennary complex-type sugar chain. A biantennary complex-type sugar chain refers to those having a monoantennary sugar chain consisting of 0-3 sugars in bound to each of the two mannoses at the end of the basic structure. The biantennary complex-type sugar chain is preferably e.g. the disialo sugar chain shown below:

[Chemical Formula 9]
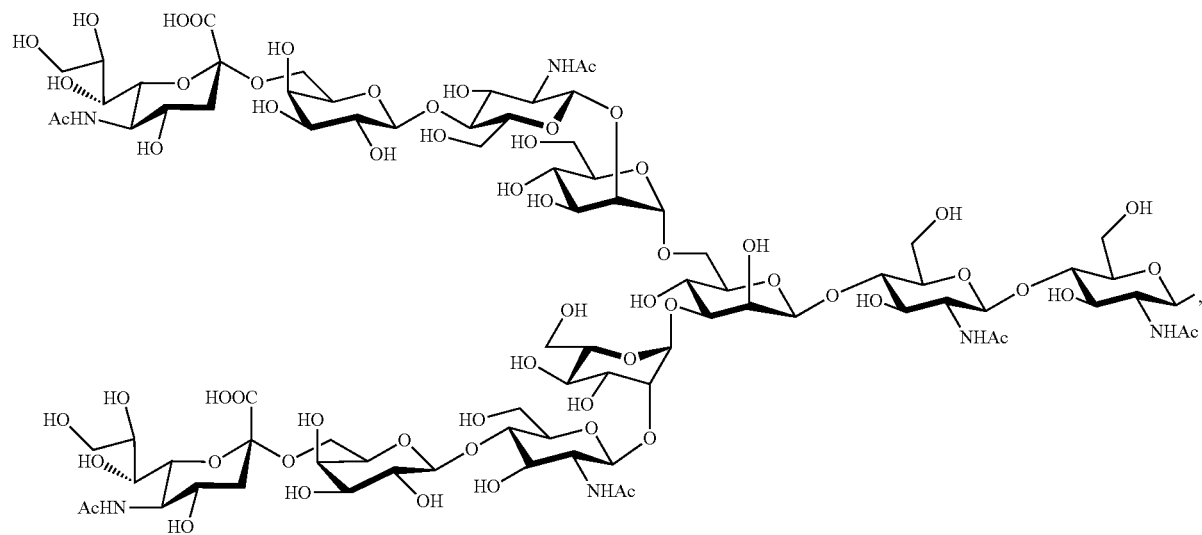
a monosialo sugar chain: OH
[Chemical Formula 10]
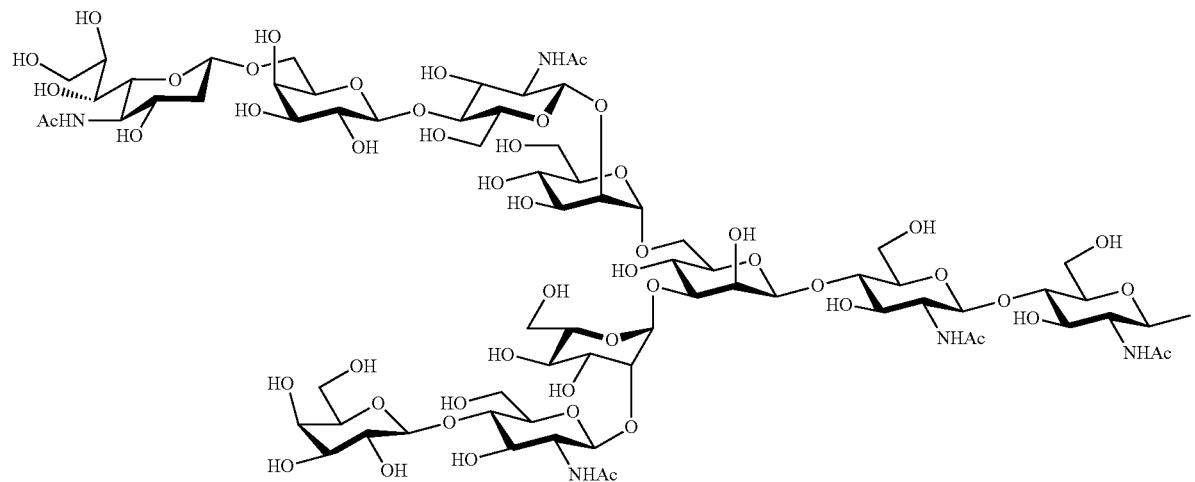
[Chemical Formula 10A]
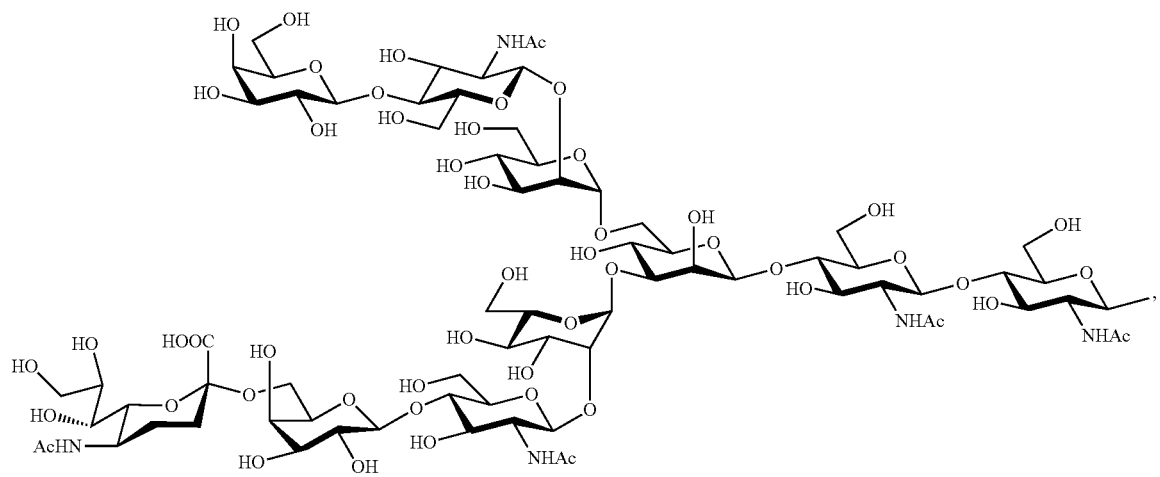

an asialo sugar chain:

[Chemical Formula 11]

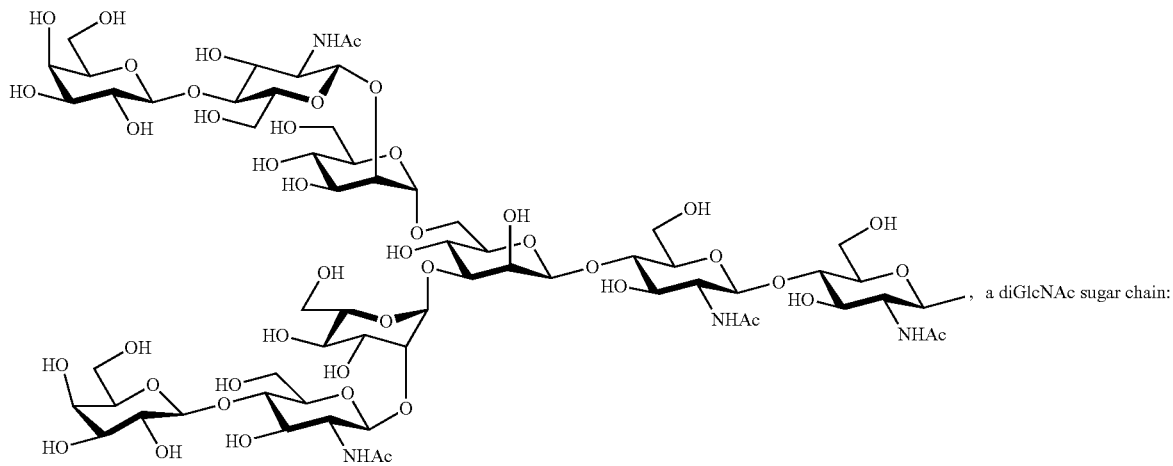

, a diGlcNAc sugar chain:

[Chemical Formula 12]

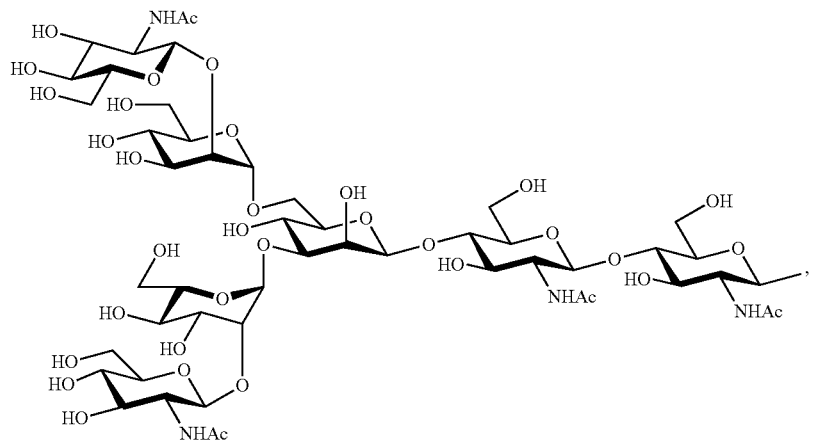

and a dimannose sugar chain:

[Chemical Formula 13]

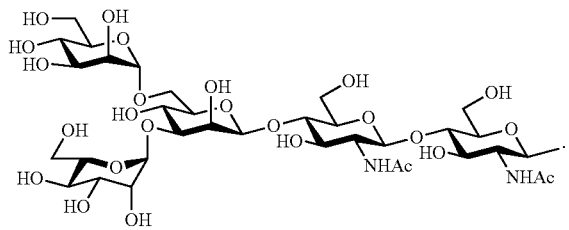

A disialo sugar chain or an asialo sugar chain is preferred as the biantennary complex-type sugar chain, most preferably a disialo sugar chain.

Moreover, the complex-type sugar chain of the present invention includes not only the above biantennary complex-type sugar chain (double-branched complex-type sugar chain), but also a triantennary complex-type sugar chain (triple-branched complex-type sugar chain) and a tetraantennary complex-type sugar chain (quadruple-branched complex-type sugar chain). For example, triantennary and tetraantennary complex-type sugar chains can include a trisialo sugar chain represented by the structural formula below:

[Chemical Formula 14]
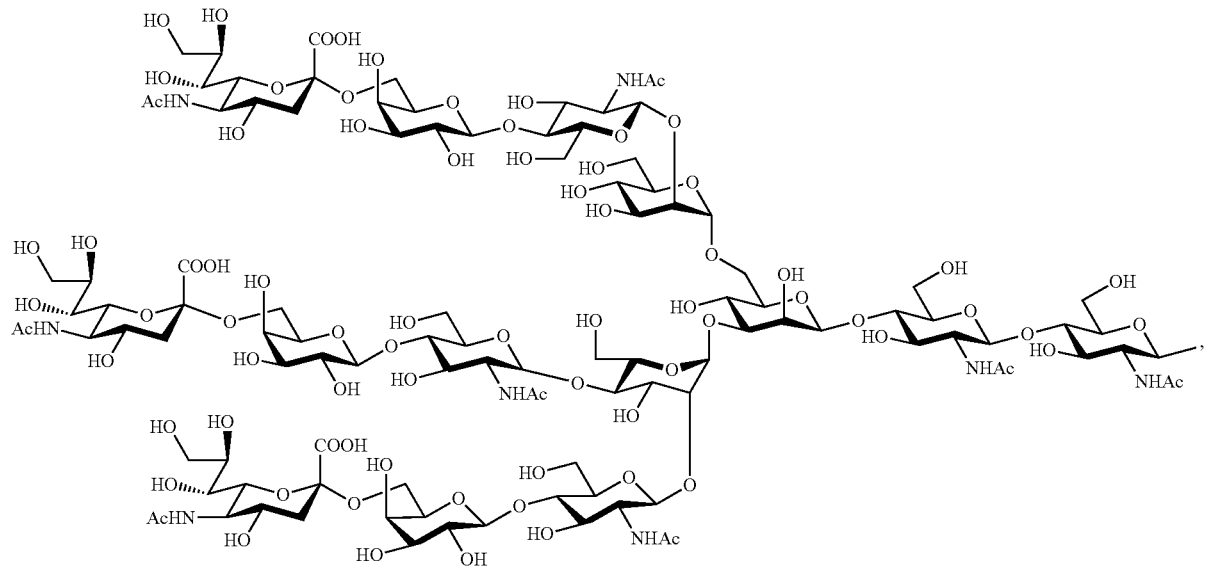
[Chemical Formula 15]
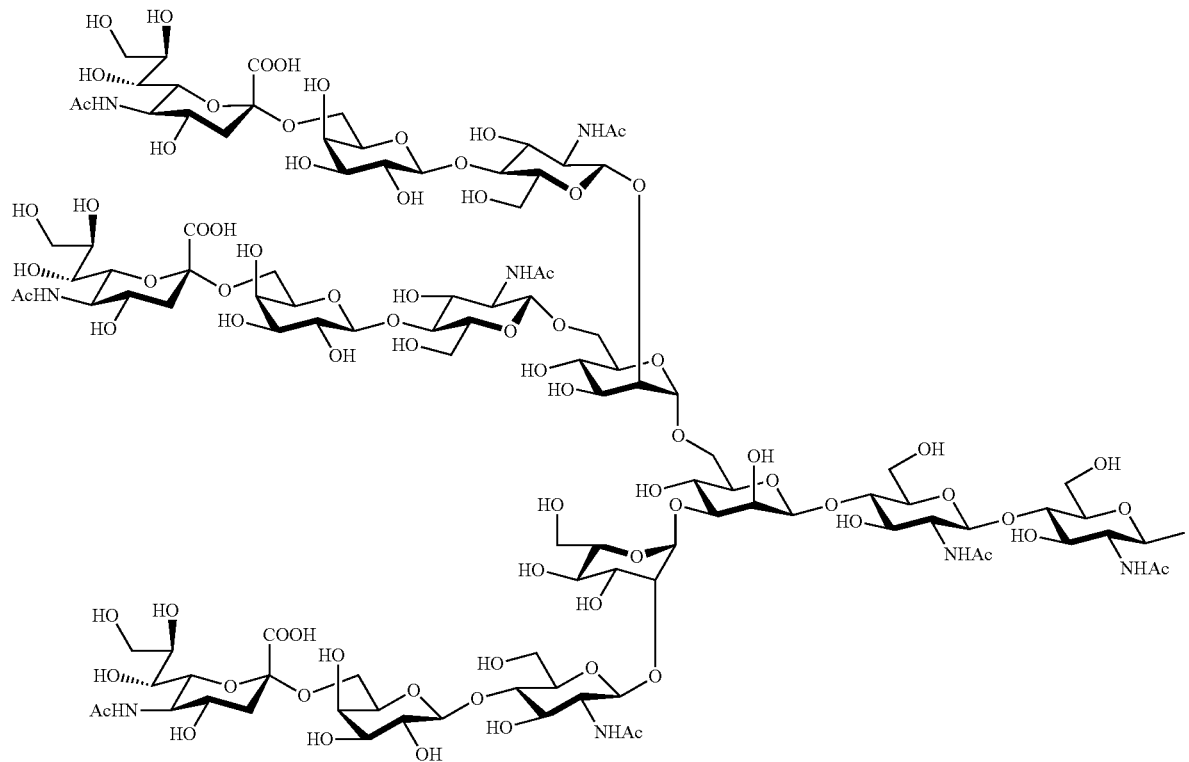

and a tetrasialo sugar chain represented by the structural formula below:

[Chemical Formula 16]

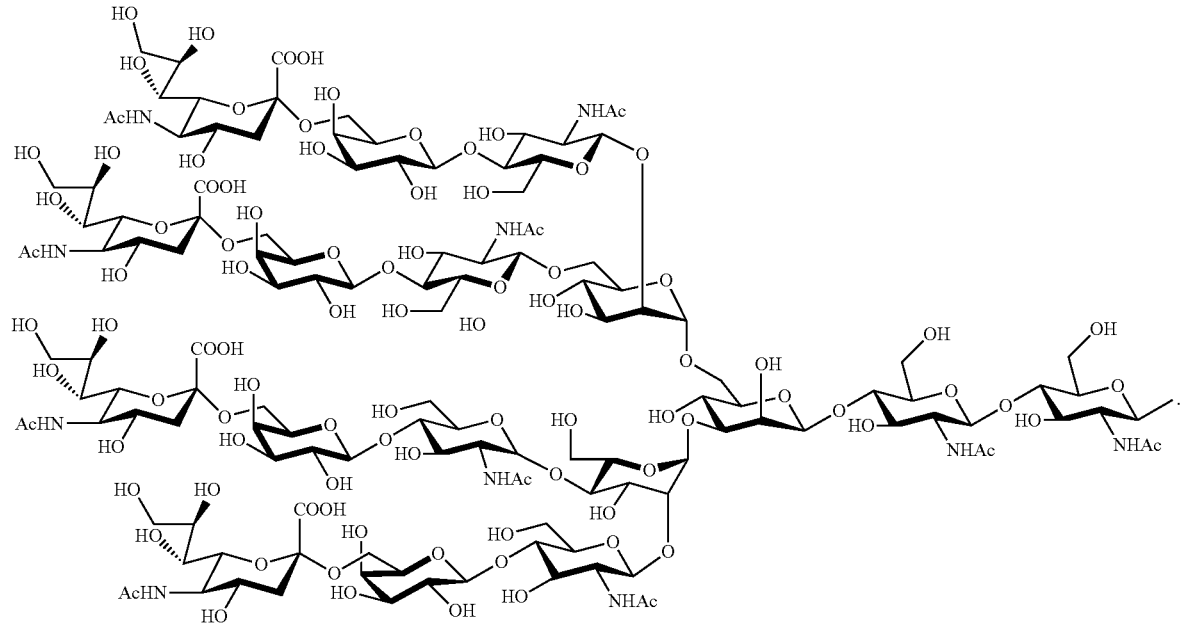

Moreover, triantennary and tetraantennary complex-type sugar chains can also include a sugar chain having one or more sugars deleted from the non-reducing terminal of these trisialo and tetrasialo sugar chains.

Further, the complex-type sugar chain of the present invention includes those with a fucose added. Complex-type sugar chains with a fucose added can include a fucose-containing complex-type sugar chain represented by the structural formula below:

[Chemical Formula 17]

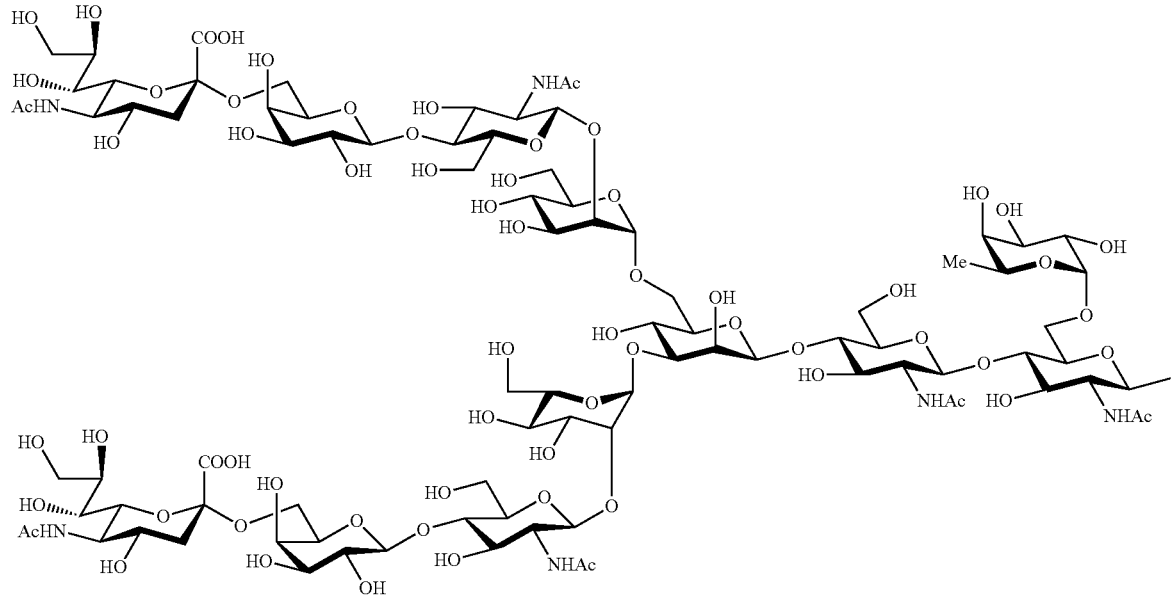

[Chemical Formula 18]
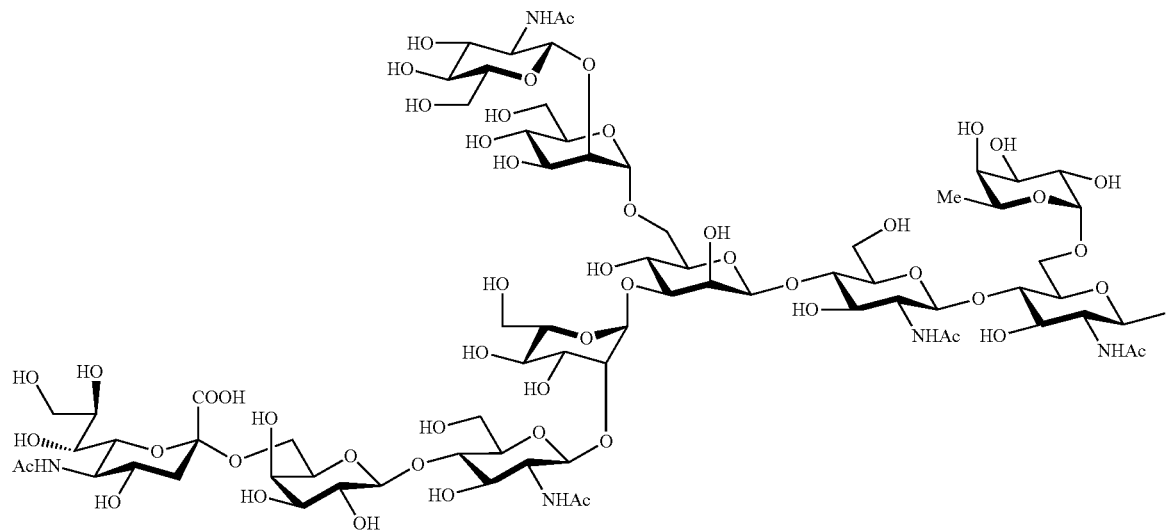
[Chemical Formula 19]
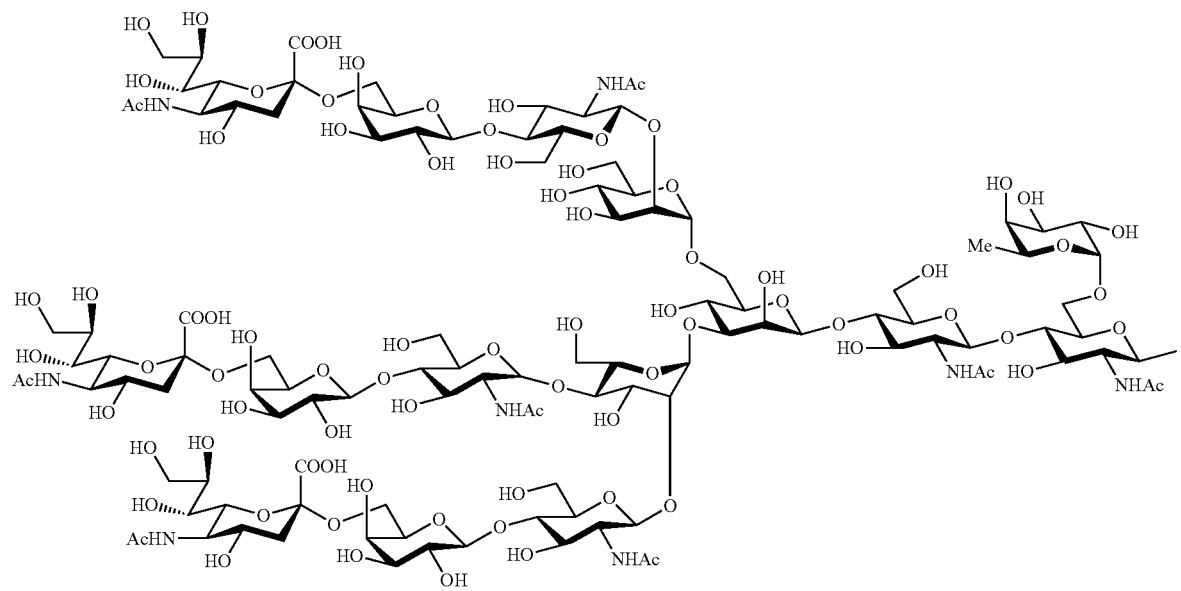

[Chemical Formula 20]

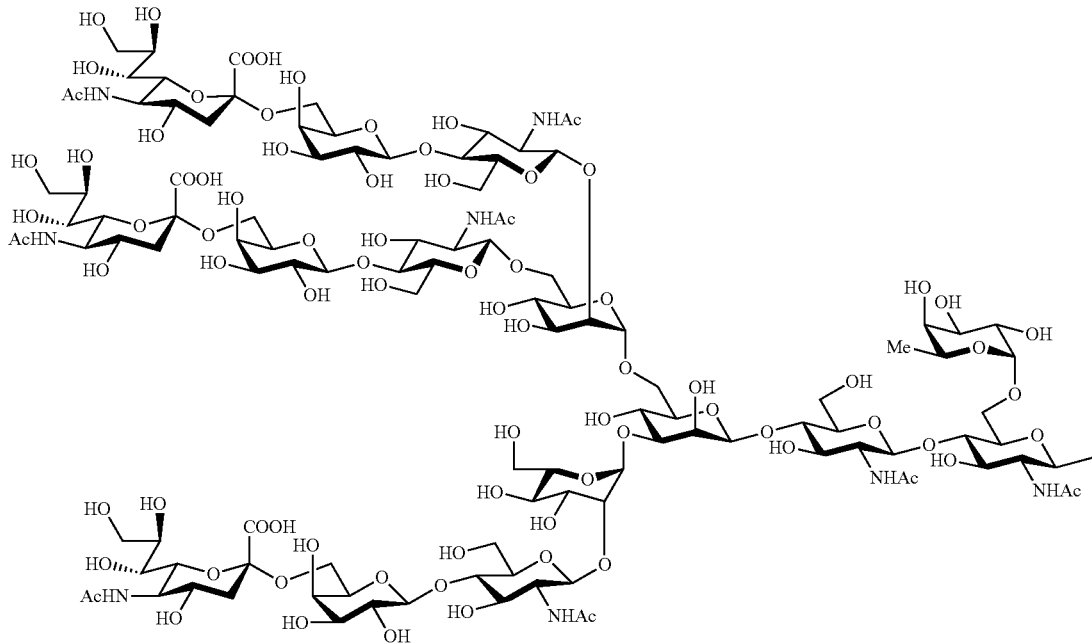

[Chemical Formula 21]

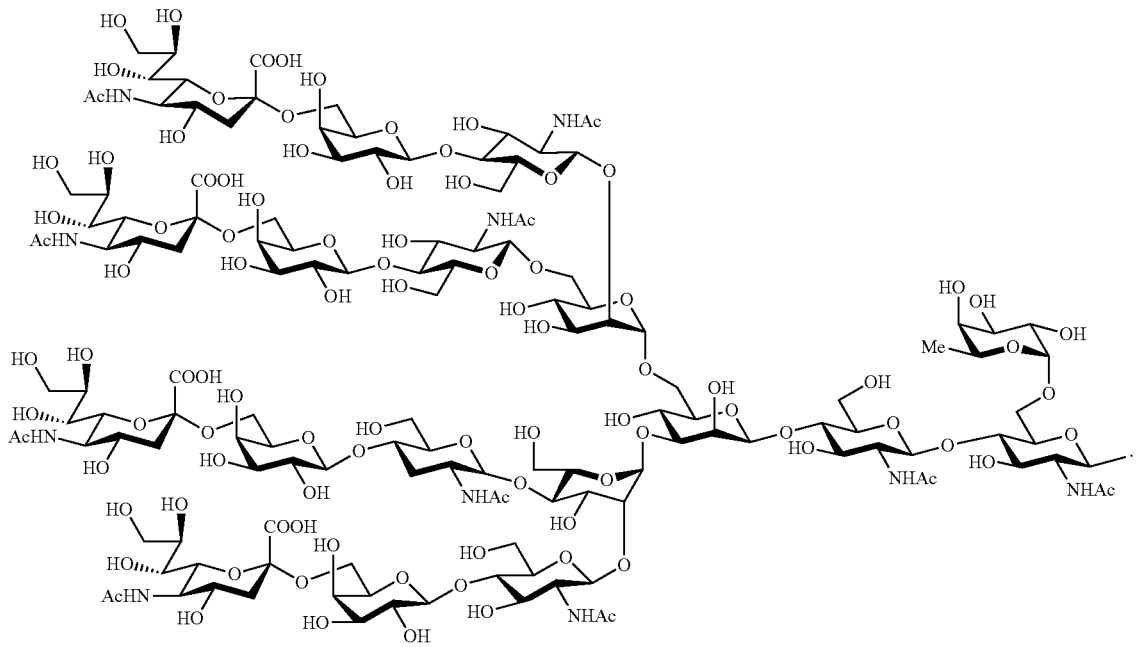

Moreover, a sugar chain having one or more sugars deleted from the non-reducing terminal of these fucose-containing complex-type sugar chain can also be included.

Moreover, a "biantennary complex-type sugar chain," a "disialo sugar chain," a "monosialo sugar chain," an "asialo sugar chain," a "diGlcNAc sugar chain," a "dimannose sugar chain," a "triantennary complex-type sugar chain," a "tetraantennary complex-type sugar chain," and a "fucose-containing complex-type sugar chain" herein include not only those shown in the above chemical formulae, but also those with a binding mode different from examples shown in the chemical formulae, and such sugar chains are also preferably employed as a sugar chain of the present invention. Examples of such sugar chains include, e.g., a disialo or monosialo sugar chain in which sialic acid and galactose are bound with an (α2→3) bond.

Moreover, the complex-type sugar chain of the present invention also comprises a sugar chain having a polylactosamine structure or a sialyl polylactosamine structure represented by the following formula.

[Chemical Formula 22]

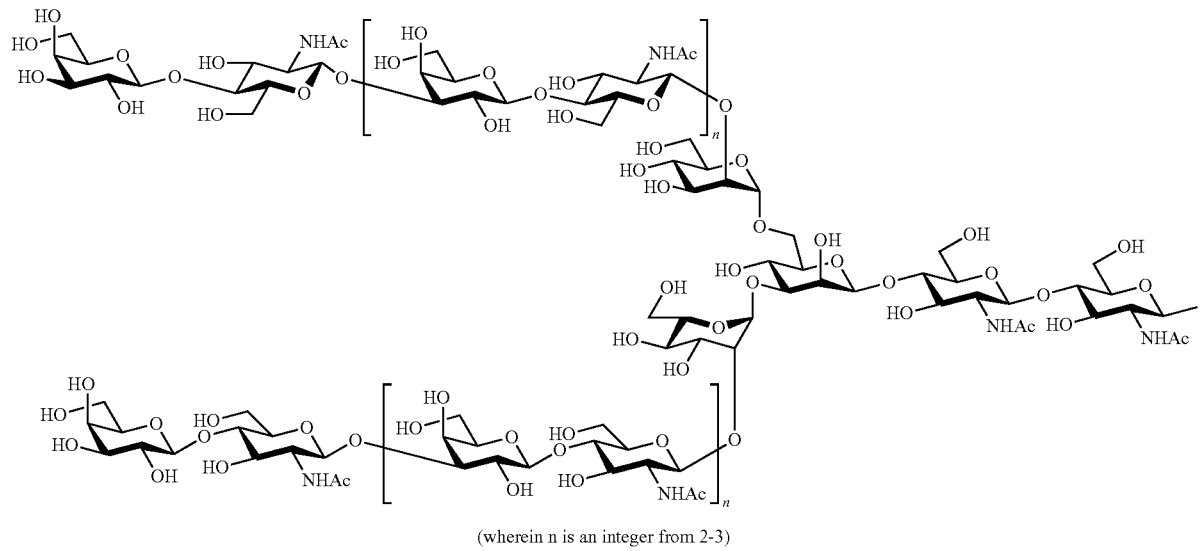

(wherein n is an integer from 2-3)

[Chemical Formula 23]

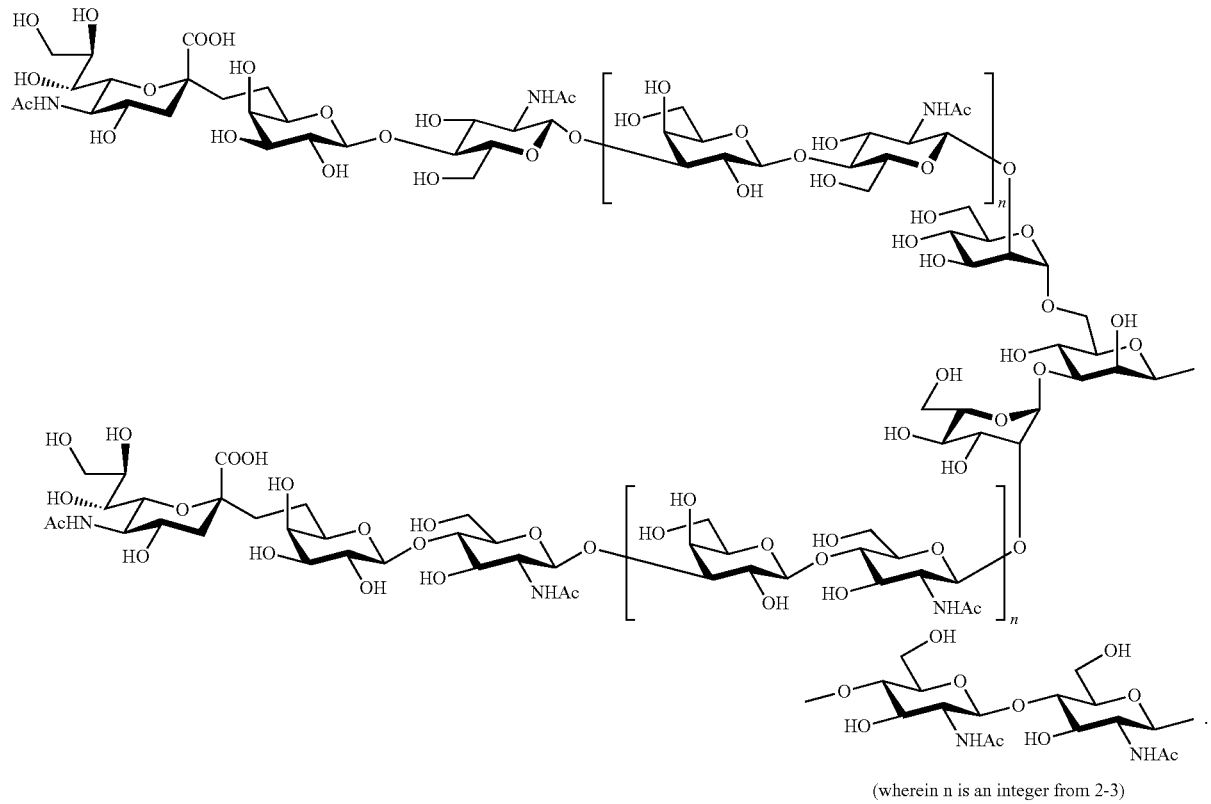

(wherein n is an integer from 2-3)

Moreover, the high-mannose sugar chain employed herein is a sugar chain having two or more mannoses further bound to the basic structure of the complex-type sugar chain described above. Because high-mannose sugar chains are bulky, stability in blood may become higher by binding a high-mannose sugar chain to the peptide. A sugar chain comprising 5-9 mannoses such as a mammalian high-mannose sugar chain is preferred, but it may be a sugar chain comprising more mannoses such as a yeast high-mannose sugar chain. Examples of high-mannose sugar chains preferably employed herein can include, e.g., high-mannose-5 (M-5):

[Chemical Formula 24]

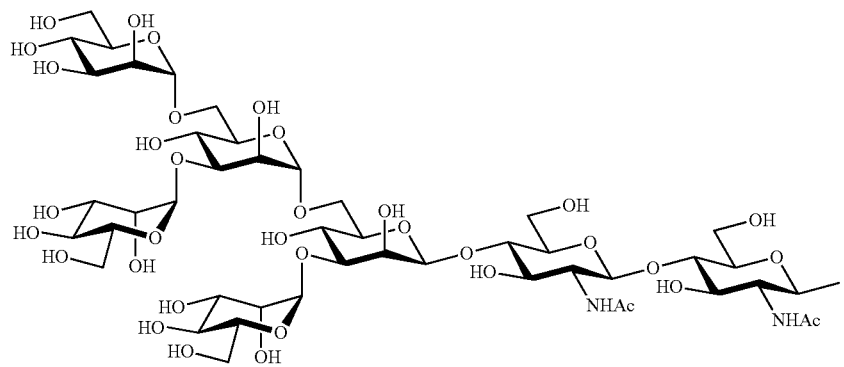

and high-mannose-9 (M-9):

[Chemical Formula 25]

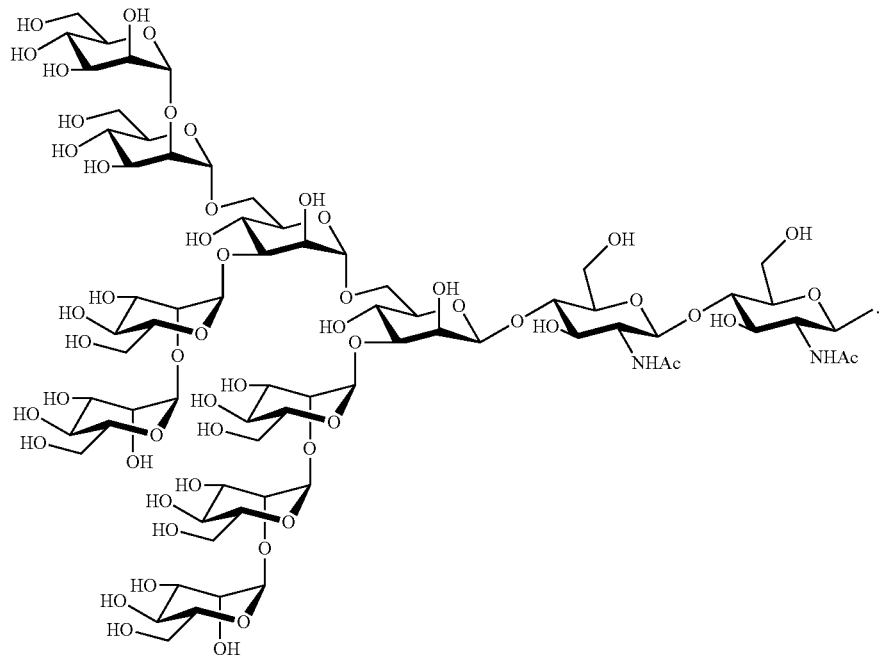

Preferred sugar chains herein can also include, e.g., a sugar chain having an identical structure (a sugar chain in which the type of constituent sugar and the binding mode thereof are identical) with a sugar chain that exists in a human body as a glycoprotein bound to a protein (such as a sugar chain described in "FEBS LETTERS Vol. 50, No. 3, February 1975"), or a sugar chain having one or more sugars deleted from the non-reducing terminal of the same. Specifically, sugar chains listed below can be included.

[Chemical Formula 26]
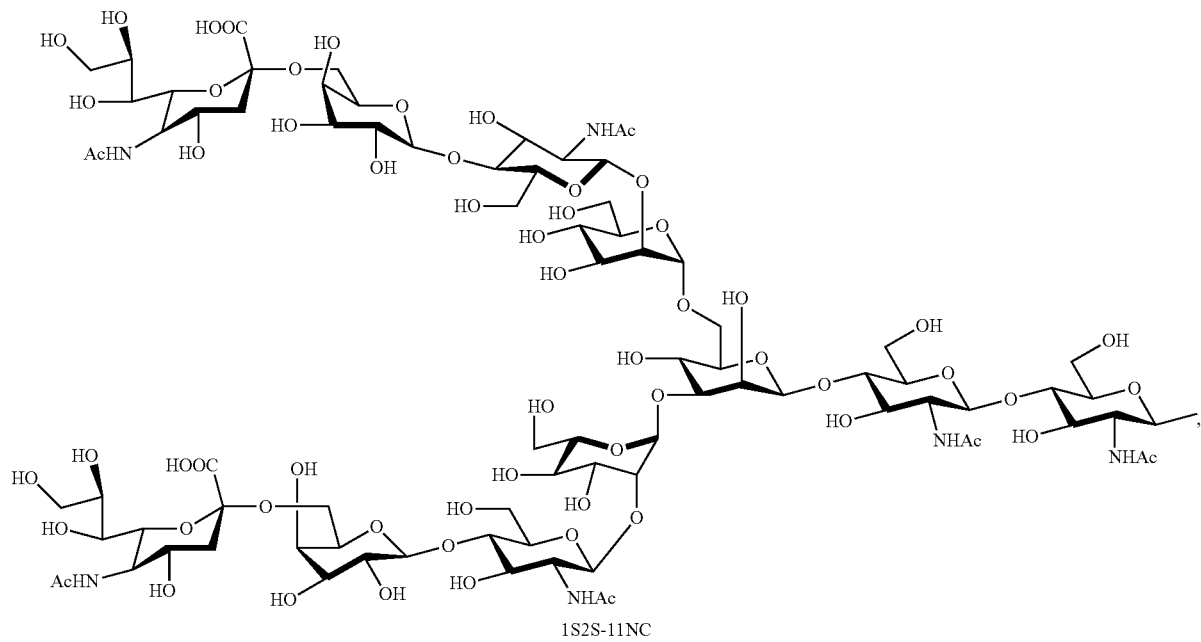
1S2S-11NC
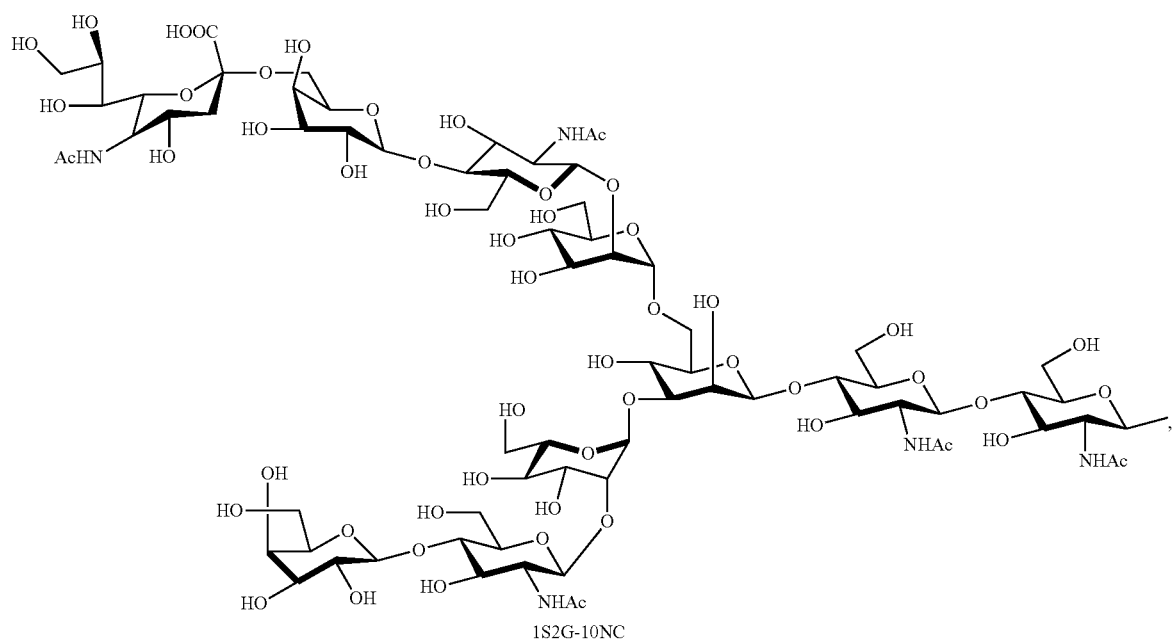
1S2G-10NC

-continued
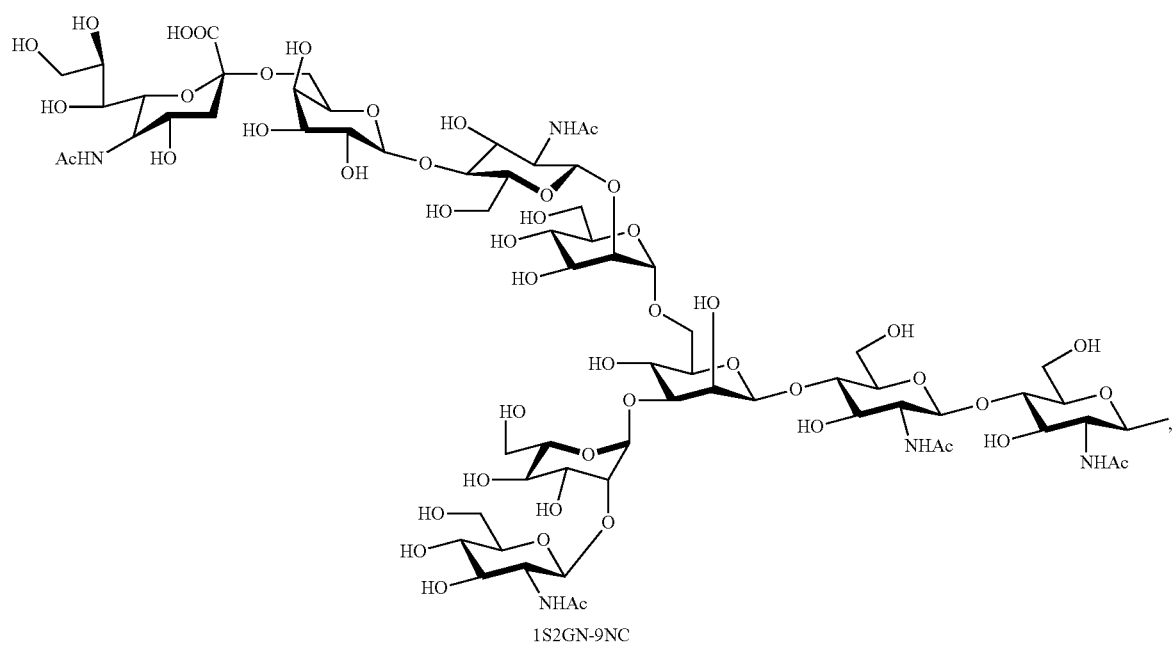
1S2GN-9NC
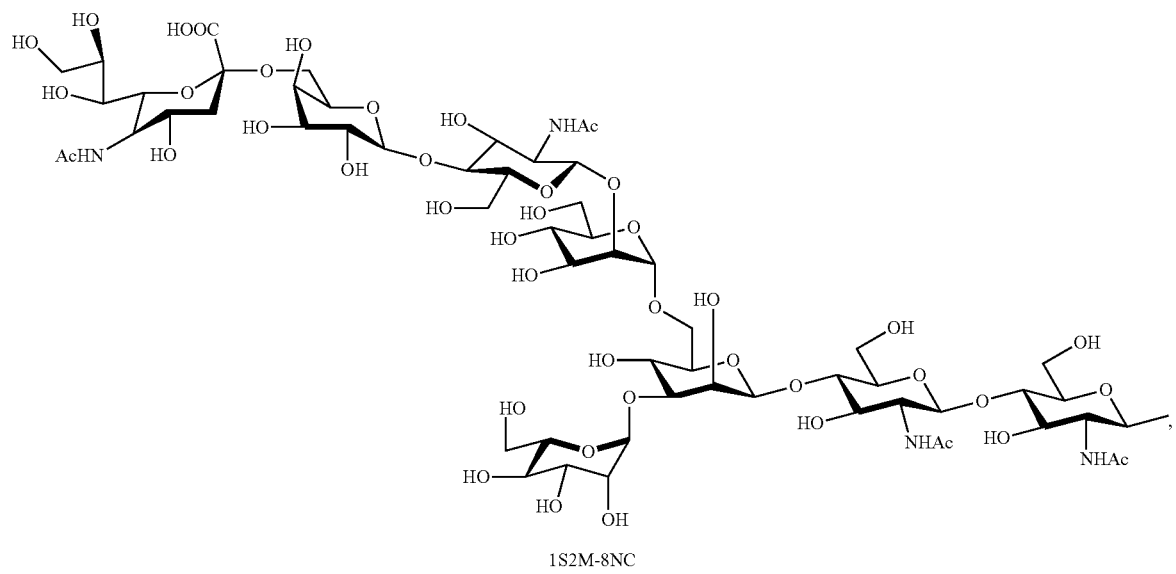
1S2M-8NC

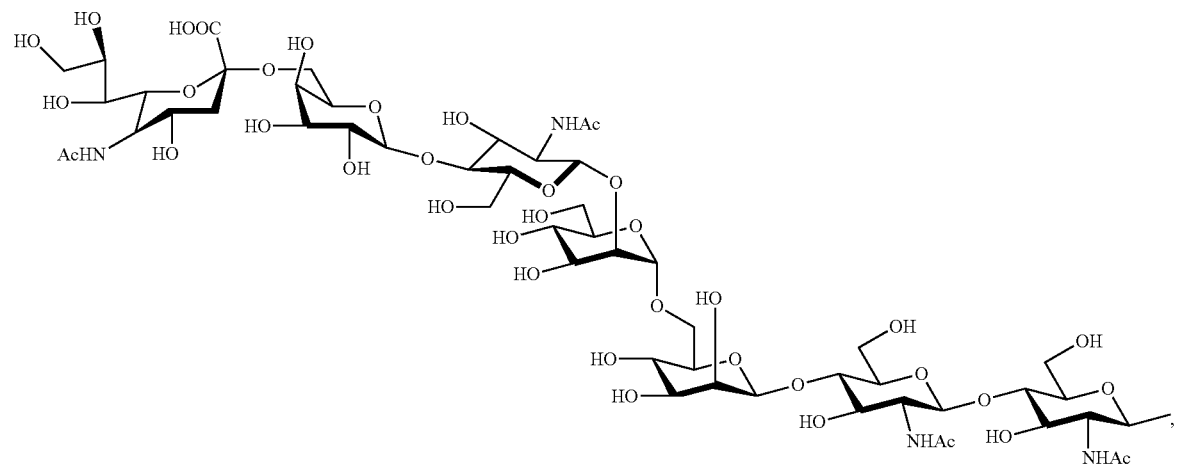
1S-7NC
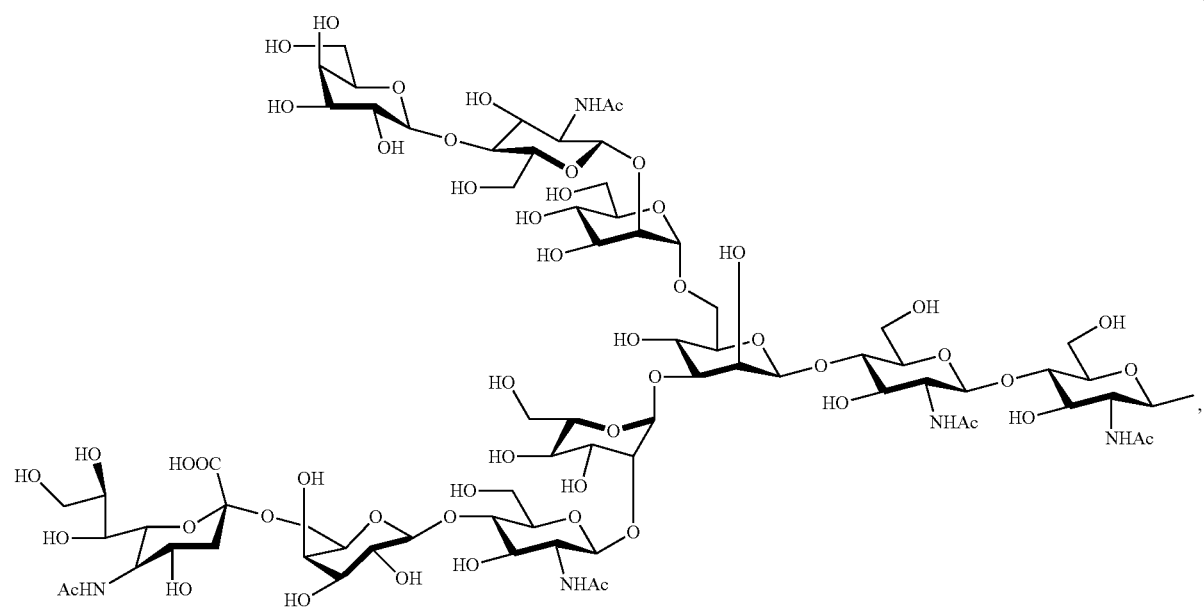
1G2S-10NC

-continued
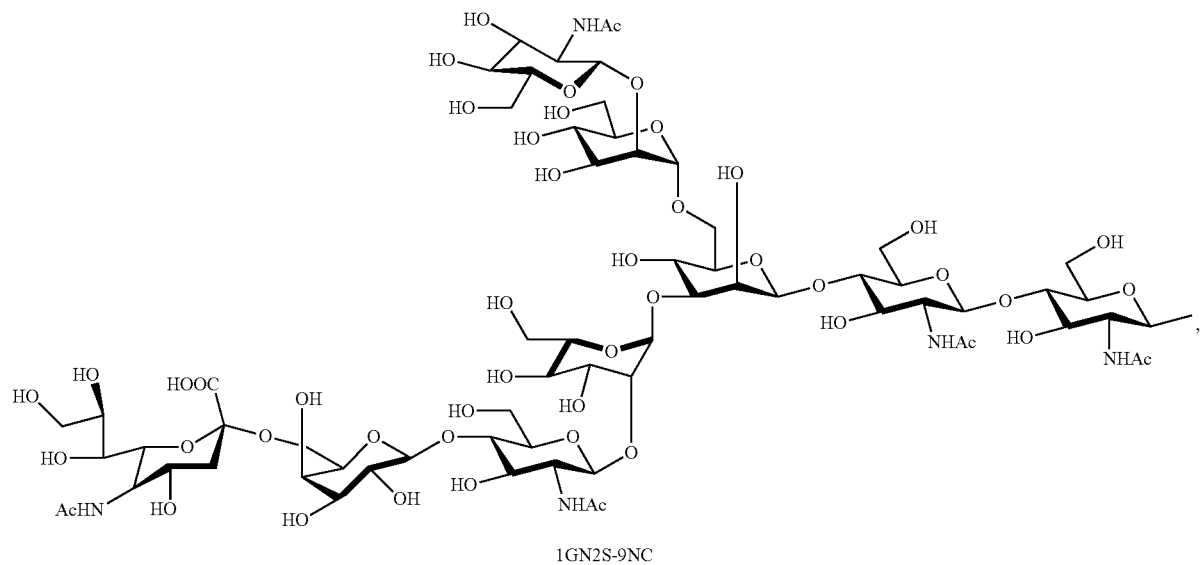
1GN2S-9NC
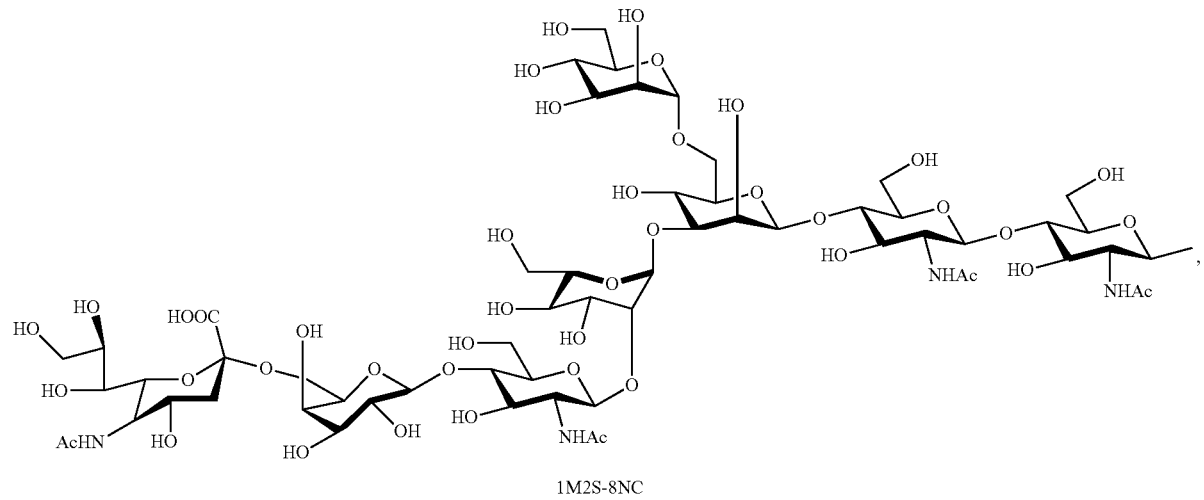
1M2S-8NC
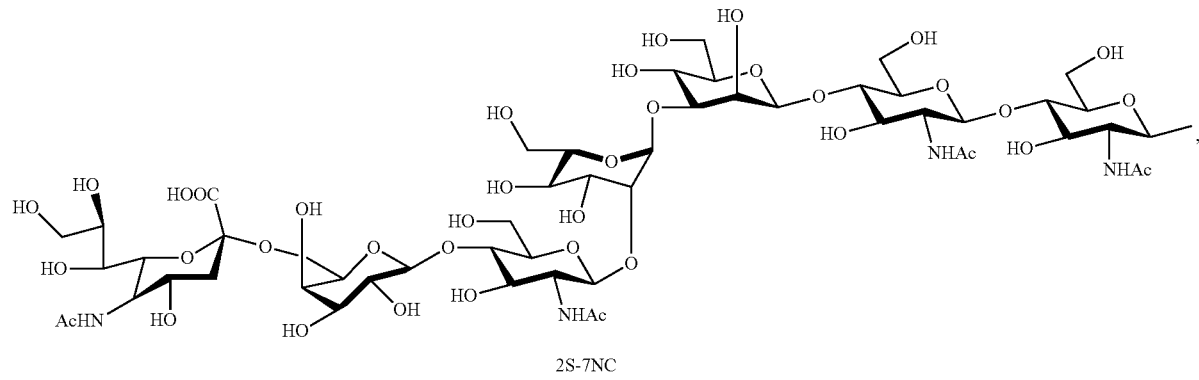
2S-7NC

-continued
[Chemical Formula 27]
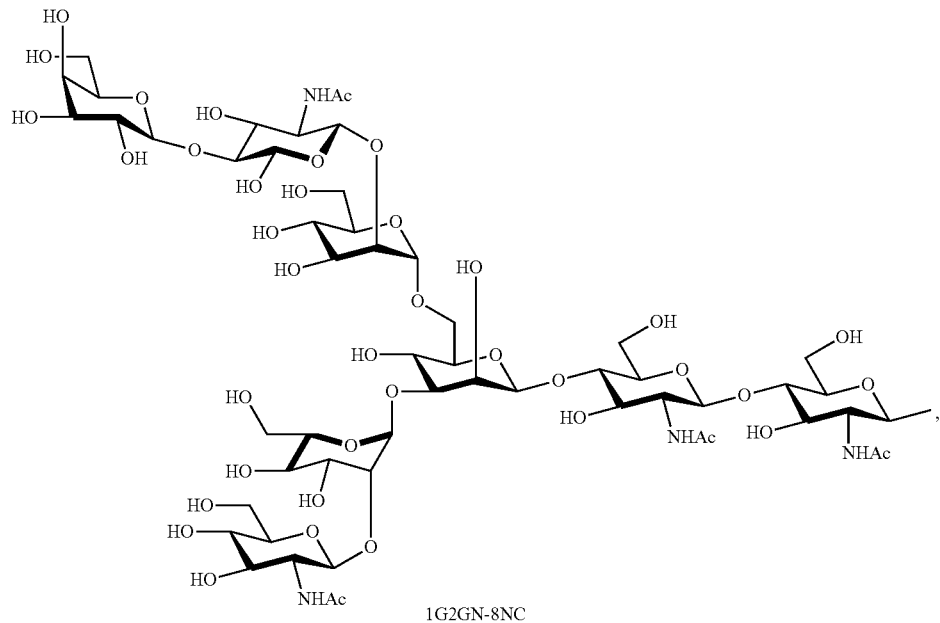
1G2GN-8NC
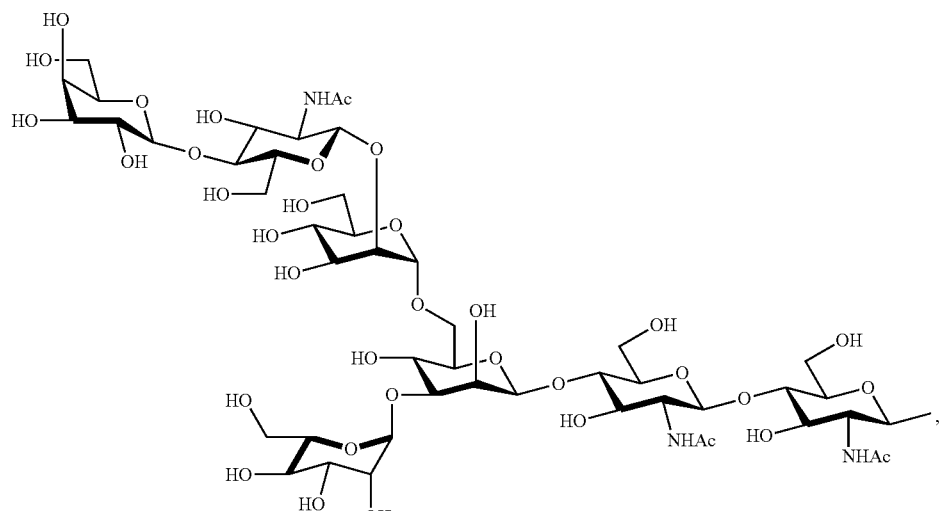
1G2M-7NC

-continued
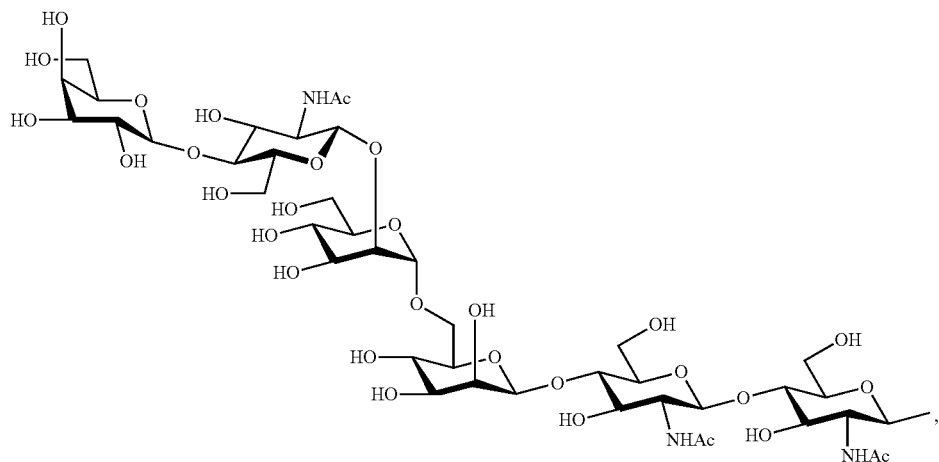
1G-6NC
12
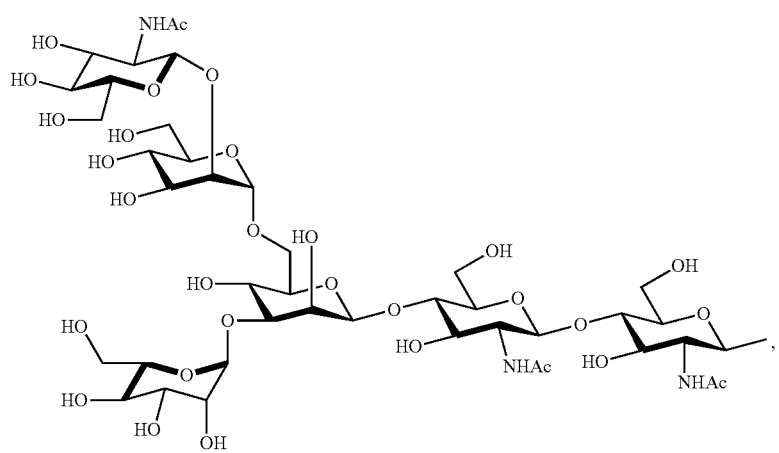
1GN2M-6NC
13
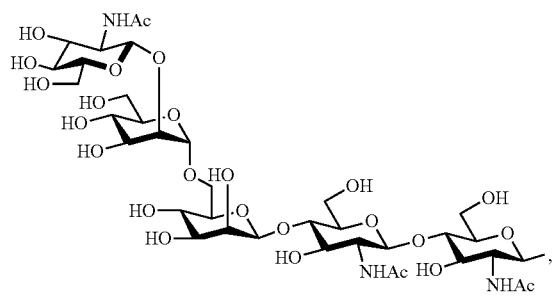
1GN-5NC
14
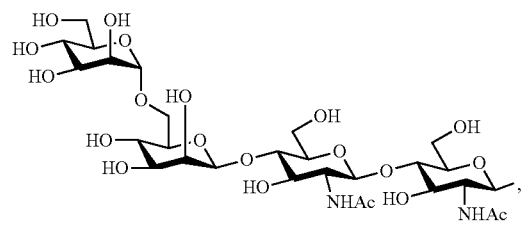
1M-4NC
15

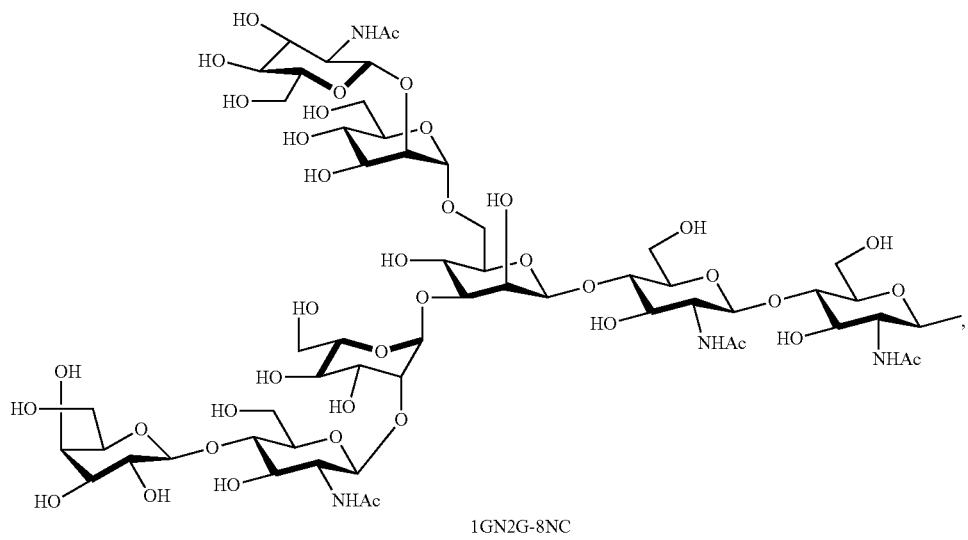
1GN2G-8NC
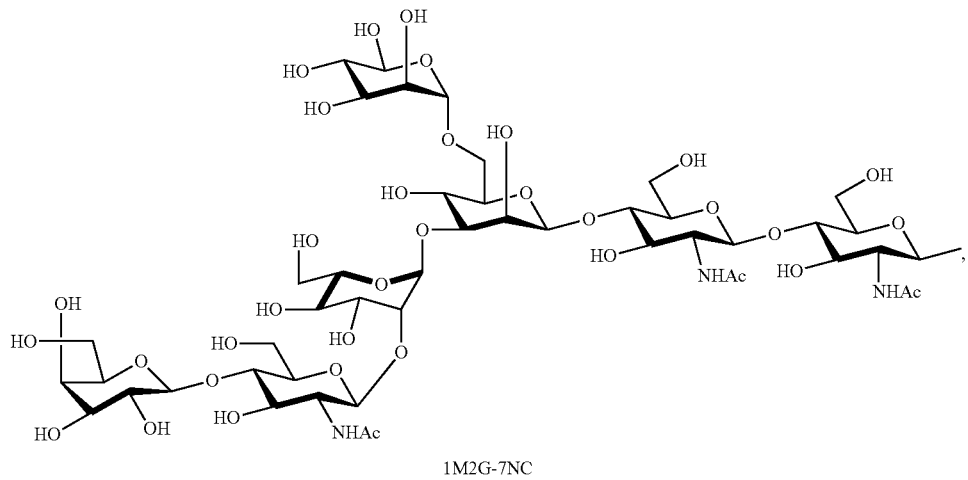
1M2G-7NC
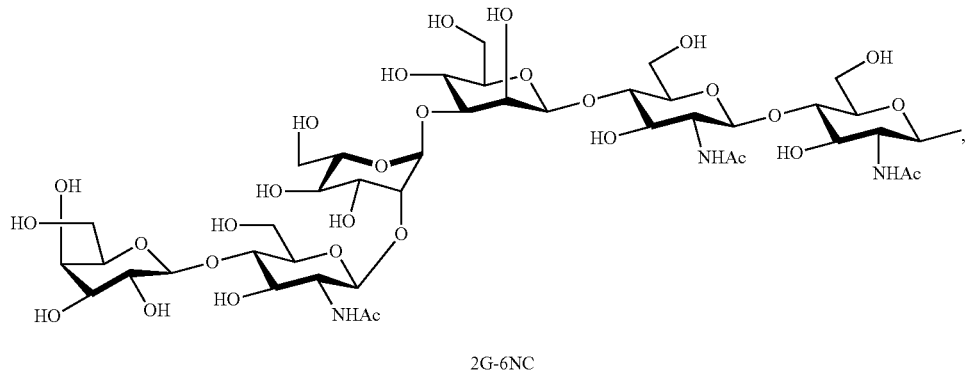
2G-6NC

-continued
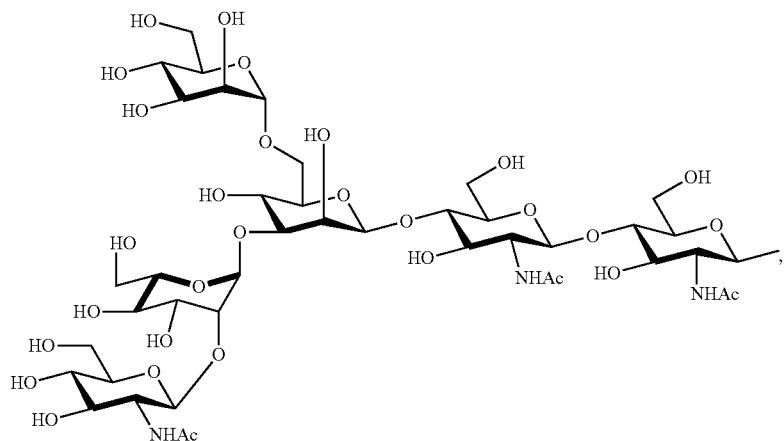
1M2GN-5NC
19
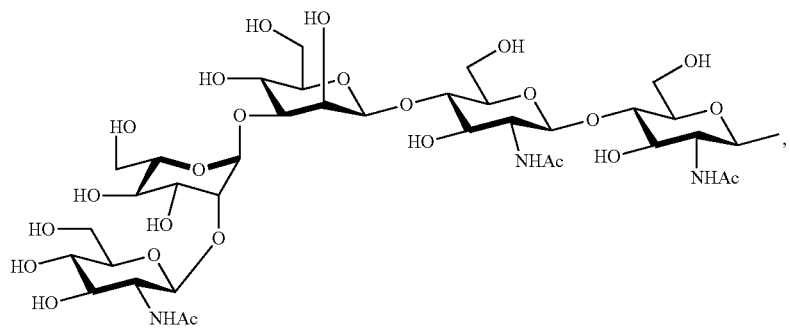
2GN-5NC
20
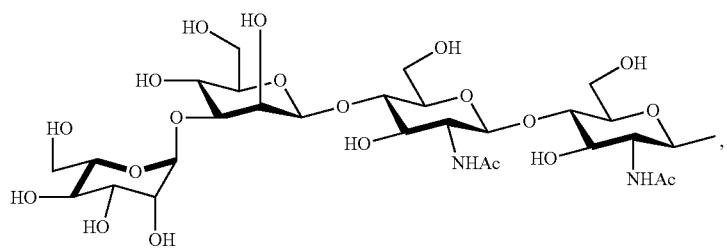
2M-4NC
21

-continued
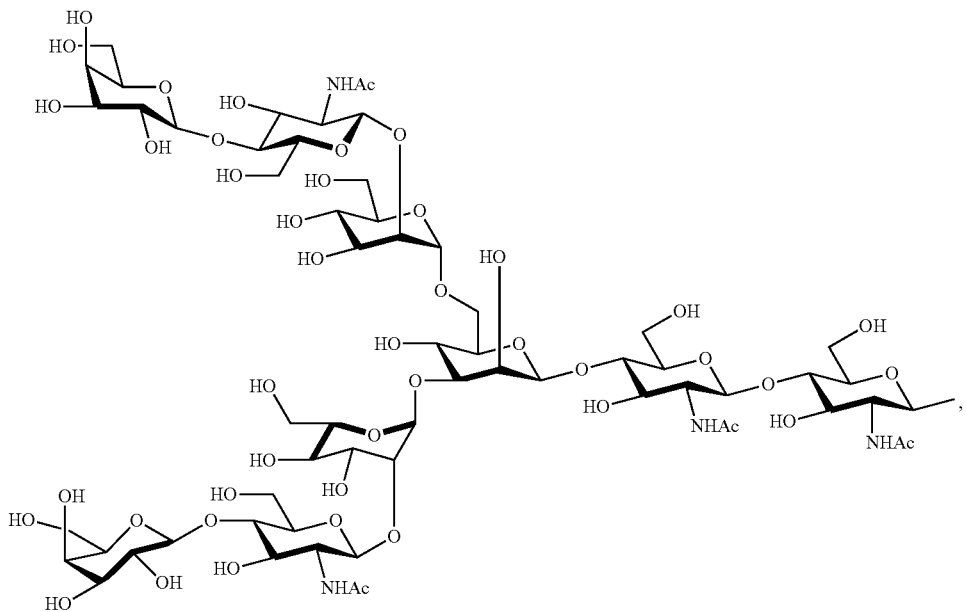
1G2G-9NC
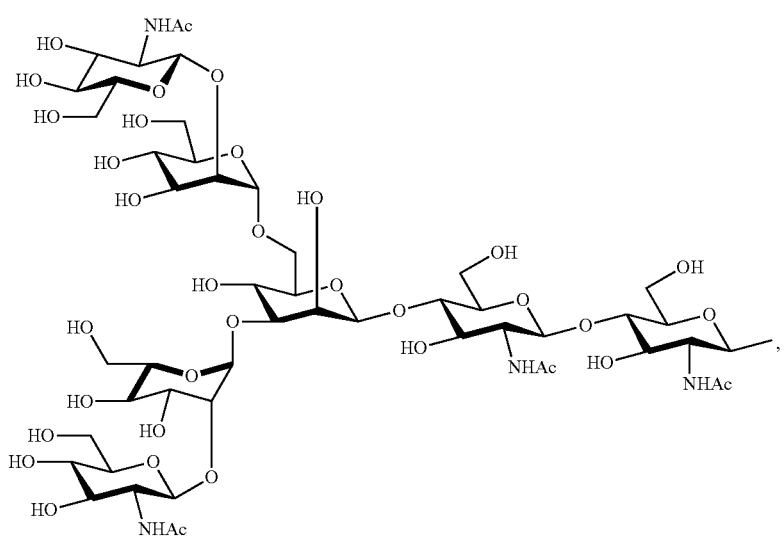
1GN2GN-7NC
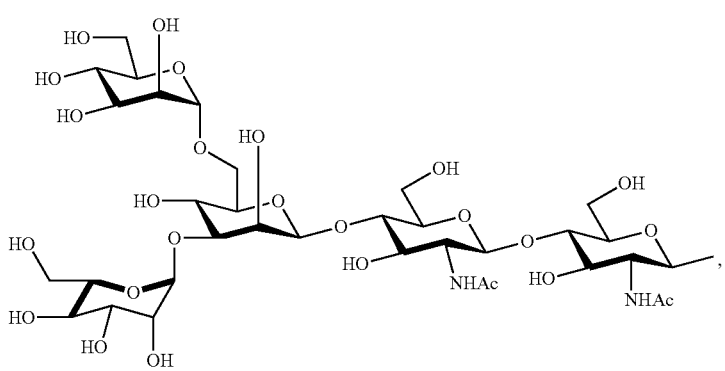
1M2M-5NC

[Chemical Formula 28]
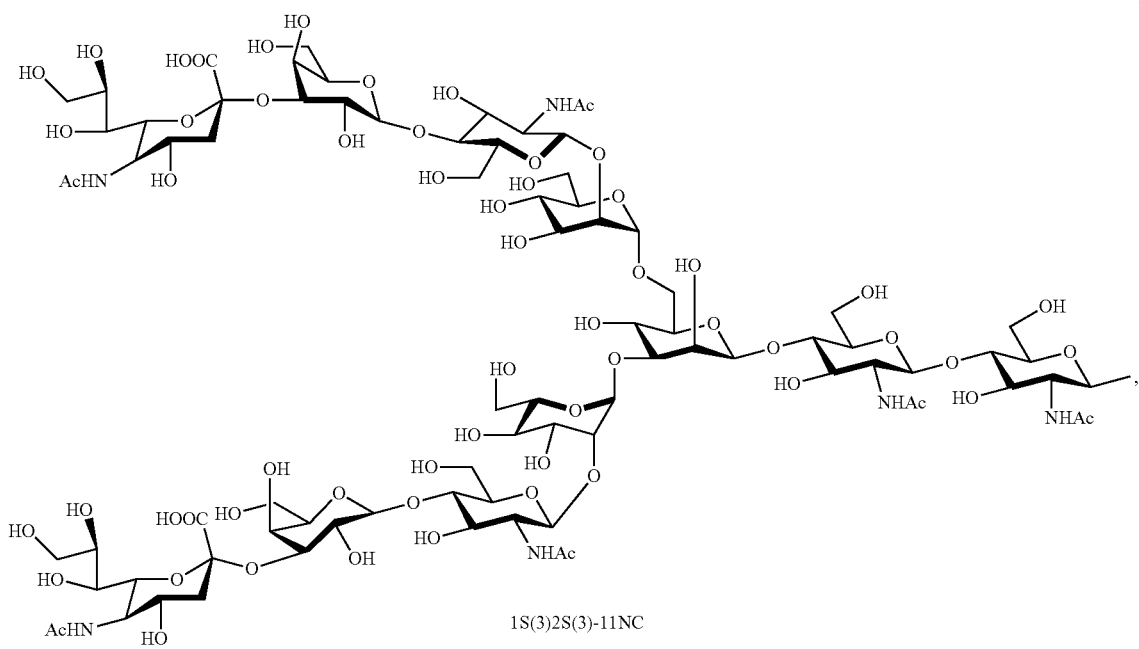
1S(3)2S(3)-11NC
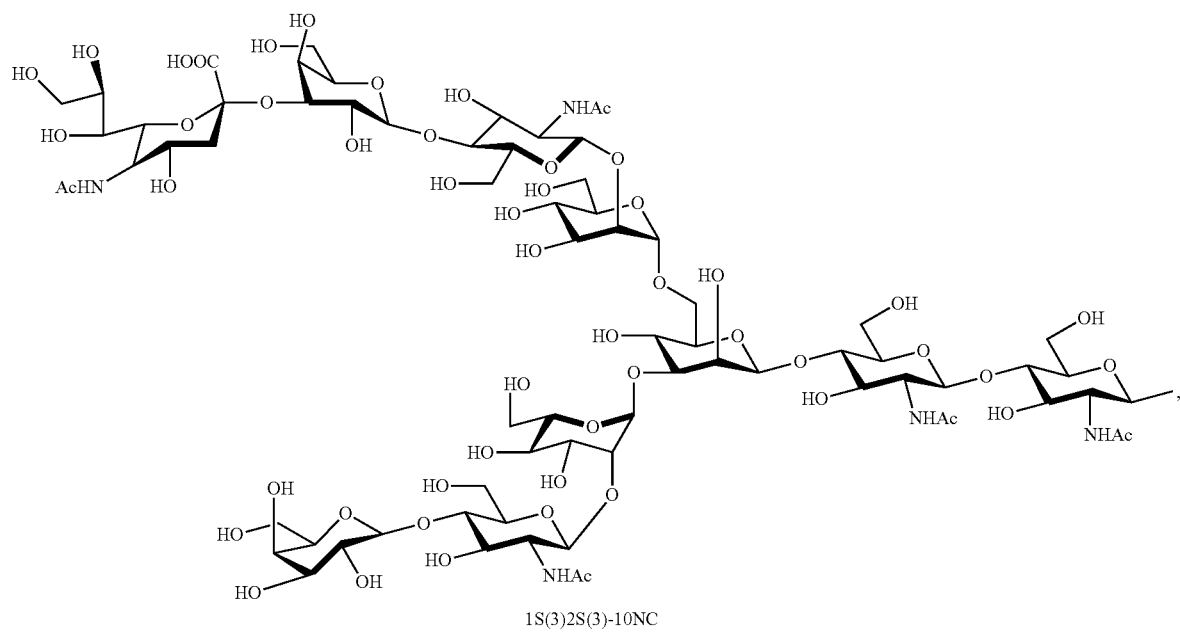
1S(3)2S(3)-10NC

-continued
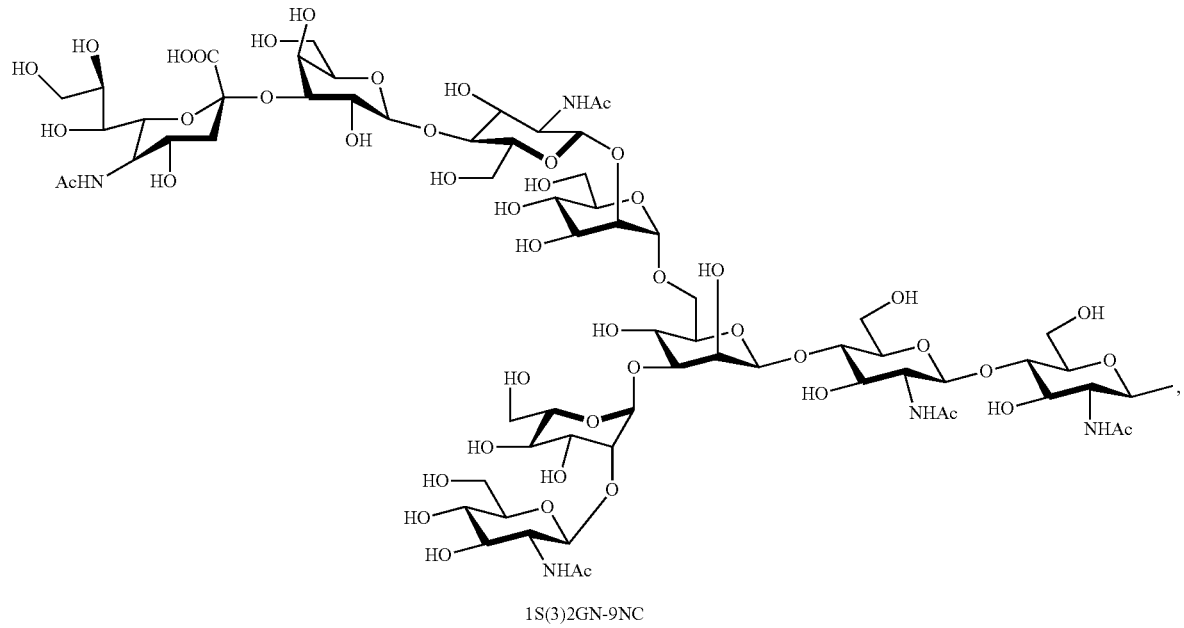
1S(3)2GN-9NC
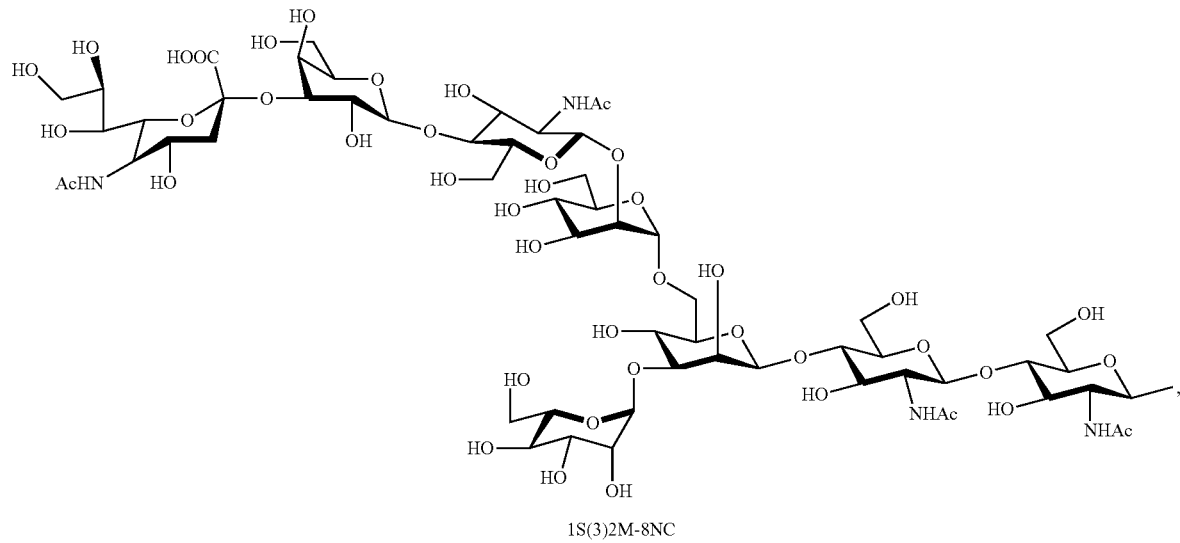
1S(3)2M-8NC
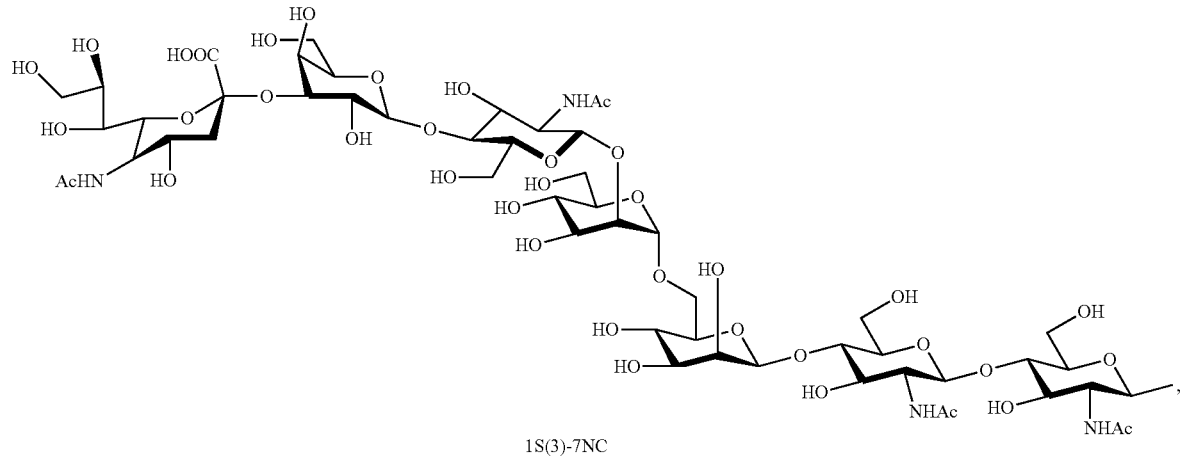
1S(3)-7NC

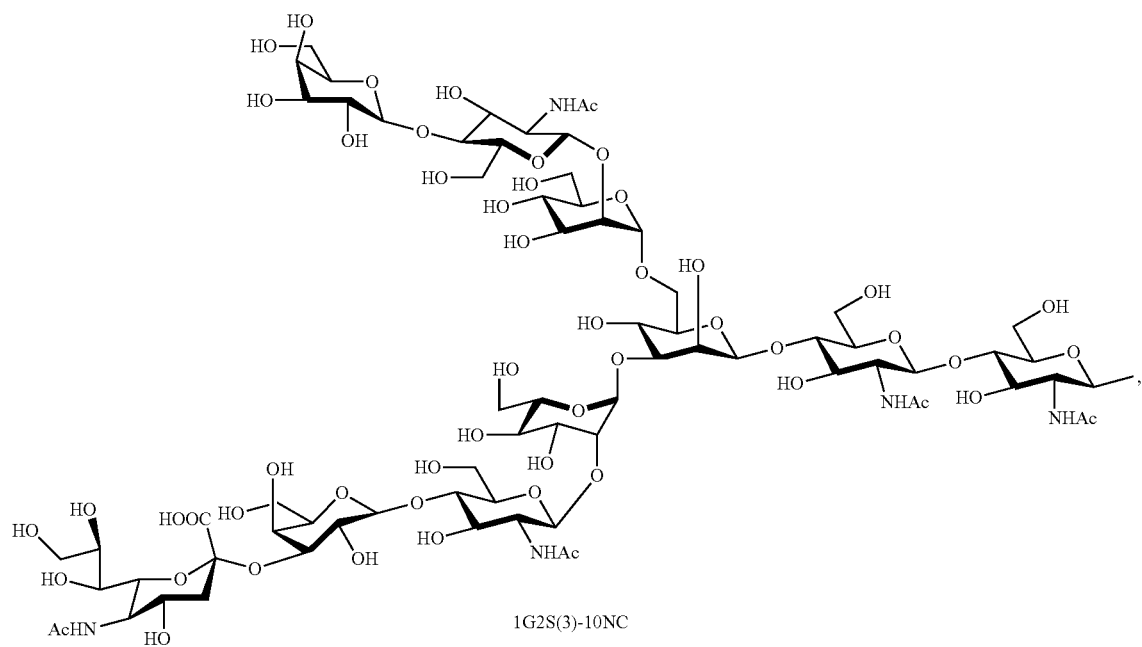
1G2S(3)-10NC
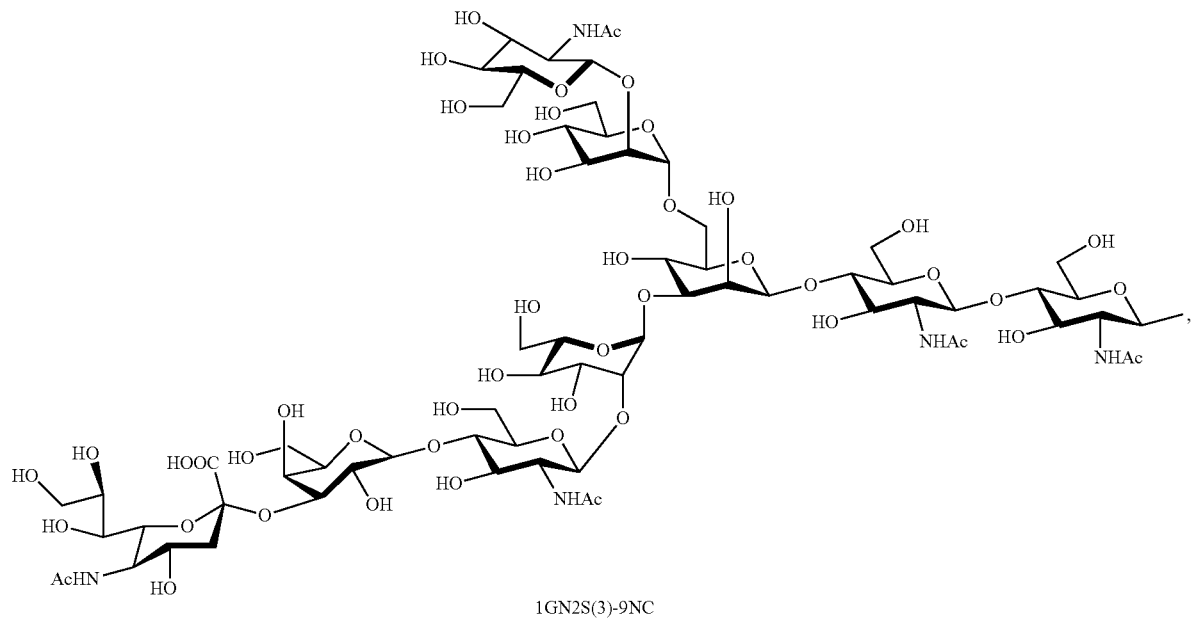
1GN2S(3)-9NC

-continued
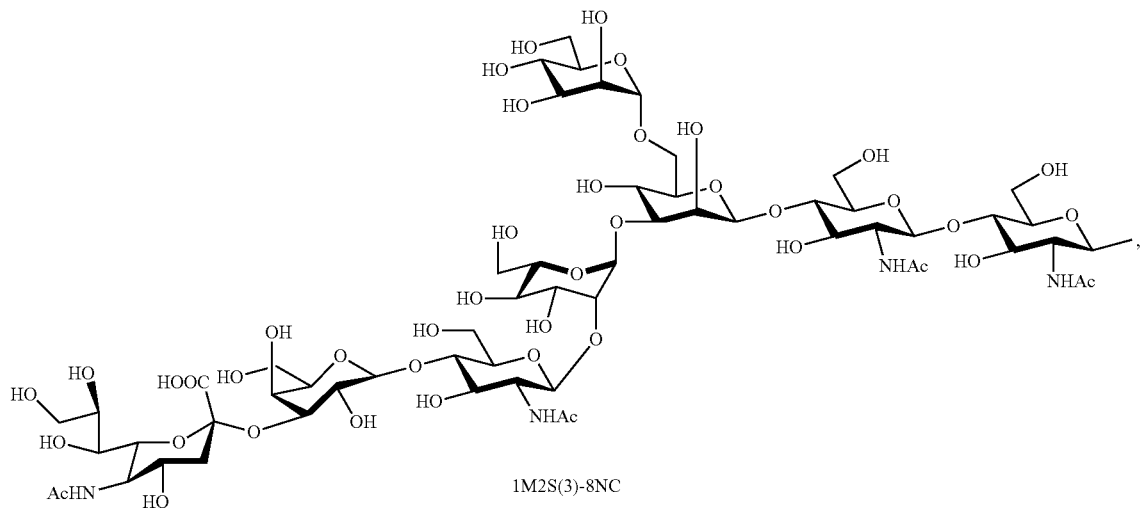
1M2S(3)-8NC
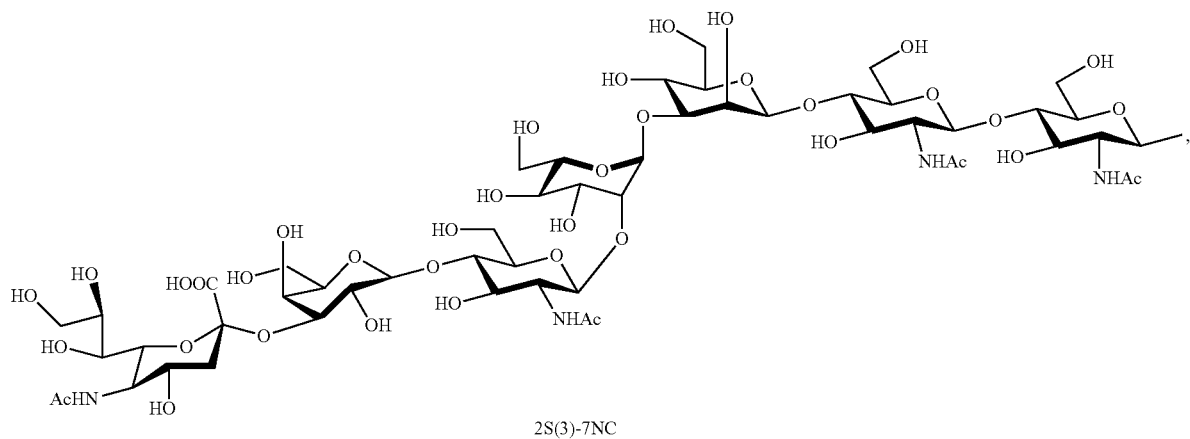
2S(3)-7NC
[Chemical Formula 29]
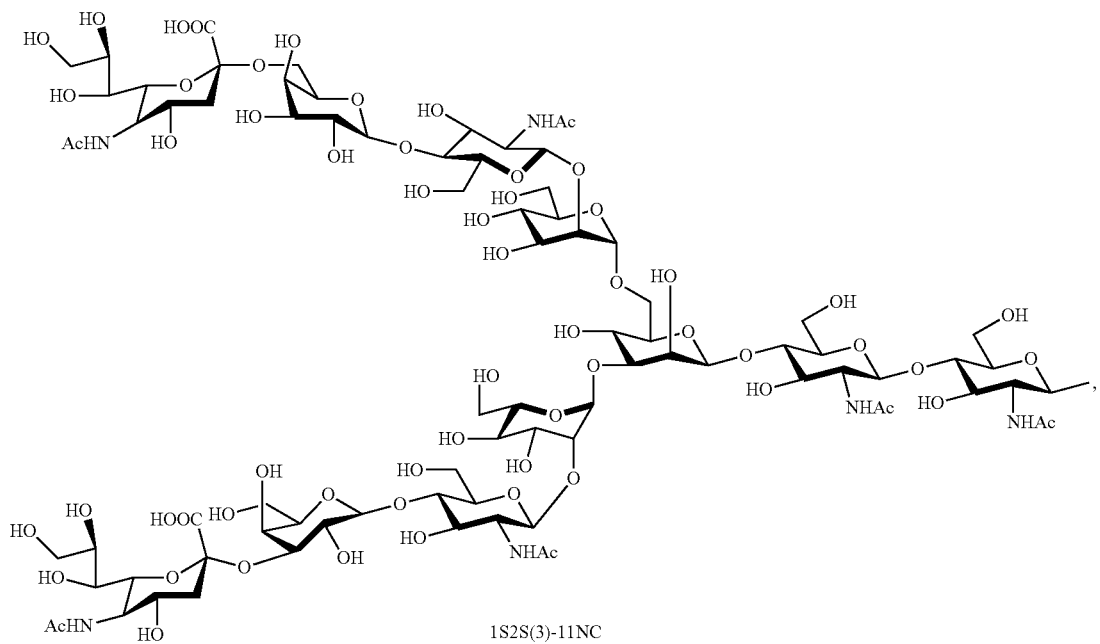
1S2S(3)-11NC

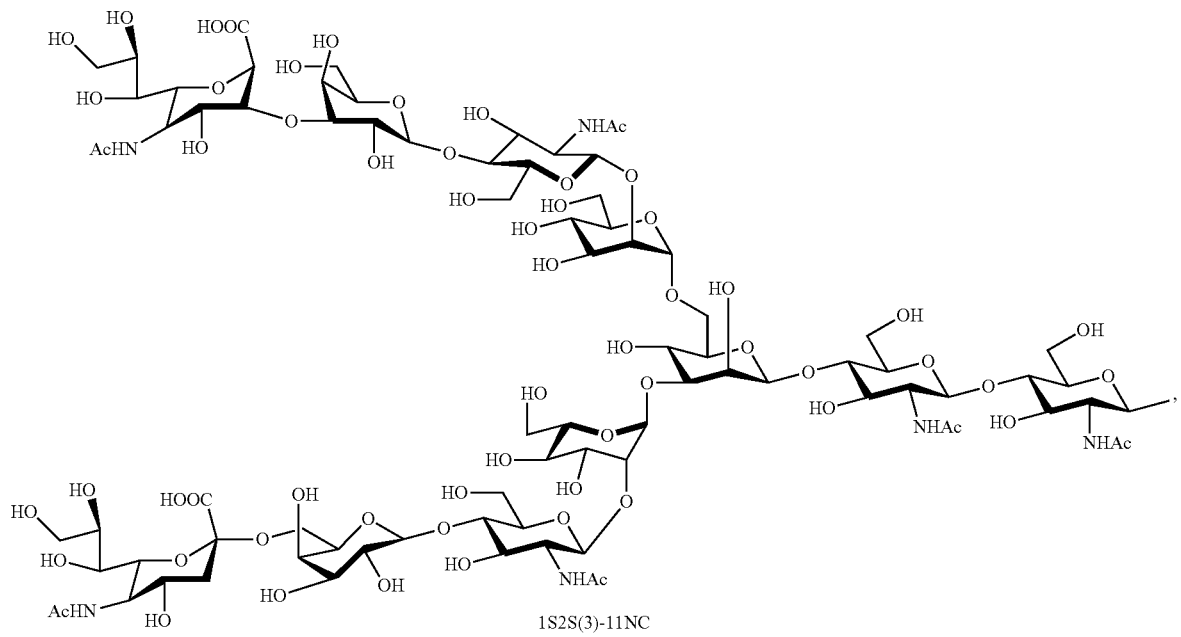

1S2S(3)-11NC

In one embodiment of the present invention, the sugar chain may have the carboxy group of the sialic acid placed at the non-reducing terminal modified. Examples of such a sugar chain can include, among the sugar chains listed above, a sugar chain having a sialic acid at the non-reducing terminal, wherein the hydrogen atom of the carboxy group (—COOH) of said sialic acid in the sugar chain is substituted with Bn, Et, Me, CH₂COPh, CH₂PhOMe, CH₂Ph(OMe)₂, CH₂PhNO₂, or CH₂Ph(NO₂)₂ (i.e. the carboxy group of said sialic acid is represented by —COOBn, —COOEt, —COOMe, —COOCH₂COPh, —COOCH₂PhOMe, —COOCH₂Ph(OMe)₂, —COOCH₂PhNO₂, or —COOCH₂Ph(NO₂)₂).

Moreover, in one aspect of the present invention, a preferred sugar chain is a sugar chain having a linear structure. An example of such a sugar chain includes oligohyaluronic acid. An oligohyaluronic acid herein refers to a sugar chain having 2-32 sugars, preferably 2-16 sugars, and more preferably 4-8 sugars of alternately bound N-acetylglucosamine and glucuronic acid in a linear line.

Among the oligohyaluronic acids employed in the present invention, particularly preferred examples include, when a unit consisting of N-acetylglucosamine and glucuronic acid is set as 1 unit, a sugar chain of 2 units (4 sugars) or more to 8 units (16 sugars) or less, further preferably 2 units (4 sugars)-4 units (8 sugars), and most preferably 2 units (4 sugars).

Examples of a hyaluronic acid preferably employed in the present invention include, e.g., an 4-sugar oligohyaluronic acid,

[Chemical Formula 30]

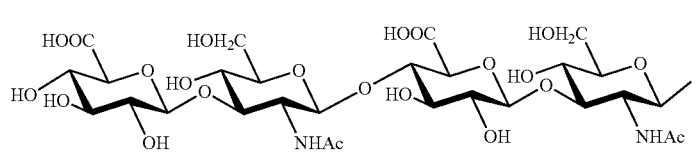

and an 8-sugar oligohyaluronic acid.

[Chemical Formula 31]

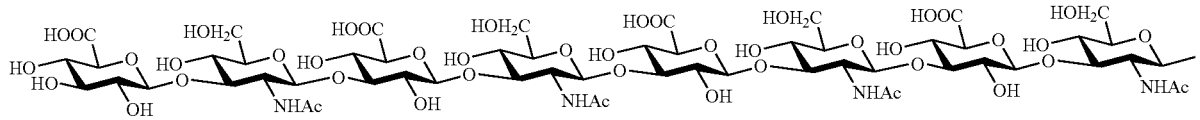

The amino acid to be glycosylated in the glycosylated polypeptide of the present invention is, similarly to a naturally-occurring interferon β, preferably the amino acid corresponding to position 80 in interferon β. Moreover, the amino acid to be glycosylated is preferably asparagine.

In one preferred aspect of the present invention, the sugar chains of the glycosylated polypeptide of the present invention are preferably uniform. As used herein, sugar chains are uniform in a glycosylated polypeptide refers to the fact that the glycosylation sites in the peptide, the type of each sugar constituting the sugar chain, the binding order, and the binding mode between sugars are identical when sugar chains are compared between glycosylated polypeptides. Specifically, it refers to the fact that the sugar chain structure is uniform between glycosylated polypeptides in at least 90% or more, preferably 95% or more, and more preferably 99% or more.

Moreover, as used herein, the glycosylated polypeptides in the composition are uniform in a composition comprising a glycosylated polypeptide refers to the fact that the glycosylation sites in the peptide, the type of each sugar constituting the sugar chain, the binding order of the sugar chain, the binding mode between sugars, the type of amino acids constituting the polypeptide, and the amino acid sequence order are identical when sugar chain and polypeptide portions are compared between glycosylated polypeptides comprised in said composition. Specifically, it refers to the fact that the sugar chain structure and polypeptide portions are uniform between glycosylated polypeptides comprised in the composition in at least 90% or more, preferably 95% or more, and more preferably 99% or more.

In particular, a composition etc. comprising a glycopeptide having uniform sugar chains between glycopeptides have constant quality, and is particularly preferred in the fields of pharmaceuticals manufacture or assays etc. The proportion of uniform sugar chains or the proportion of uniform glycosylated polypeptides can be measured for example by a method employing e.g. HPLC, capillary electrophoresis, NMR, and mass spectrometry.

The glycosylated polypeptide of the present invention is manufactured by linking a glycosylated peptide fragment and at least two peptide fragments.

(Peptide Fragment)

As described above, such glycosylated peptide fragments and peptide fragments constituting the glycosylated polypeptide of the present invention each have a portion of the amino acid sequence of interferon β. In other words, each fragment has the amino acid sequence of each of the sequence of 166 amino acids of interferon β divided into at least three portions.

In regards to the number of fragments and the length of each fragment, it is preferred to select the amino acid sequence of each fragment with the preferred number of fragments and at the preferred amino acid position considering the reduction in yield due to elongation during synthesis of each fragment, the type of amino acid necessary for linking each fragment, and the reduction in yield due to the number of linking steps.

The length of each fragment will vary according to the method for preparing the fragment, but is e.g. preferably 9-84 long, more preferably 67-78 long.

Moreover, in regards to the method for linking each fragment, the linking can be performed with a well-known method such as Thiol-free ligation, Staudinger Ligation, Sugar-Assisted Ligation, and Thiol auxiliary ligation (Chem. Commu., 2011, 47, 6201-6207), (Chem. Commu., 2010, 46, 21-43), preferably with native chemical ligation method (NCL).

When employing the native chemical ligation method, the N-terminal of each fragment selected from the amino acid sequence of interferon β must be Cys. When an amino acid other than Cys is to be selected as the N-terminal amino acid of each fragment, Ala, His, Lys, Phe, Ser, Thr, Val, or Met can be selected. For example, when the N-terminal of the fragment is Ala, it is possible to synthesize a fragment having Cys introduced at the N-terminal instead of Ala, and then reduce the Cys into Ala after ligation with other fragments. Moreover, when the N-terminal of the fragment is Phe or Val, it is possible to employ a non-natural amino acid having a thiol group at the β position as the amino acid to be introduced for ligation, and then subject to reduction treatment. When Ser or Thr is designed as the N-terminal of the fragment, cysteine can be introduced as the N-terminal, and this can be converted into Ser or Thr after ligation by methylation of the thiol group of said cysteine residue, followed by a cyanogen bromide treatment. Moreover, when His or Lys is designed as the N-terminal of the fragment, it is possible to form the desired amide bond by a ligation reaction utilizing the nucleophilic attack of the amino group after introducing these amino acids as the N-terminal. When other amino acids are the N-terminal of the fragment, the ultimate glycosylated polypeptide can also be constituted by applying the native chemical ligation method with a well-known method.

Alternatively, when cysteine is absent at the desired position in the amino acid sequence of interferon β, it is also possible to introduce a cysteine at the desired position as the N-terminal of the fragment, as long as the final product glycosylated polypeptide has interferon β activity. Moreover, the introduced cysteine can also be substituted to Ala, Ser, or Thr as above after the ligation step between each peptide fragment as desired.

In the manufacture of the glycosylated polypeptide of the present invention, the amino acid selected as the N-terminal of the fragment is preferably selected from Ala, Phe, Val, Ser, or Thr in regards to the number of fragments or the yield of the final product, and more preferably selected from Ala, Phe, or Val which can be substituted by a reduction reaction. As a more specific example, positions 1-67 in interferon β can be the first fragment, positions 68-88 having Ala at position 68 at the N-terminal can be the second fragment, and positions 89-166 having Ala at position 89 at the N-terminal can be the third fragment. Moreover, for example, the above third fragment of positions 89-166 can also be manufactured as divided into a fragment of positions 89-133 and a fragment of positions 134-166 having Ala at position 134 at the N-terminal.

(Method for Manufacturing Fragment)

Such a peptide fragment manufacturing method can be manufactured by methods such as biosynthesis, chemical synthesis, or cell-free synthesis. In particular, the synthesis of a peptide fragment having a sugar chain is preferably manufactured by chemical synthesis in order to have uniform sugar chains. A method for manufacturing a glycosylated polypeptide by applying well-known peptide synthesis methods such as solid and liquid phase synthesis can be employed as the manufacturing method by chemical synthesis. Moreover, when Ala is selected as the N-terminal of each fragment, since it is necessary to reduce a particular Cys introduced at the N-terminal instead of Ala into Ala after ligating each fragment, it is preferred to selectively protect in advance the Cys that is not to be reduced. Accordingly, in such a case, it is easy and preferred to manufacture the peptide fragment by chemical synthesis.

As a specific example of the glycosylated peptide fragment manufacturing method of the present invention which is a stable manufacturing method for a glycosylated polypeptide having uniform sugar chain structure, as with peptide fragments, a method for manufacturing a glycosylated peptide fragment by using glycosylated Asn as the glycosylated amino acid and applying a well-known peptide synthesis method such as solid and liquid phase synthesis can be employed. Such a method is described in e.g. Angew. Chem. Int. Ed. 2008, 47, 6851-6855. It is also described in International Publication No. 2004/005330 (US2005222382 (A1)), the disclosure of which is incorporated herein by reference in its entirety.

The glycosylated polypeptide can be manufactured by for example a solid phase synthesis employing glycosylated asparagine, the outline of which is shown below.

(1) The carboxy group of an amino acid having the amino group nitrogen protected with a lipophilic protecting group is bound to a resin. In this case, since the amino group nitrogen of the amino acid is protected with a lipophilic protecting group, self-condensation between amino acids is prevented, and the resin reacts with the amino acid to cause binding.

(2) The lipophilic protecting group of the reactant obtained is detached to form a free amino group.

(3) This free amino group and the carboxy group of any amino acid having the amino group nitrogen protected with a lipophilic protecting group are subjected to amidation reaction.

(4) The lipophilic protecting group is detached to form a free amino group.

(5) By repeating the above steps (3) and (4) once or more, a peptide in which any number of any amino acid are linked and having a resin bound at one end and a free amino group at the other end is obtained.

(6) Finally, by cleaving the resin with an acid, a peptide having the desired amino acid sequence can be obtained.

In (1), if glycosylated asparagine having the amino group nitrogen protected with a lipophilic protecting group is employed instead of the amino acid having the amino group nitrogen protected with a lipophilic protecting group, and the carboxy group of said asparagine portion is reacted with the hydroxyl group of the resin, a glycosylated peptide fragment having glycosylated asparagine at the C-terminal can be obtained.

Moreover, after (2), or after repeating (3) and (4) for any number of times that is once or more, if glycosylated asparagine having the amino group nitrogen protected with a lipophilic protecting group is employed instead of the amino acid having the amino group nitrogen protected with a lipophilic protecting group in (3), a sugar chain can be added at any position. Moreover, (3) and (4) can also be further repeated after adding the glycosylated asparagine to elongate the peptide.

After binding the glycosylated amino acid, if the lipophilic protecting group is detached to form a free amino group, and step (6) is performed immediately thereafter, a peptide having glycosylated asparagine at the N-terminal peptide can be obtained.

The sugar chains described above having identical structure are employed as the sugar chain bound in the above synthesis method. Such sugar chains can be obtained by any well-known method. Examples of specific methods that can be utilized are, but are not limited to, chemical synthesis of sugar chains (see, e.g., J. Seifert et al. Angew Chem Int. Ed. 2000, 39, p 531-534) or those separated from a natural or artificial sugar chain source or those commercially available. The glycosylated amino acids having identical structure in the said method are not limited, and for example, separation of sugar chains of identical structure from a natural or artificial sugar chain source can be performed by the method described in e.g. WO 2004/058789. Specifically, a mixture comprising glycosylated asparagine (sialylglycopeptide (SGP)) is isolated from a natural sugar chain source such as a hen egg with the method described in e.g. Seko et al., Biochim Biophys Acta. 1997; 1335 (1-2):23-32, a lipophilic protecting group (such as Fmoc) is introduced into said glycosylated asparagine to obtain a glycosylated asparagine derivative mixture, this is subjected to chromatography, and sugar chains having various structures comprised in said mixture can be separated according to its structure. Moreover, a glycosylated asparagine having a particular structure with or without various protecting groups can be available from e.g. Otsuka Chemical Co., Ltd.

The resin may be a resin generally used in solid phase synthesis, and for example, 2-chlorotrityl chloride resin (from Merck) functionalized with chlorine, Amino-PEGA resin (from Merck) functionalized with an amino group, NovaSyn TGT alcohol resin (from Merck) having a hydroxyl group, Wang resin (from Merck), and HMPA-PEGA resin (from Merck) etc. can be employed. Moreover, a linker may exist between the Amino-PEGA resin and the amino acid, and examples of such linkers can include, e.g., 4-hydroxymethylphenoxyacetic acid (HMPA) and 4-(4-hydroxymethyl-3-methoxyphenoxy)-butylacetic acid (HMPB). H-Cys(Trt)-Trityl NovaPEG resin (from Merck) etc. in which the C-terminal amino acid is bound to the resin in advance can also be employed.

Moreover, when the C-terminal is to be amidated, e.g. Rink-Amide-PEGA resin (from Merck) functionalized with an amino group can be employed. By cleaving this resin and the peptide with an acid, the C-terminal amino acid of the peptide can be amidated.

In the binding between the resin and the amino acid having the amino group nitrogen protected with a lipophilic protecting group, for example, in order to use a resin having a hydroxyl group or a resin functionalized with chlorine, the carboxy group of the amino acid is bound to the resin via an ester bond. Moreover, if a resin functionalized with an amino group is to be used, the carboxy group of an amino acid is bound to the resin via an amide bond.

The 2-chlorotrityl chloride resin is preferred in that it can prevent the racemization of the terminal Cys when elongating the peptide chain in solid phase synthesis.

Any amino acid can be employed as the amino acid, and examples can include the natural amino acids serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro).

Examples of lipophilic protecting groups can include, e.g., carbonate- or amide-based protecting groups such as a 9-fluorenylmethoxycarbonyl (Fmoc) group, a t-butyloxycarbonyl (Boc) group, a benzyl group, an allyl group, an allyloxycarbonyl group, and an acetyl group. When introducing a lipophilic protecting group into an amino acid, e.g. when introducing an Fmoc group, introduction can be carried out by adding 9-fluorenylmethyl-N-succinimidyl carbonate and sodium hydrogen carbonate and allowing reaction. The reaction may be performed at 0-50° C., preferably at room temperature for approximately about 1-5 hours.

As the amino acid protected with a lipophilic protecting group, those commercially available can also be used. Examples can include Fmoc-Ser-OH, Fmoc-Asn-OH, Fmoc-Val-OH, Fmoc-Leu-OH, Fmoc-Ile-OH, Fmoc-Ala-OH, Fmoc-Tyr-OH, Fmoc-Gly-OH, Fmoc-Lys-OH, Fmoc-Arg-OH, Fmoc-His-OH, Fmoc-Asp-OH, Fmoc-Glu-OH, Fmoc-Gln-OH, Fmoc-Thr-OH, Fmoc-Cys-OH, Fmoc-Met-OH, Fmoc-Phe-OH, Fmoc-Trp-OH, Fmoc-Pro-OH, Boc-Ser-OH, Boc-Asn-OH, Boc-Val-OH, Boc-Leu-OH, Boc-Ile-OH, Boc-Ala-OH, Boc-Tyr-OH, Boc-Gly-OH, Boc-Lys-OH, Boc-Arg-OH, Boc-His-OH, Boc-Asp-OH, Boc-Glu-OH, Boc-Gln-OH, Boc-Thr-OH, Boc-Cys-OH, Boc-Met-OH, Boc-Phe-OH, Boc-Trp-OH, and Boc-Pro-OH.

Moreover, an amino acid protected with a lipophilic protecting group wherein the protecting group is introduced into the side chain can include, e.g., Fmoc-Ala-OH, Fmoc-Arg(Pbf)-OH, Fmoc-Asn(Trt)-OH, Fmoc-Asp(OtBu)-OH, Fmoc-Cys(Acm)-OH, Fmoc-Cys(tBu)-OH, Fmoc-Cys(Trt)-OH, Fmoc-Glu(OtBu)-OH, Fmoc-Gln(Trt)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH, Boc-Met-OH, and Boc-Thz-OH. Thz herein indicates a thiazolidine-type Cys (Thiazolidine-4-carboxylic acid).

When the peptide fragment is synthesized by e.g. solid phase synthesis, it is preferred to preferred to have an amino acid protected with a Boc group at the N-terminal in that the side reaction by the nucleophilic reaction caused by the amino group can be suppressed when thioesterification is necessary after the peptide fragment synthesis.

Moreover, if it is desired to add a linker in the amino acid sequence of a glycosylated polypeptide, the linker can be inserted at a preferred position by using a linker protected with a lipophilic protecting group instead of the above amino acid protected with a lipophilic protecting group in the process of solid phase synthesis.

When employing a resin having a hydroxyl group, e.g. well-known dehydration condensation agents such as 1-mesitylenesulfonyl-3-nitro-1,2,4-triazole (MSNT), dicyclohexylcarbodiimide (DCC), and diisopropylcarbodiimide (DIP-CDI) can be employed as the esterification catalyst. Moreover, When employing a 2-chlorotrityl chloride resin, esterification can be performed with a base such as diisopropylethylamine (DIPEA), triethylamine, pyridine, and 2,4,6-collidine. The proportion of the amino acid and the dehydration condensation agent used is 1 part by weight of the former to generally 1-10 parts by weight, preferably 2-5 parts by weight of the latter.

The esterification reaction is preferably performed by for example placing the resin in a solid phase column, washing this resin with a solvent, and then adding the amino acid solution. Examples of washing solvents can include, e.g., dimethylformamide (DMF), 2-propanol, and dichloromethane. Examples of solvents for dissolving the amino acid can include, e.g., dimethyl sulfoxide (DMSO), DMF, and dichloromethane. The esterification reaction may be performed at 0-50° C., preferably at room temperature for approximately about 10 minutes-30 hours, preferably for approximately 15 minutes-24 hours.

Moreover, it is also preferred to acetylate and cap the unreacted hydroxyl groups on the solid phase at this time with e.g. acetic anhydride.

The detachment of the lipophilic protecting group can be performed by for example treatment with a base. Examples of bases can include, e.g., piperidine and morpholine. In such a case, it is preferred that this is performed in the presence of a solvent. Examples of solvents can include, e.g., DMSO, DMF, and methanol.

The amidation reaction of the free amino group with the carboxy group of any amino acid having the amino group nitrogen protected with a lipophilic protecting group is preferably performed in the presence of an activator and a solvent.

Examples of activators can include, e.g., dicyclohexylcarbodiimide (DCC), 1-ethyl-3-(3-dimethylaminopropyl) carbodiimide hydrochloride (WSC/HCl), diphenylphosphorylazide (DPPA), carbonyldiimidazole (CDI), diethylcyanophosphonate (DEPC), benzotriazol-1-yloxytrispyrrolidinophosphonium (DIPCI), benzotriazol-1-yloxytrispyrrolidinophosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazol-1-yl)-1,1,3,3-tetramethyluronium hexafluorophosphate (HBTU), 1-[bis(dimethylamino)methylene]-5-chloro-1H-benzotriazolium 3-oxide hexafluorophosphate (HCTU), O-(7-azabenzotriazol-1-yl)-1,1,3,3-tetramethyluronium hexafluorophosphonate (HATU), O-benzotriazol-1-yl-1,1,3,3-tetramethyluronium tetrafluoroborate (TBTU), and 3,4-dihydro-3-hydrodi-4-oxa-1,2,3-benzotriazine (Dhbt).

The amount of the activator used may be 1-20 equivalents, preferably 1-10 equivalents, and further preferably 1-5 equivalents to any amino acid having the amino group nitrogen protected with a lipophilic protecting group.

Examples of solvents can include, e.g., DMSO, DMF, and dichloromethane. The reaction may be performed at 0-50° C., preferably at room temperature for approximately about 10-30 hours, preferably for approximately 15 minutes-24 hours. The detachment of the lipophilic protecting group can be performed similarly to the above.

Treatment with an acid is preferred in order to cleave the peptide chain from the resin. Examples of acids can include, e.g., a mixed solution of trifluoroethanol and acetic acid (1:1), trifluoroacetic acid (TFA), and hydrogen fluoride (HF).

The peptide fragment can be prepared by chemical synthesis such as solid phase synthesis as above, but it can also be prepared by a biosynthesis method well-known to those skilled in the art. For example, the peptide fragment of interest can be expressed by introducing the gene of interest into a recombinant vector. The recombinant vector employed herein may be any that may transform a host cell, and animal viral vectors such as a plasmid for *E. coli*, a plasmid for *Bacillus subtilis*, and a plasmid for yeasts, retrovirus, vaccinia virus, and baculovirus etc. are employed depending on the host cell. Those having a regulatory sequence such as a promoter that may appropriately express the protein in the host cell are preferred. Moreover, the host cell may be any that can express a foreign gene in a recombinant vector, and *E. coli, Bacillus subtilis*, yeast, an insect cell, and an animal cell etc. are generally employed.

The method for transfecting the host cell with a recombinant vector employed may be those routinely used in general, and e.g. heat shock method, calcium chloride method, or electroporation method for *E. coli*, and lithium chloride method or electroporation for yeasts can be utilized. Moreover, transformation of an animal cell can be performed with a physical method such as electroporation, or a chemical method such as liposome method or calcium phosphate method, or a viral vector such as a retrovirus.

Moreover, after the introduction of the vector, it is preferred to confirm that the DNA sequence of interest is properly integrated by a method well-known to those skilled in the art. In regards to the culturing format of the transformant host cell, the culture condition may be selected in light of the nutrient physiological nature of the host.

Moreover, the peptide to be prepared by biosynthesis is preferably purified. The purification method of the peptide can be performed by an ordinary general purification. For example, in the case of a recombinant protein, after culturing the bacteria or cell expressing the recombinant protein used herein, a crude extract of the peptide is prepared by collecting the bacteria or cell with a well-known method, suspending this in an appropriate buffer, destructing the bacteria or cell by e.g. ultrasonic wave, lysozyme and/or freeze-thawing, and then subjecting to centrifugal separation or filtration. The buffer may include a protein denaturing agent such as urea or guanidine hydrochloride, or a surfactant such as Triton X-100™. The purification of the extract in this way or the peptide comprised in the culture supernatant can be performed by a well-known purification method. For example, affinity chromatography, ion exchange chromatography, filter, ultrafiltration, gel filtration, electrophoresis, salt precipitation, and dialysis etc. are appropriately selected and combined to enable separation and purification of the peptide.

Moreover, in order to facilitate the purification of the recombinant protein, various tags may also be integrated into the expression vector. Examples of a tag that can be used include tags known to those skilled in the art such as a tag that improves expression efficiency or a tag that improves purification efficiency, and examples include, e.g. thioredoxin, a GST tag, a Myc tag, a FLAG tag, and a maltose-binding protein (MBP).

Moreover, when the cysteine to be used for ligation to the desired N-terminal of the peptide fragment is absent, cysteine can also be introduced to said site. For example, it is possible to mutate a desired site into cystein in a nucleic acid molecule to be introduced into a host cell by any mutagenesis method known in the present technical field, including, but are not limited to, error-prone PCR, site-specific mutagenesis, assembly PCR, DNA shuffling, in vivo mutagenesis, cassette mutagenesis, recursive ensemble mutagenesis, and exponential ensemble mutagenesis.

Moreover, when protection of the amino acid side chain is preferred in the peptide fragment prepared by biosynthesis as above, the protection can be achieved with a method well-known to those skilled in the art. For example, when protecting cysteine, the N-terminal cysteine is protected with e.g. formaldehyde, and the Cys residue side chain thiol group in the peptide can be selectively protected with e.g. S-9-Fluorenylmethyl thioether (Fm-SR).

(Linking of Each Fragment)

Any well-known method that can link two peptide fragment chains as described above can be employed for a step of linking a glycosylated peptide fragment and a peptide fragment prepared in a method as above, an example of which can include native chemical ligation (NCL, see, e.g., Japanese Translation of PCT International Application Publication No. 2004-518621). NCL is a method of mixing peptide fragment A having a thioester at the C-terminal and peptide fragment B having cysteine at the N-terminal in a buffer solution, detaching the thioester group at the C-terminal of peptide A by the nucleophilic attack of the sulfhydryl group of cysteine at the N-terminal of peptide fragment B, and linking the two peptides with each other via a natural peptide bond by a subsequent nucleophilic attack of amine.

Accordingly, as described above, when employing NCL in the linking step, a step of thioesterifying the C-terminal of the polypeptide to be positioned at the N-terminal is necessary before the linking step. Such thioesterification can be achieved for example by activating the C-terminal carboxylic acid with PyBOP and DIPEA, and adding excess alkylthiol. When employing this method, the addition of the alkylthiol is preferably performed at a low temperature of 10° C.--80° C., more preferably at a temperature of 0° C.--40° C. in order to suppress the configuration of the α carbon of the amino acid at the fragment terminal. In particular, in the above thioesterification reaction, it is preferred to employ a thiophenol instead of an alkylthiol. The thioesterification reaction by the addition of thiophenol has a fast reaction rate and can almost fully complete the reaction. Accordingly, the side reaction of the cyclization reaction of the peptide fragment during the thioester reaction can be suppressed and is thus preferred.

Moreover, the above thioesterification can also be performed by e.g. the Fmoc or Boc methods described in Yamamoto et al., J. Am. Chem. Soc. 2008, 130 (2), 501-510.

NCL is performed by mixing preferably equimolar amounts of the polypeptide chain of the sugar chain binding portion and the polypeptide chain of the non-sugar chain binding portion in a buffer solution. In a preferred aspect, the ligation reaction is carried out in a buffer having pH 6-8, and the preferred pH range is 6.5-7.5. This buffer may be aqueous, organic, or a mixture thereof. The ligation reaction can further comprise one or two or more types of catalysts and/or one or two or more types of reductants, lipids, and other denaturing agents or solubilizers etc. Examples of a preferred catalyst include, e.g., a thiol- and phosphine-containing substance such as thiophenol, benzyl mercaptan, TCEP, and alkyl phosphine. Examples of a denaturing agent and/or a solubilizer include guanidine, urea aqueous solution or an organic solvent solution such as TFE, HFIP, DMF, and NMP, water, or acetonitrile mixed with guanidine and urea aqueous solution. The speed of the ligation reaction can be adjusted with temperature, and can be generally performed at 5-55° C., preferably at 15-40° C. In particular, the ligation reaction of IFN-β is preferably performed under the condition of 6-8 M guanidine. For example, it proceeds well in a reaction system employing a buffer comprising 6 M guanidine at pH 6.8-7.8 and 1-3% thiophenol.

If the separation of the product after the ligation step and the source material is difficult, for example, the thiol group of cysteine which was the ligation linking point can be deliberately thioesterified by utilizing an excess amount of a C-terminal thiophenyl ester body having high reactivity. In this way, by thioesterifying the thiol group of the peptide side chain produced by ligation, the lipophilicity or water solubility of the product can be increased to facilitate separation.

If an excessively thioesterified thiol group was produced by this operation, it can be easily restored to a thiol group with e.g. sodium mercaptoethanesulfonate.

When each fragment was designed with Ala as the N-terminal, a glycosylated polypeptide having Cys instead of Ala at the N-terminal position is manufactured by the above method. Accordingly, in such a case, it is preferred to restore the amino acid that needs reduction (Cys) to Ala by a reduction reaction during the preparation of the glycosylated polypeptide.

A method such as radical reduction and hydride reduction can be used as such a method for reducing Cys to Ala, particularly preferably radical reduction.

The reaction of the radical reduction can be performed by e.g. adding tBuSH, sodium 2-mercaptoethanesulfonate, or glutathione etc. to a solvent such as TCEP comprising the peptide fragment. Examples of the solvent used in the radical reduction reaction employed can include water, an organic solvent (such as acetonitrile), or a buffer (such as a phosphate buffer), and a specific example can include Tris-carboxyethyl phosphine solution (TCEP solution). Moreover, the solvent can include a solubilizer. For example, it is preferred to comprise 6 M-8 M guanidine. Moreover, the radical reduction reaction is preferably performed at a pH range of 7.5-pH 8.0, and the reaction temperature is preferably −15-40° C. When the pH is lower than 7.5, the reaction will not be fully completed and is thus not preferred. Moreover, the reaction time can be 2-6 hours. When it is longer than 6 hours, peak attenuation begins and is thus not preferred. As an example of the radical reduction reaction, the reaction can be performed with 7 M guanidine and 0.25 M TCEP under the condition of pH 7.5, 20° C., and 4 hours.

In the radical reduction reaction, the Cys that is not preferred to be reduced can be protected by a protecting group. As such a protecting group, a well-known protecting group such as an Acm group, an alkoxymethyl group, a triphenylmethyl group, a t-butyl group, a benzyl group, and an ethyl group having the 3 position substituted can be employed.

Moreover, a reaction container that will allow little dead volume for placing the reaction solution is preferably employed for the radical reduction reaction in order to fully complete the reaction.

Moreover, when a Cys protected with an Acm group etc. exists after the above reduction step, deprotection of Cys is performed.

In regards to the deprotection step, for example, when the protecting group of Cys is an Acm group, it can be deprotected by reacting with e.g. iodine, mercury acetate (II), silver nitrate (I), or silver acetate (I) in water, methanol, acetic acid, or a mixed solution thereof. Moreover, when the protecting group is an alkoxymethyl group, it can be deprotected e.g. with acid hydrolysis or by employing a silver or mercury salt. When the protecting group is a triphenylmethyl group, it can be deprotected with e.g. a mercury (II) salt.

The above reaction may be performed generally at 0-80° C., preferably at 5-60° C., and further preferably at 10-35° C. The reaction time is preferably approximately 5 minutes-24 hours in general. Other protecting groups can also be deprotected by a method well-known to those skilled in the art. Moreover, after completion of the reaction, it may be treated with e.g. dithiothreitol (DTT) or hydrochloric acid, and then purified with a well-known method (such as high performance liquid column chromatography (HPLC)) as appropriate.

Moreover, when each fragment was designed with Ser as the N-terminal, a glycosylated polypeptide having Cys instead of Ser at the N-terminal position is manufactured by the above method. Accordingly, in such a case, the amino acid that needs conversion into Ser (Cys) is converted into Ser after ligation during the preparation of the glycosylated polypeptide.

Such a conversion step can be performed by e.g. a methylation reaction of the —SH group on Cys, a cyanidation reaction, and a subsequent intramolecular acyl translocation reaction.

More specifically, the above conversion step comprises (1) a step of reacting the —SH group of Cys in a peptide comprising Cys with a methylation agent to form a —SMe group (methylation), and (2) a step of reacting the —SMe group on the peptide obtained in step (1) with a cyanidation agent (cyanidation reaction), and after the reaction, converting the —SMe group into an —OH group via a reaction intermediate by placing said peptide under basic conditions (intramolecular acyl translocation reaction). Such a conversion step is described e.g. in International Publication 2009/017154, the disclosure of which is incorporated herein by reference in its entirety.

Examples of a methylation agent employed for the methylation reaction of the —SH group of Cys is not particularly limited as long as it can convert an —SH group into an —SMe group, and can include, e.g., iodomethane and methyl-4-nitrobenzene sulfonate.

The amount of the methylation agent used is 1-1000 equivalents to one cysteine residue of the source material peptide or glycopeptide. It may preferably be 10-100 and further preferably 15-30 equivalents. The methylation reaction may be performed at 0-50° C., preferably at 20-30° C. for approximately about 10 minutes-30 hours, and preferably for approximately 15 minutes-1 hour.

The solvent may be a buffer solution, the pH of which may be 7-9, preferably 8-9. For example, an example can include a buffer solution at pH 8.6 adjusted with 6 M guanidine hydrochloride solution, 0.25 M Tris-hydrochloric acid solution, and 3.3 mM EDTA solution.

Moreover, examples of a cyanidation agent that can be employed with respect to stability etc. are e.g. cyanogen bromide and phenylcyanate. Preferably, an easily available cyanogen bromide can be employed.

The amount of the cyanidation agent used can be 1-1000 equivalents, preferably 10-100 equivalents, and more preferably 15-30 equivalents to one residue of the —SMe group. The reaction with the cyanidation agent is desirably performed at 0-50° C., preferably at 30-40° C. for approximately about 30 minutes-100 hours, preferably for approximately 12 hours-50 hours.

The reaction with the cyanidation agent is performed under acidic conditions, particularly preferably at pH 2-3. The reaction can be performed under acidic conditions by the use of an acidic water-soluble substance, specifically, formic acid, trifluoroacetic acid, and methanesulfonic acid etc. In doing so, the acidic water-soluble substance used is particularly preferably degassed in order to prevent the oxidation of the sulfur atom. Moreover, the reaction is preferably performed under protection from light with respect to the stability of the cyanidation agent.

As the solvent, a water-soluble solvent showing pH 2-3 described above, e.g. 80% formic acid solution, 70% formic acid solution, and 2% trifluoroacetic acid/39% acetonitrile-containing aqueous solution etc. can be optimally employed.

When the peptide comprises a methionine residue as an amino acid, it is preferred to discriminate the —SMe group of the methionine residue from the —SMe group obtained from the methylation reaction. This discrimination can be performed by e.g. the introduction of a protecting group. As used herein, a methionine having a protecting group introduced (protected methionine) is not particularly limited as long as it is a compound that does not react with the cyanidation agent in the cyanidation reaction, an example of which can include a sulfoxide-type methionine (Met(O): —$CH_2$—$CH_2$—S(=O)—$CH_3$). The protected methionine residue can be converted into a methionine residue after the cyanidation reaction or the intramolecular acyl translocation reaction. The deprotection method can be performed as appropriate by a method well-known to those skilled in the art.

The intramolecular acyl translocation reaction can be performed by permorming under a more basic condition compared to the cyanidation reaction. This gives a peptide comprising an amino acid residue having an —OH group.

The basic condition in the intramolecular acyl translocation reaction may be acidic or neutral as long as it is placed under a more basic condition compared to the cyanidation reaction, more specifically, as long as it is a condition in which the —NH$_2$ group on the C atom adjacent to the ester bond of the reaction intermediate obtained in the cyanidation reaction is not protonated. With respect to efficiently performing the conversion from the reaction intermediate to the peptide having an —OH group, a weak or strong basic condition can be employed.

The basic condition can be achieved by adding a basic compound that is a pH adjusting agent well-known to those skilled in the art (such as guanidine, disodium phosphate, Tris, sodium hydrogen carbonate, hydrazine hydrate, and 50 mM sodium hydroxide aqueous solution). In doing so, the amount of the basic compound used can be 0.5-1000 equivalents, preferably 10-100 equivalents, and more preferably 15-30 equivalents to the source material peptide.

The intramolecular acyl translocation is desirably performed at 0-50° C., preferably at 20-30° C. for approximately about 5 minutes-30 hours, preferably for 5 minutes-1 hour, and more preferably for approximately 5 minutes-10 minutes.

The quenching of the reaction can be performed by reducing the pH. Alternatively, it is also possible to directly move on to a purification step by e.g. HPLC without changing the pH.

When Thr was selected as the N-terminal of the peptide fragment, a residue of a threonine (Thr) derivative having an —SH group instead of Cys (or a threonine derivative having said —SH group protected by a disulfide bond etc.) can be introduced to the N-terminal of the peptide fragment. The peptide fragment having a threonine derivative introduced can be subjected to the above methylation reaction, cyanidation reaction, and intramolecular acyl translocation reaction after ligation in order to substitute the threonine derivative in said peptide fragment to threonine.

When introducing a sugar chain having a sialic acid to a peptide fragment, it is preferred that the carboxy group of the sialic acid on the sugar chain to be introduced employed is, e.g., a sialic acid-containing sugar chain protected by e.g. an aryl group including e.g. a benzyl (Bn) group, an alkyl group including e.g. an ethyl group (Et) or a methyl group (Me), and a phenacyl group having the side chain of the carbon forming the ring structure substituted by e.g. a diphenylmethyl group, a phenacyl group, an alkoxy group, or a nitro group. More specifically, e.g., a protecting group that protects the carboxy group of the sialic acid as represented by —COOBn, —COOEt, —COOMe, —COOCH(Ph)$_2$, —COOCH$_2$COPh, —COOCH$_2$PhOMe, —COOCH$_2$Ph(OMe)$_2$, —COOCH$_2$PhNO$_2$, or —COOCH$_2$Ph(NO$_2$)$_2$ is preferred. In this way, by protecting the carboxy group of the sialic acid with a benzyl group etc., it is possible to prevent the detachment of an acid-labile sialic acid. In particular, the detachment of the sialic acid from the sugar chain non-reducing terminal can be prevented also when performing the heat treatment described below. Moreover, the introduction of the protecting group to the carboxy group of the sialic acid will facilitate the separation and purification step by HPLC etc. in the manufacture step.

The protection reaction of the carboxy group of the sialic acid on the sugar chain can be performed by a method well-known to those skilled in the art. For example, the deprotection of the protecting group of the carboxy group of the sialic acid protected by a benzyl group, a diphenylmethyl group, or a phenacyl group can also be performed by a method well-known to those skilled in the art. For example, the deprotection reaction can be performed by hydrolysis under basic conditions, although not particularly limited to the following. The deprotection reaction may be performed generally at 0-50° C., preferably at 0-40° C., and further preferably at 0-30° C. The reaction time is preferably for approximately 5 minutes-5 hours in general. After completion of the reaction, it may be neutralized with a weak acid such as phosphoric or acetic acid, and then purified with a well-known method (such as high performance liquid column chromatography (HPLC)) as appropriate. The step of deprotecting the protecting group of the carboxy group of the sialic acid can be performed before or after the folding step.

Each step of the manufacture of interferon β shown above can be a one-pot synthesis. For example, when interferon β is manufactured by preparing multiple fragments and by multiple ligation steps, the multiple ligation steps can be a one-pot synthesis. Further, the reduction step of cysteine is necessary after linking the fragments, the multiple ligation steps as well as the subsequent reduction step of cysteine can also be a one-pot synthesis.

Further, the deprotection step of cysteine and the deprotection step of the sugar chain sialic acid which are necessary after the ligation step (such as the reduction step of cysteine if necessary) can also be a one-pot synthesis. For example, by allowing the first step ligation and the second step ligation described in Examples 2 and 3 in the present specification to be one-pot, it is possible to improve the yield by about 1.6-folds.

In this way, allowing the manufacture step to be one-pot is preferred since reduction of the time for the manufacture step and facilitation by elimination of the HPLC step can be attempted, and further the yield can be improved.

(Folding Step)

The glycosylated peptide fragment and the peptide fragment are bound by the above method, and a step of substituting the necessary amino acid, or a step of folding the glycosylated polypeptide having all the portions linked after the deprotection step can be included. Various well-known methods can be employed as the folding step, and can comprise, but is not limited to, e.g. dialysis in a folding buffer. The folding buffer is not limited, and can be, e.g., glutathione, cystine-cysteine, and a compound having a guanidine group such as guanidine or a salt thereof, and the pH can be 6.0-9.0. Dialysis can be performed multiple times, and the composition or pH of the folding buffer for each dialysis treatment may be identical or different.

More specifically, e.g., when the folding step is performed by three rounds of dialysis, the first dialysis can be performed in a solution comprising 8 M guanidine at pH 8.0-9.0 for 0.5-6 hours, the second dialysis condition can be performed in a solution comprising 2 M-4 M guanidine at pH 8.0-9.0 for 6-24 hours, and the third dialysis can be performed in a solution comprising 1 mM-20 mM acetic acid aqueous solution at pH 2.0-4.0 for 6-24 hours.

Moreover, when the folding buffer employed for the folding step comprises oxidized and reduced glutathione, it is preferred to vary the concentration ratio of the oxidized and reduced as appropriate depending on the type of sugar chain added to the polypeptide. For example, when the sugar chain is a disialo sugar chain, the ratio of the oxidized glutathione and the reduced glutathione comprised in the folding buffer is preferably in the range of 1:1-4:1, more preferably 1:1-3:1, and particularly preferably 2:1. Moreover, when the sugar chain is an asialo sugar chain, the ratio of the oxidized glutathione and the reduced glutathione is preferably in the range of 4:1-16:1, more preferably in the range of 6:1-10:1, and particularly preferably 8:1.

The formation of a disulfide bond at an unintended site or aggregation etc. can be suppressed by having the source material at a low concentration when dissolving the source material before folding.

Confirmation of the polypeptide folding can be achieved by any method that analyzes the polypeptide conformation, examples of which include, but are not limited to, the disulfide mapping method, the evaluation of binding to an antibody specific to the conformational epitope, and X-ray analysis.

(Heat Treatment)

Moreover, the glycosylated polypeptide manufactured by the above method can also be heat-treated. The heat treatment is preferably performed before the folding step. Moreover, when a sialic acid is present at the non-reducing terminal of the sugar chain in the glycosylated polypeptide, it is preferred that the heat treatment is performed with the carboxy group of the sialic acid protected with a benzyl group etc.

The heat treatment can be performed e.g. in a buffer solution comprising 6 M-10 M guanidine (Gn) at pH 3.5-7 under a temperature condition of 40° C.-60° C. for about 24-72 hours. Inactivation of an enveloped virus such as HIV, HCV, and HBV that has a suspicion of contamination can be achieved by heat treatment. In addition, the glycosylated polypeptide of the present invention can maintain its interferon β activity even when heat treatment is applied.

Moreover, since it is likely that the thiol group of cysteine will produce a side reaction by heat treatment, the thiol group of cysteine is preferably protected with an Acm group etc. in the heat treatment step.

(Activity)

The glycosylated polypeptide of the present invention has interferon β activity. An "interferon β activity" herein means having at least one activity among well-known activities such as immunomodulation action, antiviral activity, and antitumor activity.

For example, interferon β activity of the glycosylated polypeptide can be measured with e.g. the antitumor activity measurement test described in Example 12.

The antitumor activity measurement test can be examined by e.g. subcutaneously administering the subject glycosylated polypeptide to a mouse having a tumor and measuring the tumor volume over time.

The glycosylated polypeptide of the present invention can be provided as 90% or more pure. Moreover, the glycosylated polypeptide of the present invention more preferably is 95%, 97%, 98%, 99.0%, or 99.5% or more pure.

The purity of the glycosylated polypeptide herein refers to the value of the yield (g) excluding impurities such as unreacted material from the total yield (g) when preparing the glycosylated polypeptide of interest, divided by the total yield of when preparing the glycosylated polypeptide, multiplied by 100. More specifically, the total yield when preparing the glycosylated polypeptide refers to the yield of the glycosylated polypeptide fraction of interest obtained in the product separation step by HPLC after the folding step. Moreover, impurities etc. also include a glycosylated polypeptide that does not have identical sugar chain structure.

In a composition comprising the glycosylated polypeptide of the present invention, the purity of the glycosylated polypeptide refers to the purity of the glycosylated polypeptide per se that is comprised in the composition as one ingredient, separately from other ingredients comprised in the composition.

Accordingly, a high purity composition comprising a glycosylated polypeptide has constant quality, and is particularly preferred in the fields of pharmaceuticals manufacture or assays etc.

Moreover, the purity of the glycosylated polypeptide can be measured by HPLC analysis. The purity of the glycosylated polypeptide as measured by HPLC can be shown in HPLC area size %.

(Pharmaceutical Composition)

Next, a pharmaceutical composition containing the glycosylated polypeptide of the present invention as the active ingredient will be described.

The pharmaceutical composition containing the glycosylated polypeptide of the present invention as the active ingredient is effective for the treatment or prevention of interferon β-related diseases. As described above, various actions are known for interferon β, and these action-related diseases also vary. For example, examples of interferon β-related diseases include, e.g., a brain tumor such as glioblastoma, medulloblastoma, and astrocytoma, cutaneous malignant melanoma, chronic active hepatitis B, chronic hepatitis C, subacute sclerosing panencephalitis, compensated cirrhosis C, and multiple sclerosis. The pharmaceutical composition containing the glycosylated polypeptide of the present invention as the active ingredient is effective for the treatment or prevention of the above diseases.

Moreover, the administration subject of the pharmaceutical composition containing the glycosylated polypeptide of the present invention as the active ingredient means any individual of an organism, preferably an animal, further preferably a mammal, and further preferably a human individual.

The above pharmaceutical composition is one formulated into the form of an ordinary pharmaceutical composition with a diluent or an excipient such as a generally used filler, expander, binder, moisturizer, disintegrant, surfactant, and lubricant.

Examples of such pharmaceutical compositions include, e.g., tablets, pills, powders, liquids, suspensions, emulsions, granules, capsules, suppositories, inhalants, ophthalmic solutions, and injections.

The amount of the glycosylated polypeptide of the present invention contained in the pharmaceutical composition is not particularly limited and can be selected as appropriate from a broad range, but in general, 1-90% by weight of the glycosylated polypeptide of the present invention is preferably contained, and more preferably 1-70% by weight is contained in the pharmaceutical composition.

The pharmaceutical composition containing the glycosylated polypeptide of the present invention as the active ingredient can either further contain other active ingredients, or it can be employed in combination with a pharmaceutical composition containing other active ingredients. Moreover, the pharmaceutical composition containing the glycosylated polypeptide of the present invention as the active ingredient can either comprise the glycosylated polypeptide as a pharmaceutically acceptable salt, or further contain one or more different glycosylated polypeptides of the present invention as active ingredients. Moreover, it can also be employed in combination with the pharmaceutical composition containing one or more different glycosylated polypeptides of the present invention as the active ingredient. Moreover, Examples of other ingredients that can be contained in the pharmaceutical composition can include a pharmaceutically acceptable carrier known to those skilled in the art.

The method for administering the pharmaceutical composition according to the present invention is not particularly restricted, and administration is achieved with a method according to various drug formulations, age, sex, and the disease condition of the patient, and other conditions. The method of administration for tablets, pills, liquids, suspensions, emulsions, granules, and capsules include e.g. oral administration. Moreover, in case of injections, it can be intravenously, intramuscularly, intradermally, subcutaneously, or intraperitoneally administered alone or mixed with an ordinary fluid replacement such as glucose or amino acid. In case of suppositories, it is intrarectally administered. In case of ophthalmic solutions, it is applied to an eye tissue such as the conjuctival sac. In case of inhalants, it is applied to the bronchial tube or the lung.

The administration dose of the above pharmaceutical composition may be selected as appropriate according to usage, age, sex, and the disease extent of the patient, and other conditions, and for example can be an administration dose that will be 0.001-9 nmol of the glycosylated polypeptide of the present invention, preferably 0.01-0.2 nmol per 1 kg of body weight.

The administration frequency of the above pharmaceutical composition may be selected as appropriate according to usage, age, sex, and the disease extent of the patient, and other conditions, and 3 times/day, twice/day, once/day, and further at a less frequent administration frequency according to stability in blood thereof (such as once/week and once/month) may be selected. Preferably, the administration frequency of the above pharmaceutical composition is once or less per day.

The sugar chain added to the glycosylated polypeptide of the present invention is easily degraded by the metabolic system in the body. Moreover, in one aspect of the present invention, said sugar chain has a structure that is present as bound to a glycopeptide (or a glycoprotein) in vivo. Accordingly, the glycosylated polypeptide of the present invention and a pharmaceutical composition comprising said peptide as the active ingredient have advantages such as not showing side effects or antigenicity even when administered in vivo, and having less concern for losing drug effect due to allergic reactions or antibody production.

Further, the glycosylated polypeptide of the present invention can be stably and easily supplied in large amounts, and it is extremely useful with respect to providing pharmaceuticals having stable and high quality.

Moreover, the present invention also provides a method for treating or preventing an interferon β-related disease, characterized in administering an effective amount of the glycosylated polypeptide of the present invention.

The terms used herein are to be employed to describe particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having consistent meanings with the meanings herein and related technical fields, and shall not be construed as having idealized or excessively formal meanings.

The embodiments of the present invention may be described referring to schematic diagrams. In case of schematic diagrams, they may be exaggerated in presentation in order to allow clear description.

Terms such as first and second are employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The present invention will now be described in further detail referring to Examples. However, the present invention can be embodied by various aspects, and shall not be construed as being limited to the Examples described herein.

EXAMPLES

The following Examples exemplify a method of manufacturing the 1-166 amino acids in the amino acid sequence of interferon β divided into three fragments of peptide fragment A having amino acids at positions 1-67, glycopeptide fragment B having amino acids at positions 68-88, and peptide fragment C having amino acids at positions 89-166.

More specifically, a manufacturing method comprising the following steps is exemplified:

(I) A step of preparing peptide fragment A represented by the following formula (d), glycopeptide fragment B represented by the following formula (e), and peptide fragment C represented by the following formula (f).

[Chemical Formula 32]

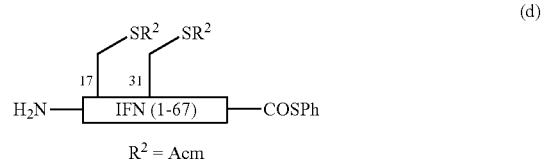

[Chemical Formula 33]

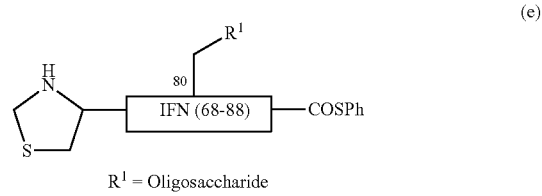

[Chemical Formula 34]

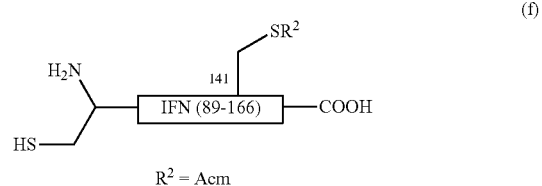

(II) A step of linking fragment B and fragment C by ligation to prepare fragment (B+C), and converting the thiazolidine-type cysteine at the N-terminal of fragment (B+C) into cysteine (see FIG. 1).

(III) A step of linking fragment A and fragment (B+C) by ligation to prepare fragment (A+B+C) (see FIG. 2).

(IV) A step of reducing the cysteine employed for ligation in fragment (A+B+C) into alanine (see FIG. 3).

(IV) A step of deprotecting the protecting group of cysteine (see FIG. 4).

In each fragment, the C-terminal used for linking by ligation is thioesterified, and the N-terminal used for linking by ligation has a cysteine. Moreover, in glycopeptide fragment B represented by the above formula (II), the N-terminal side cysteine is a thiazolidine-type in order to avoid a side reaction the ligation step at the C-terminal.

The N-terminal amino acid of the above fragments B and C is alanine at positions 68 and 89 in interferon β. However, since cysteine is required for ligation, in the above manufacturing example, the fragments were synthesized with cysteine instead of alanine at the N-terminal amino acid of fragments B and C, and then reduced to alanine after ligation.

Moreover, for example, fragment (A+B) herein shows fragment A and fragment B linked together.

Example 1 Synthesis of Each Peptide Fragment (1-1. Synthesis of Peptide Fragment A-SPh)

Amino-PEGA resin (from Merck) (100 µmol) was placed into a column for solid phase synthesis, sufficiently washed with methylene chloride (DCM) and DMF, and then sufficiently swelled with DMF. 4-hydroxymethyl-3-methoxyphenoxy butyric acid (HMPB) (0.25 mmol), TBTU (0.25 mmol), and N-ethylmorpholine (0.25 mmol) were dissolved in DMF (2 ml) and placed in the column, and this was stirred at room temperature for 4 hours. The resin was sufficiently washed with DMF and DCM, the HMPB-PEGA resin was obtained, and this was employed as the solid phase for solid phase synthesis.

Fmoc-Phe (0.50 mmol), MSNT (0.50 mmol), and N-methylimidazole (0.375 mmol) were dissolved in DCM (2 ml), placed into the column for solid phase synthesis, and stirred at 25° C. for 4 hours.

After stirring, the resin was washed with DCM and DMF. The Fmoc group was treated with 20% piperidine/DMF solution (2 ml) for 15 minutes for deprotection. After washing with DMF, the amino acids were sequentially condensed with the method shown below for subsequent peptide chain elongation.

The amino acid having the amino group protected with an Fmoc group was dissolved in N-methylpyrrolidone (NMP) (1 ml), 0.45 M HCTU.HOBT/NMP (0.4 mmol) was added, this was added to the column for solid phase synthesis, and subsequently 0.9 M DIPEA/NMP (0.8 mmol) was added to the column for solid phase synthesis. After stirring at room temperature for 20 minutes, the resin was washed with DCM and DMF, the Fmoc group was treated with 20% piperidine/DMF solution (2 ml) for 15 minutes for deprotection. This operation was repeated, and amino acids protected with Fmoc and Boc groups (0.5 mmol) were used to sequentially condense the amino acids.

As amino acids protected with Fmoc and Boc groups, Fmoc-Phe, Fmoc-Ile, Fmoc-Asn(Trt), Fmoc-Gln(Trt), Fmoc-Leu, Fmoc-Met, Fmoc-Glu(OtBu), Fmoc-Tyr(tBu), Fmoc-Ile, Fmoc-Leu-Thr(ψMe, MePro), Fmoc-Ala, Fmoc-Ala, Fmoc-Asp(OtBu), Fmoc-Glu(OtBu), Fmoc-Lys(Boc), Fmoc-Gln(Trt), Fmoc-Phe, Fmoc-Gln(Trt), Fmoc-Gln(Trt), Fmoc-Leu, Fmoc-Gln(Trt), Fmoc-Lys(Boc), Fmoc-Ile, Fmoc-Glu(OtBu), Fmoc-Glu(OtBu), Fmoc-Pro, Fmoc-Ile, Fmoc-Asp(OtBu), Fmoc-Phe, Fmoc-Asn(Trt), Fmoc-Met, Fmoc-Arg(Pbf), Fmoc-Asp(OtBu), Fmoc-Lys(Boc), Fmoc-Leu, Fmoc-Cys(Acm), Fmoc-Tyr(tBu), Fmoc-Glu(OtBu), Fmoc-Leu, Fmoc-Arg(Pbf), Fmoc-Gly, Fmoc-Asn(Trt), Fmoc-Leu, Fmoc-Gln(Trt), Fmoc-Trp(Boc), Fmoc-Leu, Fmoc-Leu, Fmoc-Lys(Boc), Fmoc-Gln(Trt), Fmoc-Cys (Acm), Fmoc-Gln(Trt), Fmoc-Phe, Fmoc-Asn(Trt), Fmoc-Ser(tBu)-Ser(ψMe, MePro), Fmoc-Arg(Pbf), Fmoc-Gln (Trt), Fmoc-Leu, Fmoc-Phe, Fmoc-Gly, Fmoc-Leu, Fmoc-Leu, Fmoc-Asn(Trt), Fmoc-Tyr(tBu), Fmoc-Ser(tBu), and Boc-Met were sequentially employed and linked to the solid phase resin. As a result, a 67-residue peptide (1) of Phe-Ile-Asn(Trt)-Gln(Trt)-Leu-Met-Glu(OtBu)-Tyr(tBu)-Ile-Thr (ψMe, MePro)-Leu-Ala-Ala-Asp(OtBu)-Glu(OtBu)-Lys (Boc)-Gln(Trt)-Phe-Gln(Trt)-Gln(Trt)-Leu-Gln(Trt)-Lys (Boc)-Ile-Glu(OtBu)-Glu(OtBu)-Pro-Ile-Asp(OtBu)-Phe-Asn (Trt)-Met-Arg(Pbf)-Asp(OtBu)-Lys(Boc)-Leu-Cys (Acm)-Tyr(tBu)-Glu(OtBu)-Leu-Arg(Pbf)-Gly-Asn(Trt)-Leu-Gln(Trt)-Trp(Boc)-Leu-Leu-Lys(Boc)-Gln(Trt)-Cys (Acm)-Gln(Trt)-Phe-Asn(Trt)-Ser(ψMe, MePro)-Ser(tBu)-Arg(Pbf)-Gln(Trt)-Leu-Phe-Gly-Leu-Leu-Asn(Trt)-Tyr (tBu)-Ser(tBu)-Met-BocNH (SEQ ID NO. 2) was obtained on the solid phase resin.

After washing the peptide (1) obtained above with DCM and DMF, a mixed solution of trifluoroethanol and acetic acid (1:1) was added until the resin was sufficiently soaked, and this was stirred for 18 hours at room temperature to cleave between the resin and peptide 1. The cleaved resin was filtered off, and the reaction solution was concentrated under reduced pressure. The residue obtained was concentrated, and a peptide having the amino acid side chain protected (1) (SEQ ID NO. 3): Phe-Ile-Asn(Trt)-Gln(Trt)-Leu-Met-Glu(OtBu)-Tyr(tBu)-Ile-Thr(ψMe, MePro)-Leu-Ala-Ala-Asp(OtBu)-Glu(OtBu)-Lys(Boc)-Gln(Trt)-Phe-Gln(Trt)-Gln(Trt)-Leu-Gln(Trt)-Lys(Boc)-Ile-Glu(OtBu)-Glu(OtBu)-Pro-Ile- Asp(OtBu)-Phe-Asn (Trt)-Met-Arg (Pbf)-Asp(OtBu)-Lys(Boc)-Leu-Cys(Acm)-Tyr(tBu)-Glu (OtBu)-Leu-Arg(Pbf)-Gly-Asn(Trt)-Leu-Gln(Trt)-Trp (Boc)-Leu-Leu-Lys(Boc)-Gln(Trt)-Cys(Acm)-Gln(Trt)-Phe-Asn(Trt)-Ser(ψMe, MePro)-Ser(tBu)-Arg(Pbf)-Gln (Trt)-Leu-Phe-Gly-Leu-Leu-Asn(Trt)-Tyr(tBu)-Ser(tBu)-Met-BocNH was obtained.

One hundred µmol equivalents of peptide (1) having a 67-residue amino acid and having the amino acid side chain protected was transferred to a recovery flask, dissolved in DMF (3.0 mL), and then cooled to −15° C.--−20° C. under nitrogen atmosphere. To this was added thiophenol (308 µl, 3.0 mmol), and then PyBOP (260.0 mg, 0.50 mmol) then DIPEA (85.0 µl, 0.5 mmol) were added. After stirring at −15° C.--−20° C. for 2 hours, trifluoroacetic acid (0.1 mL) was added, and this was gradually restored to room temperature. After being restored to room temperature, the reaction solution was concentrated under reduced pressure. To the residue obtained was added trifluoroacetic acid:water: TIPS (=95:2.5:2.5), and this was stirred at room temperature. After 2 hours, this solution was added again to the diethyl ether (150 ml) for precipitation, and then centrifuged in order to remove the solution portion to obtain the residue comprising the peptide thioester. This residue obtained was purified with HPLC [column: SHISEIDO proteonavi (C4, 5 µm), φ20×250 mm, flow rate: 7.0 mL/min, eluting solution A: 0.1% TFA water, B: 0.09% TFA/10% water/90% AN, gradient A:B=55:45→55:45 (5 minutes)→25:75 (35 minutes)→5:95 (36 minutes), isocratic elution for 5 min and then linear gradient], and peptide fragment A-SPh (1) having a thiophenyl ester at the C-terminal (SEQ ID NO. 4): H2N-Met-Ser-Tyr-Asn-Leu-Leu-Gly-Phe-Leu-Gln-Arg-Ser-Ser-Asn-Phe-Gln-Cys(Acm)-Gln-Lys-Leu-Leu-Trp-Gln-Leu-Asn-Gly-Arg-Leu-Glu-Tyr-Cys(Acm)-Leu-Lys-Asp-Arg-Met-Asn-Phe-Asp-Ile-Pro-Glu-Glu-Ile-Lys-Gln-Leu-Gln-Gln-Phe-Gn-Lys-Gu-Asp-Ala-Ala-Leu-Thr-Ile-Tyr-Glu-Met-Leu-Gln-Asn-Ile-Phe-SPh was obtained.

ESI-MS: Calcd for $C_{378}H_{581}N_{97}O_{108}S_6$: $[M+4H]^{4+}$ 2094.16, $[M+5H]^{5+}$ 1675.53, $[M+6H]^{6+}$ 1396.44, found. 2094.06, 1675.43, 1396.17.

(1-2. Synthesis of Disialo Sugar Chain Attached Peptide Fragment B—SPh)

Amino-PEGA resin (from Merck) (100 μmol) was placed into a column for solid phase synthesis, sufficiently washed with methylene chloride (DCM) and DMF, and then sufficiently swelled with DMF. 4-hydroxymethyl-3-methoxyphenoxy butyric acid (HMPB) (0.25 mmol), TBTU (0.25 mmol), and N-ethylmorpholine (0.25 mmol) were dissolved in DMF (2 ml) and placed in the column, and this was stirred at room temperature for 4 hours. The resin was sufficiently washed with DMF and DCM, the HMPB-PEGA resin was obtained, and this was employed as the solid phase for solid phase synthesis.

Fmoc-Leu (0.50 mmol), MSNT (0.50 mmol), and N-methylimidazole (0.375 mmol) were dissolved in DCM (2 ml), placed into the column for solid phase synthesis, and stirred at 25° C. for 4 hours.

After stirring, the resin was washed with DCM and DMF. The Fmoc group was treated with 20% piperidine/DMF solution (2 ml) for 15 minutes for deprotection. After washing with DMF, the amino acids were sequentially condensed with the method shown below for subsequent peptide chain elongation.

The amino acid having the amino group protected with an Fmoc group was dissolved in N-methylpyrrolidone (NMP) (1 ml), 0.45 M HCTU-HOBT/NMP (0.4 mmol) was added, this was added to the column for solid phase synthesis, and subsequently 0.9 M DIPEA/NMP (0.8 mmol) was added to the column for solid phase synthesis. After stirring at room temperature for 20 minutes, the resin was washed with DCM and DMF, the Fmoc group was treated with 20% piperidine/DMF solution (2 ml) for 15 minutes for deprotection. This operation was repeated, and amino acids protected with an Fmoc group (0.5 mmol) were used to sequentially condense the amino acids.

Fmoc-Leu, Fmoc-Leu, Fmoc-Asn(Trt), Fmoc-Glu(OtBu), Fmoc-Val, Fmoc-Ile, Fmoc-Thr(tBu), and Fmoc-Glu(OtBu) were sequentially employed as amino acids protected with an Fmoc group, and an 8-residue peptide was obtained on the Leu-Leu-Asn(Trt)-Glu(OtBu)-Val-Ile-Thr(tBu)-Glu(OtBu) (SEQ ID NO: 51). To this 8-residue peptide, the Fmoc group was treated with 20% piperidine/DMF solution (2 ml) for 15 minutes for deprotection. After washing with DMF, dibenzyl disialo sugar chain asparagine (g) (547.8 mg, 200 μmol) and DEPBT (59.9 mg, 200 μmol) were dissolved in DMF/DMSO (1:1 mixed solution, 3.33 ml) in the centrifuge tube, placed into the column for solid phase synthesis, DIPEA (52.3 μl, 300 μmoL) was added, and this was stirred at room temperature for 18 hours. Washing with DMF and DCM yielded a 9-residue sugar chain peptide of Leu-Leu-Asn(Trt)-Glu(OtBu)-Val-Ile-Thr(tBu)-Glu(OtBu)-Asn (dibenzyl-disialooligosaccharide)-FmocNH (SEQ ID NO. 5) on the solid phase.

[Chemical Formula 35]

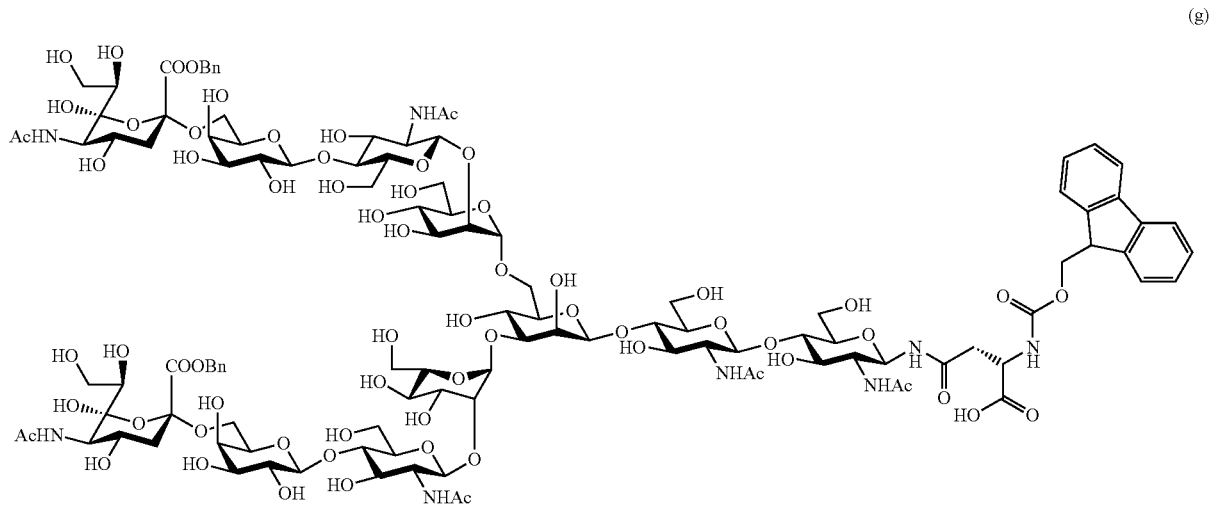

(g)

For subsequent glycopeptide chain elongation, the lipophilic protecting group of the 9-residue sugar chain peptide on the solid phase resin obtained above was deprotected with 20% piperidine/DMF solution (2 ml), and then amino acids were sequentially condensed with the method shown below.

The amino acid having the amino acid protected with an Fmoc group as well as HOBt (67.6 mg, 0.50 mmol) and DIPCI (73.1 μl, 0.475 mmol) were dissolved in DMF (6.3 ml), activated for 15 minutes, and then placed into the column for sold phase synthesis. After stirring at room temperature for 1 hour, the Fmoc group was treated with 20% piperidine/DMF solution (2 ml) for 20 minutes for deprotection. This operation was repeated to sequentially condense the amino acids. As amino acids protected with Fmoc and Boc groups, Fmoc-Trp(Boc), Fmoc-Gly, Fmoc-Thr(tBu), Fmoc-Ser(tBu)-Ser(ψMe, MePro), Fmoc-Ser(tBu), Fmoc-Asp(OtBu), Fmoc-Gln(Trt), Fmoc-Arg(Pbf), Fmoc-Phe, Fmoc-Ile, and Boc-L-thiazolidine-4-carboxylic acid were sequentially employed and linked to the solid phase resin. As a result, a 21-residue glycosylated peptide fragment (2) of Leu-Leu-Asn(Trt)-Glu(OtBu)-Val-Ile-Thr(tBu)-Glu(OtBu)-Asn(dibenzyl-disialooligosaccharide)-Trp(Boc)-Gly-Thr(tBu)-Ser(ψMe, MePro)-Ser(tBu)-Ser(tBu)-Asp(OtBu)-Gln(Trt)-Arg(Pbf)-Phe-Ile-Thz-BocN (SEQ ID NO. 6) was obtained on the solid phase resin.

Then, after washing with DCM and DMF, a mixed solution of trifluoroethanol and acetic acid (1:1) was added until the resin was sufficiently soaked, and this was stirred for 18 hours at room temperature to cleave between the resin and the glycosylated peptide fragment. The cleaved resin was filtered off, and the reaction solution was concentrated under reduced pressure. The residue obtained was concentrated, and a 21-residue sugar chain peptide (2) having the amino acid side chain protected (SEQ ID NO. 7): Leu-Leu-Asn(Trt)-Glu(OtBu)-Val-Ile-Thr(tBu)-Glu(OtBu)-Asn(dibenzyl-disialooligosaccharide)-Trp(Boc)-Gly-Thr(tBu)-Ser(ψMe, MePro)-Ser(tBu)-Ser(tBu)-Asp(OtBu)-Gln(Trt)-Arg(Pbf)-Phe-Ile-Thz-BocN was obtained.

One hundred μmol equivalents of glycosylated peptide fragment (2) having a 21-residue amino acid and having the amino acid side chain protected was transferred to a recovery flask, dissolved in DMF (3.0 mL), and then cooled to −15° C.--20° C. under nitrogen atmosphere. To this was added thiophenol (308 μl, 3.0 mmol), and then PyBOP (260.0 mg, 0.50 mmol) then DIPEA (85.0 μl, 0.5 mmol) were added. After stirring at −15° C.--20° C. for 2 hours, trifluoroacetic acid (0.1 mL) was added, and this was gradually restored to room temperature. After being restored to room temperature, the reaction solution was concentrated under reduced pressure. To the residue obtained was added trifluoroacetic acid:water:TIPS (=95:2.5:2.5), and this was stirred at room temperature. After 2 hours, this solution was added to the diethyl ether (150 ml) for precipitation, and then centrifuged in order to remove the solution portion to obtain the residue comprising the glycosylated peptide thioester. This residue obtained was purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, gradient A:B=65:35→52:48 (26 minutes)→5:95 (28 minutes), linear gradient], and disialo sugar chain attached peptide fragment B—SPh (2) having a thiophenyl ester at the C-terminal (SEQ ID NO. 8): HN-Thz-Ile-Phe-Arg-Gln-Asp-Ser-Ser-Ser-Thr-Gly-Trp-Asn(dibenzyl-disialooligosaccharide)-Glu-Thr-Ile-Val-Glu-Asn-Leu-Leu-SPh was obtained.

ESI-MS: Calcd for $C_{209}H_{314}N_{34}O_{96}S_2$: $[M+3H]^{3+}$ 1635.34, $[M+4H]^{4+}$ 1226.76, found. 1635.04, 1226.51.

(1-3. Synthesis of Asialo Glycosylated Peptide Fragment B—SPh)

Amino-PEGA resin (from Merck) (100 μmol) was placed into a column for solid phase synthesis, sufficiently washed with methylene chloride (DCM) and DMF, and then sufficiently swelled with DMF. 4-hydroxymethyl-3-methoxyphenoxy butyric acid (HMPB) (0.25 mmol), TBTU (0.25 mmol), and N-ethylmorpholine (0.25 mmol) were dissolved in DMF (2 ml) and placed in the column, and this was stirred at room temperature for 4 hours. The resin was sufficiently washed with DMF and DCM, the HMPB-PEGA resin was obtained, and this was employed as the solid phase for solid phase synthesis.

Fmoc-Leu (0.50 mmol), MSNT (0.50 mmol), and N-methylimidazole (0.375 mmol) were dissolved in DCM (2 ml), placed into the column for solid phase synthesis, and stirred at 25° C. for 4 hours.

After stirring, the resin was washed with DCM and DMF. The Fmoc group was treated with 20% piperidine/DMF solution (2 ml) for 15 minutes for deprotection. After washing with DMF, the amino acids were sequentially condensed with the method shown below for subsequent peptide chain elongation.

The amino acid having the amino group protected with an Fmoc group was dissolved in N-methylpyrrolidone (NMP) (1 ml), 0.45 M HCTU.HOBT/NMP (0.4 mmol) was added, this was added to the column for solid phase synthesis, and subsequently 0.9 M DIPEA/NMP (0.8 mmol) was added to the column for solid phase synthesis. After stirring at room temperature for 20 minutes, the resin was washed with DCM and DMF, the Fmoc group was treated with 20% piperidine/DMF solution (2 ml) for 15 minutes for deprotection. This operation was repeated, and amino acids protected with an Fmoc group (0.5 mmol) were used to sequentially condense the amino acids.

As amino acids protected with an Fmoc group, Fmoc-Leu, Fmoc-Leu, Fmoc-Asn(Trt), Fmoc-Glu(OtBu), Fmoc-Val, Fmoc-Ille, Fmoc-Thr(tBu), and Fmoc-Glu(OtBu) were sequentially employed and linked on the solid phase resin. As a result, an 8-residue peptide fragment of Leu-Leu-Asn(Trt)-Glu(OtBu)-Val-Ile-Thr(tBu)-Glu(OtBu) (SEQ ID NO. 9) was obtained on the solid phase resin. The Fmoc group of this 8-residue peptide fragment was treated with 20% piperidine/DMF solution (1 ml) for 15 minutes for deprotection. After washing with DMF, asialo sugar chain asparagine derivative (h) (547.8 mg, 200 μmol) and DEPBT (59.9 mg, 200 μmol) were dissolved in DMF/DMSO (1:1 mixed solution, 3.33 ml) in the centrifuge tube, placed into the column for solid phase synthesis, DIPEA (52.3 μl, 300 μmoL) was added, and this was stirred at room temperature for 18 hours. Washing with DMF and DCM yielded a 9-residue glycosylated peptide fragment of Leu-Leu-Asn(Trt)-Glu(OtBu)-Val-Ile-Thr(tBu)-Glu(OtBu)-Asn(Asialooligosaccharide)-FmocNH (SEQ ID NO. 10) on the solid phase.

[Chemical Formula 36]

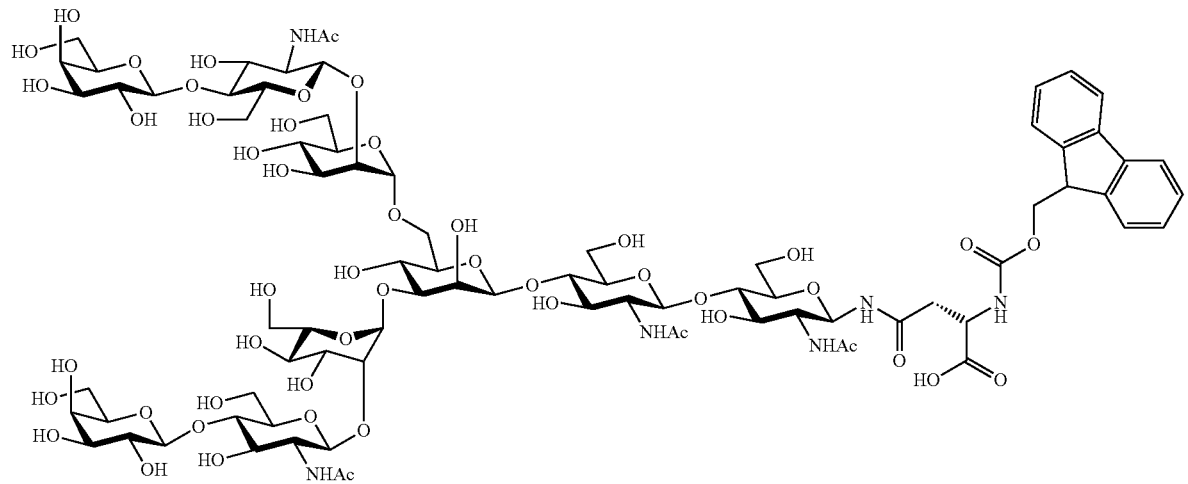

(h)

For subsequent glycopeptide chain elongation, the lipophilic protecting group of the 9-residue sugar chain peptide on the solid phase resin obtained above was deprotected with 20% piperidine/DMF solution (2 ml), and then amino acids were sequentially condensed with the method shown below. The amino acid having the amino acid protected with an Fmoc group as well as HOBt (67.6 mg, 0.50 mmol) and DIPCI (73.1 μl, 0.475 mmol) were dissolved in DMF (6.3 ml), activated for 15 minutes, and then placed into the column for solid phase synthesis. After stirring at room temperature for 1 hour, the Fmoc group was treated with 20% piperidine/DMF solution (2 ml) for 20 minutes for deprotection. This operation was repeated to sequentially condense the amino acids. As amino acids protected with Fmoc and Boc groups, Fmoc-Trp(Boc), Fmoc-Gly, Fmoc-Thr(tBu), Fmoc-Ser(tBu)-Ser(ψMe, MePro), Fmoc-Ser(tBu), Fmoc-Asp(OtBu), Fmoc-Gln(Trt), Fmoc-Arg(Pbf), Fmoc-Phe, Fmoc-Ile, and Boc-L-thiazolidine-4-carboxylic acid were sequentially employed and linked on the solid phase resin. As a result, a 21-residue glycosylated peptide fragment (3) having the amino acid side chain protected, Leu-Leu-Asn(Trt)-Glu(OtBu)-Val-Ile-Thr(tBu)-Glu(OtBu)-Asn(Asialooligosaccharide)-Trp(Boc)-Gly-Thr(tBu)-Ser(ψMe, MePro)-Ser(tBu)-Ser(tBu)-Asp(OtBu)-Gln(Trt)-Arg(Pbf)-Phe-Ile-Thz-BocN (SEQ ID NO. 11) was obtained on the solid phase resin.

After washing with DCM and DMF, a mixed solution of trifluoroethanol and acetic acid (1:1) was added until the resin was sufficiently soaked, and this was stirred for 18 hours at room temperature to cleave between the resin and glycosylated peptide fragment (3). The cleaved resin was filtered off, and the reaction solution was concentrated under reduced pressure. The residue obtained was concentrated, and glycosylated peptide fragment (3) having the amino acid side chain protected (SEQ ID NO. 12): Leu-Leu-Asn(Trt)-Glu(OtBu)-Val-Ile-Thr(tBu)-Glu(OtBu)-Asn(Asialooligosaccharide)-Trp(Boc)-Gly-Thr(tBu)-Ser(ψMe, MePro)-Ser(tBu)-Ser(tBu)-Asp(OtBu)-Gln(Trt)-Arg(Pbf)-Phe-Ile-Thz-BocN was obtained.

One hundred μmol equivalents of a 21-residue glycosylated peptide fragment (3) having the amino acid side chain protected was transferred to a recovery flask, dissolved in DMF (3.0 mL), and then cooled to −15° C.--20° C. under nitrogen atmosphere. To this was added thiophenol (308 μl, 3.0 mmol), and then PyBOP (260.0 mg, 0.50 mmol) then DIPEA (85.0 μl, 0.5 mmol) were added. After stirring at −15° C.--20° C. for 2 hours, trifluoroacetic acid (0.1 mL) was added, and this was gradually restored to room temperature. After being restored to room temperature, the reaction solution was concentrated under reduced pressure. To the residue obtained was added trifluoroacetic acid:water:TIPS (=95:2.5:2.5), and this was stirred at room temperature. After 2 hours, this solution was added again to the diethyl ether (150 ml) for precipitation, and then centrifuged in order to remove the solution portion to obtain the residue comprising the glycosylated peptide thioester. This residue obtained was purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, gradient A:B=65:35→52:48 (26 minutes)→5:95 (28 minutes), linear gradient], and asialo glycosylated peptide fragment B—SPh (3) having a thiophenyl ester at the C-terminal (SEQ ID NO. 13): HN-Thz-Ile-Phe-Arg-Gln-Asp-Ser-Ser-Ser-Thr-Gly-Trp-Asn(Asialooligosaccharide)-Glu-Thr-Ile-Val-Glu-Asn-Leu-Leu-SPh was obtained.

ESI-MS: Calcd for $C_{173}H_{28}N_{32}O_{80}S_2$: $[M+3H]^{3+}$ 1381.09, $[M+4H]^{4+}$ 1036.07, found. 1380.90, 1035.92.

(1-4. Synthesis of Peptide Fragment C)

Amino-PEGA resin (from Merck) (100 μmol) was placed into a column for solid phase synthesis, sufficiently washed with methylene chloride (DCM) and DMF, and then sufficiently swelled with DMF. 4-hydroxymethyl-3-methoxyphenoxy butyric acid (HMPB) (0.25 mmol), TBTU (0.25 mmol), and N-ethylmorpholine (0.25 mmol) were dissolved in DMF (2 ml) and placed in the column, and this was stirred at room temperature for 4 hours. The resin was sufficiently washed with DMF and DCM, the HMPB-PEGA resin was obtained, and this was employed as the solid phase for solid phase synthesis.

Fmoc-Asn(Trt) (0.50 mmol), MSNT (0.50 mmol), and N-methylimidazole (0.375 mmol) were dissolved in DCM (2 ml), placed into the column for solid phase synthesis, and stirred at 25° C. for 4 hours.

After stirring, the resin was washed with DCM and DMF. The Fmoc group was treated with 20% piperidine/DMF solution (2 ml) for 15 minutes for deprotection. After washing with DMF, the amino acids were sequentially condensed with the method shown below for subsequent peptide chain elongation.

The amino acid having the amino group protected with an Fmoc group was dissolved in N-methylpyrrolidone (NMP) (1 ml), 0.45 M HCTU-HOBT/NMP (0.4 mmol) was added, this was added to the column for solid phase synthesis, and subsequently 0.9 M DIPEA/NMP (0.8 mmol) was added to the column for solid phase synthesis. After stirring at room temperature for 20 minutes, the resin was washed with DCM and DMF, the Fmoc group was treated with 20% piperidine/DMF solution (2 ml) for 15 minutes for deprotection. This operation was repeated, and amino acids protected with an Fmoc group (0.5 mmol) were used to sequentially condense the amino acids. As amino acids protected with Fmoc and Boc groups, Fmoc-Asn(Trt), Fmoc-Arg(Pbf), Fmoc-Leu, Fmoc-Tyr(tBu), Fmoc-Gly, Fmoc-Thr(tBu), Fmoc-Leu, Fmoc-Arg(Pbf), Fmoc-Asn(Trt), Fmoc-Ile, Fmoc-Phe, Fmoc-Tyr(tBu), Fmoc-Phe, Fmoc-Asn(Trt), Fmoc-Arg(Pbf), Fmoc-Leu, Fmoc-Ile, Fmoc-Glu(OtBu), Fmoc-Val, Fmoc-Arg(Pbf), Fmoc-Val, Fmoc-Ile, Fmoc-Thr(tBu), Fmoc-Trp(Boc), Fmoc-Ala, Fmoc-Cys(Acm), Fmoc-His(Trt), Fmoc-Tyr(tBu)-Ser(ψMe, MePro), Fmoc-Glu(OtBu), Fmoc-Lys(Boc), Fmoc-Ala, Fmoc-Lys(Boc), Fmoc-Leu, Fmoc-Tyr(tBu), Fmoc-His(Trt), Fmoc-Leu, Fmoc-Ile, Fmoc-Arg(Pbf), Fmoc-Gly, Fmoc-Tyr(tBu), Fmoc-Tyr(tBu), Fmoc-Arg(Pbf), Fmoc-Lys(Boc), Fmoc-Leu, Fmoc-His(Trt), Fmoc-Leu, Fmoc-Ser(tBu)-Ser(ψMe, MePro), Fmoc-Met, Fmoc-Leu, Fmoc-Lys(Boc), Fmoc-Gly, Fmoc-Arg(Pbf), Fmoc-Phe-Thr(ψMe, MePro), Fmoc-Asp(OtBu), Fmoc-Glu(OtBu), Fmoc-Lys(Boc), Fmoc-Glu(OtBu), Fmoc-Leu, Fmoc-Lys(Boc), Fmoc-Glu(OtBu), Fmoc-Glu(OtBu), Fmoc-Leu, Fmoc-Val, Fmoc-Lys(Boc)-Thr(ψMe, MePro), Fmoc-Leu, Fmoc-His(Trt), Fmoc-Asn(Trt), Fmoc-Ile, Fmoc-Gln(Trt), Fmoc-His(Trt), Fmoc-Tyr(tBu), Fmoc-Val, Fmoc-Asn(Trt), and Boc-Cys(Trt) were sequentially employed and linked on the solid phase resin. As a result, a 78-residue peptide fragment (4) of Asn(Trt)-Arg(Pbf)-Leu-Tyr(tBu)-Gly-Thr(tBu)-Leu-Arg(Pbf)-Asn(Phe-Tyr(tBu)-Phe-Asn(Trt)-Arg(Pbf)-Leu-Ile-Glu(OtBu)-Val-Arg(Pbf)-Val-Ile-Thr(tBu)-Trp(Boc)-Ala-Cys(Acm)-His(Trt)-Ser(ψMe, MePro)-Tyr(tBu)-Glu(OtBu)-Lys(Boc)-Ala-Lys(Boc)-Leu-Tyr(tBu)-His(Trt)-Leu-Ile-Arg(Pbf)-Gly-Tyr(tBu)-Tyr(tBu)-Arg(Pbf)-Lys(Boc)-Leu-His(Trt)-Leu-Ser(ψMe, MePro)-Ser(tBu)-Met-Leu-Lys(Boc)-Gly-Arg(Pbf)-Thr(ψMe, MePro)-Phe-Asp(OtBu)-Glu(OtBu)-Lys(Boc)-

Glu(OtBu)-Leu-Lys(Boc)-Glu(OtBu)-Glu(OtBu)-Leu-Val-Thr(ψMe, MePro)-Lys(Boc)-Leu-His(Trt)-Asn(Trt)-Ile-Gln(Trt)-His(Trt)-Tyr(tBu)-Val-Asn(Trt)-Cys(Trt)-BocNH (SEQ ID NO. 14) was obtained on the solid phase resin.

To peptide fragment (4) obtained above was added trifluoroacetic acid:water:TIPS (=95:2.5:2.5), and this was stirred at room temperature for 3.5 hours to cleave between the resin and peptide fragment (4). Then, this was added to the diethyl ether (150 ml) for precipitation, and then subjected to a centrifugal separation operation to separate the precipitate comprising peptide fragment (4) of interest and the solution portion. Then, after removing the solution portion, the target substance was confirmed with HPLC, and then purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, gradient A:B=65:35→65:35 (5 minutes)→30:70 (35 minutes)→5:95 (45 minutes), isocratic elution for 5 min and then linear gradient] to obtain peptide fragment C (4) of interest (SEQ ID NO. 15): H₂N-Cys-Asn-Val-Tyr-His-Gln-Ile-Asn-His-Leu-Lys-Thr-Val-Leu-Glu-Glu-Lys-Leu-Glu-Lys-Glu-Asp-Phe-Thr-Arg-Gly-Lys-Leu-Met-Ser-Ser-Leu-His-Leu-Lys-Arg-Tyr-Tyr-Gly-Arg-Ile-Leu-His-Tyr-Leu-Lys- Ala-Lys-Glu-Tyr-Ser-His-Cys(Acm)-Ala-Trp-Thr-Ile-Val-Arg-Val-Glu-Ile-Leu-Arg-Asn-Phe-Tyr-Phe-Ile-Asn-Arg-Leu-Thr-Gly-Tyr-Leu-Arg-Asn.

ESI-MS: Calcd for $C_{441}H_{688}N_{124}O_{114}S_3$: $[M+8H]^{8+}$ 1206.89, $[M+9H]^{9+}$ 1072.90, $[M+10H]^{10+}$ 965.71, $[M+11H]^{11+}$ 804.93, found. 1206.85, 1072.87, 965.58, 877.90, 804.90.

Example 2 Synthesis of Asialo IFN-β

Active IFN-3 having an asialo sugar chain was synthesized in a total of 5 steps shown below.

(2-1. First Step: Linking of Asialo Glycosylated Peptide Fragment B and Peptide Fragment C)

Two types of fragments, a 21-residue asialo glycosylated peptide fragment B with a thiophenyl ester C-terminal (3) (1.8 mg) and a 78-residue peptide fragment C (4) (2.5 mg) were placed in the same recovery flask, dissolved in a buffer solution at pH 7.2 (0.26 ml) (prepared with 8 M guanidine hydrochloride solution, 0.2 mM phosphoric acid solution, and 20 mM Tris-carboxyethyl phosphine solution (TCEP solution)). Thiophenol (7.8 μl) was then added and reacted at room temperature. After 24 hours, the reaction was confirmed with HPLC, then to the reaction solution was added 0.2 M methoxyamine solution (0.39 ml) (prepared by adding 20 mM TCEP solution to 0.2 M methoxyamine solution), and this was reacted at room temperature. After 12 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, and the filtrate portion comprising the glycopeptide fragment was purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, gradient A:B=65:35→65:35 (5 minutes)→30:70 (35 minutes)→5:95 (45 minutes), isocratic elution for 5 min and then linear gradient] to obtain peptide fragment (11) of interest having an asialo sugar chain at the position corresponding to position 80 of interferon β (SEQ ID NO. 16) (FIGS. 5 and 6).

ESI-MS: Calcd for $C_{607}H_{950}N_{156}O_{194}S_4$: $[M+10H]^{10+}$ 1367.52, $[M+11H]^{11+}$ 1243.29, $[M+12H]^{12+}$ 1139.77, $[M+13H]^{13+}$ 1052.17, $[M+14H]^{14+}$ 977.09, $[M+15H]^{15+}$ 912.02, $[M+16H]^{16+}$ 855.08, $[M+17H]^{17+}$ 804.84, $[M+18H]^{18+}$ 760.18, found. 1367.64, 1243.33, 1139.80, 1052.20, 977.10, 912.03, 855.09, 804.84, 760.18

(2-2. Second Step: Linking of Peptide Fragment a and Asialo Glycosylated Peptide Fragment (B+C))

Two types of fragments, the 67-residue peptide with a thiophenyl ester C-terminal (1) obtained in the above first step (2.3 mg) and peptide fragment (11) of interest having an asialo sugar chain at the position corresponding to position 80 of interferon β (asialo glycosylated peptide fragment (B+C)) (68-166) (1.9 mg) were placed in the same recovery flask, dissolved in a buffer solution at pH 7.2 (0.14 ml) (prepared with 8 M guanidine hydrochloride solution, 0.2 mM phosphoric acid solution, and 20 mM TCEP solution). Thiophenol (4.2 μl) was then added and reacted at room temperature. After 24 hours, the reaction was confirmed with HPLC, sodium mercaptoethanesulfonate (1.1 mg) was then added, and this was reacted at room temperature. After 12 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, and the filtrate portion comprising the target substance was purified with HPLC [column: SHISEIDO proteonavi (C4, 5 μm), (φ20× 250 mm, flow rate: 7.0 mL/min, eluting solution A: 0.1% TFA water, B: 0.09% TFA/10% water/90% AN, A:B= 55:45 →55:45 (5 minutes)→25:75 (35 minutes)→5:95 (36 minutes), isocratic elution for 5 min and then linear gradient] to obtain a 166-residue glycosylated polypeptide (12) having a free thiol group at Cys at positions 68 and 89 and having an asialo sugar chain at Asn at position 80 (SEQ ID NO. 17) (FIGS. 7 and 8).

ESI-MS: Calcd for $C_{979}H_{1525}N_{253}O_{300}S_9$: $[M+17H]^{17+}$ 1290.86, $[M+18H]^{18+}$ 1219.20, $[M+19H]^{19+}$ 1155.09, $[M+20H]^{20+}$ 1097.38, $[M+21H]^{21+}$ 1045.18, $[M+22H]^{22+}$ 997.71, $[M+23H]^{23+}$ 954.38, $[M+24H]^{24+}$ 914.65, $[M+25H]^{25+}$ 878.11, $[M+26H]^{26+}$ 844.37, $[M+27H]^{27+}$ 813.14, $[M+28H]^{28+}$ 784.13, $[M+29H]^{29+}$ 757.13, found. 1219.21, 1155.11, 1097.43, 1045.23, 997.71, 954.43, 914.67, 878.11, 844.37, 813.17, 784.13, 757.16

(2-3. Third Step: Reduction of Cys to Ala)

The 166-residue glycosylated polypeptide (12) having a free thiol group at Cys at positions 68 and 89 and having an asialo sugar chain at Asn at position 80 obtained in the above second step (1.0 mg) was placed in a recovery flask, dissolved in a buffer solution at pH 7.5 (0.10 ml) (prepared with 8 M guanidine hydrochloride solution and 0.2 mM phosphoric acid solution), then 0.5 M Tris-ethylcarboxy phosphine solution (TCEP solution) at pH 7.5 (0.10 ml) (prepared with TECP, 6 M guanidine hydrochloride solution, 0.2 mM phosphoric acid solution, and triethylamine), tBuSH (4.2 μl), and 0.1 M VA-044 solution (4.2 μl) (prepared by dissolving VA-044 in water) were added, and this was reacted at room temperature. After 4 hours, the production of the target substance was confirmed with HPLC and ESI-MS. The reaction solution was transferred to a centrifuge tube, tBuSH was extracted with diethyl ether, then the aqueous layer comprising the target substance was filtered with a membrane filter, and the filtrate portion comprising the target substance was purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, A:B=55:45→55:45 (5 minutes)→ 25:75 (35 minutes)→5:95 (36 minutes), isocratic elution for 5 min and then linear gradient] to obtain a 166-residue glycosylated polypeptide (13) having Cys at positions 68 and 89 converted to Ala and having an asialo sugar chain at Asn at position 80 (SEQ ID NO. 18) (FIGS. 9 and 10).

ESI-MS: Calcd for $C_{979}H_{1525}N_{253}O_{300}S_7$: $[M+17H]^{17+}$ 1287.09, $[M+18H]^{18+}$ 1215.64, $[M+19H]^{19+}$ 1151.71, $[M+20H]^{20+}$ 1094.18, $[M+21H]^{21+}$ 1042.12, $[M+22H]^{22+}$ 994.80, $[M+23H]^{23+}$ 951.59, $[M+24H]^{24+}$ 911.98, $[M+25H]^{25+}$ 875.54, $[M+26H]^{26+}$ 841.91, $[M+27H]^{27+}$ 810.76, $[M+28H]^{28+}$ 781.84, $[M+29H]^{29+}$ 754.92, found. 1287.05, 1215.71, 1151.76, 1094.23, 1042.17, 994.88, 951.64, 911.99, 875.61, 841.95, 810.77, 781.85, 754.94

(2-4. Fourth Step: Deprotection of Acm Group)

The 166-residue glycosylated polypeptide (13) having an asialo sugar chain at Asn at position 80 obtained in the above third step (0.3 mg) was placed in an Eppendorf tube, dissolved in 90% acetic acid aqueous solution (0.03 ml), silver acetate (0.10 mg) was then added, and this was reacted at room temperature with protection from light. After 3.5 hours, the production of the target substance was confirmed with HPLC and ESI-MS. To the reaction solution was added dithiothreitol (1.0 mg), this was stirred at room temperature for 5 minutes and then centrifuged, and the supernatant excluding the precipitate was collected. This collected supernatant was filtered with a membrane filter, and the filtrate portion comprising the target substance was purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, gradient A:B=50:50→50:50 (5 minutes)→20:80 (35 minutes)→5:95 (35.5 minutes), isocratic elution for 5 min and then linear gradient] to obtain glycosylated polypeptide (14) having an asialo sugar chain at Asn at position 80, having the Acm group of cysteine at positions 17, 31, and 141 deprotected (SEQ ID NO. 19) (FIGS. 11 and 12).

ESI-MS: Calcd for $C_{970}H_{1510}N_{250}O_{297}S_7$: $[M+17H]^{17+}$ 1274.55, $[M+18H]^{18+}$ 1203.80, $[M+19H]^{19+}$ 1140.49, $[M+20H]^{20+}$ 1083.52, $[M+21H]^{21+}$ 1031.97, $[M+22H]^{22+}$ 985.11, $[M+23H]^{23+}$ 942.32, $[M+24H]^{24+}$ 903.10, $[M+25H]^{25+}$ 867.01, $[M+26H]^{26+}$ 833.70, $[M+27H]^{27+}$ 802.86, $[M+28H]^{28+}$ 774.23, $[M+29H]^{29+}$ 747.56, found. 1274.62, 1203.82, 1140.53, 1083.55, 1032.01, 985.15, 942.38, 903.12, 867.05, 833.72, 802.91, 774.29, 747.55

(2-5. Fifth Step: Folding Step)

Glycosylated polypeptide (14) having an asialo sugar chain at Asn at position 80 obtained in the above fourth step (0.32 mg) was placed in a centrifuge tube, dissolved in a buffer solution at pH 8.5 (3.5 ml) (prepared with 8 M guanidine hydrochloride solution and 0.1 mM Tris solution), and then left at room temperature. After 1 hour, this solution was transferred to a dialysis membrane (Spectra/Pro, MWCO: 8000). This dialysis membrane was placed in dialysis external solution A (prepared with 3 M guanidine hydrochloride solution, 0.1 mM Tris solution, 8 mM reduced glutathione solution, and 1 mM glutathione solution) and dialyzed at 4° C. After 12 hours, this dialysis membrane was replaced in dialysis external solution B (prepared with 1 M guanidine hydrochloride solution and 0.1 mM Tris solution) and dialyzed at 4° C. After 12 hours, this dialysis membrane was placed in dialysis external solution C (10 mM acetic acid solution) and dialyzed at 4° C. After 24 hours, this dialysis membrane was removed from the dialysis external solution, and the dialysis membrane internal solution was transferred to a centrifuge tube. The dialysis membrane internal solution was analyzed with HPLC, and the major peak elution time was reduced from 17.4 minutes at the starting time of the stepwise dialysis operation to 11.6 minutes at the end of the stepwise dialysis operation. This peak was measured with ESI-MS, and a molecular weight that was reduced by 2 Da from the molecular weight before the start of the stepwise dialysis operation was confirmed. This was thus directly purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, gradient A:B=50:50 →50:50 (5 minutes)→20:80 (35 minutes)→5:95 (35.5 minutes), isocratic elution for 5 min and then linear gradient] to obtain glycosylated polypeptide (15) (SEQ ID NO. 20) (FIGS. 13 and 14). Moreover, the purity of this fraction was determined with HPLC to be 99.00% (HPLC area size %) (FIG. 15). Then, lyophilization of the obtained glycosylated polypeptide (15) was performed. This lyophilizate was redissolved in 10 mM acetic acid aqueous solution, the glycoprotein was then quantified with a spectrophotometer (ultraviolet absorption method), and the concentration was defined as an in vitro activity sample. Moreover, an in vivo activity sample was prepared by dissolving 10 mM acetic acid aqueous solution comprising glycosylated polypeptide (15) with a defined glycoprotein concentration in a buffer separately prepared for formulation (prepared with human serum albumin (30 mg), sodium chloride (24.4 mg), dibasic sodium phosphate hydrate (7.53 mg), and crystalline sodium dihydrogenphosphate (1.41 mg)), lyophilizing again, and then dissolving in Japanese Pharmacopeia water for injection.

ESI-MS after stepwise dialysis and after HPLC purification: Calcd for $C_{970}H_{1508}N_{250}O_{297}S_7$: $[M+9H]^{9+}$ 2406.37, $[M+10H]^{10+}$ 2165.83, $[M+11H]^{11+}$ 1969.03, $[M+12H]^{12+}$ 1805.03, $[M+13H]^{13+}$ 1666.25, $[M+14H]^{14+}$ 1547.31, $[M+15H]^{15+}$ 1444.22, $[M+16H]^{16+}$ 1354.02, $[M+17H]^{17+}$ 1274.43, $[M+18H]^{18+}$ 1203.68, found. 2406.21, 2165.68, 1968.85, 1804.85, 1666.09, 1547.16, 1444.05, 1353.93, 1274.39, 1203.63

Example 3. Synthesis of Disialo IFN-β

Active IFN-β having a disialo sugar chain was synthesized in a total of 6 steps shown below.

(3-1. First Step: Linking of Dibenzyl Disialo Sugar Chain Attached Peptide Fragment B and Peptide Fragment C)

Two types of fragments, a 21-residue dibenzyl disialo sugar chain attached peptide fragment B with a thiophenyl ester C-terminal (2) (2.2 mg) and a 78-residue peptide fragment C (4) (2.5 mg) were placed in the same recovery flask, dissolved in a buffer solution at pH 7.3 (0.21 ml) (prepared with 8 M guanidine hydrochloride solution, 0.2 mM phosphoric acid solution, and 20 mM Tris-carboxyethyl phosphine solution (TCEP solution)), thiophenol (6.2 μl) was then added, and this was reacted at room temperature. After 24 hours, the reaction was confirmed with HPLC, then to the reaction solution was added 0.2 M methoxyamine solution (0.31 ml) (prepared by adding 20 mM TCEP solution to 0.2 M methoxyamine solution), and this was reacted at room temperature. After 12 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, and the filtrate portion comprising the glycopeptide fragment was purified with HPLC [column: SHISEIDO proteonavi (C4, 5 μm), (φ20× 250 mm, flow rate: 7.0 mL/min, eluting solution A: 0.1% TFA water, B: 0.09% TFA/10% water/90% AN, A:B=55: 45→55:45 (5 minutes)→25:75 (35 minutes)→5:95 (36 minutes), isocratic elution for 5 min and then linear gradient] to obtain peptide fragment (B+C) (5) of interest having a dibenzyl disialo sugar chain at the position corresponding to position 80 of interferon β (SEQ ID NO. 21) (FIGS. 16 and 17).

ESI-MS: Calcd for $C_{643}H_{996}N_{158}O_{210}S_4$: $[M+10H]^{10+}$ 1443.10, $[M+11H]^{11+}$ 1312.63, $[M+12H]^{12+}$ 1203.33, $[M+13H]^{13+}$ 1110.84, $[M+14H]^{14+}$ 1031.57, $[M+15H]^{15+}$ 962.87, $[M+16H]^{16+}$ 902.75, $[M+17H]^{17+}$ 849.70, $[M+18H]^{18+}$ 802.55, $[M+19H]^{19+}$ 760.37, found. 1443.78, 1312.66, 1203.36, 1110.84, 1031.58, 962.86, 902.76, 849.70, 802.55, 760.36

(3-2. Second Step: Linking of Peptide Fragment a and Dibenzyl Disialo Sugar Chain Attached Peptide Fragment (B+C))

Two types of fragments, a 67-residue peptide fragment with a thiophenyl ester C-terminal A (1) (2.9 mg) and the peptide fragment having a dibenzyl disialo sugar chain at the position corresponding to position 80 of interferon β (dibenzyl disialo sugar chain attached peptide fragment (B+C)) (5) obtained in the above first step (3.3 mg) were placed in the same recovery flask, dissolved in a buffer solution at pH 7.2 (0.22 ml) (prepared with 8 M guanidine hydrochloride solution, 0.2 mM phosphoric acid solution, and 20 mM TCEP solution). Thiophenol (7.0 µl) was then added and reacted at room temperature. After 24 hours, the reaction was confirmed with HPLC, sodium mercaptoethanesulfonate (2.0 mg) was then added, and this was reacted at room temperature. After 12 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, and the filtrate portion comprising the target substance was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, A:B=55:45→55:45 (5 minutes)→25:75 (35 minutes)→5:95 (36 minutes), isocratic elution for 5 min and then linear gradient] to obtain a 166-residue glycosylated polypeptide (6) having a free thiol group at Cys at positions 68 and 89 and having a dibenzyl disialo sugar chain at Asn at position 80 (SEQ ID NO. 22) (FIGS. 18 and 19).

ESI-MS: Calcd for $C_{1015}H_{1571}N_{255}O_{318}S_9$: $[M+16H]^{16+}$ 1419.15, $[M+17H]^{17+}$ 1335.73, $[M+18H]^{18+}$ 1261.58, $[M+19H]^{19+}$ 1195.23, $[M+20H]^{20+}$ 1135.52, $[M+21H]^{21+}$ 1081.50, $[M+22H]^{22+}$ 1032.38, $[M+23H]^{23+}$ 987.54, $[M+24H]^{24+}$ 946.44, $[M+25H]^{25+}$ 908.62, $[M+26H]^{26+}$ 873.71, $[M+27H]^{27+}$ 841.39, $[M+28H]^{28+}$ 811.37, $[M+29H]^{29+}$ 783.43, $[M+30H]^{30+}$ 757.35, found. 1419.12, 1335.73, 1261.55, 1195.21, 1135.48, 1081.49, 1032.35, 987.51, 946.42, 908.61, 873.70, 841.39, 811.36, 783.42, 757.36

(3-3. Third Step: Reduction of Cys to Ala)

The 166-residue glycosylated polypeptide (6) having a free thiol group at Cys at positions 68 and 89 and having a dibenzyl disialo sugar chain at Asn at position 80 obtained in the above second step (4.0 mg) was placed in a recovery flask, dissolved in a buffer solution at pH 7.5 (0.28 ml) (prepared with 8 M guanidine hydrochloride solution and 0.2 mM phosphoric acid solution), then 0.5 M Tris-ethylcarboxy phosphine solution (TCEP solution) at pH 7.5 (0.28 ml) (prepared with TECP, 6 M guanidine hydrochloride solution, 0.2 mM phosphoric acid solution, and triethylamine), tBuSH (28 µl), and 0.1 M VA-044 solution (28 µl) (prepared by dissolving VA-044 in water) were added, and this was reacted at room temperature. After 4 hours, the production of the target substance was confirmed with HPLC and ESI-MS. The reaction solution was transferred to a centrifuge tube, tBuSH was extracted with diethyl ether, then the aqueous layer comprising the target substance was filtered with a membrane filter, and the filtrate portion comprising the target substance was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, A:B=55:45→55:45 (5 minutes)→25:75 (35 minutes)→5:95 (36 minutes), isocratic elution for 5 min and then linear gradient] to obtain a 166-residue glycosylated polypeptide (7) having Cys at positions 68 and 89 converted to Ala and having a dibenzyl disialo sugar chain at Asn at position 80 (SEQ ID NO. 23) (FIGS. 20 and 21).

ESI-MS: Calcd for $C_{1015}H_{1571}N_{255}O_{318}S_7$: $[M+18H]^{18+}$ 1258.02, $[M+19H]^{19+}$ 1191.86, $[M+20H]^{20+}$ 1132.32, $[M+21H]^{21+}$ 1078.44, $[M+22H]^{22+}$ 1029.47, $[M+23H]^{23+}$ 984.75, $[M+24H]^{24+}$ 943.76, $[M+25H]^{25+}$ 906.05, $[M+26H]^{26+}$ 871.24, $[M+27H]^{27+}$ 839.01, $[M+28H]^{28+}$ 809.08, $[M+29H]^{29+}$ 781.22, found. 1258.02, 1191.86, 1132.31, 1078.39, 1029.43, 984.73, 943.76, 906.04, 871.25, 839.01, 809.06, 781.17

(3-4. Fourth Step: Deprotection of Acm Group)

The 166-residue glycosylated polypeptide (7) having a dibenzyl disialo sugar chain at Asn at position 80 obtained in the above third step (2.9 mg) was placed in an Eppendorf tube, dissolved in 90% acetic acid aqueous solution (0.13 ml), silver acetate (0.43 mg) was then added, and this was reacted at room temperature with protection from light. After 3.5 hours, the production of the target substance was confirmed with HPLC and ESI-MS. To the reaction solution was added dithiothreitol (3.0 mg), this was stirred at room temperature for 5 minutes and then centrifuged, and the supernatant excluding the precipitate was collected. This collected supernatant was filtered with a membrane filter, and the filtrate portion comprising the target substance was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, gradient A:B=50:50→50:50 (5 minutes)→20:80 (35 minutes)→5:95 (35.5 minutes), isocratic elution for 5 min and then linear gradient] to obtain a 166-residue glycosylated polypeptide (8) having a dibenzyl disialo sugar chain at Asn at position 80, having the Acm groups at positions 17, 31, and 141 deprotected (SEQ ID NO. 24) (FIGS. 22 and 23).

ESI-MS: Calcd for $C_{1006}H_{1556}N_{252}O_{313}S_7$: $[M+18H]^{18+}$ 1246.17, $[M+19H]^{19+}$ 1180.64, $[M+20H]^{20+}$ 1121.65, $[M+21H]^{21+}$ 1068.29, $[M+22H]^{22+}$ 1019.78, $[M+23H]^{23+}$ 975.48, $[M+24H]^{24+}$ 934.88, $[M+25H]^{25+}$ 897.52, $[M+26H]^{26+}$ 863.04, $[M+27H]^{27+}$ 831.11, $[M+28H]^{28+}$ 801.47, $[M+29H]^{29+}$ 773.86, found. 1246.16, 1180.60, 1121.62, 1068.27, 1019.74, 975.44, 934.85, 897.49, 863.00, 831.08, 801.45, 773.81

(3-5. Fifth Step: Deprotection of Benzyl Group)

The 166-residue glycosylated polypeptide (8) having a dibenzyl disialo sugar chain at Asn at position 80 obtained in the above fourth step (1.9 mg) was placed in a recovery flask, dissolved in 8 M guanidine solution (0.17 ml) (prepared with guanidine hydrochloride and 20 mM TCEP), and then stirred at room temperature. After cooling with ice-water, 50 mM sodium hydroxide aqueous solution (0.85 ml) was slowly added. After reacting in ice-water for 20 minutes, this was neutralized with a buffer (2.1 ml) (prepared with 8 M guanidine solution and 0.2 M acetic acid sodium aqueous solution). The reaction was confirmed with HPLC and ESI-MS to have produced the target substance. The reaction solution was directly purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, gradient A:B=50:50→50:50 (5 minutes)→20:80 (35 minutes)→5:95 (35.5 minutes), isocratic elution for 5 min and then linear gradient] to obtain a 166-residue glycosylated polypeptide (9) having a disialo sugar chain at Asn at position 80 (SEQ ID NO. 25) (FIGS. 24 and 25).

ESI-MS: Calcd for $C_{992}H_{1544}N_{252}O_{313}S_7$: $[M+17H]^{17+}$ 1308.81, $[M+18H]^{18+}$ 1236.16, $[M+19H]^{19+}$ 1171.15, $[M+20H]^{20+}$ 1112.64, $[M+21H]^{21+}$ 1059.71, $[M+22H]^{22+}$ 1011.58, $[M+23H]^{23+}$ 967.64, $[M+24H]^{24+}$ 927.37, $[M+25H]^{25+}$ 890.31, $[M+26H]^{26+}$ 856.11, $[M+27H]^{27+}$ 824.44, $[M+28H]^{28+}$ 795.03, $[M+29H]^{29+}$ 767.65, $[M+30H]^{30+}$ 742.09, found. 1308.80, 1236.17, 1171.12, 1112.63, 1059.67, 1011.56, 967.63, 927.34, 890.29, 856.09, 824.42, 795.01, 767.63, 742.08

(3-6. Sixth step: Folding step)

Glycosylated polypeptide (9) having a disialo sugar chain at Asn at position 80 obtained in the above fifth step (1.3 mg) was placed in a centrifuge tube, dissolved in a buffer solution at pH 8.5 (13 ml) (prepared with 8 M guanidine hydrochloride solution and 0.1 mM Tris solution), and then left at room temperature. After 1 hour, this solution was transferred to a dialysis membrane (Spectra/Pro, MWCO: 8000). This dialysis membrane was placed in dialysis external solution A (prepared with 3 M guanidine hydrochloride solution, 0.1 mM Tris solution, 2 mM reduced glutathione solution, and 1 mM glutathione solution) and dialyzed at 4° C. After 12 hours, this dialysis membrane was replaced in dialysis external solution B (prepared with 1 M guanidine hydrochloride solution and 0.1 mM Tris solution) and dialyzed at 4° C. After 12 hours, this dialysis membrane was placed in dialysis external solution C (10 mM acetic acid solution) and dialyzed at 4° C. After 24 hours, this dialysis membrane was removed from the dialysis external solution, and the dialysis membrane internal solution was transferred to a centrifuge tube. The dialysis membrane internal solution was analyzed with HPLC, and the major peak elution time was reduced from 28.0 minutes at the starting time of the stepwise dialysis operation to 26.1 minutes at the end of the stepwise dialysis operation. This peak was measured with ESI-MS, and a molecular weight that was reduced by 2 Da from the molecular weight before the start of the stepwise dialysis operation was confirmed. This was thus directly purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, gradient A:B=46:54→46:54 (5 minutes)→34.5:65.5 (28 minutes)→5:95 (28.5 minutes), isocratic elution for 5 min and then linear gradient] to obtain glycosylated polypeptide (10) (SEQ ID NO. 26) (FIGS. 26 and 27). Moreover, the purity of this fraction was determined with HPLC to be 99.36% (HPLC area size %) (FIG. 28). Then, lyophilization of the obtained glycosylated polypeptide (10) was performed. This lyophilizate was redissolved in 10 mM acetic acid aqueous solution, the glycoprotein was then quantified with a spectrophotometer (ultraviolet absorption method), and the concentration was defined as an in vitro activity sample.

Moreover, an in vivo activity sample was prepared by dissolving 10 mM acetic acid aqueous solution comprising glycosylated polypeptide 10 with a defined glycoprotein concentration in a buffer separately prepared for formulation (prepared with human serum albumin (30 mg), sodium chloride (24.4 mg), dibasic sodium phosphate hydrate (7.53 mg), and crystalline sodium dihydrogenphosphate (1.41 mg)), lyophilizing again, and then dissolving in Japanese Pharmacopeia water for injection.

ESI-MS after stepwise dialysis and after HPLC purification: Calcd for $C_{992}H_{1542}N_{252}O_{313}S_7$: $[M+10H]^{10+}$ 2224.08, $[M+11H]^{11+}$ 2021.98, $[M+12H]^{12+}$ 1853.57, $[M+13H]^{13+}$ 1711.06, $[M+14H]^{14+}$ 1588.92, $[M+15H]^{15+}$ 1483.05, $[M+16H]^{16+}$ 1390.43, $[M+17H]^{17+}$ 1308.69, $[M+18H]^{18+}$ 1236.05, found. 2223.88, 2021.80, 1853.43, 1710.91, 1588.77, 1482.92, 1390.35, 1308.61, 1236.01

The amino acid sequence of interferon β was manufactured by dividing into three fragments in the above Examples 2 and 3, but Examples 4-6 below show examples of manufacturing the amino acid sequence of interferon β divided into four fragments.

In Examples 4-6, the glycosylated polypeptide is manufactured from a total of four peptide fragments by further dividing peptide fragment C having amino acids at positions 89-166 in interferon β into fragment C1 of positions 89-134 and fragment C2 of positions 135-166 having Ala at position 134 at the N-terminal.

Example 4. Synthesis of Peptide Fragment (C1+C2)

(4-1. Synthesis of Peptide Fragment C1-SPh)

Amino-PEGA resin (from Merck) (100 μmol) was placed into a column for solid phase synthesis, sufficiently washed with methylene chloride (DCM) and DMF, and then sufficiently swelled with DMF. 4-hydroxymethyl-3-methoxyphenoxy butyric acid (HMPB) (0.25 mmol), TBTU (0.25 mmol), and N-ethylmorpholine (0.25 mmol) were dissolved in DMF (2 ml) and placed in the column, and this was stirred at room temperature for 4 hours. The resin was sufficiently washed with DMF and DCM, the HMPB-PEGA resin was obtained, and this was employed as the solid phase for solid phase synthesis.

Fmoc-Lys(Boc) (0.50 mmol), MSNT (0.50 mmol), and N-methylimidazole (0.375 mmol) were dissolved in DCM (2 ml), placed into the column for solid phase synthesis, and stirred at 25° C. for 4 hours.

After stirring, the resin was washed with DCM and DMF. The Fmoc group was treated with 20% piperidine/DMF solution (2 ml) for 15 minutes for deprotection. After washing with DMF, the amino acids were sequentially condensed with the method shown below for subsequent peptide chain elongation.

The amino acid having the amino group protected with an Fmoc group was dissolved in N-methylpyrrolidone (NMP) (1 ml), 0.45 M HCTU-HOBT/NMP (0.4 mmol) was added, this was added to the column for solid phase synthesis, and subsequently 0.9 M DIPEA/NMP (0.8 mmol) was added to the column for solid phase synthesis. After stirring at room temperature for 20 minutes, the resin was washed with DCM and DMF, the Fmoc group was treated with 20% piperidine/DMF solution (2 ml) for 15 minutes for deprotection. This operation was repeated, and amino acids protected with an Fmoc group (0.5 mmol) were used to sequentially condense the amino acids.

As amino acids protected with an Fmoc or Boc group, Fmoc-Lys(Boc), Fmoc-Leu, Fmoc-Tyr(tBu), Fmoc-His(Trt), Fmoc-Leu, Fmoc-Ile, Fmoc-Arg(Pbf), Fmoc-Gly, Fmoc-Tyr(tBu), Fmoc-Tyr(tBu), Fmoc-Arg(Pbf), Fmoc-Lys(Boc), Fmoc-Leu, Fmoc-His(Trt), Fmoc-Leu, Fmoc-Ser(tBu)-Ser(ψMe, MePro), Fmoc-Met, Fmoc-Leu, Fmoc-Lys(Boc), Fmoc-Gly, Fmoc-Arg(Pbf), Fmoc-Phe-Thr(ψMe, MePro), Fmoc-Asp(OtBu), Fmoc-Glu(OtBu), Fmoc-Lys (Boc), Fmoc-Glu(OtBu), Fmoc-Leu, Fmoc-Lys(Boc), Fmoc-Glu(OtBu), Fmoc-Glu(OtBu), Fmoc-Leu, Fmoc-Val, Fmoc-Lys(Boc)-Thr(ψMe, MePro), Fmoc-Leu, Fmoc-His (Trt), Fmoc-Asn(Trt), Fmoc-Ile, Fmoc-Gln(Trt), Fmoc-His (Trt), Fmoc-Tyr(tBu), Fmoc-Val, and Fmoc-Asn(Trt) were used, and as the amino acid protected with a Boc group, Boc-L-thiazolidine-4-carboxylic acid was sequentially employed and linked on the solid phase resin. As a result, a 46-residue peptide fragment (16) of Lys(Boc)-Leu-Tyr (tBu)-His(Trt)-Leu-Ile-Arg(Pbf)-Gly-Tyr(tBu)-Tyr(tBu)-Arg(Pbf)-Lys(Boc)-Leu-His(Trt)-Leu-Ser(ψMe, MePro)-Ser(tBu)-Met-Leu-Lys(Boc)-Gly-Arg (Pbf)-Thr(ψMe, MePro)-Phe-Asp(OtBu)-Glu(OtBu)-Lys(Boc)-Glu(OtBu)-Leu-Lys(Boc)-Glu(OtBu)-Glu(OtBu)-Leu-Val-Thr(ψMe, MePro)-Lys(Boc)-Leu-His(Trt)-Asn(Trt)-Ile-Gln(Trt)-His (Trt)-Tyr(tBu)-Val-Asn(Trt)-Thz-BocN (SEQ ID NO. 27) was obtained on the solid phase resin.

The solid phase resin having peptide fragment (16) obtained above was washed with DCM and DMF, then a mixed solution of trifluoroethanol and acetic acid (1:1) was added until the resin was sufficiently soaked, and this was stirred for 18 hours at room temperature to cleave between the resin and peptide fragment (16). The cleaved resin was filtered off, and the reaction solution was concentrated under reduced pressure. The residue obtained was concentrated, and peptide fragment (16) having the amino acid side chain protected (SEQ ID NO. 28): Lys(Boc)-Leu-Tyr(tBu)-His (Trt)-Leu-Ile-Arg(Pbf)-Gly-Tyr(tBu)-Tyr(tBu)-Arg(Pbf)-Lys(Boc)-Leu-His(Trt)-Leu-Ser(ψMe, MePro)-Ser(tBu)-Met-Leu-Lys(Boc)-Gly-Arg(Pbf)-Thr(ψMe, MePro)-Phe-Asp(OtBu)-Glu(OtBu)-Lys(Boc)-Glu(OtBu)-Leu-Lys (Boc)-Glu(OtBu)-Glu(OtBu)-Leu-Val-Thr(ψMe, MePro)-Lys(Boc)-Leu-His(Trt)-Asn(Trt)-Ile-Gln(Trt)-His(Trt)-Tyr (tBu)-Val-Asn(Trt)-Thz-BocN was obtained.

One hundred µmol equivalents of a 46-residue protected peptide fragment (16) was transferred to a recovery flask, dissolved in DMF (3.0 mL), and then cooled to −15° C.−−20° C. under nitrogen atmosphere. To this was added thiophenol (308 µl, 3.0 mmol), and then PyBOP (260.0 mg, 0.50 mmol) then DIPEA (85.0 µl, 0.5 mmol) were added. After stirring at −15° C.−−20° C. for 2 hours, trifluoroacetic acid (0.1 mL) was added, and this was gradually restored to room temperature. After being restored to room temperature, the reaction solution was concentrated under reduced pressure. To the residue obtained was added trifluoroacetic acid:water:TIPS (=95:2.5:2.5), and this was stirred at room temperature. After 2 hours, this solution was added to the diethyl ether (150 ml) for precipitation, and then centrifuged in order to remove the solution portion to obtain the residue comprising the peptide thioester. This residue obtained was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, gradient A:B=65:35→65:35 (5 minutes)→30:70 (35 minutes)→5:95 (45 minutes), isocratic elution for 5 min and then linear gradient], and peptide fragment C1-SPh (16) having a thiophenyl ester at the C-terminal (SEQ ID NO. 29): HN-Thz-Asn-Val-Tyr-His-Gln-Ile-Asn-His-Leu-Lys-Thr-Val-Leu-Glu-Glu-Lys-Leu-Glu-Lys-Glu-Asp-Phe-Thr-Arg-Gly-Lys-Leu-Met-Ser-Ser-Leu-His-Leu-Lys-Arg-Tyr-Tyr-Gly-Tyr-Arg-Ile-Leu-His-Tyr-Leu-Lys-SPh was obtained.

ESI-MS: Calcd for $C_{263}H_{412}N_{72}O_{67}S_3$: $[M+4H]^{4+}$ 1438.68, $[M+5H]^{5+}$ 1151.14, $[M+6H]^{6+}$ 959.45, $[M+7H]^{7+}$ 822.53, $[M+8H]^{8+}$ 719.84, found. 1438.51, 1151.00, 959.34, 822.43, 719.74

(4-2. Synthesis of Peptide Fragment C2)

Amino-PEGA resin (from Merck) (100 µmol) was placed into a column for solid phase synthesis, sufficiently washed with methylene chloride (DCM) and DMF, and then sufficiently swelled with DMF. 4-hydroxymethyl-3-methoxyphenoxy butyric acid (HMPB) (0.25 mmol), TBTU (0.25 mmol), and N-ethylmorpholine (0.25 mmol) were dissolved in DMF (2 ml) and placed in the column, and this was stirred at room temperature for 4 hours. The resin was sufficiently washed with DMF and DCM, the HMPB-PEGA resin was obtained, and this was employed as the solid phase for solid phase synthesis.

Fmoc-Asn(Trt) (0.50 mmol), MSNT (0.50 mmol), and N-methylimidazole (0.375 mmol) were dissolved in DCM (2 ml), placed into the column for solid phase synthesis, and stirred at 25° C. for 4 hours.

After stirring, the resin was washed with DCM and DMF. The Fmoc group was treated with 20% piperidine/DMF solution (2 ml) for 15 minutes for deprotection. After washing with DMF, the amino acids were sequentially condensed with the method shown below for subsequent peptide chain elongation.

The amino acid having the amino group protected with an Fmoc group was dissolved in N-methylpyrrolidone (NMP) (1 ml), 0.45 M HCTU-HOBT/NMP (0.4 mmol) was added, this was added to the column for solid phase synthesis, and subsequently 0.9 M DIPEA/NMP (0.8 mmol) was added to the column for solid phase synthesis. After stirring at room temperature for 20 minutes, the resin was washed with DCM and DMF, the Fmoc group was treated with 20% piperidine/DMF solution (2 ml) for 15 minutes for deprotection. This operation was repeated, and amino acids protected with an Fmoc group (0.5 mmol) were used to sequentially condense the amino acids. As amino acids protected with an Fmoc or Boc group, Fmoc-Asn(Trt), Fmoc-Arg(Pbf), Fmoc-Leu, Fmoc-Tyr(tBu), Fmoc-Gly, Fmoc-Thr(tBu), Fmoc-Leu, Fmoc-Arg(Pbf), Fmoc-Asn(Trt), Fmoc-Ile, Fmoc-Phe, Fmoc-Tyr(tBu), Fmoc-Phe, Fmoc-Asn(Trt), Fmoc-Arg (Pbf), Fmoc-Leu, Fmoc-Ile, Fmoc-Glu(OtBu), Fmoc-Val, Fmoc-Arg(Pbf), Fmoc-Val, Fmoc-Ile, Fmoc-Thr(tBu), Fmoc-Trp(Boc), Fmoc-Ala, Fmoc-Cys(Acm), Fmoc-His (Trt), Fmoc-Tyr(tBu)-Ser(ψMe, MePro), Fmoc-Glu(OtBu), Fmoc-Lys(Boc), and Boc-Cys(Trt) were sequentially employed and linked on the solid phase resin. As a result, a 32-residue peptide fragment (17) of Asn(Trt)-Arg(Pbf)-Leu-Tyr(tBu)-Gly-Thr(tBu)-Leu-Arg(Pbf)-Asn(Trt)-Ile-Phe-Tyr (tBu)-Phe-Asn(Trt)-Arg(Pbf)-Leu-Ile-Glu(OtBu)-Val-Arg (Pb)-Val-Ile-Thr(tBu)-Trp(Boc)-Ala-Cys(Acm)-His(Trt)-Ser(ψMe, MePro)-Tyr(tBu)-Glu(OtBu)-Lys(Boc)-Cys(Trt)-BocNH (SEQ ID NO. 30) was obtained on the solid phase resin.

To peptide fragment (17) obtained above was added trifluoroacetic acid:water:TIPS (95:2.5:2.5), and this was stirred at room temperature for 3.5 hours to cleave between the resin and peptide fragment (17). Then, this was added to the diethyl ether (150 ml) for precipitation, and then subjected to a centrifugal separation operation to separate the precipitate comprising the peptide of interest and the solution portion. Then, after removing the solution portion, the target substance was confirmed with HPLC, and then purified with HPLC [column: SHISEIDO proteonavi (C4, 5 µm), φ20×250 mm, flow rate: 7.0 mL/min, eluting solution A: 0.1% TFA water, B: 0.09% TFA/10% water/90% AN, gradient A:B=65:35→65:35 (5 minutes)→30:70 (35 minutes)→5:95 (45 minutes), isocratic elution for 5 min and then linear gradient] to obtain peptide fragment C2 (17) of interest (SEQ ID NO. 31): H₂N-Cys-Lys-Glu-Tyr-Ser-His- Cys(Acm)-Ala-Trp-Thr-Ile-Val-Arg-Val-Glu-Ile-Leu-Arg-Asn-Phe-Tyr-Phe-Ile-Asn-Arg-Leu-Thr-Gly-Tyr-Leu-Arg-Asn.

ESI-MS: ESI-MS: Calcd for $C_{185}H_{282}N_{52}O_{47}S_2$: $[M+3H]^{3+}$ 1351.22, $[M+4H]^{4+}$ 1013.67, $[M+5H]^{5+}$ 811.13, found. 1351.02, 1013.51, 811.01.

Example 5. Linking of Peptide Fragment C1 and Peptide Fragment C2

Two types of fragments, a 46-residue peptide fragment with a thiophenyl ester C-terminal C1-SPh (16) (8.7 mg) and a 32-residue peptide fragment C2 (17) (3.5 mg) were placed in the same recovery flask, dissolved in a buffer solution at pH 6.8 (1.0 ml) (prepared with 8 M guanidine hydrochloride solution, 0.2 mM phosphoric acid solution, and 20 mM Tris-carboxyethyl phosphine solution (TCEP solution)), thiophenol (30 µl) was then added, and this was reacted at room temperature. After 24 hours, the reaction was confirmed with HPLC, then to the reaction solution was added 0.2 M methoxyamine solution (1.5 ml) (prepared by adding 20 mM TCEP solution to 0.2 M methoxyamine solution), and this was reacted at room temperature. After 12 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, the filtrate portion comprising the target fragment was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, gradient A:B=65:35→65:35 (5 minutes)→30:70 (35 minutes)→5:95 (45 minutes), isocratic elution for 5 min and then linear gradient] to obtain peptide fragment (18) of interest (SEQ ID NO. 32) (peptide fragment (C1+C2)) (89-166) (FIG. 29).

ESI-MS: Calcd for $C_{441}H_{688}N_{124}O_{114}S_4$: $[M+8H]^{8+}$ 1210.90, $[M+9H]^{9+}$ 1076.47, $[M+10H]^{10+}$ 968.92, $[M+11H]^{11+}$ 880.93, $[M+12H]^{12+}$ 807.60, $[M+13H]^{13+}$ 745.55, $[M+14H]^{14+}$ 692.37, found. 1210.77, 1076.46, 968.91, 880.92, 808.50, 745.47, 692.37

Example 6. Asialo IFN-β Synthesis Method 2

(6-1. Linking of Asialo Glycosylated Peptide Fragment B and Peptide Fragment (C1+C2))

Two types of fragments, a 21-residue asialo glycosylated peptide fragment B with a thiophenyl ester C-terminal (3) (1.5 mg) and a 78-residue peptide fragment (18) (peptide fragment C1.C2) (2.4 mg) were placed in the same recovery flask, dissolved in a buffer solution at pH 7.2 (0.25 ml) (prepared with 8 M guanidine hydrochloride solution, 0.2 mM phosphoric acid solution, and 20 mM Tris-carboxyethyl phosphine solution (TCEP solution)). Thiophenol (7.4 µl) was then added and reacted at room temperature. After 24 hours, the reaction was confirmed with HPLC, then to the reaction solution was added 0.2 M methoxyamine solution (0.37 ml) (prepared by adding 20 mM TCEP solution to 0.2 M methoxyamine solution), and this was reacted at room temperature. After 12 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, and the filtrate portion comprising the glycopeptide fragment was purified with HPLC [column: SHISEIDO proteonavi (C4, 5 µm), <φ20×250 mm, flow rate: 7.0 mL/min, eluting solution A: 0.1% TFA water, B: 0.09% TFA/10% water/90% AN, gradient A:B=65:35→65:35 (5 minutes)→30:70 (35 minutes)→5:95 (45 minutes), isocratic elution for 5 min and then linear gradient] to obtain peptide fragment (19) of interest having an asialo sugar chain at the position corresponding to position 80 of interferon β (SEQ ID NO. 33) (asialo glycosylated peptide fragment (B+C1+C2)) (68-166) (FIG. 30).

ESI-MS: Calcd for $C_{607}H_{950}N_{156}O_{194}S_5$: $[M+10H]^{10+}$ 1370.73, $[M+11H]^{11+}$ 1246.21, $[M+12H]^{12+}$ 1142.44, $[M+13H]^{13+}$ 1054.64, $[M+14H]^{14+}$ 979.38, $[M+15H]^{15+}$ 914.15, $[M+16H]^{16+}$ 857.08, $[M+17H]^{17+}$ 806.72, $[M+18H]^{18+}$ 761.96, $[M+19H]^{19+}$ 721.91, found. 1370.66, 1246.14, 1142.38, 1054.56, 979.38, 914.08, 856.99, 806.65, 761.92, 721.86

(6-2 Linking of Peptide Fragment a and Glycopeptide Fragment B+C1+C2)

Two types of fragments, a 67-residue peptide fragment with a thiophenyl ester C-terminal A (1) (3.0 mg) and peptide fragment (19) of interest having an asialo sugar chain at the position corresponding to position 80 of interferon β (asialo glycosylated peptide fragment B+C1+C2) obtained in the above 6-1. (68-166) (3.3 mg) were placed in the same recovery flask, dissolved in a buffer solution at pH 7.2 (0.24 ml) (prepared with 8 M guanidine hydrochloride solution, 0.2 mM phosphoric acid solution, and 20 mM TCEP solution). Thiophenol (7.2 µl) was then added and reacted at room temperature. After 24 hours, the reaction was confirmed with HPLC, sodium mercaptoethanesulfonate (2.1 mg) was then added, and this was reacted at room temperature. After 12 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, and the filtrate portion comprising the target substance was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, A:B=55:45→55:45 (5 minutes)→25:75 (35 minutes)→5:95 (36 minutes), isocratic elution for 5 min and then linear gradient] to obtain a 166-residue glycosylated polypeptide (20) having a free thiol group at Cys at positions 68, 89, and 135 and having an asialo sugar chain at Asn at position 80 (SEQ ID NO. 34) (FIG. 31).

ESI-MS: Calcd for $C_{979}H_{1525}N_{253}O_{299}S_{11}$: $[M+17H]^{17+}$ 1293.69, $[M+18H]^{18+}$ 1221.88, $[M+19H]^{19+}$ 1157.62, $[M+20H]^{20+}$ 1099.79, $[M+21H]^{21+}$ 1047.47, $[M+22H]^{22+}$ 999.90, $[M+23H]^{23+}$ 956.47, $[M+24H]^{24+}$ 916.66, $[M+25H]^{25+}$ 880.03, $[M+26H]^{26+}$ 846.22, $[M+27H]^{27+}$ 814.92, $[M+28H]^{28+}$ 785.85, found. 1292.75, 1221.01, 1156.79, 1098.99, 1046.71, 999.19, 955.78, 916.00, 879.39, 845.63, 814.34, 785.29

(6-3 Reduction of Cys to Ala)

The 166-residue glycosylated polypeptide (20) having a free thiol group at Cys at positions 68, 89, and 135 and having an asialo sugar chain at Asn at position 80 obtained in the above 6-2. (1.1 mg) was placed in a recovery flask, dissolved in a buffer solution at pH 7.5 (0.20 ml) (prepared with 8 M guanidine hydrochloride solution and 0.2 mM phosphoric acid solution), then 0.5 M Tris-ethylcarboxy phosphine solution (TCEP solution) at pH 7.5 (0.20 ml) (prepared with TECP, 6 M guanidine hydrochloride solution, 0.2 mM phosphoric acid solution, and triethylamine), tBuSH (20 µl), and 0.1 M VA-044 solution (20 µl) (prepared by dissolving VA-044 in water) were added, and this was reacted at room temperature. After 4 hours, the production of the target substance was confirmed with HPLC and ESI-MS. The reaction solution was transferred to a centrifuge tube, tBuSH was extracted with diethyl ether, then the aqueous layer comprising the target substance was filtered with a membrane filter, and the filtrate portion comprising the target substance was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, A:B=55:45→55:45 (5 minutes)→25:75 (35 minutes)→5:95 (36 minutes), isocratic elution for 5 min and then linear gradient] to obtain a 166-residue glycosylated polypeptide (21) having Cys at positions 68, 89, and 135 converted to Ala and having an asialo sugar chain at Asn at position 80 (SEQ ID NO. 35) (FIG. 32).

ESI-MS: Calcd for $C_{979}H_{1525}N_{253}O_{300}S_7$: $[M+17H]^{17+}$ 1287.09, $[M+18H]^{18+}$ 1215.64, $[M+19H]^{19+}$ 1151.71, $[M+20H]^{20+}$ 1094.18, $[M+21H]^{21+}$ 1042.12, $[M+22H]^{22+}$ 994.80, $[M+23H]^{23+}$ 951.59, $[M+24H]^{24+}$ 911.98, $[M+25H]^{25+}$ 875.54, $[M+26H]^{26+}$ 841.91, $[M+27H]^{27+}$ 810.76, $[M+28H]^{28+}$ 781.84, $[M+29H]^{29+}$ 754.92, found. 1287.11, 1215.69, 1151.72, 1094.20, 1042.16, 994.83, 951.61, 911.98, 875.57, 841.93, 810.80, 781.88, 754.88

Glycosylated polypeptide (15) can be obtained by applying the steps of Acm group deprotection and folding that have similar conditions as the steps described in 2-4. and 2-5. to glycosylated polypeptide (21) obtained in the above 6-3.

Example 7. Disialo IFN-β Synthesis Method 2

(7-1 Linking of Dibenzyl Disialo Sugar Chain Attached Peptide Fragment B and Peptide Fragment (C1+C2))

Two types of fragments, a 21-residue dibenzyl disialo sugar chain attached peptide fragment B with a thiophenyl ester C-terminal (2) (17.9 mg) and a 78-residue peptide fragment (18) (peptide fragment (C1+C2)) (22.9 mg) were placed in the same recovery flask, dissolved in a buffer solution at pH 7.2 (2.37 ml) (prepared with 8 M guanidine hydrochloride solution, 0.2 mM phosphoric acid solution, and 20 mM Tris-carboxyethyl phosphine solution (TCEP solution)). Thiophenol (71.1 µl) was then added and reacted at room temperature. After 24 hours, the reaction was confirmed with HPLC, then to the reaction solution was added 0.2 M methoxyamine solution (3.55 ml) (prepared by adding 20 mM TCEP solution to 0.2 M methoxyamine solution), and this was reacted at room temperature. After 12 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, and the filtrate portion comprising the glycopeptide fragment was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, A:B=55:45→55:45 (5 minutes)→25:75 (35 minutes)→5:95 (36 minutes), isocratic elution for 5 min and then linear gradient] to obtain peptide fragment (22) of interest having a dibenzyl disialo sugar chain at the position corresponding to position 80 of interferon β (SEQ ID NO. 36) (FIG. 33).

ESI-MS: Calcd for $C_{643}H_{996}N_{158}O_{210}S_4$: $[M+12H]^{12+}$ 1315.55, $[M+12H]^{12+}$ 1206.00, $[M+13H]^{13+}$ 1113.31, $[M+14H]^{14+}$ 1033.86, $[M+15H]^{15+}$ 965.00, $[M+16H]^{16+}$ 904.75, $[M+17H]^{17+}$ 851.59, $[M+18H]^{18+}$ 804.34, $[M+19H]^{19+}$ 762.06, found. 1315.59, 1205.97, 1113.28, 1033.83, 964.98, 904.74, 851.57, 804.32, 762.02

(7-2 Peptide Fragment a and Dibenzyl Disialo Sugar Chain Attached Peptide Fragment (B+C1+C2))

Two types of fragments, a 67-residue peptide fragment with a thiophenyl ester C-terminal A (1) (4.7 mg) and peptide fragment (22) of interest having a dibenzyl disialo sugar chain at the position corresponding to position 80 of interferon β obtained in the above 7-1. (5.2 mg) were placed in the same recovery flask, dissolved in a buffer solution at pH 7.2 (0.35 ml) (prepared with 8 M guanidine hydrochloride solution, 0.2 mM phosphoric acid solution, and 20 mM TCEP solution). Thiophenol (11 µl) was then added and reacted at room temperature. After 24 hours, the reaction was confirmed with HPLC, sodium mercaptoethanesulfonate (3.3 mg) was then added, and this was reacted at room temperature. After 12 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, and the filtrate portion comprising the target substance was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, A:B=55:45→55:45 (5 minutes)→25:75 (35 minutes)→5:95 (36 minutes), isocratic elution for 5 min and then linear gradient] to obtain a 166-residue peptide fragment (23) having a free thiol group at Cys at positions 68, 89, and 135 and having a dibenzyl disialo sugar chain at Asn at position 80 (SEQ ID NO. 37) (FIG. 34).

ESI-MS: Calcd for $C_{1015}H_{1571}N_{255}O_{316}S_{10}$: $[M+16H]^{16+}$ 1421.16, $[M+17H]^{17+}$ 1337.62, $[M+18H]^{18+}$ 1263.36, $[M+19H]^{19+}$ 1196.92, $[M+20H]^{20+}$ 1137.13, $[M+21H]^{21+}$ 1083.02, $[M+22H]^{22+}$ 1033.84, $[M+23H]^{23+}$ 988.93, $[M+24H]^{24+}$ 947.77, $[M+25H]^{25+}$ 909.90, $[M+26H]^{26+}$ 874.94, $[M+27H]^{27+}$ 842.57, $[M+28H]^{28+}$ 812.52, $[M+29H]^{29+}$ 784.53, found. 1421.13, 1337.57, 1263.35, 1196.90, 1137.08, 1082.99, 1033.80, 988.89, 947.73, 909.87, 874.92, 842.55, 812.51, 784.50

(7-3 Reduction of Cys to Ala)

The 166-residue peptide fragment (23) having a free thiol group at Cys at positions 68, 89, and 135 and having a dibenzyl disialo sugar chain at Asn at position 80 obtained in the above 7-2. (6.1 mg) was placed in a recovery flask, dissolved in a buffer solution at pH 7.5 (0.27 ml) (prepared with 8 M guanidine hydrochloride solution and 0.2 mM phosphoric acid solution), then 0.5 M Tris-carboxyethyl phosphine solution at pH 7.5 (TCEP solution) (0.27 ml) (prepared with TECP, 6 M guanidine hydrochloride solution, 0.2 mM phosphoric acid solution, and triethylamine), tBuSH (100 µl), and 0.1 M VA-044 solution (100 µl) (prepared by dissolving VA-044 in water) were added, and this was reacted at room temperature. After 4 hours, the production of the target substance was confirmed with HPLC and ESI-MS. The reaction solution was transferred to a centrifuge tube, thiophenol was extracted with diethyl ether, then the aqueous layer comprising the target substance was filtered with a membrane filter, and the filtrate portion comprising the target substance was purified with HPLC [column: SHISEIDO proteonavi (C4, 5 µm), (φ20×250 mm, flow rate: 7.0 mL/min, eluting solution A: 0.1% TFA water, B: 0.09% TFA/10% water/90% AN, A:B=55:45→55:45 (5 minutes)→25:75 (35 minutes)→5:95 (36 minutes), isocratic elution for 5 min and then linear gradient] to obtain a 166-residue peptide fragment (24) having Cys at positions 68, 89, and 135 converted to Ala and having a dibenzyl disialo sugar chain at Asn at position 80 (SEQ ID NO. 38) (FIG. 35).

101

ESI-MS: Calcd for $C_{1015}H_{1571}N_{255}O_{316}S_7$: $[M+18H]^{18+}$ 1258.02, $[M+19H]^{19+}$ 1191.86, $[M+20H]^{20+}$ 1132.32, $[M+21H]^{21+}$ 1078.44, $[M+22H]^{22+}$ 1029.47, $[M+23H]^{23+}$ 984.75, $[M+24H]^{24+}$ 943.76, $[M+25H]^{25+}$ 906.05, $[M+26H]^{26+}$ 871.24, $[M+27H]^{27+}$ 839.01, $[M+28H]^{28+}$ 809.08, $[M+29H]^{29+}$ 781.22, found. 1258.05, 1191.87, 1132.37, 1078.47, 1029.51, 984.77, 943.79, 906.05, 871.25, 839.04, 809.05, 781.24

Glycosylated polypeptide (10) can be obtained by applying the steps of Acm group deprotection, benzyl group deprotection, and folding that have similar conditions as the steps described in 3-4, 3-5, and 3-6 to the glycosylated polypeptide (24) obtained in the above 7-3.

In the above Examples 1-3, a peptide fragment having Ala at the N-terminal was designed and employed for ligation. Accordingly, in Examples 1-3, a peptide fragment having Cys introduced at the position of Ala placed at the N-terminal of said peptide fragment was synthesized, ligated, and then Cys was reduced to Ala.

In the following Example, a peptide fragment having Ser at the N-terminal was designed. In other words, an example is shown wherein a peptide fragment having Cys introduced at the position of Ser was synthesized, ligated, and then Cys was converted to Ser. More specifically, an example is shown wherein peptide fragment B having amino acids at positions 68-88 in the amino acid sequence of interferon β is synthesized by dividing into fragment B2 of positions 68-75 and fragment B1 of positions 76-88 having Cys at the N-terminal instead of Ser at position 76, and after a ligation step of synthesizing peptide fragment (B1+B2)-SR having Cys as the amino acid at the position corresponding to position 76 of interferon β (hereinafter referred to as peptide fragment (B1+B2)-SR (Cys body)) by ligation and a step of converting Cys at the position corresponding to position 76 of interferon β in peptide fragment (B1+B2)-SR (Cys body) to Ser, peptide fragment (B1+B2)-SR having Ser as the amino acid at the position corresponding to position 76 of interferon β is synthesized.

In other words, more specifically, a manufacturing method comprising the following steps is exemplified:

(I) A step of preparing peptide fragment B1 represented by the following formula (i).

[Chemical Formula 37]

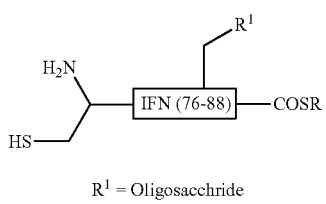

$R^1$ = Oligosacchride (II) A step of preparing glycopeptide B2 represented by the following formula (j).

[Chemical Formula 38]

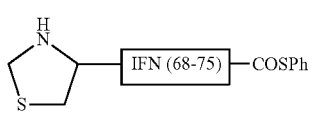

102

(III) A step of preparing a glycopeptide represented by the following formula (k) by linking peptide B1 and glycopeptide B2, and then converting a particular cysteine on said peptide to serine (see FIGS. 43-45)

[Chemical Formula 39]

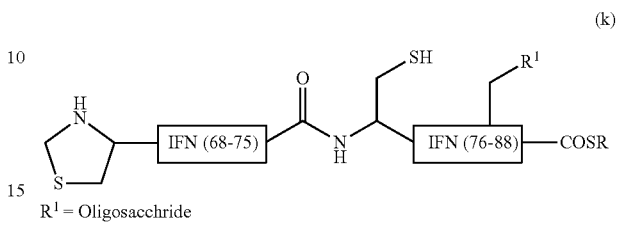

$R^1$ = Oligosacchride

Example 8. Synthesis of Disialo Sugar Chain Attached Peptide Fragment (B1+B2)-SR (8-1 Synthesis of Peptide Fragment B1-SR)

HMPB-Chem Matrix (from Biotage) (0.10 mmol) was placed into a column for solid phase synthesis, sufficiently washed with methylene chloride (DCM) and DMF, and then sufficiently swelled with DCM.

Fmoc-Leu (0.50 mmol), MSNT (0.50 mmol), and N-methylimidazole (0.375 mmol) were dissolved in DCM (2 ml), placed into the column for solid phase synthesis, and stirred at 25° C. for 4 hours.

After stirring, the resin was washed with DCM and DMF. The Fmoc group was treated with 20% piperidine/DMF solution (2 ml) for 15 minutes for deprotection. After washing with DMF, the amino acids were sequentially condensed with the method shown below for subsequent peptide chain elongation.

The amino acid having the amino group protected with an Fmoc group was dissolved in N-methylpyrrolidone (NMP) (1 ml), 0.45 M HCTU.HOBT/NMP (0.4 mmol) was added, this was added to the column for solid phase synthesis, and subsequently 0.9 M DIPEA/NMP (0.8 mmol) was added to the column for solid phase synthesis. After stirring at room temperature for 20 minutes, the resin was washed with DCM and DMF, the Fmoc group was treated with 20% piperidine/DMF solution (2 ml) for 15 minutes for deprotection. This operation was repeated, and amino acids protected with an Fmoc group (0.5 mmol) were used to sequentially condense the amino acids.

Fmoc-Leu, Fmoc-Leu, Fmoc-Asn(Trt), Fmoc-Glu(OtBu), Fmoc-Val, Fmoc-Ile, Fmoc-Thr(tBu), and Fmoc-Glu(OtBu) were sequentially employed as amino acids protected with an Fmoc group, and an 8-residue peptide was obtained on the Leu-Leu-Asn(Trt)-Glu(OtBu)-Val-Ile-Thr(tBu)-Glu (OtBu) (SEQ ID NO: 51). To this 8-residue peptide, the Fmoc group was treated with 20% piperidine/DMF solution (2 ml) for 15 minutes for deprotection. After washing with DMF, dibenzyl disialo sugar chain asparagine derivative (g) (547.8 mg, 200 μmol) and DEPBT (59.9 mg, 200 μmol) were dissolved in DMF/DMSO (1:1 mixed solution, 3.33 ml) in the centrifuge tube, placed into the column for solid phase synthesis, DIPEA (52.3 μl, 300 μmoL) was added, and this was stirred at room temperature for 18 hours. Washing with DMF and DCM yielded a 9-residue sugar chain peptide of Leu-Leu-Asn(Trt)-Glu(OtBu)-Val-Ile-Thr(tBu)-Glu (OtBu)-Asn(dibenzyl-disialooligosaccharide)-FmocNH (SEQ ID NO. 39) on the solid phase.

[Chemical Formula 40]

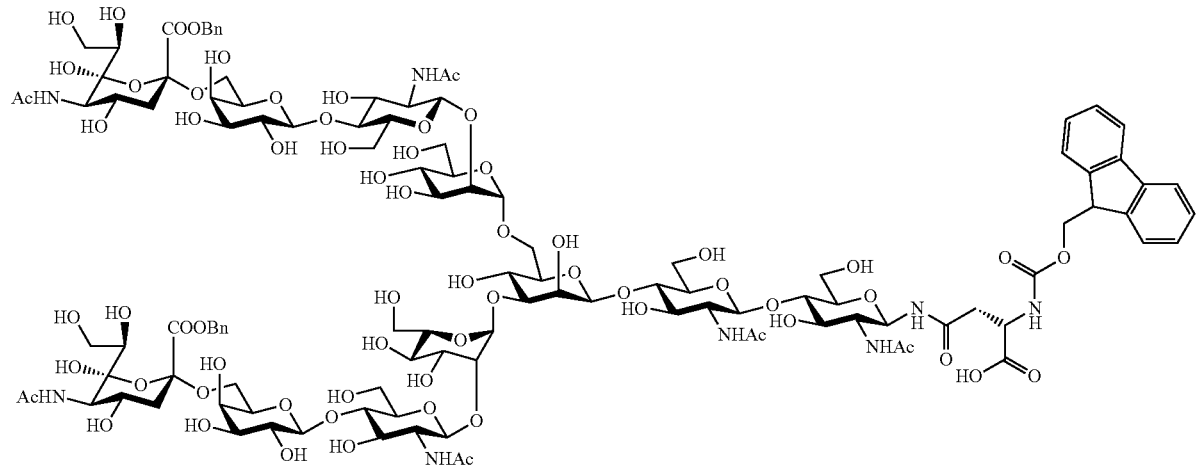

(g)

For subsequent glycopeptide chain elongation, the lipophilic protecting group of the 9-residue sugar chain peptide on the solid phase resin obtained above was deprotected with 20% piperidine/DMF solution (2 ml), and then amino acids were sequentially condensed with the method shown below.

The amino acid having the amino acid protected with an Fmoc group as well as HOBt (67.6 mg, 0.50 mmol) and DIPCI (73.1 μl, 0.475 mmol) were dissolved in DMF (6.3 ml), activated for 15 minutes, and then placed into the column for solid phase synthesis. After stirring at room temperature for 1 hour, the Fmoc group was treated with 20% piperidine/DMF solution (2 ml) for 20 minutes for deprotection. This operation was repeated to sequentially condense the amino acids. As amino acids protected with Fmoc and Boc groups, Fmoc-Trp(Boc), Fmoc-Gly, Fmoc-Thr(tBu), and Boc-Cys(Trt) were sequentially employed and linked to the solid phase resin. As a result, a 13-residue glycosylated peptide fragment (25) of Leu-Leu-Asn(Trt)-Glu(OtBu)-Val-Ile-Thr(tBu)-Glu(OtBu)-Asn(dibenzyl-disialooligosaccharide)-Trp(Boc)-Gly-Thr(tBu)-Cys(Trt)-BocNH (SEQ ID NO. 40) was obtained on the solid phase resin.

Then, after washing with DCM and DMF, a mixed solution of trifluoroethanol and acetic acid (1:1) was added until the resin was sufficiently soaked, and this was stirred for 18 hours at room temperature to cleave between the resin and the glycosylated peptide fragment. The cleaved resin was filtered off, and the reaction solution was concentrated under reduced pressure. The residue obtained was concentrated, and glycosylated peptide (25) having the amino acid side chain protected (SEQ ID NO. 41): Leu-Leu-Asn(Trt)-Glu(OtBu)-Val-Ile-Thr(tBu)-Glu(OtBu)-Asn(dibenzyl-disialooligosaccharide)-Trp(Boc)-Gly-Thr(tBu)-Cys(Trt)-BocNH was obtained.

One hundred μmol equivalents of glycosylated peptide fragment (25) having a 13-residue amino acid and having the amino acid side chain protected was transferred to a recovery flask, dissolved in DMF (3.0 mL), and then cooled to −15° C.--20° C. under nitrogen atmosphere. To this was added sodium 2-mercaptoethanesulfonate (492.5 mg, 3.0 mmol), and then PyBOP (260.0 mg, 0.50 mmol) then DIPEA (85.0 μl, 0.5 mmol) were added. After stirring at −15° C.--20° C. for 2 hours, trifluoroacetic acid (0.1 mL) was added, and this was gradually restored to room temperature. After being restored to room temperature, the reaction solution was concentrated under reduced pressure. To the residue obtained was added trifluoroacetic acid:water:TIPS (=95:2.5:2.5), and this was stirred at room temperature. After 2 hours, this solution was added again to the diethyl ether (150 ml) for precipitation, and then centrifuged in order to remove the solution portion to obtain the residue comprising the peptide thioester. This residue obtained was purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, gradient A:B=72:28→59:41 (26 minutes), linear gradient] to obtain dibenzyl disialo sugar chain attached peptide fragment B1-SR (25) having an alkyl thioester as the C-terminal (SEQ ID NO. 42): H₂N-Cys-Thr-Gly-Trp-Asn(dibenzyl-disialooligosaccharide)-Glu-Thr-Ile-Val-Glu-Asn-Leu-Leu-SR (FIG. 46). -SR shows an ethyl sulfonate thioester.

(8-2 Synthesis of Peptide Fragment B2-SPh)

HMPB-Chem Matrix (from Biotage) (0.10 mmol) was placed into a column for solid phase synthesis, sufficiently washed with methylene chloride (DCM) and DMF, and then sufficiently swelled with DCM.

Fmoc-Ser(tBu) (0.50 mmol), MSNT (0.50 mmol), and N-methylimidazole (0.375 mmol) were dissolved in DCM (2 ml), placed into the column for solid phase synthesis, and stirred at 25° C. for 4 hours.

After stirring, the resin was washed with DCM and DMF. The Fmoc group was treated with 20% piperidine/DMF solution (2 ml) for 15 minutes for deprotection. After washing with DMF, the amino acids were sequentially condensed with the method shown below for subsequent peptide chain elongation.

The amino acid having the amino group protected with an Fmoc group was dissolved in N-methylpyrrolidone (NMP) (1 ml), 0.45 M HCTU-HOBT/NMP (0.4 mmol) was added, this was added to the column for solid phase synthesis, and subsequently 0.9 M DIPEA/NMP (0.8 mmol) was added to the column for solid phase synthesis. After stirring at room temperature for 20 minutes, the resin was washed with DCM and DMF, the Fmoc group was treated with 20% piperidine/DMF solution (2 ml) for 15 minutes for deprotection. This operation was repeated, and amino acids protected with an Fmoc group (0.5 mmol) were used to sequentially condense the amino acids.

Fmoc-Ser(tBu), Fmoc-Ser(tBu), Fmoc-Asp(OtBu), Fmoc-Gln(Trt), Fmoc-Arg(Pbf), Fmoc-Phe, Fmoc-Ile, and Boc-L-thiazolidine-4-carboxylic acid were sequentially employed as amino acids protected with an Fmoc group and linked to the solid phase resin. As a result, an 8-residue peptide fragment (26) of Ser(tBu)-Ser(tBu)-Asp(OtBu)-Gln(Trt)-Arg(Pbf)-Phe-Ile-Thz-BocN (SEQ ID NO. 43) was obtained on the solid phase resin.

Then, after washing with DCM and DMF, a mixed solution of trifluoroethanol and acetic acid (1:1) was added until the resin was sufficiently soaked, and this was stirred for 18 hours at room temperature to cleave between the resin and the peptide fragment. The cleaved resin was filtered off, and the reaction solution was concentrated under reduced pressure. The residue obtained was concentrated, and peptide (26) having the amino acid side chain protected (SEQ ID NO. 44): Ser(tBu)-Ser(tBu)-Asp(OtBu)-Gln(Trt)-Arg(Pbf)-Phe-Ile-Thz-BocN was obtained.

One hundred μmol equivalents of peptide fragment (26) having an 8-residue amino acid and having the amino acid side chain protected was transferred to a recovery flask, dissolved in DMF (3.0 mL), and then cooled to −15° C.--−20° C. under nitrogen atmosphere. To this was added thiophenol (308 μl, 3.0 mmol), and then PyBOP (260.0 mg, 0.50 mmol) then DIPEA (85.0 μl, 0.5 mmol) were added. After stirring at −15° C.--−20° C. for 2 hours, trifluoroacetic acid (0.1 mL) was added, and this was gradually restored to room temperature. After being restored to room temperature, the reaction solution was concentrated under reduced pressure. To the residue obtained was added trifluoroacetic acid:water:TIPS (=95:2.5:2.5), and this was stirred at room temperature. After 2 hours, this solution was added again to the diethyl ether (150 ml) for precipitation, and then centrifuged in order to remove the solution portion to obtain the residue comprising the peptide thioester. This residue obtained was purified with HPLC [column: SHISEIDO proteonavi (C4, 5 μm), φ20×250 mm, flow rate: 7.0 mL/min, eluting solution A: 0.1% TFA water, B: 0.09% TFA/10% water/90% AN, gradient A:B=78:22→68:32 (20 minutes), linear gradient] to obtain peptide fragment B2-SPh (26) having a thiophenyl ester at the C-terminal (SEQ ID NO. 45): HN-Thz-Ile-Phe-Arg-Gln-Asp-Ser-Ser-SPh (FIG. 47).

(8-3 Linking of Dibenzyl Disialo Sugar Chain Attached Peptide Fragment B1-SR and Peptide Fragment B2-SPh)

Two types of fragments, a 13-residue dibenzyl disialo sugar chain attached peptide fragment B1-SR with an alkyl thioester C-terminal (0.60 mg) and an 8-residue peptide fragment B2-SPh (0.16 mg) were placed in the same recovery flask, dissolved in a buffer solution at pH 7.2 (0.15 ml) (prepared with 8 M guanidine hydrochloride solution, 0.2 mM phosphoric acid solution, and 20 mM Tris-carboxyethyl phosphine solution (TCEP solution)), and reacted at room temperature. After 14.5 hours, the production of the target substance was confirmed with HPLC and ESI-MS. The reaction solution was filtered with a membrane filter, and the filtrate portion comprising the glycopeptide fragment was purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, A:B=78:22 →56:44 (22 minutes), isocratic elution for 5 min and then linear gradient] to obtain glycosylated peptide fragment (B1+B2)-SR (Cys body) (27) of interest having a dibenzyl disialo sugar chain and having the C-terminal alkyl thioesterified (SEQ ID NO. 46) (FIG. 48).

(8-4 Methylation of Cys)

5.3 mg (1.03 μmol) of the 21-residue peptide alkyl thioester (27) obtained was placed in an Eppendorf tube, dissolved in a buffer solution at pH 8.6 (1.09 mL) (prepared with 8 M guanidine hydrochloride solution, 0.25 Tris-hydrochloric acid solution, and 3.3 mM EDTA solution) and acetonitrile (0.36 mL), and methyl-4-nitrobenzene sulfonate (5.1 mg) was then added at 25° C. After 30 minutes, 10% TFA solution (0.2 mL) was added to pH 4, and then the reaction solution was purified with HPLC [column: SHISEIDO proteonavi (C4, 5 μm), (φ20×250 mm, flow rate: 7.0 mL/min, eluting solution A: 0.1% TFA water, B: 0.09% TFA/10% water/90% AN, A:B=72:55→55:45 (34 minutes), isocratic elution for 5 min and then linear gradient] to obtain glycosylated peptide fragment (B1+B2)-SR (Cys body) (28) having a dibenzyl disialo sugar chain having the sulfur atom of the cysteine residue comprised in the source material methylated and having the C-terminal alkyl thioesterified (SEQ ID NO. 47) (FIG. 49).

(8-5 Cyanidation of Methylated Cys and Intramolecular Acyl Transfer Reaction Following Cyanidation)

Peptide fragment (28) having dibenzyl disialo sugar chain having the sulfur atom of the cysteine residue methylated obtained was placed in an Eppendorf tube, dissolved in 0.1 mM 80% formic acid solution (3.3 mL), and cyanogen bromide 23.2 mg (219 μmol) was then added at 25° C. After the reaction container was protected from light, reaction was allowed at 37° C., and after 26.5 hours, the reaction solution was concentrated under reduced pressure.

The residue obtained was dissolved in a buffer solution at pH 8.0 (prepared with 8 M guanidine hydrochloride solution and 0.2 M phosphoric acid solution) (0.33 mL), and then reacted at 37° C. After 1 hour, 20% piperidine/DMF solution (3.3 μL, 1% v/v) was added, and after confirming the completion of the reaction with HPLC, this was purified by HPLC [column: SHISEIDO proteonavi (C4, 5 μm), (φ20× 250 mm, flow rate: 7.0 mL/min, eluting solution A: 0.1% TFA water, B: 0.09% TFA/10% water/90% AN, A:B=72: 55→55:45 (34 minutes), isocratic elution for 5 min and then linear gradient] to obtain the reaction intermediate glycosylated peptide fragment (B1+B2)-SR (29) having a 21-residue dibenzyl disialo sugar chain and having the C-terminal alkyl thioesterified (SEQ ID NO. 48) (FIG. 50). -SR shows an ethyl sulfonate thioester.

Disialo IFN-β can by synthesized similarly to Example 3 by employing the glycosylated polypeptide obtained in the above 8-5. (29) as the dibenzyl disialo sugar chain attached peptide fragment B in Example 3.

Example 9 Heat Treatment Method (9-1. Heat Treatment of 17,31,141Cys(Acm)-80N(Dibenzyl-Disialooligosaccharide)-IFN-β)

The glycosylated polypeptide obtained in the above 3-3. (7) (17,31,141Cys(Acm)-80N(dibenzyl-disialooligosaccharide)-IFN-β) (3.7 mg) was placed in a 10 mL recovery flask, and 0.2 M phosphate buffer at pH 7.0 (comprising 8 M guanidine) (3.3 mL; substrate concentration: 50 mM) was introduced. A glass stopper was plugged in the recovery flask, and this was then warmed in an oil bath to 60° C. After 10 hours, this was restored to room temperature, and then HPLC analysis was performed. After confirming that there was no degradation by HPLC and ESI-MS (FIG. 36), this was desalted with HPLC [column: SHISEIDO proteonavi (C4, 5 μm), (φ20×250 mm, flow rate: 7.0 mL/min, eluting solution A: 0.1% TFA water, B: 0.09% TFA/10% water/90%

AN, gradient A:B=50:50 →50:50 (5 minutes)→20:80 (35 minutes)→5:95 (35.5 minutes)], and a heat treatment sample (4.0 mg) was obtained.

(9-2. Heat Treatment of 80N(Dibenzyl-Disialooligosaccharide)-IFN-β)

The glycosylated polypeptide obtained in the above 3-4.(8) (80N(dibenzyl-disialooligosaccharide)-IFN-β (30 μg)) was placed in a 0.5 mL Eppendorf tube, and 0.2 M phosphate buffer at pH 7.0 (comprising 8 M guanidine) (30 μL; substrate concentration: 50 mM) was introduced. This was covered and heated in an oil bath to 60° C. After 10 hours, this was restored to room temperature and subjected to HPLC analysis [column: SHISEIDO proteonavi (C4, 5 μm), φ20×250 mm, flow rate: 7.0 mL/min, eluting solution A: 0.1% TFA water, B: 0.09% TFA/10% water/90% AN, gradient A:B=50:50→50:50 (5 minutes)→20:80 (35 minutes) →5:95 (35.5 minutes), isocratic elution for 5 min and then linear gradient], and the purity was confirmed by HPLC and ESI-MS (FIG. 37).

Comparing the HPLC and ESI-MS data with glycosylated polypeptide (7) having Cys protected used in the heating test in the above 9-1., the recovery amount of glycosylated polypeptide (8) having cysteine unprotected was reduced by the heat treatment.

Example 10 Receptor Affinity Analysis

Receptor affinity analysis of non-heated or heat-treated chemically synthesized IFN-β against IFN-α/β receptor 2 was performed.

The binding affinity of the non-heated or heat-treated chemically synthesized IFN-β against IFN-α/p receptor 2 was measured with ProteOn XPR36 (Bio-rad) employing SPR (Surface Plasmon Resonance technology).

Specifically, 10 μg/mL of IFN-α/β receptor 2 (10 mM acetic acid buffer, pH 4.5) was fixed to a GLM chip (Bio-rad) according to instructions by employing an amine coupling kit (Bio-rad) and flowing 0.005% Tween 20/PBS at a flow rate of 30 μL/min. The non-heated disialo sugar chain attached polypeptide (10) prepared in Example 3, or the heat-treated disialo sugar chain attached polypeptide obtained by subjecting the disialo sugar chain attached polypeptide heat-treated in the above 9-1. to the de-Acm step, the benzyl group deprotection step, and the folding step described in the above 3-4.-3-6. were adjusted to 0.31-25 nM with 0.1% BSA and 2 mM EDTA/PBS, and added to the chip at a flow rate 50 of μL/min. The analysis with glycosylated polypeptide (10) was carried out at each of five concentrations of 0.31 nM, 0.93 nM, 2.8 nM, 8.3 nM, and 25 nM. The binding constant (ka), the dissociation constant (kd), and the binding dissociation constant (Kd) were analyzed with ProteOn Manager software. The results thereof are shown in FIG. 38, FIG. 39, and Table 1.

FIG. 38 shows the graph of analyzing the binding affinity of the non-heated disialo sugar chain attached polypeptide (10) against IFN-α/β receptor 2. Moreover, FIG. 39 shows the graph of analyzing the binding affinity of the heat-treated disialo sugar chain attached polypeptide against IFN-α/β receptor 2. As shown in FIG. 38, FIG. 39, and Table 1, the chemically synthesized glycosylated polypeptide of the present invention had receptor affinity equivalent to that of a non-heat-treated glycosylated polypeptide even after heat treatment.

TABLE 1

|  | Non-heat-treated | Heat-treated |
| --- | --- | --- |
| ka [1/M · sec] | $5.5 \times 10^{6}$ | $4.3 \times 10^{6}$ |
| kd [1/sec] | $2.7 \times 10^{-3}$ | $2.3 \times 10^{-3}$ |
| Kd [M] | $4.9 \times 10^{-10}$ | $5.3 \times 10^{-10}$ |

Example 11 Pharmacokinetics Analysis

An Example of a pharmacokinetics analysis when the glycosylated polypeptides according to the present invention prepared by the above Examples were intravenously and subcutaneously administered is shown below.

(11-1. Preparation of Administration Fluid and Reagent)

The asialo glycosylated polypeptide (15) (asialo IFN-β) prepared in Example 2 and the disialo sugar chain attached polypeptide (10) (disialo IFN-β) prepared in Example 3 were employed as the chemically synthesized IFN-β. BSA and phosphate buffer solution were added and lyophilization was performed. An administration fluid was prepared by dissolving this with 60 μL of milli-Q water immediately before administration and adjusting to 500,000 IU/mL with Phosphate buffered saline solution (PBS, Wako Pure Chemical Industries, Ltd.). Moreover, IFNβ Mochida for injection prepared by biosynthesis (Mochida Pharmaceutical Co., Ltd.) was employed as the control IFN-β. The provided water for injection was employed for dissolving to 12 million IU/mL, and then adjusted to 500,000 IU/mL with PBS. For EDTA-PBS, PBS was added so that EDTA-2Na (Wako Pure Chemical Industries, Ltd.) will be 2 mM. The chemically synthesized glycosylated polypeptide employed for the pharmacokinetics analysis of the present Example was those that were not heat-treated. Moreover, IFN Mochida is IFNβ-1a derived from human fibroblast that was prepared by biosynthesis.

(11-2. Administration and Blood Collection)

Administration was to mice (BALB/c mouse, male, body weight 20.45-25.28 g) at a dosage of 2 million IU/kg under food satiation from the orbital vein or dorsal subcutaneous with an Insulin Syringe Myjector 29 G×½ (Terumo Corporation) at a volume of 4 mL/kg. 75 μL of blood was collected from the orbital vein with a heparin treatment Hematocrit Capillary Tube (HIRSHMANN LABORGERATE) before administration as well as at 2, 10, and 30 minutes and 1, 3, 6, and 8 hours after administration for intravenous administration, and before administration as well as at 10 and 30 minutes and 1, 2, 4, 6, and 8 hours after administration for subcutaneous administration. This was promptly mixed with EDTA-PBS of the same volume as the collected blood and centrifuged (15000 rpm, 4° C., 10 minutes). 90 μL of the supernatant was taken as the plasma sample. Plasma samples were frozen in storage until employed for measurement. Tips and tubes used were low absorbent products from BM Equipment Co., Ltd.

(11-3. Measurement of Blood Concentration)

Human interferon-β ELISA kit (Kamakura Techno-Science, Inc.) was employed for the measurement of the blood concentration of the glycosylated polypeptide (IFN-β). In other words, dilutions of the plasma sample at 360, 120, and 12-folds as necessary were prepared with the diluting solution supplied in the kit as measurement samples. As a standard for preparing a standard curve, the chemically synthesized IFN-β in the same lot as that employed for administration and IFNβ Mochida for injection were employed to allow preparation at 200, 100, 50, 25, 12.5, 6.25, and 3.125 IU/mL with the diluting solution supplied in the kit. Blank plasma was added to the standard curve depending on the dilution ratio of the plasma sample so that the delivered amount will be equal. By multiplying the results obtained and the dilution ratio, and further multiplying the dilution ratio 2 in EDTA-PBS as the anticoagulation treatment, the blood concentration was calculated. The plasma IFN-β concentration transition obtained is shown in FIG. 40.

(11-4. Calculation of Pharmacokinetics Parameter)

From the transition of IFN-β concentration obtained, the area under the plasma concentration curve (AUC) was calculated by the trapezoidal rule employing the moment analysis method. Moreover, the predicted initial concentration was determined by the extrapolation method for intravenous administration (C0), and the maximum plasma concentration (Cmax) was determined from the half-life in plasma (t½), the mean residence time (MRT), and the actual value for subcutaneous administration. The pharmacokinetics parameters obtained are shown in Table 2.

From FIG. 40, it is seen that the glycosylated polypeptide prepared by the chemical synthesis according to the present invention shows an equivalent blood kinetics compared to IFN-β prepared by biosynthesis.

TABLE 2

|  | Intravenous administration | | | | Subcutaneous administration | | | |
| --- | --- | --- | --- | --- | --- | --- | --- | --- |
|  | $t_{1/2}$ | AUC | MRT | $C_0$ | $t_{1/2}$ | AUC | MRT | $C_{max}$ |
| IFNβ Mochida | 84 | 232831 | 50 | 20723 | 121 | 120287 | 170 | 606 |
| Asialo IFN-β | 68 | 85183 | 43 | 6754 | 222 | 39853 | 319 | 149 |
| Disialo IFN-β | 96 | 254544 | 70 | 15204 | 300 | 97078 | 345 | 403 |

($t_{1/2}$: min, AUC: min · IU/mL, MRT: min, $C_0$: IU/mL, $C_{max}$: IU/mL)

Example 12 Antitumor Activity Measurement Test (12-1. Cell Culture and Preparation of Reagent)

Daudi cells which are human Burkitt's lymphoma were employed for the antitumor activity test. The medium employed was RPMI 1640 (Invitrogen) supplemented with 10% of Fetal Bovine Serum (GIBCO) subjected to an inactivating treatment at 56° C. for 30 minutes and penicillin/streptomycin (SIGMA). Non-treat dish (IWAKI) was employed as the culture plate, culturing was performed at 37° C. under a condition of 5% $CO_2$ concentration, and passaged once every 2-3 days.

(12-2. Method for Preparing Tumor-Bearing Mouse)

The Daudi cells cultured in the above 12-1. were collected in a tube and centrifuged (1300 rpm, 4° C., 3 minutes). The supernatant was removed with an aspirator, HBSS (Nacalai) was added, and the cells were suspended. Next, this was centrifuged again and the supernatant was removed. This cell washing treatment was performed for a total of three times. The number of cells was counted with a hemocytometer, and a cell suspension at $2\times10^8$ cells/mL was prepared with HBSS. Immediately before Daudi cell inoculation, Matrigel (BD) at the same volume as the cell suspension was added to make a 2-folds dilution to prepare a cell suspension for inoculation. The cell suspension for inoculation was stored on ice until immediately before inoculation. Somnopentyl (Kyoritsuseiyaku Corporation) diluted to 5 mg/mL with PBS was employed as the anesthetic drug. 250-300 μL of the anesthetic drug was intraperitoneally administered to an SCID mouse (C. B-17/Icr-scid/scid Jcl mouse, male) (CLEA Japan, Inc.) with an Insulin Syringe Myjector 29 G×½ (Terumo). After confirming the introduction of anesthesia, hair on the right frank of the mouse was shaved with an electrical shaver. 100 μL of the cell suspension for inoculation was subcutaneously inoculated with a 26 G ½ injection needle (Terumo) and a 1 mL glass syringe (Terumo).

(12-3. Methods for Measuring Antitumor Activity and Evaluation)

About 30 days after the cell inoculation treatment of the above 11-3., the major axis (mm) and the minor axis (mm) of the tumor tissue formed were measured with a caliper (Mitsutoyo). The tumor volume ($mm^3$) was determined with the values obtained. The tumor volume was calculated with the formula: tumor volume ($mm^3$)=major axis (mm)×minor axis (mm)×minor axis (mm)×0.5. The tumor volume was calculated over time and plotted on a graph for evaluation as the antitumor activity power.

(12-4. Methods for Preparing Administration Fluid and Administration)

The asialo glycosylated polypeptide (15) synthesized in Example 2 and the disialo sugar chain attached polypeptide (10) synthesized in Example 3 were prepared at 5 million IU/mL with PBS. IFN Mochida for injection prepared by biosynthesis (Mochida Pharmaceutical Co., Ltd.) was employed as the control IFN-β. The provided water for injection was employed for dissolving to 12 million IU/mL, and then adjusted to 5 million IU/mL with PBS. The preparation of the administration fluid was performed immediately before administration. Tumor-bearing mice were divided into 4 groups employing the tumor volume measured in the above 12-3. (n=4/group). The tumor volume at the time of grouping was approximately 800 $mm^3$. Administration was with the prepared administration fluid to the dorsal subcutaneous at a volume of 4 mL/kg so that the dosage will be 20 million IU/kg, with an Insulin Syringe Myjector 29 G×½. For the vehicle administration group, PBS employed for preparing the administration fluid was administered at a volume of 4 mL/kg. Grouping and first administration was set as day 0, and a total of 10 dorsal subcutaneous administrations were given every day until day 9.

(12-5. Evaluation of Antitumor Activity Power)

The tumor volume was calculated on days 3, 6, 8, 10, 13, 15, and 17 with the method shown in 12-3., and the change of tumor volume over time is shown in FIG. 41.

From FIG. 41, it is seen that the glycosylated polypeptide prepared by the chemical synthesis according to the present invention showed equivalent or superior antitumor activity compared to IFN-3 prepared by biosynthesis. In particular, the glycosylated polypeptide (19) of the present invention wherein the attached disialo sugar chains are substantially uniform showed superior antitumor activity compared to IFN-β prepared by biosynthesis.

Example 13 Evaluation of Cell Proliferation Suppression Ability after Heat Treatment Moreover, the cell proliferation suppression ability of the heat-treated disialo sugar chain attached polypeptide obtained by subjecting the disialo sugar chain attached polypeptide heat-treated in the above 9-1. to the de-Acm step, the benzyl group deprotection step, and the folding step described in the above 3-4.-3-6. was evaluated.

Specific evaluation of cell proliferation suppression ability was performed as follows.

Human Burkitt's lymphoma cell strain, Daudi, was suspended in RPMI 1640 medium containing 10% Fatal Bovine Serum, 100 U/mL penicillin, and 100 μg/mL streptomycin (10% FCS-RPMI 1640) to $1.25\times10^5$ cells/mL. $1\times10^4$/80 μL/well of the cell suspension was seeded in a 96-well flat-bottomed plate, 20 μL/well of complete chemically synthesized IFN-β diluted with 10% FCS-RPMI 1640 was further added, and cultured in an $CO_2$ incubator with $CO_2$ concentration adjusted to 5% at 37° C. for 3 days. The cell proliferation suppression ability was measured with Cell counting kit-8 (DOJINDO) according to the manual provided in the kit, with mitochondria dehydrogenase activity at day 3 of culture as the indicator.

Moreover, the non-heat-treated disialo sugar chain attached polypeptide (10) was used as the control. The results thereof are shown in FIG. 42. As shown in FIG. 42, cell proliferation suppression ability equivalent to a non-heat-treated glycosylated polypeptide was shown in the glycosylated polypeptide even after heat treatment.

SEQUENCE LISTING

OCKP1104F sequence listing.txt

The invention claimed is:

1. A composition comprising glycosylated polypeptides and/or pharmaceutically acceptable salts thereof, wherein the polypeptides are selected from the group consisting of:
   (a) a polypeptide consisting of the amino acid sequence of SEQ ID NO:1;
   (b) a polypeptide having 1 to 10 amino acids conservatively substituted from the amino acid sequence of SEQ ID NO:1 and having interferon β activity; and
   (c) any combination of (a) and/or (b);
   wherein the polypeptide has a complex-type sugar chain at the amino acid corresponding to position 80 in interferon β,
   the sugar chains are 90% or more uniform among said glycosylated polypeptides, and
   cysteines corresponding to positions 31 and 141 of interferon β form a disulfide bond.

2. The composition according to claim 1, wherein the glycosylated polypeptides in said composition are 90% or more pure prior to addition to the composition.

3. A method for treating or reducing the risk of developing an interferon β-related disease, comprising administering to a subject in need thereof an effective amount of the composition of claim 1, thereby treating or reducing the risk of developing the interferon beta-related disease.

4. The method according to claim 3, wherein said interferon β-related disease is at least one disease selected from the group consisting of a brain tumor including multi-glioblastoma, medulloblastoma, and astrocytoma, cutaneous malignant melanoma, chronic active hepatitis B, chronic hepatitis C, subacute sclerosing panencephalitis, compensated cirrhosis C, and multiple sclerosis.

5. The method according to claim 3, wherein the composition is a pharmaceutical composition comprising:
   (I) the composition according claim 1, and
   (II) a pharmaceutically acceptable carrier.

6. The composition according to claim 1, wherein the sugar chain in said glycosylated polypeptide is an asparagine-linked sugar chain.

7. The composition according to claim 1, wherein the sugar chain in said glycosylated polypeptide is a disialo sugar chain of the following formula (a) or an asialo sugar chain of the following formula (b):

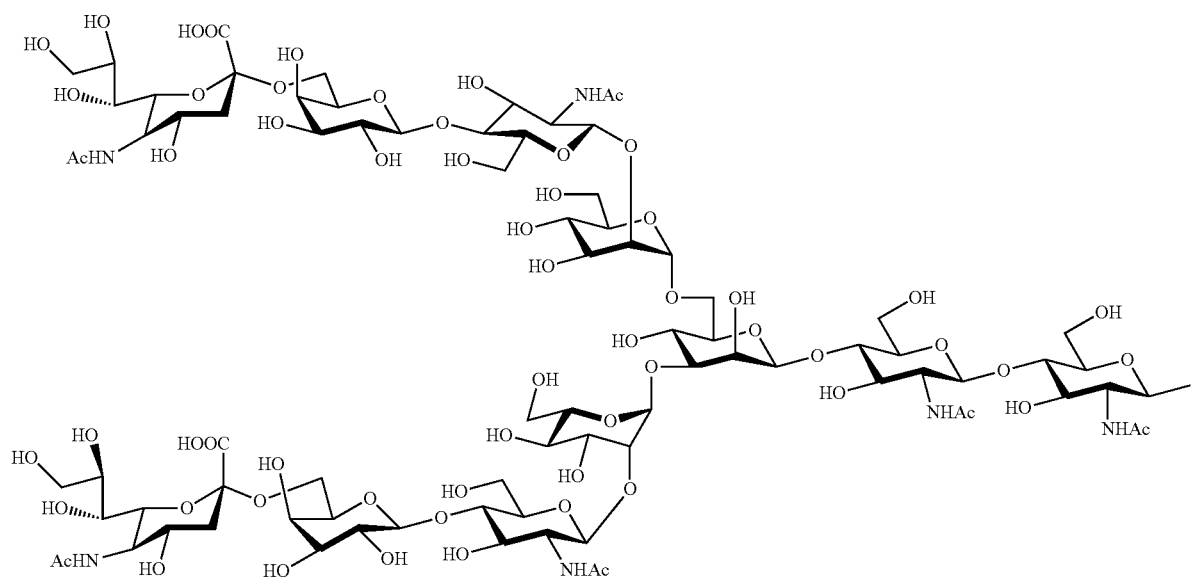

(a)

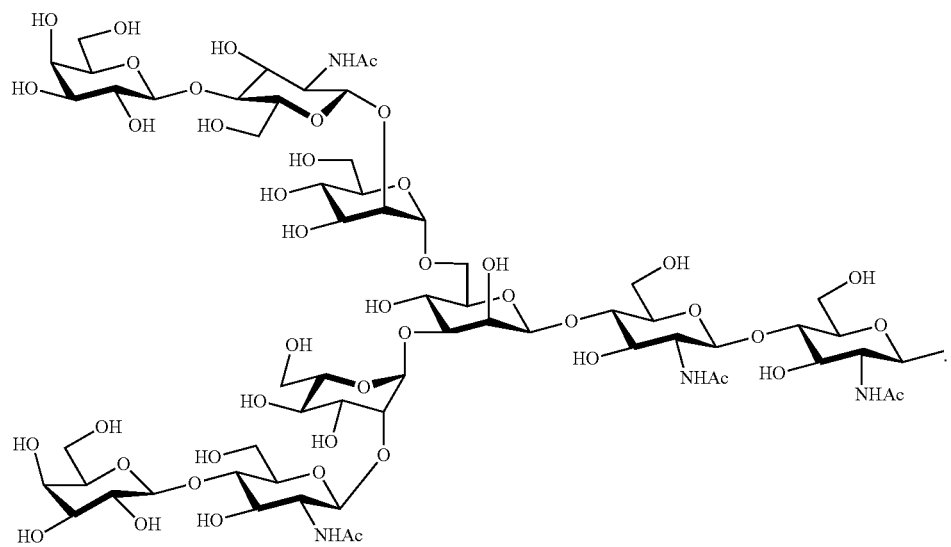

(b)

8. A pharmaceutical composition comprising:
(I) the composition according claim 1, and
(II) a pharmaceutically acceptable carrier.

9. The pharmaceutical composition according to claim 8, wherein said glycosylated polypeptides are 90% or more pure prior to being added to the composition.

10. The pharmaceutical composition according to claim 8, wherein the sugar chain in said glycosylated polypeptide is an asparagine-linked sugar chain.

11. The pharmaceutical composition according to claim 8, wherein the sugar chain in said glycosylated polypeptide is a disialo sugar chain of the following formula (a) or an asialo sugar chain of the following formula (b):

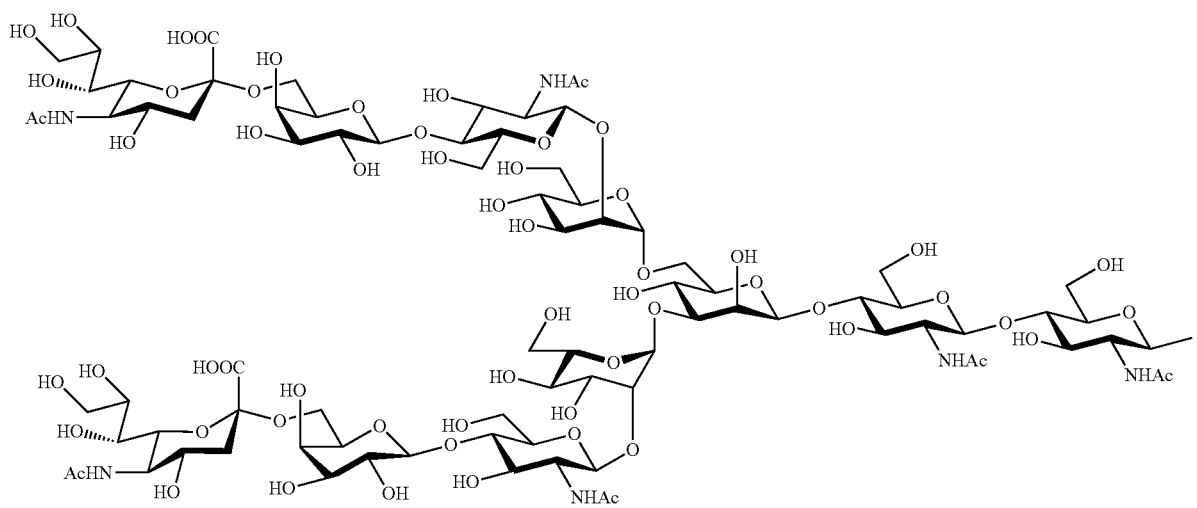

(a)

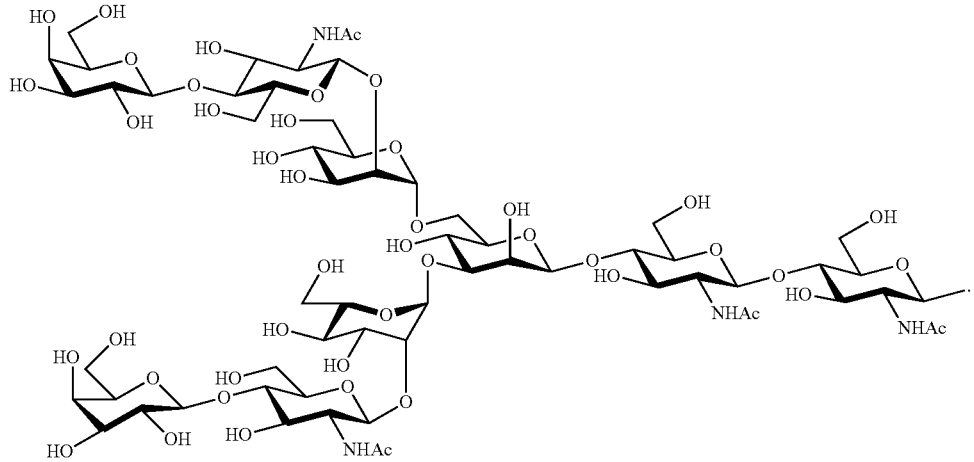

(b)

12. The composition according to claim 8, wherein the composition is stable to heat treatment.

13. The composition according to claim 8, wherein the composition is free of viral and genetic material.

14. The composition according to claim 1, wherein the composition is stable to heat treatment.

15. The composition of claim 1, wherein the polypeptides are selected from the group consisting of:
   (a) a polypeptide consisting of the amino acid sequence of SEQ ID NO:1;
   (b) a polypeptide having 1 to 5 amino acids conservatively substituted from the amino acid sequence of SEQ ID NO:1 and having interferon β activity; and
   (c) any combination of (a) and/or (b);
   wherein the polypeptide has a complex-type sugar chain at the amino acid corresponding to position 80 in interferon β, and
   the sugar chains are 90% or more uniform among said glycosylated polypeptides.

16. A composition comprising glycosylated polypeptides and/or pharmaceutically acceptable salts thereof, wherein the polypeptides are selected from the group consisting of:
   a polypeptide consisting of the amino acid sequence of SEQ ID NO:1,
   wherein the polypeptide has a complex-type sugar chain at the amino acid corresponding to position 80 in interferon β,
   the sugar chains are 90% or more uniform among said glycosylated polypeptides, and cysteines corresponding to positions 31 and 141 of interferon β form a disulfide bond.

17. The composition according to claim 16, wherein the glycosylated polypeptides in said composition are 90% or more pure prior to addition to the composition.

18. The composition according to claim 16, wherein the sugar chain in said glycosylated polypeptide is an asparagine-linked sugar chain.

19. The composition according to claim 16, wherein the sugar chain in said glycosylated polypeptide is a disialo sugar chain of the following formula (a) or an asialo sugar chain of the following formula (b):

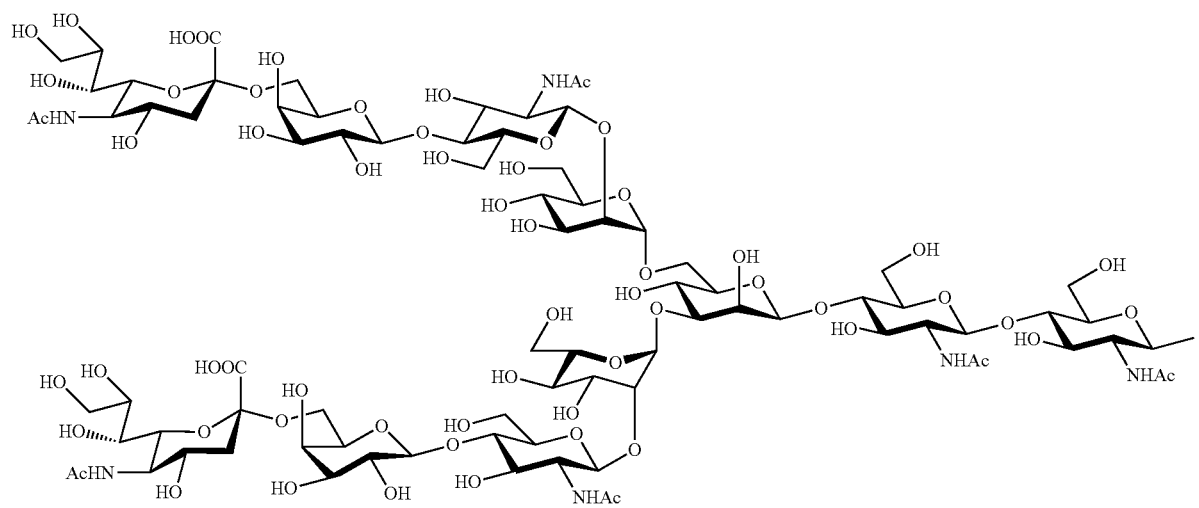
(a)

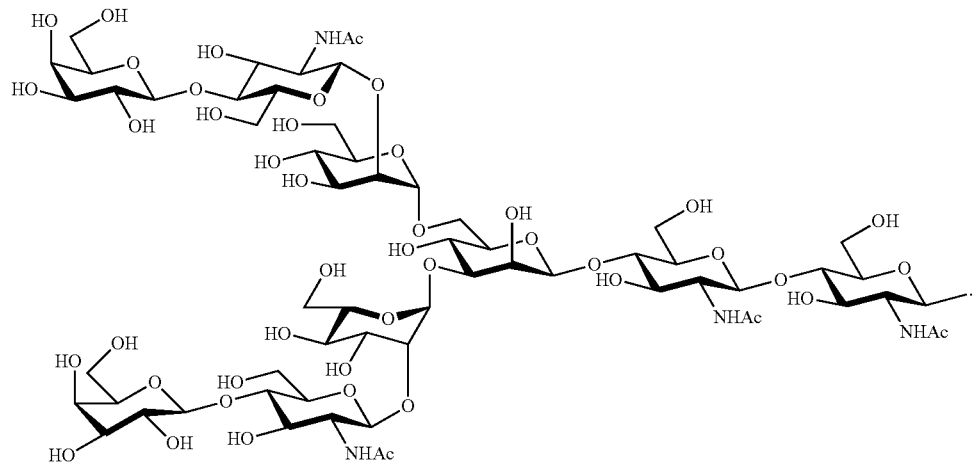
(b)

20. The composition according to claim 16, wherein the composition is stable to heat treatment.

21. A pharmaceutical composition comprising:
(I) the composition according claim 16, and
(II) a pharmaceutically acceptable carrier.

22. The pharmaceutical composition according to claim 21, wherein said glycosylated polypeptides are 90% or more pure prior to being added to the composition.

* * * * *

UNITED STATES PATENT AND TRADEMARK OFFICE
CERTIFICATE OF CORRECTION

PATENT NO.        : 10,358,470 B2
APPLICATION NO.   : 14/347222
DATED             : July 23, 2019
INVENTOR(S)       : Sakamoto et al.

Page 1 of 3

It is certified that error appears in the above-identified patent and that said Letters Patent is hereby corrected as shown below:

In the Specification

Column 9, Line 7: Please correct "13" to read -- β --

Column 15, Line 2: Please correct "3-hydroxy" to read -- β-hydroxy --

Column 19, Formula 9: Please correct "a monosialo sugar chain: OH" to read -- a monosialo sugar chain: --

Column 19, Formula 10: Please delete Formula 10 and replace with:

[Chemical Formula 10]

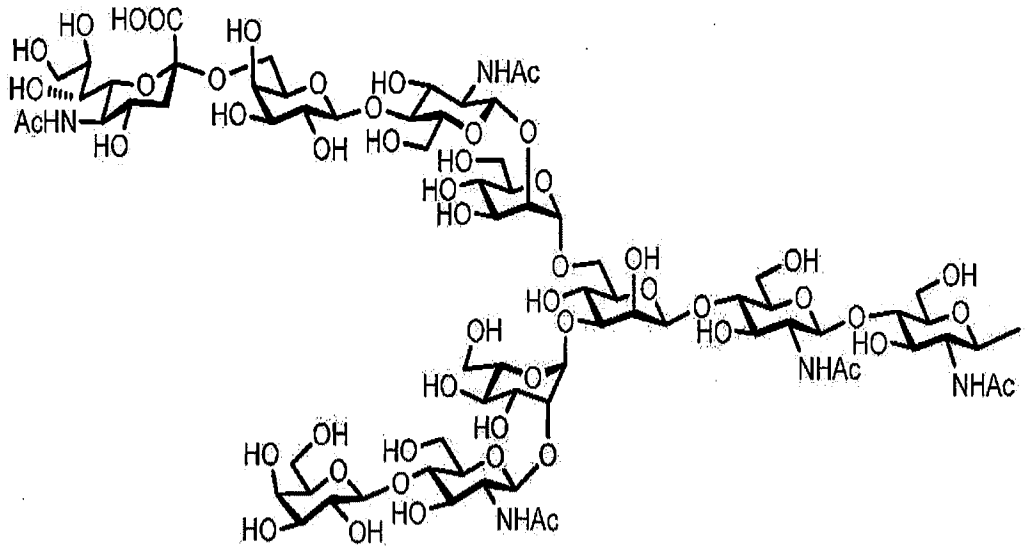

Signed and Sealed this
Seventeenth Day of December, 2019

Andrei Iancu
*Director of the United States Patent and Trademark Office*

Column 19, Formula 10A: Please delete Formula 10A and replace with:

[Chemical Formula 10A]

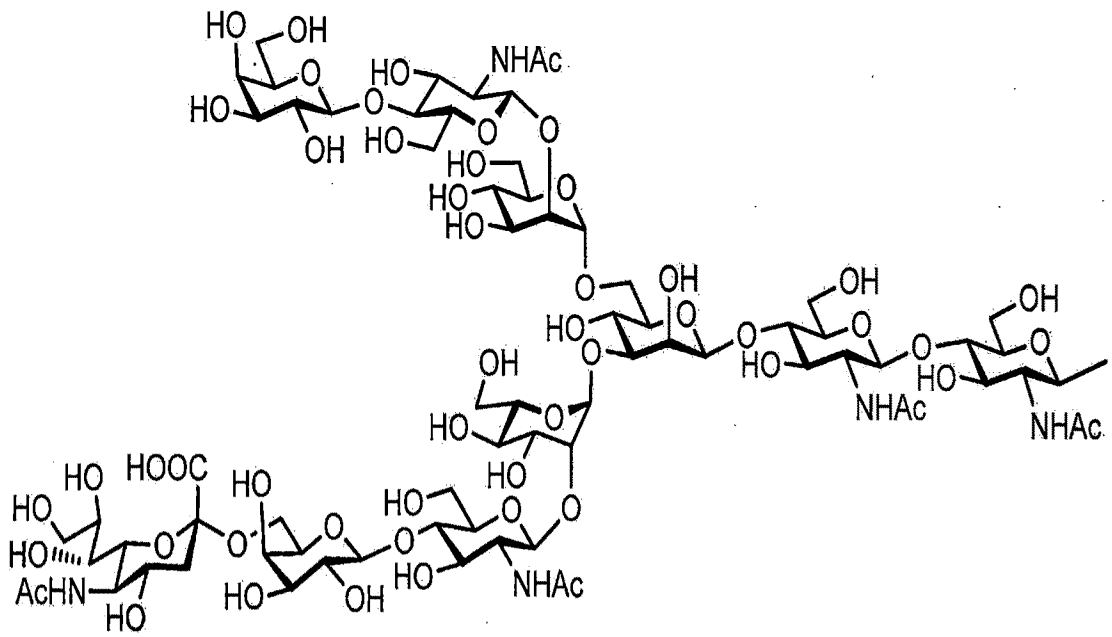

Column 61, Formula 29: Please correct "1S2S(3)-11NC" to read -- 1S(3)2S-11NC --

Column 71, Line 26: Please correct "3" to read -- β --

Column 79, Line 47: Please correct "HCTU.HOBT/NMP" to read -- HCTU•HOBT/NMP --

Column 79, Line 62: Please correct "Fmoc-lie" to read -- Fmoc-Ile --

Column 80, Line 66: Please correct "Gn-Lys-Gu" to read -- Gln-Lys-Glu --

Column 81, Line 1: Please correct "$O_{108}$" to read -- $O_{106}$ --

Column 81, Line 52: Please correct "HCTU-HOBT/NMP" to read -- HCTU•HOBT/NMP --

Column 84, Line 16: Please correct "HCTU.HOBT/NMP" to read -- HCTU•HOBT/NMP --

Column 84, Line 27: Please correct "Fmoc-Ille" to read -- Fmoc-Ile --

Column 85, Line 65: Please correct "Asia" to read -- Asn --

Column 86, Line 1: Please correct "$H_{28}$" to read -- $H_{268}$ --

Column 86, Line 27: Please correct "HCTU-HOBT/NMP" to read -- HCTU•HOBT/NMP --

Column 86, Line 60: Please correct "Asn(Phe-Tyr(tBu)-" to read -- Asn(Trt)-Ile-Phe-Tyr(tBu)- --

CERTIFICATE OF CORRECTION (continued)
U.S. Pat. No. 10,358,470 B2

Column 87, Line 34: Please correct "IFN-3" to read -- IFN-β --

Column 92, Line 16: Please correct "$O_{318}$" to read -- $O_{316}$ --

Column 94, Line 50: Please correct "HCTU-HOBT/NMP" to read -- HCTU•HOBT/NMP --

Column 96, Line 25: Please correct "HCTU-HOBT/NMP" to read -- HCTU•HOBT/NMP --

Column 96, Line 48: Please correct "(Pb)" to read -- (Pbf) --

Column 97, Line 50: Please correct "C1.C2" to read -- C1•C2 --

Column 99, Line 62: Please correct "$[M+12H]^{12+}$" to read -- $[M+11H]^{11+}$ --

Column 102, Line 40: Please correct "HCTU.HOBT/NMP" to read -- HCTU•HOBT/NMP --

Column 104, Line 61: Please correct "HCTU-HOBT/NMP" to read -- HCTU•HOBT/NMP --

Column 107, Line 35: Please correct "IFN-α/p" to read -- IFN-α/β --

Column 108, Line 35: Please correct "IFN" to read -- IFNβ --

Column 110, Line 53: Please correct "IFN-3" to read -- IFN-β --

```
                        SEQUENCE LISTING

<160> NUMBER OF SEQ ID NOS: 51

<210> SEQ ID NO 1
<211> LENGTH: 166
<212> TYPE: PRT
<213> ORGANISM: Homo sapiens

<400> SEQUENCE: 1

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term BocNH
<220> FEATURE:
<221> NAME/KEY: MOD_RES
<222> LOCATION: (2)..(2)
<223> OTHER INFORMATION: Ser(tBu)
<220> FEATURE:
<221> NAME/KEY: MOD_RES
<222> LOCATION: (3)..(3)
<223> OTHER INFORMATION: Tyr(tBu)
```

-continued

```
<220> FEATURE:
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (10)..(10)
<223> OTHER INFORMATION: Gln(Trt)
<220> FEATURE:
<221> NAME/KEY: MOD_RES
<222> LOCATION: (11)..(11)
<223> OTHER INFORMATION: Arg(Pbf)
<220> FEATURE:
<221> NAME/KEY: MOD_RES
<222> LOCATION: (12)..(12)
<223> OTHER INFORMATION: Ser(tBu)
<220> FEATURE:
<221> NAME/KEY: MOD_RES
<222> LOCATION: (13)..(13)
<223> OTHER INFORMATION: Ser(psiMe, MePro)
<220> FEATURE:
<221> NAME/KEY: MOD_RES
<222> LOCATION: (14)..(14)
<223> OTHER INFORMATION: Asn(Trt)
<220> FEATURE:
<221> NAME/KEY: MOD_RES
<222> LOCATION: (16)..(16)
<223> OTHER INFORMATION: Gln(Trt)
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (18)..(18)
<223> OTHER INFORMATION: Gln(Trt)
<220> FEATURE:
<221> NAME/KEY: MOD_RES
<222> LOCATION: (19)..(19)
<223> OTHER INFORMATION: Lys(Boc)
<220> FEATURE:
<221> NAME/KEY: MOD_RES
<222> LOCATION: (22)..(22)
<223> OTHER INFORMATION: Trp(Boc)
<220> FEATURE:
<221> NAME/KEY: MOD_RES
<222> LOCATION: (23)..(23)
<223> OTHER INFORMATION: Gln(Trt)
<220> FEATURE:
<221> NAME/KEY: MOD_RES
<222> LOCATION: (25)..(25)
<223> OTHER INFORMATION: Asn(Trt)
<220> FEATURE:
<221> NAME/KEY: MOD_RES
<222> LOCATION: (27)..(27)
<223> OTHER INFORMATION: Arg(Pbf)
<220> FEATURE:
<221> NAME/KEY: MOD_RES
<222> LOCATION: (29)..(29)
<223> OTHER INFORMATION: Glu(OtBu)
<220> FEATURE:
<221> NAME/KEY: MOD_RES
<222> LOCATION: (30)..(30)
<223> OTHER INFORMATION: Tyr(tBu)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (33)..(33)
<223> OTHER INFORMATION: Lys(Boc)
<220> FEATURE:
<221> NAME/KEY: MOD_RES
<222> LOCATION: (34)..(34)
<223> OTHER INFORMATION: Asp(OtBu)
```

```
<220> FEATURE:
<221> NAME/KEY: MOD_RES
<222> LOCATION: (35)..(35)
<223> OTHER INFORMATION: Arg(Pbf)
<220> FEATURE:
<221> NAME/KEY: MOD_RES
<222> LOCATION: (37)..(37)
<223> OTHER INFORMATION: Asn(Trt)
<220> FEATURE:
<221> NAME/KEY: MOD_RES
<222> LOCATION: (39)..(39)
<223> OTHER INFORMATION: Asp(OtBu)
<220> FEATURE:
<221> NAME/KEY: MOD_RES
<222> LOCATION: (42)..(42)
<223> OTHER INFORMATION: Glu(OtBu)
<220> FEATURE:
<221> NAME/KEY: MOD_RES
<222> LOCATION: (43)..(43)
<223> OTHER INFORMATION: Glu(OtBu)
<220> FEATURE:
<221> NAME/KEY: MOD_RES
<222> LOCATION: (45)..(45)
<223> OTHER INFORMATION: Lys(Boc)
<220> FEATURE:
<221> NAME/KEY: MOD_RES
<222> LOCATION: (46)..(46)
<223> OTHER INFORMATION: Gln(Trt)
<220> FEATURE:
<221> NAME/KEY: MOD_RES
<222> LOCATION: (48)..(48)
<223> OTHER INFORMATION: Gln(Trt)
<220> FEATURE:
<221> NAME/KEY: MOD_RES
<222> LOCATION: (49)..(49)
<223> OTHER INFORMATION: Gln(Trt)
<220> FEATURE:
<221> NAME/KEY: MOD_RES
<222> LOCATION: (51)..(51)
<223> OTHER INFORMATION: Gln(Trt)
<220> FEATURE:
<221> NAME/KEY: MOD_RES
<222> LOCATION: (52)..(52)
<223> OTHER INFORMATION: Lys(Boc)
<220> FEATURE:
<221> NAME/KEY: MOD_RES
<222> LOCATION: (53)..(53)
<223> OTHER INFORMATION: Glu(OtBu)
<220> FEATURE:
<221> NAME/KEY: MOD_RES
<222> LOCATION: (54)..(54)
<223> OTHER INFORMATION: Asp(OtBu)
<220> FEATURE:
<221> NAME/KEY: MOD_RES
<222> LOCATION: (58)..(58)
<223> OTHER INFORMATION: Thr(psiMe, MePro)
<220> FEATURE:
<221> NAME/KEY: MOD_RES
<222> LOCATION: (60)..(60)
<223> OTHER INFORMATION: Tyr(tBu)
<220> FEATURE:
<221> NAME/KEY: MOD_RES
<222> LOCATION: (61)..(61)
<223> OTHER INFORMATION: Glu(OtBu)
<220> FEATURE:
<221> NAME/KEY: MOD_RES
<222> LOCATION: (64)..(64)
<223> OTHER INFORMATION: Gln(Trt)
<220> FEATURE:
<221> NAME/KEY: MOD_RES
<222> LOCATION: (65)..(65)
<223> OTHER INFORMATION: Asn(Trt)
<220> FEATURE:
<221> NAME/KEY: misc_feature
<222> LOCATION: (67)..(67)
<223> OTHER INFORMATION: Resin modified
```

-continued

```
<400> SEQUENCE: 2

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe
65

<210> SEQ ID NO 3
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term BocNH
<220> FEATURE:
<221> NAME/KEY: MOD_RES
<222> LOCATION: (2)..(2)
<223> OTHER INFORMATION: Ser(tBu)
<220> FEATURE:
<221> NAME/KEY: MOD_RES
<222> LOCATION: (3)..(3)
<223> OTHER INFORMATION: Tyr(tBu)
<220> FEATURE:
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (10)..(10)
<223> OTHER INFORMATION: Gln(Trt)
<220> FEATURE:
<221> NAME/KEY: MOD_RES
<222> LOCATION: (11)..(11)
<223> OTHER INFORMATION: Arg(Pbf)
<220> FEATURE:
<221> NAME/KEY: MOD_RES
<222> LOCATION: (12)..(12)
<223> OTHER INFORMATION: Ser(tBu)
<220> FEATURE:
<221> NAME/KEY: MOD_RES
<222> LOCATION: (13)..(13)
<223> OTHER INFORMATION: Ser(psiMe, MePro)
<220> FEATURE:
<221> NAME/KEY: MOD_RES
<222> LOCATION: (14)..(14)
<223> OTHER INFORMATION: Asn(Trt)
<220> FEATURE:
<221> NAME/KEY: MOD_RES
<222> LOCATION: (16)..(16)
<223> OTHER INFORMATION: Gln(Trt)
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (18)..(18)
<223> OTHER INFORMATION: Gln(Trt)
<220> FEATURE:
<221> NAME/KEY: MOD_RES
<222> LOCATION: (19)..(19)
<223> OTHER INFORMATION: Lys(Boc)
<220> FEATURE:
<221> NAME/KEY: MOD_RES
<222> LOCATION: (22)..(22)
<223> OTHER INFORMATION: Trp(Boc)
```

```
<220> FEATURE:
<221> NAME/KEY: MOD_RES
<222> LOCATION: (23)..(23)
<223> OTHER INFORMATION: Gln(Trt)
<220> FEATURE:
<221> NAME/KEY: MOD_RES
<222> LOCATION: (25)..(25)
<223> OTHER INFORMATION: Asn(Trt)
<220> FEATURE:
<221> NAME/KEY: MOD_RES
<222> LOCATION: (27)..(27)
<223> OTHER INFORMATION: Arg(Pbf)
<220> FEATURE:
<221> NAME/KEY: MOD_RES
<222> LOCATION: (29)..(29)
<223> OTHER INFORMATION: Glu(OtBu)
<220> FEATURE:
<221> NAME/KEY: MOD_RES
<222> LOCATION: (30)..(30)
<223> OTHER INFORMATION: Tyr(tBu)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (33)..(33)
<223> OTHER INFORMATION: Lys(Boc)
<220> FEATURE:
<221> NAME/KEY: MOD_RES
<222> LOCATION: (34)..(34)
<223> OTHER INFORMATION: Asp(OtBu)
<220> FEATURE:
<221> NAME/KEY: MOD_RES
<222> LOCATION: (35)..(35)
<223> OTHER INFORMATION: Arg(Pbf)
<220> FEATURE:
<221> NAME/KEY: MOD_RES
<222> LOCATION: (37)..(37)
<223> OTHER INFORMATION: Asn(Trt)
<220> FEATURE:
<221> NAME/KEY: MOD_RES
<222> LOCATION: (39)..(39)
<223> OTHER INFORMATION: Asp(OtBu)
<220> FEATURE:
<221> NAME/KEY: MOD_RES
<222> LOCATION: (42)..(42)
<223> OTHER INFORMATION: Glu(OtBu)
<220> FEATURE:
<221> NAME/KEY: MOD_RES
<222> LOCATION: (43)..(43)
<223> OTHER INFORMATION: Glu(OtBu)
<220> FEATURE:
<221> NAME/KEY: MOD_RES
<222> LOCATION: (45)..(45)
<223> OTHER INFORMATION: Lys(Boc)
<220> FEATURE:
<221> NAME/KEY: MOD_RES
<222> LOCATION: (46)..(46)
<223> OTHER INFORMATION: Gln(Trt)
<220> FEATURE:
<221> NAME/KEY: MOD_RES
<222> LOCATION: (48)..(48)
<223> OTHER INFORMATION: Gln(Trt)
<220> FEATURE:
<221> NAME/KEY: MOD_RES
<222> LOCATION: (49)..(49)
<223> OTHER INFORMATION: Gln(Trt)
<220> FEATURE:
<221> NAME/KEY: MOD_RES
<222> LOCATION: (51)..(51)
<223> OTHER INFORMATION: Gln(Trt)
<220> FEATURE:
<221> NAME/KEY: MOD_RES
<222> LOCATION: (52)..(52)
<223> OTHER INFORMATION: Lys(Boc)
```

```
<220> FEATURE:
<221> NAME/KEY: MOD_RES
<222> LOCATION: (53)..(53)
<223> OTHER INFORMATION: Glu(OtBu)
<220> FEATURE:
<221> NAME/KEY: MOD_RES
<222> LOCATION: (54)..(54)
<223> OTHER INFORMATION: Asp(OtBu)
<220> FEATURE:
<221> NAME/KEY: MOD_RES
<222> LOCATION: (58)..(58)
<223> OTHER INFORMATION: Thr(psiMe, MePro)
<220> FEATURE:
<221> NAME/KEY: MOD_RES
<222> LOCATION: (60)..(60)
<223> OTHER INFORMATION: Tyr(tBu)
<220> FEATURE:
<221> NAME/KEY: MOD_RES
<222> LOCATION: (61)..(61)
<223> OTHER INFORMATION: Glu(OtBu)
<220> FEATURE:
<221> NAME/KEY: MOD_RES
<222> LOCATION: (64)..(64)
<223> OTHER INFORMATION: Gln(Trt)
<220> FEATURE:
<221> NAME/KEY: MOD_RES
<222> LOCATION: (65)..(65)
<223> OTHER INFORMATION: Asn(Trt)

<400> SEQUENCE: 3

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe
65

<210> SEQ ID NO 4
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (31)..(31)
<223> OTHER INFORMATION: Cys(Acm)
<220> FEATURE:
<223> OTHER INFORMATION: C-term SPh

<400> SEQUENCE: 4

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45
```

Gln Phe Gln Lys Glu Asp Ala Ala Leu Thr Ile Tyr Glu Met Leu Gln
            50                  55                  60

Asn Ile Phe
 65

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term FmocNH
<220> FEATURE:
<221> NAME/KEY: MOD_RES
<222> LOCATION: (1)..(1)
<223> OTHER INFORMATION: Asn(dibenzyl-disialo oligosaccharide)
<220> FEATURE:
<221> NAME/KEY: MOD_RES
<222> LOCATION: (2)..(2)
<223> OTHER INFORMATION: Glu(OtBu)
<220> FEATURE:
<221> NAME/KEY: MOD_RES
<222> LOCATION: (3)..(3)
<223> OTHER INFORMATION: Thr(tBu)
<220> FEATURE:
<221> NAME/KEY: MOD_RES
<222> LOCATION: (6)..(6)
<223> OTHER INFORMATION: Glu(OtBu)
<220> FEATURE:
<221> NAME/KEY: MOD_RES
<222> LOCATION: (7)..(7)
<223> OTHER INFORMATION: Asn(Trt)
<220> FEATURE:
<221> NAME/KEY: misc_feature
<222> LOCATION: (9)..(9)
<223> OTHER INFORMATION: Resin modified

<400> SEQUENCE: 5

Asn Glu Thr Ile Val Glu Asn Leu Leu
 1               5

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term BocN
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (5)..(5)
<223> OTHER INFORMATION: Gln(Trt)
<220> FEATURE:
<221> NAME/KEY: MOD_RES
<222> LOCATION: (6)..(6)
<223> OTHER INFORMATION: Asp(OtBu)
<220> FEATURE:
<221> NAME/KEY: MOD_RES
<222> LOCATION: (7)..(7)
<223> OTHER INFORMATION: Ser(tBu)

```
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Ser(psiMe, MePro)
<220> FEATURE:
<221> NAME/KEY: MOD_RES
<222> LOCATION: (10)..(10)
<223> OTHER INFORMATION: Thr(tBu)
<220> FEATURE:
<221> NAME/KEY: MOD_RES
<222> LOCATION: (12)..(12)
<223> OTHER INFORMATION: Trp(Boc)
<220> FEATURE:
<221> NAME/KEY: MOD_RES
<222> LOCATION: (13)..(13)
<223> OTHER INFORMATION: Asn(dibenzyl-disialo oligosaccharide)
<220> FEATURE:
<221> NAME/KEY: MOD_RES
<222> LOCATION: (14)..(14)
<223> OTHER INFORMATION: Glu(OtBu)
<220> FEATURE:
<221> NAME/KEY: MOD_RES
<222> LOCATION: (15)..(15)
<223> OTHER INFORMATION: Thr(tBu)
<220> FEATURE:
<221> NAME/KEY: MOD_RES
<222> LOCATION: (18)..(18)
<223> OTHER INFORMATION: Glu(OtBu)
<220> FEATURE:
<221> NAME/KEY: MOD_RES
<222> LOCATION: (19)..(19)
<223> OTHER INFORMATION: Asn(Trt)
<220> FEATURE:
<221> NAME/KEY: misc_feature
<222> LOCATION: (21)..(21)
<223> OTHER INFORMATION: Resin modified

<400> SEQUENCE: 6

Cys Ile Phe Arg Gln Asp Ser Ser Ser Thr Gly Trp Asn Glu Thr Ile
1               5                   10                  15

Val Glu Asn Leu Leu
            20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term BocN
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (5)..(5)
<223> OTHER INFORMATION: Gln(Trt)
<220> FEATURE:
<221> NAME/KEY: MOD_RES
<222> LOCATION: (6)..(6)
<223> OTHER INFORMATION: Asp(OtBu)
<220> FEATURE:
<221> NAME/KEY: MOD_RES
<222> LOCATION: (7)..(7)
<223> OTHER INFORMATION: Ser(tBu)
```

```
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Ser(psiMe, MePro)
<220> FEATURE:
<221> NAME/KEY: MOD_RES
<222> LOCATION: (10)..(10)
<223> OTHER INFORMATION: Thr(tBu)
<220> FEATURE:
<221> NAME/KEY: MOD_RES
<222> LOCATION: (12)..(12)
<223> OTHER INFORMATION: Trp(Boc)
<220> FEATURE:
<221> NAME/KEY: MOD_RES
<222> LOCATION: (13)..(13)
<223> OTHER INFORMATION: Asn(dibenzyl-disialo oligosaccharide)
<220> FEATURE:
<221> NAME/KEY: MOD_RES
<222> LOCATION: (14)..(14)
<223> OTHER INFORMATION: Glu(OtBu)
<220> FEATURE:
<221> NAME/KEY: MOD_RES
<222> LOCATION: (15)..(15)
<223> OTHER INFORMATION: Thr(tBu)
<220> FEATURE:
<221> NAME/KEY: MOD_RES
<222> LOCATION: (18)..(18)
<223> OTHER INFORMATION: Glu(OtBu)
<220> FEATURE:
<221> NAME/KEY: MOD_RES
<222> LOCATION: (19)..(19)
<223> OTHER INFORMATION: Asn(Trt)

<400> SEQUENCE: 7

Cys Ile Phe Arg Gln Asp Ser Ser Ser Thr Gly Trp Asn Glu Thr Ile
1               5                   10                  15

Val Glu Asn Leu Leu
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term HN
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (13)..(13)
<223> OTHER INFORMATION: Asn(dibenzyl-disialo oligosaccharide)
<220> FEATURE:
<223> OTHER INFORMATION: C-term SPh

<400> SEQUENCE: 8

Cys Ile Phe Arg Gln Asp Ser Ser Ser Thr Gly Trp Asn Glu Thr Ile
1               5                   10                  15

Val Glu Asn Leu Leu
            20

<210> SEQ ID NO 9
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu(OtBu)
<220> FEATURE:
<221> NAME/KEY: MOD_RES
<222> LOCATION: (2)..(2)
<223> OTHER INFORMATION: Thr(tBu)
<220> FEATURE:
<221> NAME/KEY: MOD_RES
<222> LOCATION: (5)..(5)
<223> OTHER INFORMATION: Glu(OtBu)
<220> FEATURE:
<221> NAME/KEY: MOD_RES
<222> LOCATION: (6)..(6)
<223> OTHER INFORMATION: Asn(Trt)
<220> FEATURE:
<221> NAME/KEY: misc_feature
<222> LOCATION: (8)..(8)
<223> OTHER INFORMATION: Resin modified

<400> SEQUENCE: 9

Glu Thr Ile Val Glu Asn Leu Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term FmocNH
<220> FEATURE:
<221> NAME/KEY: MOD_RES
<222> LOCATION: (1)..(1)
<223> OTHER INFORMATION: Asn(Asialo oligosaccharide)
<220> FEATURE:
<221> NAME/KEY: MOD_RES
<222> LOCATION: (2)..(2)
<223> OTHER INFORMATION: Glu(OtBu)
<220> FEATURE:
<221> NAME/KEY: MOD_RES
<222> LOCATION: (3)..(3)
<223> OTHER INFORMATION: Thr(tBu)
<220> FEATURE:
<221> NAME/KEY: MOD_RES
<222> LOCATION: (6)..(6)
<223> OTHER INFORMATION: Glu(OtBu)
<220> FEATURE:
<221> NAME/KEY: MOD_RES
<222> LOCATION: (7)..(7)
<223> OTHER INFORMATION: Asn(Trt)
<220> FEATURE:
<221> NAME/KEY: misc_feature
<222> LOCATION: (9)..(9)
<223> OTHER INFORMATION: Resin modified

<400> SEQUENCE: 10

Asn Glu Thr Ile Val Glu Asn Leu Leu
1               5

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term BocN
```

```
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (5)..(5)
<223> OTHER INFORMATION: Gln(Trt)
<220> FEATURE:
<221> NAME/KEY: MOD_RES
<222> LOCATION: (6)..(6)
<223> OTHER INFORMATION: Asp(OtBu)
<220> FEATURE:
<221> NAME/KEY: MOD_RES
<222> LOCATION: (7)..(7)
<223> OTHER INFORMATION: Ser(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Ser(psiMe, MePro)
<220> FEATURE:
<221> NAME/KEY: MOD_RES
<222> LOCATION: (10)..(10)
<223> OTHER INFORMATION: Thr(tBu)
<220> FEATURE:
<221> NAME/KEY: MOD_RES
<222> LOCATION: (12)..(12)
<223> OTHER INFORMATION: Trp(Boc)
<220> FEATURE:
<221> NAME/KEY: MOD_RES
<222> LOCATION: (13)..(13)
<223> OTHER INFORMATION: Asn(Asialo oligosaccharide)
<220> FEATURE:
<221> NAME/KEY: MOD_RES
<222> LOCATION: (14)..(14)
<223> OTHER INFORMATION: Glu(OtBu)
<220> FEATURE:
<221> NAME/KEY: MOD_RES
<222> LOCATION: (15)..(15)
<223> OTHER INFORMATION: Thr(tBu)
<220> FEATURE:
<221> NAME/KEY: MOD_RES
<222> LOCATION: (18)..(18)
<223> OTHER INFORMATION: Glu(OtBu)
<220> FEATURE:
<221> NAME/KEY: MOD_RES
<222> LOCATION: (19)..(19)
<223> OTHER INFORMATION: Asn(Trt)
<220> FEATURE:
<221> NAME/KEY: misc_feature
<222> LOCATION: (21)..(21)
<223> OTHER INFORMATION: Resin modified

<400> SEQUENCE: 11

Cys Ile Phe Arg Gln Asp Ser Ser Ser Thr Gly Trp Asn Glu Thr Ile
1               5                   10                  15

Val Glu Asn Leu Leu
            20

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term BocN
```

```
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (5)..(5)
<223> OTHER INFORMATION: Gln(Trt)
<220> FEATURE:
<221> NAME/KEY: MOD_RES
<222> LOCATION: (6)..(6)
<223> OTHER INFORMATION: Asp(OtBu)
<220> FEATURE:
<221> NAME/KEY: MOD_RES
<222> LOCATION: (7)..(7)
<223> OTHER INFORMATION: Ser(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Ser(psiMe, MePro)
<220> FEATURE:
<221> NAME/KEY: MOD_RES
<222> LOCATION: (10)..(10)
<223> OTHER INFORMATION: Thr(tBu)
<220> FEATURE:
<221> NAME/KEY: MOD_RES
<222> LOCATION: (12)..(12)
<223> OTHER INFORMATION: Trp(Boc)
<220> FEATURE:
<221> NAME/KEY: MOD_RES
<222> LOCATION: (13)..(13)
<223> OTHER INFORMATION: Asn(Asialo oligosaccharide)
<220> FEATURE:
<221> NAME/KEY: MOD_RES
<222> LOCATION: (14)..(14)
<223> OTHER INFORMATION: Glu(OtBu)
<220> FEATURE:
<221> NAME/KEY: MOD_RES
<222> LOCATION: (15)..(15)
<223> OTHER INFORMATION: Thr(tBu)
<220> FEATURE:
<221> NAME/KEY: MOD_RES
<222> LOCATION: (18)..(18)
<223> OTHER INFORMATION: Glu(OtBu)
<220> FEATURE:
<221> NAME/KEY: MOD_RES
<222> LOCATION: (19)..(19)
<223> OTHER INFORMATION: Asn(Trt)

<400> SEQUENCE: 12

Cys Ile Phe Arg Gln Asp Ser Ser Ser Thr Gly Trp Asn Glu Thr Ile
1               5                   10                  15

Val Glu Asn Leu Leu
            20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term HN
<220> FEATURE:
<221> NAME/KEY: MOD_RES
<222> LOCATION: (1)..(1)
<223> OTHER INFORMATION: Thz
```

-continued

```
<220> FEATURE:
<221> NAME/KEY: MOD_RES
<222> LOCATION: (13)..(13)
<223> OTHER INFORMATION: Asn(Asialo oligosaccharide)
<220> FEATURE:
<223> OTHER INFORMATION: C-term SPh

<400> SEQUENCE: 13

Cys Ile Phe Arg Gln Asp Ser Ser Ser Thr Gly Trp Asn Glu Thr Ile
1               5                   10                  15

Val Glu Asn Leu Leu
            20

<210> SEQ ID NO 14
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term BocNH
<220> FEATURE:
<221> NAME/KEY: MOD_RES
<222> LOCATION: (1)..(1)
<223> OTHER INFORMATION: Cys(Trt)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (4)..(4)
<223> OTHER INFORMATION: Tyr(tBu)
<220> FEATURE:
<221> NAME/KEY: MOD_RES
<222> LOCATION: (5)..(5)
<223> OTHER INFORMATION: His(Trt)
<220> FEATURE:
<221> NAME/KEY: MOD_RES
<222> LOCATION: (6)..(6)
<223> OTHER INFORMATION: Gln(Trt)
<220> FEATURE:
<221> NAME/KEY: MOD_RES
<222> LOCATION: (8)..(8)
<223> OTHER INFORMATION: Asn(Trt)
<220> FEATURE:
<221> NAME/KEY: MOD_RES
<222> LOCATION: (9)..(9)
<223> OTHER INFORMATION: His(Trt)
<220> FEATURE:
<221> NAME/KEY: MOD_RES
<222> LOCATION: (11)..(11)
<223> OTHER INFORMATION: Lys(Boc)
<220> FEATURE:
<221> NAME/KEY: MOD_RES
<222> LOCATION: (12)..(12)
<223> OTHER INFORMATION: Thr(psiMe, MePro)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (16)..(16)
<223> OTHER INFORMATION: Glu(OtBu)
<220> FEATURE:
<221> NAME/KEY: MOD_RES
<222> LOCATION: (17)..(17)
<223> OTHER INFORMATION: Lys(Boc)
<220> FEATURE:
<221> NAME/KEY: MOD_RES
<222> LOCATION: (19)..(19)
<223> OTHER INFORMATION: Glu(OtBu)
```

-continued

```
<220> FEATURE:
<221> NAME/KEY: MOD_RES
<222> LOCATION: (20)..(20)
<223> OTHER INFORMATION: Lys(Boc)
<220> FEATURE:
<221> NAME/KEY: MOD_RES
<222> LOCATION: (21)..(21)
<223> OTHER INFORMATION: Glu(OtBu)
<220> FEATURE:
<221> NAME/KEY: MOD_RES
<222> LOCATION: (22)..(22)
<223> OTHER INFORMATION: Asp(OtBu)
<220> FEATURE:
<221> NAME/KEY: MOD_RES
<222> LOCATION: (24)..(24)
<223> OTHER INFORMATION: Thr(psiMe, MePro)
<220> FEATURE:
<221> NAME/KEY: MOD_RES
<222> LOCATION: (25)..(25)
<223> OTHER INFORMATION: Arg(Pbf)
<220> FEATURE:
<221> NAME/KEY: MOD_RES
<222> LOCATION: (27)..(27)
<223> OTHER INFORMATION: Lys(Boc)
<220> FEATURE:
<221> NAME/KEY: MOD_RES
<222> LOCATION: (30)..(30)
<223> OTHER INFORMATION: Ser(tBu)
<220> FEATURE:
<221> NAME/KEY: MOD_RES
<222> LOCATION: (31)..(31)
<223> OTHER INFORMATION: Ser(psiMe, MePro)
<220> FEATURE:
<221> NAME/KEY: MOD_RES
<222> LOCATION: (33)..(33)
<223> OTHER INFORMATION: His(Trt)
<220> FEATURE:
<221> NAME/KEY: MOD_RES
<222> LOCATION: (35)..(35)
<223> OTHER INFORMATION: Lys(Boc)
<220> FEATURE:
<221> NAME/KEY: MOD_RES
<222> LOCATION: (36)..(36)
<223> OTHER INFORMATION: Arg(Pbf)
<220> FEATURE:
<221> NAME/KEY: MOD_RES
<222> LOCATION: (37)..(37)
<223> OTHER INFORMATION: Tyr(tBu)
<220> FEATURE:
<221> NAME/KEY: MOD_RES
<222> LOCATION: (38)..(38)
<223> OTHER INFORMATION: Tyr(tBu)
<220> FEATURE:
<221> NAME/KEY: MOD_RES
<222> LOCATION: (40)..(40)
<223> OTHER INFORMATION: Arg(Pbf)
<220> FEATURE:
<221> NAME/KEY: MOD_RES
<222> LOCATION: (43)..(43)
<223> OTHER INFORMATION: His(Trt)
<220> FEATURE:
<221> NAME/KEY: MOD_RES
<222> LOCATION: (44)..(44)
<223> OTHER INFORMATION: Tyr(tBu)
<220> FEATURE:
<221> NAME/KEY: MOD_RES
<222> LOCATION: (46)..(46)
<223> OTHER INFORMATION: Lys(Boc)
<220> FEATURE:
<221> NAME/KEY: MOD_RES
<222> LOCATION: (48)..(48)
<223> OTHER INFORMATION: Lys(Boc)
<220> FEATURE:
<221> NAME/KEY: MOD_RES
<222> LOCATION: (49)..(49)
<223> OTHER INFORMATION: Glu(OtBu)
```

```
-continued

<220> FEATURE:
<221> NAME/KEY: MOD_RES
<222> LOCATION: (50)..(50)
<223> OTHER INFORMATION: Tyr(tBu)
<220> FEATURE:
<221> NAME/KEY: MOD_RES
<222> LOCATION: (51)..(51)
<223> OTHER INFORMATION: Ser(psiMe, MePro)
<220> FEATURE:
<221> NAME/KEY: MOD_RES
<222> LOCATION: (52)..(52)
<223> OTHER INFORMATION: His(Trt)
<220> FEATURE:
<221> NAME/KEY: MOD_RES
<222> LOCATION: (53)..(53)
<223> OTHER INFORMATION: Cys(Acm)
<220> FEATURE:
<221> NAME/KEY: MOD_RES
<222> LOCATION: (55)..(55)
<223> OTHER INFORMATION: Trp(Boc)
<220> FEATURE:
<221> NAME/KEY: MOD_RES
<222> LOCATION: (56)..(56)
<223> OTHER INFORMATION: Thr(tBu)
<220> FEATURE:
<221> NAME/KEY: MOD_RES
<222> LOCATION: (59)..(59)
<223> OTHER INFORMATION: Arg(Pbf)
<220> FEATURE:
<221> NAME/KEY: MOD_RES
<222> LOCATION: (61)..(61)
<223> OTHER INFORMATION: Glu(OtBu)
<220> FEATURE:
<221> NAME/KEY: MOD_RES
<222> LOCATION: (64)..(64)
<223> OTHER INFORMATION: Arg(Pbf)
<220> FEATURE:
<221> NAME/KEY: MOD_RES
<222> LOCATION: (65)..(65)
<223> OTHER INFORMATION: Asn(Trt)
<220> FEATURE:
<221> NAME/KEY: MOD_RES
<222> LOCATION: (67)..(67)
<223> OTHER INFORMATION: Tyr(tBu)
<220> FEATURE:
<221> NAME/KEY: MOD_RES
<222> LOCATION: (70)..(70)
<223> OTHER INFORMATION: Asn(Trt)
<220> FEATURE:
<221> NAME/KEY: MOD_RES
<222> LOCATION: (71)..(71)
<223> OTHER INFORMATION: Arg(Pbf)
<220> FEATURE:
<221> NAME/KEY: MOD_RES
<222> LOCATION: (73)..(73)
<223> OTHER INFORMATION: Thr(tBu)
<220> FEATURE:
<221> NAME/KEY: MOD_RES
<222> LOCATION: (75)..(75)
<223> OTHER INFORMATION: Tyr(tBu)
<220> FEATURE:
<221> NAME/KEY: MOD_RES
<222> LOCATION: (77)..(77)
<223> OTHER INFORMATION: Arg(Pbf)
<220> FEATURE:
<221> NAME/KEY: MOD_RES
<222> LOCATION: (78)..(78)
<223> OTHER INFORMATION: Asn(Trt)
<220> FEATURE:
<221> NAME/KEY: misc_feature
<222> LOCATION: (78)..(78)
<223> OTHER INFORMATION: Resin modified
```

```
<400> SEQUENCE: 14

Cys Asn Val Tyr His Gln Ile Asn His Leu Lys Thr Val Leu Glu Glu
1               5                   10                  15

Lys Leu Glu Lys Glu Asp Phe Thr Arg Gly Lys Leu Met Ser Ser Leu
            20                  25                  30

His Leu Lys Arg Tyr Tyr Gly Arg Ile Leu His Tyr Leu Lys Ala Lys
        35                  40                  45

Glu Tyr Ser His Cys Ala Trp Thr Ile Val Arg Val Glu Ile Leu Arg
50                  55                  60

Asn Phe Tyr Phe Ile Asn Arg Leu Thr Gly Tyr Leu Arg Asn
65                  70                  75

<210> SEQ ID NO 15
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (53)..(53)
<223> OTHER INFORMATION: Cys(Acm)

<400> SEQUENCE: 15

Cys Asn Val Tyr His Gln Ile Asn His Leu Lys Thr Val Leu Glu Glu
1               5                   10                  15

Lys Leu Glu Lys Glu Asp Phe Thr Arg Gly Lys Leu Met Ser Ser Leu
            20                  25                  30

His Leu Lys Arg Tyr Tyr Gly Arg Ile Leu His Tyr Leu Lys Ala Lys
        35                  40                  45

Glu Tyr Ser His Cys Ala Trp Thr Ile Val Arg Val Glu Ile Leu Arg
50                  55                  60

Asn Phe Tyr Phe Ile Asn Arg Leu Thr Gly Tyr Leu Arg Asn
65                  70                  75

<210> SEQ ID NO 16
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Asn(Asialyloligosaccharide)
<220> FEATURE:
<221> NAME/KEY: MOD_RES
<222> LOCATION: (74)..(74)
<223> OTHER INFORMATION: Cys(Acm)

<400> SEQUENCE: 16

Cys Ile Phe Arg Gln Asp Ser Ser Ser Thr Gly Trp Asn Glu Thr Ile
1               5                   10                  15

Val Glu Asn Leu Leu Cys Asn Val Tyr His Gln Ile Asn His Leu Lys
            20                  25                  30

Thr Val Leu Glu Glu Lys Leu Glu Lys Glu Asp Phe Thr Arg Gly Lys
        35                  40                  45

Leu Met Ser Ser Leu His Leu Lys Arg Tyr Tyr Gly Arg Ile Leu His
50                  55                  60
```

-continued

```
Tyr Leu Lys Ala Lys Glu Tyr Ser His Cys Ala Trp Thr Ile Val Arg
 65                 70                  75                  80

Val Glu Ile Leu Arg Asn Phe Tyr Phe Ile Asn Arg Leu Thr Gly Tyr
                85                  90                  95

Leu Arg Asn

<210> SEQ ID NO 17
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (80)..(80)
<223> OTHER INFORMATION: Asn(Asialyloligosaccharide)
<220> FEATURE:
<221> NAME/KEY: MOD_RES
<222> LOCATION: (141)..(141)
<223> OTHER INFORMATION: Cys(Acm)

<400> SEQUENCE: 17

Met Ser Tyr Asn Leu Leu Gly Phe Leu Gln Arg Ser Ser Asn Phe Gln
  1               5                  10                  15

Cys Gln Lys Leu Leu Trp Gln Leu Asn Gly Arg Leu Glu Tyr Cys Leu
                 20                  25                  30

Lys Asp Arg Met Asn Phe Asp Ile Pro Glu Glu Ile Lys Gln Leu Gln
                 35                  40                  45

Gln Phe Gln Lys Glu Asp Ala Ala Leu Thr Ile Tyr Glu Met Leu Gln
     50                  55                  60

Asn Ile Phe Cys Ile Phe Arg Gln Asp Ser Ser Ser Thr Gly Trp Asn
 65                  70                  75                  80

Glu Thr Ile Val Glu Asn Leu Leu Cys Asn Val Tyr His Gln Ile Asn
                 85                  90                  95

His Leu Lys Thr Val Leu Glu Glu Lys Leu Glu Lys Glu Asp Phe Thr
                100                 105                 110

Arg Gly Lys Leu Met Ser Ser Leu His Leu Lys Arg Tyr Tyr Gly Arg
                115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 18
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (80)..(80)
<223> OTHER INFORMATION: Asn(Asialyloligosaccharide)
<220> FEATURE:
<221> NAME/KEY: MOD_RES
<222> LOCATION: (141)..(141)
<223> OTHER INFORMATION: Cys(Acm)

<400> SEQUENCE: 18

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 19
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (80)..(80)
<223> OTHER INFORMATION: Asn(Asialyloligosaccharide)

<400> SEQUENCE: 19

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60
```

```
Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 20
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (31)..(141)
<220> FEATURE:
<221> NAME/KEY: MOD_RES
<222> LOCATION: (80)..(80)
<223> OTHER INFORMATION: Asn(Asialyloligosaccharide)

<400> SEQUENCE: 20

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 21
<211> LENGTH: 99
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Asn(protected sialyloligosaccharide)
<220> FEATURE:
<221> NAME/KEY: MOD_RES
<222> LOCATION: (74)..(74)
<223> OTHER INFORMATION: Cys(Acm)

<400> SEQUENCE: 21

Cys Ile Phe Arg Gln Asp Ser Ser Ser Thr Gly Trp Asn Glu Thr Ile
1               5                  10                  15

Val Glu Asn Leu Leu Cys Asn Val Tyr His Gln Ile Asn His Leu Lys
            20                  25                  30

Thr Val Leu Glu Glu Lys Leu Glu Lys Glu Asp Phe Thr Arg Gly Lys
        35                  40                  45

Leu Met Ser Ser Leu His Leu Lys Arg Tyr Tyr Gly Arg Ile Leu His
    50                  55                  60

Tyr Leu Lys Ala Lys Glu Tyr Ser His Cys Ala Trp Thr Ile Val Arg
65                  70                  75                  80

Val Glu Ile Leu Arg Asn Phe Tyr Phe Ile Asn Arg Leu Thr Gly Tyr
                85                  90                  95

Leu Arg Asn

<210> SEQ ID NO 22
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (80)..(80)
<223> OTHER INFORMATION: Asn(protected sialyloligosaccharide)
<220> FEATURE:
<221> NAME/KEY: MOD_RES
<222> LOCATION: (141)..(141)
<223> OTHER INFORMATION: Cys(Acm)

<400> SEQUENCE: 22

Met Ser Tyr Asn Leu Leu Gly Phe Leu Gln Arg Ser Ser Asn Phe Gln
1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Cys Ile Phe Arg Gln Asp Ser Ser Ser Thr Gly Trp Asn
65                  70                  75                  80
```

```
Glu Thr Ile Val Glu Asn Leu Leu Cys Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 23
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (80)..(80)
<223> OTHER INFORMATION: Asn(protected sialyloligosaccharide)
<220> FEATURE:
<221> NAME/KEY: MOD_RES
<222> LOCATION: (141)..(141)
<223> OTHER INFORMATION: Cys(Acm)

<400> SEQUENCE: 23

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

-continued

```
<210> SEQ ID NO 24
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (80)..(80)
<223> OTHER INFORMATION: Asn(protected sialyloligosaccharide)

<400> SEQUENCE: 24

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
                100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 25
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (80)..(80)
<223> OTHER INFORMATION: Asn(sialyloligosaccharide)

<400> SEQUENCE: 25

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95
```

```
His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 26
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (80)..(80)
<223> OTHER INFORMATION: Asn(sialyloligosaccharide)
<220> FEATURE:
<221> NAME/KEY: DISULFID
<222> LOCATION: (31)..(141)

<400> SEQUENCE: 26

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 27
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term BocN
```

-continued

```
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (4)..(4)
<223> OTHER INFORMATION: Tyr(tBu)
<220> FEATURE:
<221> NAME/KEY: MOD_RES
<222> LOCATION: (5)..(5)
<223> OTHER INFORMATION: His(Trt)
<220> FEATURE:
<221> NAME/KEY: MOD_RES
<222> LOCATION: (6)..(6)
<223> OTHER INFORMATION: Gln(Trt)
<220> FEATURE:
<221> NAME/KEY: MOD_RES
<222> LOCATION: (8)..(8)
<223> OTHER INFORMATION: Asn(Trt)
<220> FEATURE:
<221> NAME/KEY: MOD_RES
<222> LOCATION: (9)..(9)
<223> OTHER INFORMATION: His(Trt)
<220> FEATURE:
<221> NAME/KEY: MOD_RES
<222> LOCATION: (11)..(11)
<223> OTHER INFORMATION: Lys(Boc)
<220> FEATURE:
<221> NAME/KEY: MOD_RES
<222> LOCATION: (12)..(12)
<223> OTHER INFORMATION: Thr(psiMe, MePro)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (16)..(16)
<223> OTHER INFORMATION: Glu(OtBu)
<220> FEATURE:
<221> NAME/KEY: MOD_RES
<222> LOCATION: (17)..(17)
<223> OTHER INFORMATION: Lys(Boc)
<220> FEATURE:
<221> NAME/KEY: MOD_RES
<222> LOCATION: (19)..(19)
<223> OTHER INFORMATION: Glu(OtBu)
<220> FEATURE:
<221> NAME/KEY: MOD_RES
<222> LOCATION: (20)..(20)
<223> OTHER INFORMATION: Lys(Boc)
<220> FEATURE:
<221> NAME/KEY: MOD_RES
<222> LOCATION: (21)..(21)
<223> OTHER INFORMATION: Glu(OtBu)
<220> FEATURE:
<221> NAME/KEY: MOD_RES
<222> LOCATION: (22)..(22)
<223> OTHER INFORMATION: Asp(OtBu)
<220> FEATURE:
<221> NAME/KEY: MOD_RES
<222> LOCATION: (24)..(24)
<223> OTHER INFORMATION: Thr(psiMe, MePro)
<220> FEATURE:
<221> NAME/KEY: MOD_RES
<222> LOCATION: (25)..(25)
<223> OTHER INFORMATION: Arg(Pbf)
<220> FEATURE:
<221> NAME/KEY: MOD_RES
<222> LOCATION: (27)..(27)
<223> OTHER INFORMATION: Lys(Boc)
```

```
<220> FEATURE:
<221> NAME/KEY: MOD_RES
<222> LOCATION: (30)..(30)
<223> OTHER INFORMATION: Ser(tBu)
<220> FEATURE:
<221> NAME/KEY: MOD_RES
<222> LOCATION: (31)..(31)
<223> OTHER INFORMATION: Ser(psiMe, MePro)
<220> FEATURE:
<221> NAME/KEY: MOD_RES
<222> LOCATION: (33)..(33)
<223> OTHER INFORMATION: His(Trt)
<220> FEATURE:
<221> NAME/KEY: MOD_RES
<222> LOCATION: (35)..(35)
<223> OTHER INFORMATION: Lys(Boc)
<220> FEATURE:
<221> NAME/KEY: MOD_RES
<222> LOCATION: (36)..(36)
<223> OTHER INFORMATION: Arg(Pbf)
<220> FEATURE:
<221> NAME/KEY: MOD_RES
<222> LOCATION: (37)..(37)
<223> OTHER INFORMATION: Tyr(tBu)
<220> FEATURE:
<221> NAME/KEY: MOD_RES
<222> LOCATION: (38)..(38)
<223> OTHER INFORMATION: Tyr(tBu)
<220> FEATURE:
<221> NAME/KEY: MOD_RES
<222> LOCATION: (40)..(40)
<223> OTHER INFORMATION: Arg(Pbf)
<220> FEATURE:
<221> NAME/KEY: MOD_RES
<222> LOCATION: (43)..(43)
<223> OTHER INFORMATION: His(Trt)
<220> FEATURE:
<221> NAME/KEY: MOD_RES
<222> LOCATION: (44)..(44)
<223> OTHER INFORMATION: Tyr(tBu)
<220> FEATURE:
<221> NAME/KEY: MOD_RES
<222> LOCATION: (46)..(46)
<223> OTHER INFORMATION: Lys(Boc)
<220> FEATURE:
<221> NAME/KEY: misc_feature
<222> LOCATION: (46)..(46)
<223> OTHER INFORMATION: Resin modified

<400> SEQUENCE: 27

Cys Asn Val Tyr His Gln Ile Asn His Leu Lys Thr Val Leu Glu Glu
1               5                   10                  15

Lys Leu Glu Lys Glu Asp Phe Thr Arg Gly Lys Leu Met Ser Ser Leu
            20                  25                  30

His Leu Lys Arg Tyr Tyr Gly Arg Ile Leu His Tyr Leu Lys
        35                  40                  45

<210> SEQ ID NO 28
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term BocN
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (2)..(2)
<223> OTHER INFORMATION: Asn(Trt)
```

-continued

```
<220> FEATURE:
<221> NAME/KEY: MOD_RES
<222> LOCATION: (4)..(4)
<223> OTHER INFORMATION: Tyr(tBu)
<220> FEATURE:
<221> NAME/KEY: MOD_RES
<222> LOCATION: (5)..(5)
<223> OTHER INFORMATION: His(Trt)
<220> FEATURE:
<221> NAME/KEY: MOD_RES
<222> LOCATION: (6)..(6)
<223> OTHER INFORMATION: Gln(Trt)
<220> FEATURE:
<221> NAME/KEY: MOD_RES
<222> LOCATION: (8)..(8)
<223> OTHER INFORMATION: Asn(Trt)
<220> FEATURE:
<221> NAME/KEY: MOD_RES
<222> LOCATION: (9)..(9)
<223> OTHER INFORMATION: His(Trt)
<220> FEATURE:
<221> NAME/KEY: MOD_RES
<222> LOCATION: (11)..(11)
<223> OTHER INFORMATION: Lys(Boc)
<220> FEATURE:
<221> NAME/KEY: MOD_RES
<222> LOCATION: (12)..(12)
<223> OTHER INFORMATION: Thr(psiMe, MePro)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (16)..(16)
<223> OTHER INFORMATION: Glu(OtBu)
<220> FEATURE:
<221> NAME/KEY: MOD_RES
<222> LOCATION: (17)..(17)
<223> OTHER INFORMATION: Lys(Boc)
<220> FEATURE:
<221> NAME/KEY: MOD_RES
<222> LOCATION: (19)..(19)
<223> OTHER INFORMATION: Glu(OtBu)
<220> FEATURE:
<221> NAME/KEY: MOD_RES
<222> LOCATION: (20)..(20)
<223> OTHER INFORMATION: Lys(Boc)
<220> FEATURE:
<221> NAME/KEY: MOD_RES
<222> LOCATION: (21)..(21)
<223> OTHER INFORMATION: Glu(OtBu)
<220> FEATURE:
<221> NAME/KEY: MOD_RES
<222> LOCATION: (22)..(22)
<223> OTHER INFORMATION: Asp(OtBu)
<220> FEATURE:
<221> NAME/KEY: MOD_RES
<222> LOCATION: (24)..(24)
<223> OTHER INFORMATION: Thr(psiMe, MePro)
<220> FEATURE:
<221> NAME/KEY: MOD_RES
<222> LOCATION: (25)..(25)
<223> OTHER INFORMATION: Arg(Pbf)
<220> FEATURE:
<221> NAME/KEY: MOD_RES
<222> LOCATION: (27)..(27)
<223> OTHER INFORMATION: Lys(Boc)
<220> FEATURE:
<221> NAME/KEY: MOD_RES
<222> LOCATION: (30)..(30)
<223> OTHER INFORMATION: Ser(tBu)
<220> FEATURE:
<221> NAME/KEY: MOD_RES
<222> LOCATION: (31)..(31)
<223> OTHER INFORMATION: Ser(psiMe, MePro)
```

```
<220> FEATURE:
<221> NAME/KEY: MOD_RES
<222> LOCATION: (33)..(33)
<223> OTHER INFORMATION: His(Trt)
<220> FEATURE:
<221> NAME/KEY: MOD_RES
<222> LOCATION: (35)..(35)
<223> OTHER INFORMATION: Lys(Boc)
<220> FEATURE:
<221> NAME/KEY: MOD_RES
<222> LOCATION: (36)..(36)
<223> OTHER INFORMATION: Arg(Pbf)
<220> FEATURE:
<221> NAME/KEY: MOD_RES
<222> LOCATION: (37)..(37)
<223> OTHER INFORMATION: Tyr(tBu)
<220> FEATURE:
<221> NAME/KEY: MOD_RES
<222> LOCATION: (38)..(38)
<223> OTHER INFORMATION: Tyr(tBu)
<220> FEATURE:
<221> NAME/KEY: MOD_RES
<222> LOCATION: (40)..(40)
<223> OTHER INFORMATION: Arg(Pbf)
<220> FEATURE:
<221> NAME/KEY: MOD_RES
<222> LOCATION: (43)..(43)
<223> OTHER INFORMATION: His(Trt)
<220> FEATURE:
<221> NAME/KEY: MOD_RES
<222> LOCATION: (44)..(44)
<223> OTHER INFORMATION: Tyr(tBu)
<220> FEATURE:
<221> NAME/KEY: MOD_RES
<222> LOCATION: (46)..(46)
<223> OTHER INFORMATION: Lys(Boc)

<400> SEQUENCE: 28

Cys Asn Val Tyr His Gln Ile Asn His Leu Lys Thr Val Leu Glu Glu
1               5                   10                  15

Lys Leu Glu Lys Glu Asp Phe Thr Arg Gly Lys Leu Met Ser Ser Leu
            20                  25                  30

His Leu Lys Arg Tyr Tyr Gly Arg Ile Leu His Tyr Leu Lys
        35                  40                  45

<210> SEQ ID NO 29
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term HN
<220> FEATURE:
<221> NAME/KEY: MOD_RES
<222> LOCATION: (1)..(1)
<223> OTHER INFORMATION: Thz
<220> FEATURE:
<223> OTHER INFORMATION: C-term SPh

<400> SEQUENCE: 29

Cys Asn Val Tyr His Gln Ile Asn His Leu Lys Thr Val Leu Glu Glu
1               5                   10                  15

Lys Leu Glu Lys Glu Asp Phe Thr Arg Gly Lys Leu Met Ser Ser Leu
            20                  25                  30

His Leu Lys Arg Tyr Tyr Gly Arg Ile Leu His Tyr Leu Lys
        35                  40                  45
```

```
<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term BocNH
<220> FEATURE:
<221> NAME/KEY: MOD_RES
<222> LOCATION: (1)..(1)
<223> OTHER INFORMATION: Cys(Trt)
<220> FEATURE:
<221> NAME/KEY: MOD_RES
<222> LOCATION: (2)..(2)
<223> OTHER INFORMATION: Lys(Boc)
<220> FEATURE:
<221> NAME/KEY: MOD_RES
<222> LOCATION: (3)..(3)
<223> OTHER INFORMATION: Glu(OtBu)
<220> FEATURE:
<221> NAME/KEY: MOD_RES
<222> LOCATION: (4)..(4)
<223> OTHER INFORMATION: Tyr(tBu)
<220> FEATURE:
<221> NAME/KEY: MOD_RES
<222> LOCATION: (5)..(5)
<223> OTHER INFORMATION: Ser(psiMe, MePro)
<220> FEATURE:
<221> NAME/KEY: MOD_RES
<222> LOCATION: (6)..(6)
<223> OTHER INFORMATION: His(Trt)
<220> FEATURE:
<221> NAME/KEY: MOD_RES
<222> LOCATION: (7)..(7)
<223> OTHER INFORMATION: Cys(Acm)
<220> FEATURE:
<221> NAME/KEY: MOD_RES
<222> LOCATION: (9)..(9)
<223> OTHER INFORMATION: Trp(Boc)
<220> FEATURE:
<221> NAME/KEY: MOD_RES
<222> LOCATION: (10)..(10)
<223> OTHER INFORMATION: Thr(tBu)
<220> FEATURE:
<221> NAME/KEY: MOD_RES
<222> LOCATION: (13)..(13)
<223> OTHER INFORMATION: Arg(Pbf)
<220> FEATURE:
<221> NAME/KEY: MOD_RES
<222> LOCATION: (15)..(15)
<223> OTHER INFORMATION: Glu(OtBu)
<220> FEATURE:
<221> NAME/KEY: MOD_RES
<222> LOCATION: (18)..(18)
<223> OTHER INFORMATION: Arg(Pbf)
<220> FEATURE:
<221> NAME/KEY: MOD_RES
<222> LOCATION: (19)..(19)
<223> OTHER INFORMATION: Asn(Trt)
<220> FEATURE:
<221> NAME/KEY: MOD_RES
<222> LOCATION: (21)..(21)
<223> OTHER INFORMATION: Tyr(tBu)
<220> FEATURE:
<221> NAME/KEY: MOD_RES
<222> LOCATION: (24)..(24)
<223> OTHER INFORMATION: Asn(Trt)
<220> FEATURE:
<221> NAME/KEY: MOD_RES
<222> LOCATION: (25)..(25)
<223> OTHER INFORMATION: Arg(Pbf)
<220> FEATURE:
<221> NAME/KEY: MOD_RES
<222> LOCATION: (27)..(27)
<223> OTHER INFORMATION: Thr(tBu)
```

```
<220> FEATURE:
<221> NAME/KEY: MOD_RES
<222> LOCATION: (29)..(29)
<223> OTHER INFORMATION: Tyr(tBu)
<220> FEATURE:
<221> NAME/KEY: MOD_RES
<222> LOCATION: (31)..(31)
<223> OTHER INFORMATION: Arg(Pbf)
<220> FEATURE:
<221> NAME/KEY: MOD_RES
<222> LOCATION: (32)..(32)
<223> OTHER INFORMATION: Asn(Trt)
<220> FEATURE:
<221> NAME/KEY: misc_feature
<222> LOCATION: (32)..(32)
<223> OTHER INFORMATION: Resin modified

<400> SEQUENCE: 30

Cys Lys Glu Tyr Ser His Cys Ala Trp Thr Ile Val Arg Val Glu Ile
1               5                   10                  15

Leu Arg Asn Phe Tyr Phe Ile Asn Arg Leu Thr Gly Tyr Leu Arg Asn
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Cys(Acm)

<400> SEQUENCE: 31

Cys Lys Glu Tyr Ser His Cys Ala Trp Thr Ile Val Arg Val Glu Ile
1               5                   10                  15

Leu Arg Asn Phe Tyr Phe Ile Asn Arg Leu Thr Gly Tyr Leu Arg Asn
            20                  25                  30

<210> SEQ ID NO 32
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (53)..(53)
<223> OTHER INFORMATION: Cys(Acm)

<400> SEQUENCE: 32

Cys Asn Val Tyr His Gln Ile Asn His Leu Lys Thr Val Leu Glu Glu
1               5                   10                  15

Lys Leu Glu Lys Glu Asp Phe Thr Arg Gly Lys Leu Met Ser Ser Leu
            20                  25                  30

His Leu Lys Arg Tyr Tyr Gly Arg Ile Leu His Tyr Leu Lys Cys Lys
        35                  40                  45

Glu Tyr Ser His Cys Ala Trp Thr Ile Val Arg Val Glu Ile Leu Arg
    50                  55                  60

Asn Phe Tyr Phe Ile Asn Arg Leu Thr Gly Tyr Leu Arg Asn
65                  70                  75
```

```
<210> SEQ ID NO 33
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Asn(asialo oligosaccharide)
<220> FEATURE:
<221> NAME/KEY: MOD_RES
<222> LOCATION: (74)..(74)
<223> OTHER INFORMATION: Cys(Acm)

<400> SEQUENCE: 33

Cys Ile Phe Arg Gln Asp Ser Ser Thr Gly Trp Asn Glu Thr Ile
1               5                   10                  15

Val Glu Asn Leu Leu Cys Asn Val Tyr His Gln Ile Asn His Leu Lys
            20                  25                  30

Thr Val Leu Glu Glu Lys Leu Glu Lys Glu Asp Phe Thr Arg Gly Lys
        35                  40                  45

Leu Met Ser Ser Leu His Leu Lys Arg Tyr Tyr Gly Arg Ile Leu His
50                  55                  60

Tyr Leu Lys Cys Lys Glu Tyr Ser His Cys Ala Trp Thr Ile Val Arg
65                  70                  75                  80

Val Glu Ile Leu Arg Asn Phe Tyr Phe Ile Asn Arg Leu Thr Gly Tyr
                85                  90                  95

Leu Arg Asn

<210> SEQ ID NO 34
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (80)..(80)
<223> OTHER INFORMATION: Asn(asialo oligosaccharide)
<220> FEATURE:
<221> NAME/KEY: MOD_RES
<222> LOCATION: (141)..(141)
<223> OTHER INFORMATION: Cys(Acm)

<400> SEQUENCE: 34

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Cys Ile Phe Arg Gln Asp Ser Ser Ser Thr Gly Trp Asn
65                  70                  75                  80
```

```
Glu Thr Ile Val Glu Asn Leu Leu Cys Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Cys Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 35
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (80)..(80)
<223> OTHER INFORMATION: Asn(asialo oligosaccharide)
<220> FEATURE:
<221> NAME/KEY: MOD_RES
<222> LOCATION: (141)..(141)
<223> OTHER INFORMATION: Cys(Acm)

<400> SEQUENCE: 35

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

-continued

```
<210> SEQ ID NO 36
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Asn(disialo oligosaccharide protected with
      dibenzyl)
<220> FEATURE:
<221> NAME/KEY: MOD_RES
<222> LOCATION: (74)..(74)
<223> OTHER INFORMATION: Cys(Acm)

<400> SEQUENCE: 36

Cys Ile Phe Arg Gln Asp Ser Ser Ser Thr Gly Trp Asn Glu Thr Ile
1               5                   10                  15

Val Glu Asn Leu Leu Cys Asn Val Tyr His Gln Ile Asn His Leu Lys
            20                  25                  30

Thr Val Leu Glu Glu Lys Leu Glu Lys Glu Asp Phe Thr Arg Gly Lys
        35                  40                  45

Leu Met Ser Ser Leu His Leu Lys Arg Tyr Tyr Gly Arg Ile Leu His
    50                  55                  60

Tyr Leu Lys Cys Lys Glu Tyr Ser His Cys Ala Trp Thr Ile Val Arg
65                  70                  75                  80

Val Glu Ile Leu Arg Asn Phe Tyr Phe Ile Asn Arg Leu Thr Gly Tyr
                85                  90                  95

Leu Arg Asn

<210> SEQ ID NO 37
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (80)..(80)
<223> OTHER INFORMATION: Asn(disialo oligosaccharide protected with
      dibenzyl)
<220> FEATURE:
<221> NAME/KEY: MOD_RES
<222> LOCATION: (141)..(141)
<223> OTHER INFORMATION: Cys(Acm)

<400> SEQUENCE: 37

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60
```

```
Asn Ile Phe Cys Ile Phe Arg Gln Asp Ser Ser Thr Gly Trp Asn
 65                  70                  75                  80

Glu Thr Ile Val Glu Asn Leu Leu Cys Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Cys Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 38
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Cys(Acm)
<220> FEATURE:
<221> NAME/KEY: MOD_RES
<222> LOCATION: (31)..(31)
<223> OTHER INFORMATION: Cys(Acm)
<220> FEATURE:
<221> NAME/KEY: MOD_RES
<222> LOCATION: (80)..(80)
<223> OTHER INFORMATION: Asn(disialo oligosaccharide protected with
      dibenzyl)
<220> FEATURE:
<221> NAME/KEY: MOD_RES
<222> LOCATION: (141)..(141)
<223> OTHER INFORMATION: Cys(Acm)

<400> SEQUENCE: 38

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140
```

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term FmocNH
<220> FEATURE:
<221> NAME/KEY: MOD_RES
<222> LOCATION: (1)..(1)
<223> OTHER INFORMATION: Asn(dibenzyl-disialo oligosaccharide)
<220> FEATURE:
<221> NAME/KEY: MOD_RES
<222> LOCATION: (2)..(2)
<223> OTHER INFORMATION: Glu(OtBu)
<220> FEATURE:
<221> NAME/KEY: MOD_RES
<222> LOCATION: (3)..(3)
<223> OTHER INFORMATION: Thr(tBu)
<220> FEATURE:
<221> NAME/KEY: MOD_RES
<222> LOCATION: (6)..(6)
<223> OTHER INFORMATION: Glu(OtBu)
<220> FEATURE:
<221> NAME/KEY: MOD_RES
<222> LOCATION: (7)..(7)
<223> OTHER INFORMATION: Asn(Trt)
<220> FEATURE:
<221> NAME/KEY: misc_feature
<222> LOCATION: (9)..(9)
<223> OTHER INFORMATION: Resin modified

<400> SEQUENCE: 39

Asn Glu Thr Ile Val Glu Asn Leu Leu
1               5

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term BocNH
<220> FEATURE:
<221> NAME/KEY: MOD_RES
<222> LOCATION: (1)..(1)
<223> OTHER INFORMATION: Cys(Trt)
<220> FEATURE:
<221> NAME/KEY: MOD_RES
<222> LOCATION: (2)..(2)
<223> OTHER INFORMATION: Thr(tBu)
<220> FEATURE:
<221> NAME/KEY: MOD_RES
<222> LOCATION: (4)..(4)
<223> OTHER INFORMATION: Trp(Boc)
<220> FEATURE:
<221> NAME/KEY: MOD_RES
<222> LOCATION: (5)..(5)
<223> OTHER INFORMATION: Asn(dibenzyl-disialo oligosaccharide)
<220> FEATURE:
<221> NAME/KEY: MOD_RES
<222> LOCATION: (6)..(6)
<223> OTHER INFORMATION: Glu(OtBu)

```
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (10)..(10)
<223> OTHER INFORMATION: Glu(OtBu)
<220> FEATURE:
<221> NAME/KEY: MOD_RES
<222> LOCATION: (11)..(11)
<223> OTHER INFORMATION: Asn(Trt)
<220> FEATURE:
<221> NAME/KEY: misc_feature
<222> LOCATION: (13)..(13)
<223> OTHER INFORMATION: Resin modified

<400> SEQUENCE: 40

Cys Thr Gly Trp Asn Glu Thr Ile Val Glu Asn Leu Leu
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term BocNH
<220> FEATURE:
<221> NAME/KEY: MOD_RES
<222> LOCATION: (1)..(1)
<223> OTHER INFORMATION: Cys(Trt)
<220> FEATURE:
<221> NAME/KEY: MOD_RES
<222> LOCATION: (2)..(2)
<223> OTHER INFORMATION: Thr(tBu)
<220> FEATURE:
<221> NAME/KEY: MOD_RES
<222> LOCATION: (4)..(4)
<223> OTHER INFORMATION: Trp(Boc)
<220> FEATURE:
<221> NAME/KEY: MOD_RES
<222> LOCATION: (5)..(5)
<223> OTHER INFORMATION: Asn(dibenzyl-disialo oligosaccharide)
<220> FEATURE:
<221> NAME/KEY: MOD_RES
<222> LOCATION: (6)..(6)
<223> OTHER INFORMATION: Glu(OtBu)
<220> FEATURE:
<221> NAME/KEY: MOD_RES
<222> LOCATION: (7)..(7)
<223> OTHER INFORMATION: Thr(tBu)
<220> FEATURE:
<221> NAME/KEY: MOD_RES
<222> LOCATION: (10)..(10)
<223> OTHER INFORMATION: Glu(OtBu)
<220> FEATURE:
<221> NAME/KEY: MOD_RES
<222> LOCATION: (11)..(11)
<223> OTHER INFORMATION: Asn(Trt)

<400> SEQUENCE: 41

Cys Thr Gly Trp Asn Glu Thr Ile Val Glu Asn Leu Leu
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: Asn(dibenzyl-disialo oligosaccharide)
<220> FEATURE:
<223> OTHER INFORMATION: C-term SR (SCH2-CH2-SO3H)

<400> SEQUENCE: 42

Cys Thr Gly Trp Asn Glu Thr Ile Val Glu Asn Leu Leu
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term BocN
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (5)..(5)
<223> OTHER INFORMATION: Gln(Trt)
<220> FEATURE:
<221> NAME/KEY: MOD_RES
<222> LOCATION: (6)..(6)
<223> OTHER INFORMATION: Asp(OtBu)
<220> FEATURE:
<221> NAME/KEY: MOD_RES
<222> LOCATION: (7)..(7)
<223> OTHER INFORMATION: Ser(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: misc_feature
<222> LOCATION: (8)..(8)
<223> OTHER INFORMATION: Resin modified

<400> SEQUENCE: 43

Cys Ile Phe Arg Gln Asp Ser Ser
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term BocN
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (5)..(5)
<223> OTHER INFORMATION: Gln(Trt)
```

```
<220> FEATURE:
<221> NAME/KEY: MOD_RES
<222> LOCATION: (6)..(6)
<223> OTHER INFORMATION: Asp(OtBu)
<220> FEATURE:
<221> NAME/KEY: MOD_RES
<222> LOCATION: (7)..(7)
<223> OTHER INFORMATION: Ser(tBu)
<220> FEATURE:
<221> NAME/KEY: MOD_RES
<222> LOCATION: (8)..(8)
<223> OTHER INFORMATION: Ser(tBu)

<400> SEQUENCE: 44

Cys Ile Phe Arg Gln Asp Ser Ser
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term HN
<220> FEATURE:
<221> NAME/KEY: MOD_RES
<222> LOCATION: (1)..(1)
<223> OTHER INFORMATION: Thz
<220> FEATURE:
<223> OTHER INFORMATION: C-term SPh

<400> SEQUENCE: 45

Cys Ile Phe Arg Gln Asp Ser Ser
1               5

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (13)..(13)
<223> OTHER INFORMATION: Asn(disialo oligosaccharide protected with
      dibenzyl)
<220> FEATURE:
<223> OTHER INFORMATION: C-term SCH2-CH2-SO3H

<400> SEQUENCE: 46

Cys Ile Phe Arg Gln Asp Ser Ser Cys Thr Gly Trp Asn Glu Thr Ile
1               5                   10                  15

Val Glu Asn Leu Leu
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (9)..(9)
<223> OTHER INFORMATION: Methyl-Cys
<220> FEATURE:
<221> NAME/KEY: MOD_RES
<222> LOCATION: (13)..(13)
<223> OTHER INFORMATION: Asn(disialo oligosaccharide protected with
      dibenzyl)
<220> FEATURE:
<223> OTHER INFORMATION: C-term SCH2-CH2-SO3H

<400> SEQUENCE: 47

Cys Ile Phe Arg Gln Asp Ser Ser Cys Thr Gly Trp Asn Glu Thr Ile
1               5                   10                  15

Val Glu Asn Leu Leu
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thz
<220> FEATURE:
<221> NAME/KEY: MOD_RES
<222> LOCATION: (13)..(13)
<223> OTHER INFORMATION: Asn(disialo oligosaccharide protected with
      dibenzyl)
<220> FEATURE:
<223> OTHER INFORMATION: C-term SCH2-CH2-SO3H

<400> SEQUENCE: 48

Cys Ile Phe Arg Gln Asp Ser Ser Ser Thr Gly Trp Asn Glu Thr Ile
1               5                   10                  15

Val Glu Asn Leu Leu
            20

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Ser Tyr Asn
1

<210> SEQ ID NO 50
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 50

Met Ser Trp Tyr Asn
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu(OtBu)
<220> FEATURE:
<221> NAME/KEY: MOD_RES
<222> LOCATION: (2)..(2)
<223> OTHER INFORMATION: Thr(tBu)
<220> FEATURE:
<221> NAME/KEY: MOD_RES
<222> LOCATION: (5)..(5)
<223> OTHER INFORMATION: Glu(OtBu)
<220> FEATURE:
<221> NAME/KEY: MOD_RES
<222> LOCATION: (6)..(6)
<223> OTHER INFORMATION: Asn(Trt)

<400> SEQUENCE: 51

Glu Thr Ile Val Glu Asn Leu Leu
1               5
```